(12) United States Patent
Shimoharada et al.

(10) Patent No.: US 8,030,498 B2
(45) Date of Patent: Oct. 4, 2011

(54) BENZOYLPYRAZOLE COMPOUNDS AND HERBICIDES CONTAINING THEM

(75) Inventors: Hiroshi Shimoharada, Kusatsu (JP); Masamitsu Tsukamoto, Kusatsu (JP); Masahiko Ikeguchi, Kusatsu (JP); Hiroshi Kikugawa, Kusatsu (JP); Makiko Sano, Kusatsu (JP); Yoshinori Kitahara, Kusatsu (JP); Hidemasa Kominami, Kusatsu (JP); Tatsuya Okita, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 474 days.

(21) Appl. No.: 12/094,734

(22) PCT Filed: Dec. 13, 2006

(86) PCT No.: PCT/JP2006/325311
§ 371 (c)(1),
(2), (4) Date: May 22, 2008

(87) PCT Pub. No.: WO2007/069771
PCT Pub. Date: Jun. 21, 2007

(65) Prior Publication Data
US 2009/0286683 A1     Nov. 19, 2009

(30) Foreign Application Priority Data

Dec. 15, 2005 (JP) ................ 2005-362226
Apr. 21, 2006 (JP) ................ 2006-118304
Aug. 31, 2006 (JP) ................ 2006-236954

(51) Int. Cl.
*C07D 231/20* (2006.01)
*A61K 31/415* (2006.01)
(52) U.S. Cl. ............ 548/366.1; 514/407; 514/404
(58) Field of Classification Search .......... None
See application file for complete search history.

(56) References Cited

U.S. PATENT DOCUMENTS 4,261,729 A    4/1981    Konotsune et al.

FOREIGN PATENT DOCUMENTS

| DE | 2513750 A1 * | 10/1975 |
|---|---|---|
| EP | 0 282 944 A2 | 9/1988 |
| EP | 0 344 775 A1 | 12/1989 |
| EP | 0 352 543 A1 | 1/1990 |
| EP | 0 990 649 | 4/2000 |
| JP | 50-126830 | 10/1975 |
| JP | 55000363 A * | 1/1980 |
| JP | 58 188858 | 11/1983 |
| JP | 2-173 | 1/1990 |
| JP | 2-288866 | 11/1990 |
| WO | WO 96/26206 | 8/1996 |
| WO | WO 98/31681 | 7/1998 |
| WO | 00 34273 | 6/2000 |
| WO | 02 090336 | 11/2002 |

OTHER PUBLICATIONS

U.S. Appl. No. 12/521,649, filed Jun. 29, 2009, Shimoharada, et al.
U.S. Appl. No. 12/525,554, filed Aug. 3, 2009, Shimoharada, et al.
U.S. Appl. No. 12/993,760, filed Nov. 19, 2010, Tsukamoto, et al.

* cited by examiner

*Primary Examiner* — Kamal Saeed
*Assistant Examiner* — Nyeemah A Grazier
(74) *Attorney, Agent, or Firm* — Oblon, Spivak, McClelland, Maier & Neustadt, L.L.P.

(57) ABSTRACT

A benzoylpyrazole compound represented by the formula (I) or its salt, useful as herbicides and intermediates thereof.

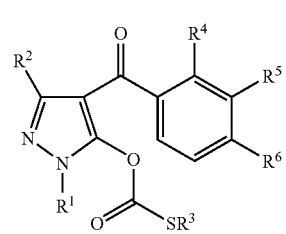

(I)

7 Claims, No Drawings

BENZOYLPYRAZOLE COMPOUNDS AND HERBICIDES CONTAINING THEM

TECHNICAL FIELD

The present invention relates to novel benzoylpyrazole compounds useful as an active ingredient of herbicides.

BACKGROUND ART

WO96/26206, JP-A-50-126830, JP-A-2-288866 and JP-A-2-173 disclose benzoylpyrazole compounds. However, they differ from benzoylpyrazole compounds represented by the following formula (I) in the chemical structure.

DISCLOSURE OF THE INVENTION

Object to be Accomplished by the Invention

Heretofore, herbicides which have excellent herbicidal activity against weeds and which are safe for crop plants, have been desired for labor saving in the operation of controlling weeds and for improvement of productivity of agricultural and horticultural plants. However, search for novel compounds suitable for such an object depends on trial and error.

Means to Accomplish the Object

The present inventors have conducted extensive studies on benzoylpyrazole compounds in order to find more excellent herbicides which accomplish the above object and as a result, accomplished the present invention.

Namely, the present invention relates to a benzoylpyrazole compound represented by the formula (I) or its salt:

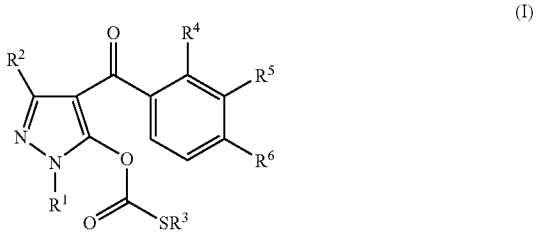

wherein $R^1$ is alkyl or cycloalkyl, $R^2$ is a hydrogen atom or alkyl, $R^3$ is alkyl; cycloalkyl; haloalkyl; alkoxyalkyl; alkoxycarbonylalkyl; alkenyl; or arylalkyl which may be substituted by $R^8$, $R^4$ is alkyl; haloalkyl; alkoxy; halogen; nitro; cyano; alkylthio; alkylsulfinyl; or alkylsulfonyl, $R^5$ is a hydrogen atom; alkyl; alkenyl; alkynyl; halogen; cyano; cyanoalkyl; cyanoalkenyl; haloalkyl; alkoxyalkyl; haloalkoxyalkyl; amino(thiocarbonyl)alkyl which may be substituted by at least one substituent selected from alkyl, cyano, cyanoalkyl, (alkylthio) carbonylalkyl, alkyl(thiocarbonyl)alkyl, —C(O)OR$^7$ and —C(O)SR$^7$; thiocyanatoalkyl; alkoxy; alkenyloxy; alkynyloxy; haloalkoxy; alkoxyalkoxy; haloalkoxyalkoxy; alkoxyhaloalkoxy; haloalkoxyhaloalkoxy; alkoxyalkoxyalkyl; alkylthio; alkoxyalkylthio; haloalkoxyalkylthio; alkoxyhaloalkylthio; haloalkoxyhaloalkylthio; alkylthioalkylthio; haloalkylthioalkylthio; alkylthiohaloalkylthio; haloalkylthiohaloalkylthio; alkylthioalkoxy; alkylsulfonyl; alkylsulfonylalkyl; alkoxycarbonylalkyl; alkoxycarbonylalkoxy; heterocyclylalkyl; heterocyclyloxy; heterocyclylalkoxy; heterocyclylalkoxyalkyl; heterocyclyloxyalkyl; cycloalkyloxy; —OC(O)SR$^7$, —OC(O)OR$^7$; —C(O)OR$^7$; —C(O)SR$^7$; —C(S)OR$^7$; —C(S)SR$^7$; aminoalkyl which may be substituted by at least one substituent selected from alkyl, cyano, cyanoalkyl, (alkylthio)carbonylalkyl, alkyl(thiocarbonyl)alkyl, —C(O)OR$^7$ and —C(O)SR$^7$; or 4,5-dihydroisoxazol-3-yl which may be substituted by R$^9$, R$^6$ is haloalkyl; halogen; nitro; cyano; alkylthio; alkylsulfinyl; or alkylsulfonyl, R$^7$ is alkyl; haloalkyl; alkoxyalkyl; alkenyl; haloalkenyl; alkynyl; or arylalkyl which may be substituted by R$^{10}$, and each of R$^8$, R$^9$ and R$^{10}$ which are independent of one another, is halogen; alkyl; or alkoxy, a process for producing it, a herbicide containing it as an active ingredient, and a method for controlling undesired plants or inhibiting their growth, which comprises applying a herbicidally effective amount of it to the undesired plants or to a place where they grow.

The compounds represented by the formula (I) have excellent herbicidal effects.

BEST MODE FOR CARRYING OUT THE INVENTION

The alkyl or alkyl moiety in each of $R^1$, $R^2$, $R^3$, $R^4$, $R^5$, $R^6$, $R^7$, $R^8$, $R^9$ and $R^{11}$ may be linear or branched, and specific examples thereof include $C_{1-9}$ alkyl such as methyl, ethyl, n-propyl, iso-propyl, n-butyl, iso-butyl, sec-butyl, tert-butyl, n-pentyl, iso-pentyl, neopentyl, tert-pentyl, n-hexyl, iso-hexyl, n-heptyl, n-octyl and n-nonyl.

Examples of the cycloalkyl or cycloalkyl moiety in each of $R^1$, $R^3$ and $R^5$ include $C_{3-6}$ cycloalkyl such as cyclopropyl, cyclobutyl, cyclopentyl and cyclohexyl.

The alkenyl or alkenyl moiety in each of $R^3$, $R^5$ and $R^7$ may be linear or branched, and specific examples thereof include $C_{2-9}$ alkenyl such as vinyl, 1-propenyl, 2-propenyl, iso-propenyl, allyl, 1-butenyl, 2-butenyl, 3-butenyl, 1,3-butadienyl, 2-pentenyl, 4-pentenyl, 2-hexenyl, 4-hexenyl, 2-heptenyl, 4-heptenyl, 2-octenyl, 6-octenyl and 2-nonenyl.

The alkynyl or alkynyl moiety in each of $R^5$ and $R^7$ may be linear or branched, and specific examples thereof include $C_{2-9}$ alkynyl such as ethynyl, propargyl, 1-propynyl, 1-pentynyl, 3-pentynyl, 1-heptynyl and 1-nonynyl.

Examples of halogen or halogen as the substituent in each of $R^3$, $R^4$, $R^5$, $R^6$, $R^7$, $R^8$, $R^9$ and $R^{10}$ include atoms of fluorine, chlorine, bromine and iodine.

The number of halogens as substituents in each of $R^3$, $R^4$, $R^5$, $R^6$ and $R^7$ may be 1 or more, and if more, they may be the same or different. Further, the positions for substitution of such halogens may be any positions.

The number of alkoxy or alkoxy moieties as substituents in each of $R^3$, $R^5$ and $R^7$ may be 1 or more, and if more, they may be the same or different. Further, the positions for substitution may be any positions.

Examples of the aryl or aryl moiety as the substituent in each of $R^3$ and $R^7$ include phenyl and naphthyl. The number of aryl or aryl moieties as substituents may be 1 or more, and if more, they may be is the same or different. Further, the positions for substitution may be any positions.

The number of $R^8$ as substituents which substitute the arylalkyl in $R^3$ may be 1 or more, and if more, they may be the same or different. Further, the positions for substitution of such substituents may be any positions.

The number of $R^{10}$ as substituents which substitute the arylalkyl in $R^7$ may be 1 or more, and if more, they may be the same or different. Further, the positions for substitution of such substituents may be any positions.

The number of $R^9$ as substituents which substitute the 4,5-dihydroisoxazol-3-yl in $R^5$ may be 1 or more, and if more, they may be the same or different. Further, the positions for substitution of such substituents may be any positions.

The alkoxyalkoxy in $R^5$ is meant for an alkoxy group having the same or different alkoxy moiety bonded thereto. The position for substitution of the alkoxy moiety which substitutes the alkoxy group may be any position. The same applies to haloalkoxyalkoxy, alkoxyhaloalkoxy, alkoxyalkoxyalkyl, alkylthioalkylthio, alkylsulfonylalkyl, alkoxycarbonylalkyl, etc.

The heterocyclyl moiety in $R^5$ may, for example, be a saturated or unsaturated 5-membered or 6-membered ring containing 1 to 4 one or more types of hetero atoms optionally selected from O, S and N, and specific examples thereof include oxolanyl, 1,3-dioxolanyl, tetrahydrofuranyl and tetrahydro-2H-pyranyl. Further, the number of heterocyclyl moieties as substituents may be 1 or more, and if more, they may be the same or different. The positions for substitution of the heterocyclyl moieties may be any positions.

The salt of the benzoylpyrazole compound represented by the above formula (I) includes all kinds of salts so long as they are agriculturally acceptable. Examples thereof include alkali metal salts such as a sodium salt and a potassium salt; alkaline earth metal salts such as a magnesium salt and a calcium salt; amine salts such as a dimethylamine salt and a triethylamine salt; inorganic acid salts such as a hydrochloride, a perchlorate, a sulfate and a nitrate; and organic acid salts such as an acetate and a methanesulfonate.

The benzoylpyrazole compound represented by the above formula (I) or its salt (hereinafter referred to simply as the compound of the present invention) can be produced by the following reactions [A] to [AG] and in accordance with a usual method for producing a salt.

The compound of the present invention represented by the above formula (I) can be produced in accordance with the following reaction [A].

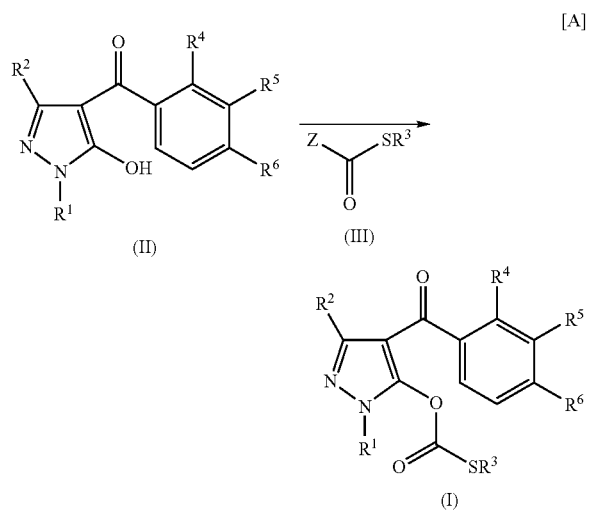

wherein $R^1$, $R^2$, $R^3$, $R^4$, $R^5$ and $R^6$ are as defined above, and Z is a leaving group such as halogen.

Namely, the compound of the present invention represented by the above formula (I) can be produced by reacting a compound represented by the formula (II) with a compound represented by the formula (III).

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried-out in the presence of a base, as the case requires. The base may be either inorganic base or organic base. Examples of the inorganic base include alkali metal hydrides such as sodium hydride and potassium hydride; alkali metal hydroxides such as sodium hydroxide and potassium hydroxide; alkali metal carbonates such as sodium carbonate and potassium carbonate; alkali metal hydrogencarbonates such as sodium hydrogencarbonate and potassium hydrogencarbonate; alkaline earth metal hydroxides such as calcium hydroxide; and alkaline earth metal carbonates such as calcium carbonate. Examples of the organic base include tertiary amines such as triethylamine and diisopropylethylamine; pyridine, 4-(dimethylamino)pyridine and 2,6-lutidine. As the base, one or more types may suitably be selected and mixed.

The above reaction can be carried out at a reaction temperature of usually from 0° C. to 150° C. for a reaction time of usually from 1 minute to 48 hours.

The above reaction may also be carried out in the two-phase system in water and a solvent insoluble in water among the above solvents in the presence of a phase transfer catalyst such as a quaternary ammonium salt.

As mentioned above; compounds represented by the above formula (II) are useful as an intermediate for preparation of the compounds represented by the formula (I). Further, some of the compounds represented by the formula (II) are novel, which are exemplified below.

Benzoylpyrazole compounds represented by the formula (II-x) or their salts:

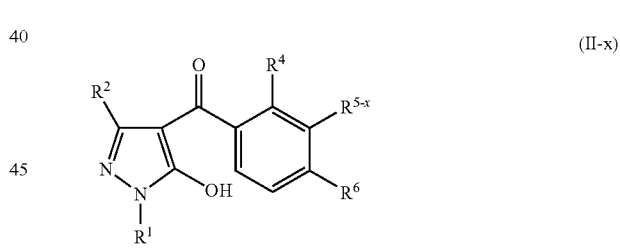

wherein $R^1$ is alkyl or cycloalkyl, $R^2$ is a hydrogen atom or alkyl, $R^4$ is alkyl; haloalkyl; alkoxy; halogen; nitro; cyano; alkylthio; alkylsulfinyl; or alkylsulfonyl, $R^{5-x}$ is alkyl substituted by at least 2 alkoxy; alkyl substituted by at least 2 haloalkoxy; amino(thiocarbonyl)alkyl which may be substituted by at least one substituent selected from alkyl, cyano, cyanoalkyl, (alkylthio)carbonylalkyl, alkyl(thiocarbonyl)alkyl, —C(O)OR$^7$ and —C(O)SR$^7$; thiocyanatoalkyl; alkoxy substituted by at least 2 alkoxy, alkoxy substituted by at least 2 haloalkoxy; alkoxyhaloalkoxy; haloalkoxyhaloalkoxy; alkoxyalkyl substituted by at least 2 alkoxy; alkylthio substituted by at least 2 alkoxy; alkylthio substituted by at least 2 haloalkoxy; alkoxyhaloalkylthio; haloalkoxyhaloalkylthio; alkylthioalkylthio; haloalkylthioalkylthio; alkylthiohaloalkylthio; haloalkylthiohaloalkylthio; alkylthiohaloalkoxy; alkyl substituted by at least 2 alkylsulfonyl; alkyl substituted by at least 2 alkoxycarbonyl; alkoxy substituted by at least 2 alkoxycarbonyl; alkyl substituted by at least 2 heterocyclyl;

alkoxy substituted by at least 2 heterocyclyl; alkyl substituted by at least 2 heterocyclylalkoxy; —OC(O)SR⁷; or aminoalkyl which may be substituted by at least one substituent selected from cyano, cyanoalkyl, (alkylthio)carbonylalkyl, alkyl(thiocarbonyl)alkyl, —C(O)OR⁷ and —C(O)SR⁷, $R^6$ is haloalkyl; halogen; nitro; cyano; alkylthio; alkylsulfinyl; or alkylsulfonyl, $R^7$ is alkyl; haloalkyl; alkoxyalkyl; alkenyl; haloalkenyl; alkynyl; or arylalkyl, which may be substituted by $R^{10}$, and $R^{10}$ is halogen; alkyl; or alkoxy.

In addition, among the compounds of the present invention represented by the above formula (I), a compound wherein $R^3$ is $R^{3-a}$ can be produced in accordance with the following reaction [B-1].

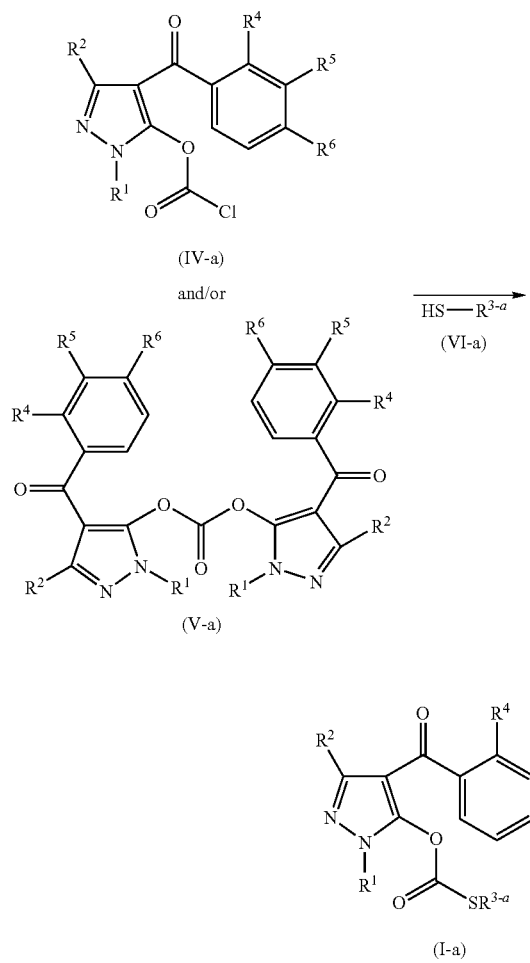

wherein $R^1$, $R^2$, $R^4$, $R^5$ and $R^6$ are as defined above, $R^{3-a}$ is alkyl; cycloalkyl; haloalkyl; alkoxyalkyl; alkoxycarbonylalkyl; alkenyl; or arylalkyl which may be substituted by $R^8$.

Namely, the compound of the present invention represented by the above formula (I-a) can be produced by reacting a compound represented by the formula (IV-a) or the formula (V-a) with a compound represented by the formula (VI-a), or by reacting a mixture of a compound represented by the formula (IV-a) and a compound represented by the formula (V-a) with a compound represented by the formula (VI-a).

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may be either inorganic base or organic base. Examples of the inorganic base include alkali metal hydrides such as sodium hydride and potassium hydride; alkali metal hydroxides such as sodium hydroxide and potassium hydroxide; alkali metal carbonates such as sodium carbonate and potassium carbonate; alkali metal hydrogencarbonates such as sodium hydrogencarbonate and potassium hydrogencarbonate; alkaline earth metal hydroxides such as calcium hydroxide; and alkaline earth metal carbonates such as calcium carbonate. Examples of the organic base include tertiary amines such as triethylamine and diisopropylethylamine; pyridine, 4-(dimethylamino)pyridine and 2,6-lutidine. As the base, one or more types may suitably be selected and mixed.

The above reaction can be carried out at a reaction temperature of usually from 0° C. to 150° C. for a reaction time of usually from 1 minute to 48 hours.

Among the compounds of the present invention represented by the above formula (I), a compound wherein $R^3$ is $R^{3-b}$ can be produced in accordance with the following reaction [B-2].

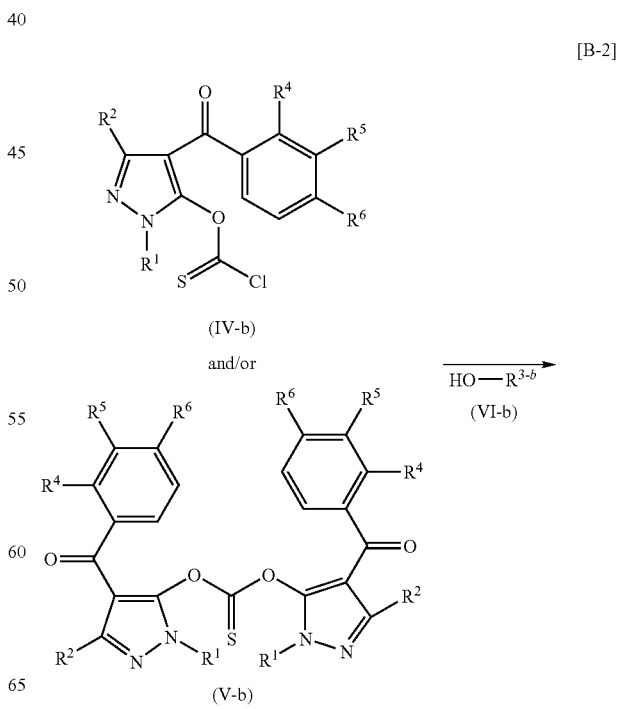

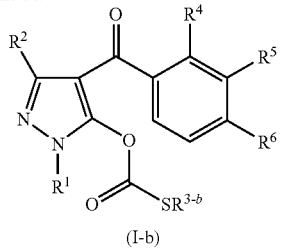

(I-b)

wherein $R^1$, $R^2$, $R^4$, $R^5$ and $R^6$ are as defined above, and $R^{3-b}$ is alkenyl.

Namely, the compound of the present invention represented by the above formula (I-b) can be produced by reacting a compound represented by the formula (IV-b) or the formula (V-b) with a compound represented by the formula (VI-b), or by reacting a mixture of a compound represented by the formula (IV-b) and a compound represented by the formula (V-b) with a compound represented by the formula (VI-b).

The above reaction can be carried out in the presence of a solvent, as the case requires. Examples of the solvent include halogenated hydrocarbons such as methylene chloride, chloroform, dichloroethane and trichloroethane; aromatic hydrocarbons such as benzene, toluene and xylene; esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may be either inorganic base or organic base. Examples of the inorganic base include alkali metal hydrides such as sodium hydride and potassium hydride; alkali metal hydroxides such as sodium hydroxide and potassium hydroxide; alkali metal carbonates such as sodium carbonate and potassium carbonate; alkali metal hydrogencarbonates such as sodium hydrogencarbonate and potassium hydrogencarbonate; alkaline earth metal hydroxides such as calcium hydroxide; and alkaline earth metal carbonates such as calcium carbonate. Examples of the organic base include tertiary amines such as triethylamine and diisopropylethylamine; pyridine, 4-(dimethylamino)pyridine and 2,6-lutidine. As the base, one or more types may suitably be selected and mixed.

The above reaction can be carried out at a reaction temperature of usually from 0° C. to 150° C. for a reaction time of usually from 1 minute to 48 hours.

The above compound represented by the formula (IV-a) or the formula (V-a) or a mixture thereof can be produced in accordance with the following reaction [C-1].

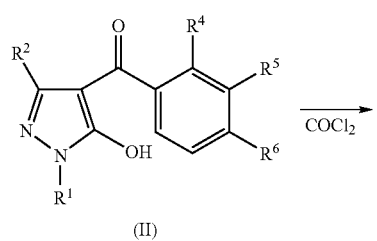

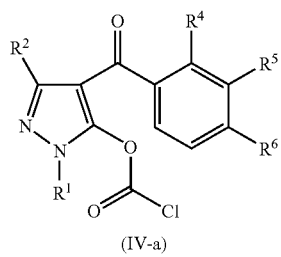

(IV-a)

and/or

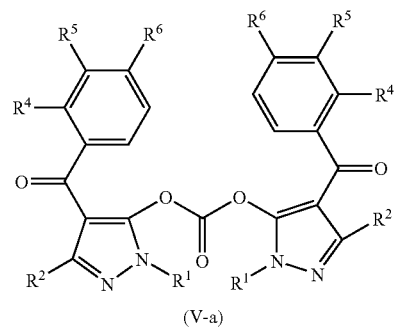

(V-a)

wherein $R^1$, $R^2$, $R^4$, $R^5$ and $R^6$ are as defined above.

Namely, the compound represented by the formula (IV-a) or the formula (V-a) or a mixture thereof can be produced by reacting a compound represented by the formula (II) with phosgene ($COCl_2$).

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene; esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may be either inorganic base or organic base. Examples of the inorganic base include alkali metal hydrides such as sodium hydride and potassium hydride; alkali metal hydroxides such as sodium hydroxide and potassium hydroxide; alkali metal carbonates such as sodium carbonate and potassium carbonate; alkali metal hydrogencarbonates such as sodium hydrogencarbonate and potassium hydrogencarbonate; alkaline earth metal hydroxides such as calcium hydroxide; and alkaline earth metal carbonates such as calcium carbonate. Examples of the organic base include tertiary amines such as triethylamine and diisopropylethylamine; pyridine, 4-(dimethylamino)pyridine and 2,6-lutidine. As the base, one or more types may suitably be selected and mixed.

The above reaction can be carried out at a reaction temperature of usually from −10° C. to 150° C. for a reaction time of usually from 1 minute to 48 hours.

The above compound represented by the formula (IV-b) or the formula (V-b) or a mixture thereof can be produced in accordance with the following reaction [C-2].

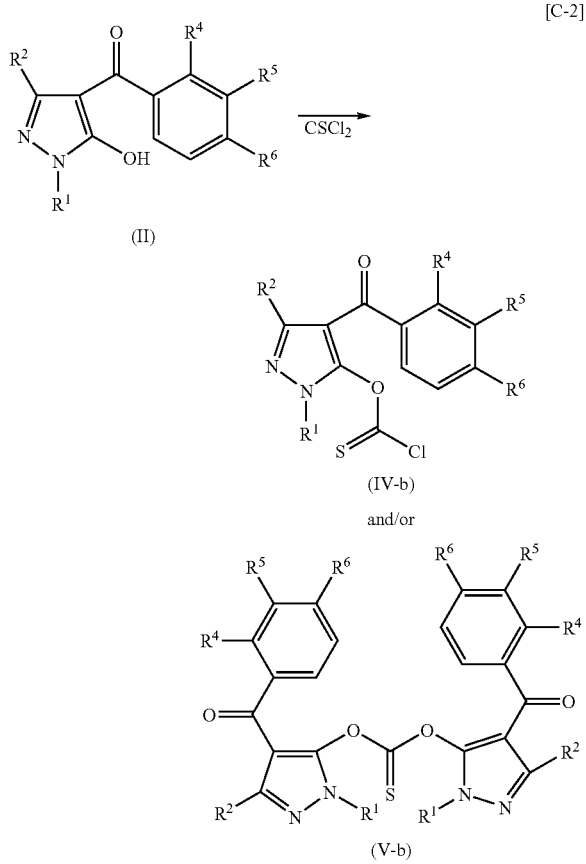

wherein $R^1$, $R^2R^4$, $R^5$ and $R^6$ are as defined above.

Namely, the compound represented by the formula (IV-b) or the formula (V-b) or a mixture thereof can be produced by reacting a compound represented by the formula (II) with thiocarbonyl chloride ($CSCl_2$).

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may be either inorganic base or organic base. Examples of the inorganic base include alkali metal hydrides such as sodium hydride and potassium hydride; alkali metal hydroxides such as sodium hydroxide and potassium hydroxide; alkali metal carbonates such as sodium carbonate and potassium carbonate; alkali metal hydrogencarbonates such as sodium hydrogencarbonate and potassium hydrogencarbonate; alkaline earth metal hydroxides such as calcium hydroxide; and alkaline earth metal carbonates such as calcium carbonate Examples of the organic base include tertiary amines such as triethylamine and diisopropylethylamine; pyridine, 4-(dimethylamino)pyridine and 2,6-lutidine. As the base, one or more types may suitably be selected and mixed.

The above reaction can be carried out at a reaction temperature of usually from −10° C. to 150° C. for a reaction time of usually from 1 minute to 48 hours.

Among the compounds represented by the above formula (II), some compounds are known compounds, such as a compound wherein $R^4$ is alkyl, $R^5$ is alkoxyalkyl, alkoxycarbonyl, alkoxyalkoxycarbonyl or haloalkoxycarbonyl, and $R^6$ is alkylsulfonyl, as disclosed in European Patent Publication No. 0282944, at pages 36 to 41, a compound wherein $R^4$ is halogen, $R^5$ is alkoxyalkoxy or heterocyclylalkoxy, and $R^6$ is alkylsulfonyl, as disclosed in European Patent Publication No. 0352543, at pages 16 to 20, a compound wherein $R^4$ is halogen, $R^5$ is alkoxyalkoxyalkyl or alkoxy, and $R^6$ is alkylsulfonyl, as disclosed in European Patent Publication No. 0344775, at pages 25 to 27, and a compound wherein $R^4$ is halogen, $R^5$ is 4,5-dihydroisoxazol-3-yl, and $R^6$ is halogen or alkylsulfonyl, as disclosed in WO98/31681, at pages 121 to 127, and they can be produced in accordance with a method disclosed in each publication or a method similar thereto.

The compound represented by the above formula (II) can be produced in accordance with the following reaction [D].

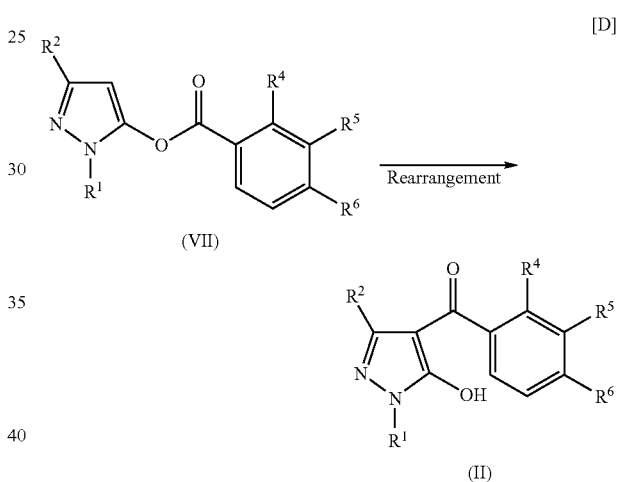

wherein $R^1$, $R^2$, $R^4$, $R^5$ and $R^6$ are as defined above.

Namely, the compound represented by the formula (II) can be produced by subjecting a compound represented by the formula (VII) to rearrangement reaction.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may be either organic base or inorganic base. Examples of the organic base include tertiary amines such as triethylamine and diisopropylethylamine; pyridine, 4-(dimethylamino)pyridine and 2,6-lutidine. Examples of the inorganic base include alkali metal carbonates such as sodium carbonate and potassium carbonate, alkali metal hydroxides such as sodium hydroxide and potassium hydroxide; and alkali metal cyanides such as sodium cyanide and potassium cyanide. As the base, one or more types may suitably be selected and mixed in an amount of from 0.01 to 100 equivalent amounts based on the compound of the formula (VII).

Further, for the above reaction, a catalyst may be added as the case requires. As the catalyst, acetone cyanohydrin can be used in an amount of from 0.01 to 10 equivalent amounts based on the compound of the formula (VII).

The above reaction can be carried out at a reaction temperature of usually from 0° C. to 150° C. for a reaction time of usually from 1 minute to 48 hours.

The compound represented by the above formula (VII) can be produced in accordance with the following reaction [E].

carbonates such as sodium carbonate and potassium carbonate; alkaline earth metal carbonates such as calcium carbonate and magnesium carbonate; alkali metal hydrogencarbonates such as sodium hydrogencarbonate and potassium hydrogencarbonate; and alkali metal hydroxides such as sodium hydroxide and potassium hydroxide. As the base, one or more types may suitably be selected and mixed in an amount of from 1 to 100 equivalent amounts based on the compound of the formula (IX).

The above reaction can be carried out at a reaction temperature of usually from 0° C. to 150° C. for a reaction time of usually from 1 minute to 48 hours.

The compound represented by the above formula (IX) can be produced in accordance with the following reaction [F].

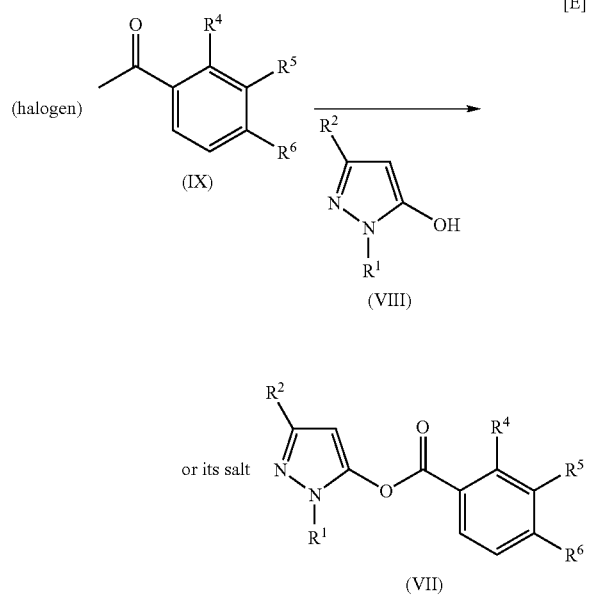

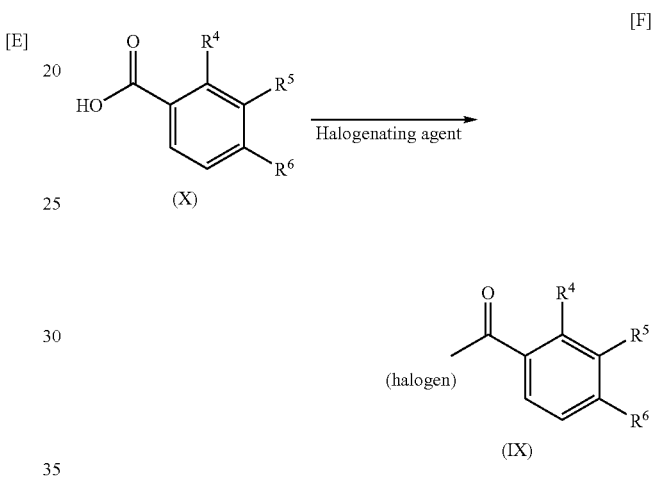

wherein $R^4$, $R^5$ and $R^6$ are as defined above.

Namely, the compound represented by the formula (IX) can be produced by reacting a compound represented by the formula (X) with a halogenating agent. This reaction is a method disclosed in literature (Organic Syntheses, Collective Volume 4, page 715, Collective Volume 9, page 516, etc.).

In the above reaction, a halogenating agent such as thionyl chloride or oxalyl chloride is reacted in an amount of from 1 to 100 equivalent amounts based on the compound represented by the formula (X).

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

For the above reaction, a catalyst can be used, as the case requires. The catalyst may, for example, be DMF.

The above reaction can be carried out at a reaction temperature of usually from 0° C. to 150° C. for a reaction time of usually from 1 minute to 48 hours.

wherein $R^1$, $R^2$, $R^4$, $R^5$ and $R^6$ are as defined above.

Namely, the compound represented by the formula (VII) can be produced by reacting a compound represented by the formula (VIII) or its salt, such as a hydrochloride, a sulfate or a nitrate, with a compound represented by the formula (IX).

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above-reaction can be carried out in the presence of a base, as the case requires. The base may be either inorganic base or organic base. Examples of the organic base include tertiary amines such as triethylamine and diisopropylethylamine; pyridine, 4-(dimethylamino)pyridine and 2,6-lutidine. Examples of the inorganic base include alkali metal In addition to the above processes, the compound represented by the formula (VII) can be produced in is accordance with the following reaction [G].

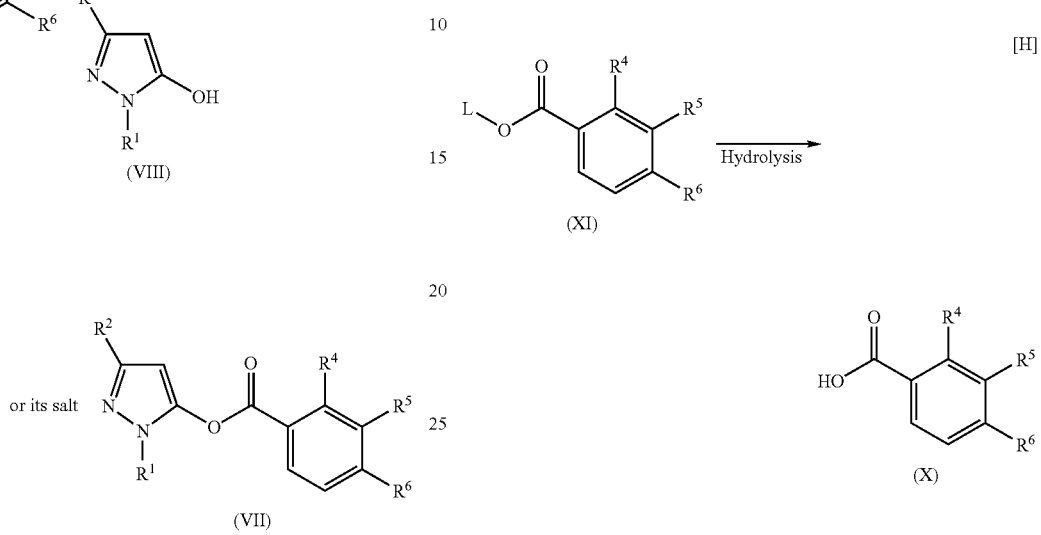

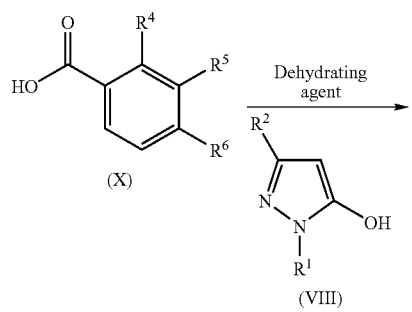

wherein $R^1$, $R^2$, $R^4$, $R^5$ and $R^6$ are as defined above.

Namely, the compound represented by the formula (VII) can be produced by reacting a compound represented by the formula (VIII) or its salt, such as a hydrochloride, a sulfate or a nitrate, with a compound represented by the formula (X) by means of a dehydrating agent.

The dehydrating agent to be used for the above reaction may, for example, be DCC (dicyclohexylcarbodiimide) or 1-ethyl-3-(3-dimethylaminopropyl)-carbodiimide hydrochloride.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. Examples of the base include tertiary amines such as triethylamine and diisopropylethylamine; pyridine, 4-(dimethylamino)pyridine and 2,6-lutidine. As the base, one or more types may suitably be selected and mixed in an amount of from 1 to 100 equivalent amounts based on the compound represented by the formula (X).

The above reaction can be carried out at a reaction temperature of usually from 0° C. to 150° C. for a reaction time of usually from 1 minute to 48 hours.

Among the compounds represented by the formula (X), compounds wherein $R^4$ is alkyl, $R^5$ is haloalkoxy, and $R^6$ is alkylthio or alkylsulfonyl, are known compounds disclosed in WO96/14285, pages 31 and 32, etc. They can be produced in accordance with a method disclosed in the publication, etc. or a method similar thereto.

The compound represented by the above formula (X) can be produced in accordance with the following reaction [H].

wherein $R^4$, $R^5$ and $R^6$ are as defined above, and L is a protective group such as alkyl.

The compound represented by the formula (X) can be produced by subjecting a compound represented by the formula (XI) to hydrolysis.

The above reaction can be carried out in the presence of a solvent, as the case requires. Examples include aromatic hydrocarbons such as benzene, toluene and xylene; aprotic polar solvents such as acetonitrile, N,N-dimethylformamide, dimethylsulfoxide, sulfolane and dimethoxyethane; ethers such as diethyl ether, dioxane and tetrahydrofuran; alcohols such as methanol and ethanol; and water. As the solvent, one or more types may suitably be selected.

The above reaction can be carried out in the presence of a base or an acid, as the case requires. The base may be either inorganic base or organic base. Examples of the inorganic base include alkali metal hydroxides such as lithium hydroxide and sodium hydroxide; alkali metal carbonates such as potassium carbonate and sodium carbonate; and alkaline earth metal carbonates such as calcium carbonate and barium carbonate. Examples of the organic base include tertiary amines such as triethylamine and diisopropylethylamine. Examples of the acid include hydrochloric acid, sulfuric acid and perchloric acid. As the base or acid, one or more types may suitably be selected and mixed in an amount of from 1 to 100 equivalent amounts based on the compound represented by the formula (XI).

The above reaction can be carried out at a reaction temperature of usually from 0° C. to 150° C. for a reaction time of usually from 1 minute to 48 hours.

Among the compounds represented by the above formula (XI), a compound represented by the formula (XI-a-1) wherein $R^5$ is $R^{5-a-1}$ can be produced in accordance with the following reaction [I].

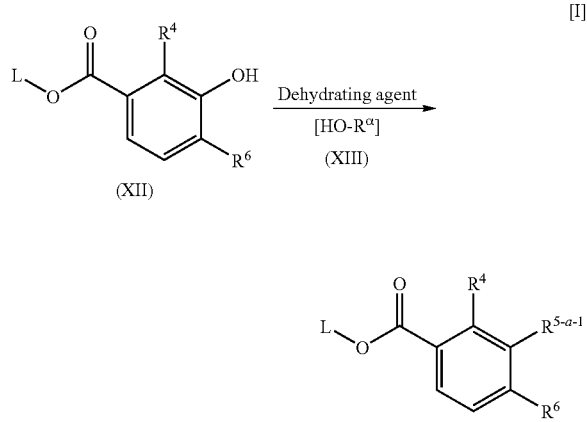

(XII)

(XI-a-1)

wherein $R^4$, $R^6$ and L are as defined above, $R^{5-a-1}$ alkoxy, haloalkoxy, alkoxyalkoxy, haloalkoxyalkoxy, alkoxyhaloalkoxy, haloalkoxyhaloalkoxy, heterocyclyloxy, heterocyclylalkoxy, cycloalkyloxy, —OC(O)SR$^7$, —OC(O)OR$^7$, alkylthioalkoxy, alkoxycarbonylalkoxy, alkenyloxy or alkynyloxy and $R^\alpha$ is alkyl, haloalkyl, alkoxyalkyl, haloalkoxyalkyl, alkoxyhaloalkyl, haloalkoxyhaloalkyl, heterocyclyl, heterocyclylalkyl, cycloalkyl, —C(O)SR$^7$, —C(O)OR$^7$, alkylthioalkyl, alkoxycarbonylalkyl, alkenyl or alkynyl.

Namely, the compound represented by the formula (XI-a-1) can be produced by reacting a compound represented by the formula, (XII) with a compound represented by the formula (XIII) by means of a dehydrating agent.

The dehydrating agent to be used in the above reaction may, for example, be DCC (dicyclohexylcarbodiimide), 1-ethyl-3-(3-dimethylaminopropyl)-carbodiimide hydrochloride or diethylazodicarboxylate.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. Examples of the base include tertiary amines such as triethylamine and diisopropylethylamine; pyridine, 4-(dimethylamino)pyridine and 2,6-lutidine. As the base, one or more types may suitably be selected and mixed in an amount of from 1 to 100 equivalent amounts based on the compound represented by the formula (XII).

The above reaction can be carried out at a reaction temperature of usually from 0° C. to 150° C. for a reaction time of usually from 1 minute to 48 hours.

Among the compounds represented by the above formula (XII), compounds wherein $R^4$ is alkyl, and $R^6$ is alkylthio or alkylsulfonyl, are known compounds disclosed in WO97/35851, at pages 54 to 55, etc. They can be produced in accordance with a method disclosed in the publication, etc. or a method similar thereto.

In addition to the above processes, the compound represented by the formula (XI-a-1) can also be produced in accordance with the following reaction [J].

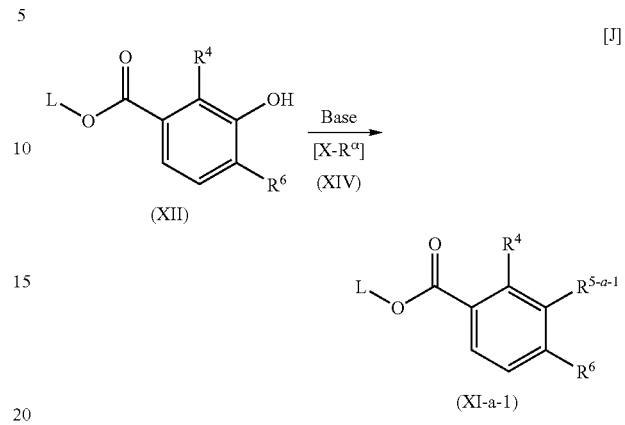

wherein $R^4$, $R^{5-a-1}$, $R^6$, $R^\alpha$ and L are as defined above, and X is a leaving group such as halogen or a methanesulfonyloxy group.

Namely, the compound represented by the formula (XI-a-1) can be produced by reacting a compound represented by the formula (XII) with a compound represented by the formula (XIV) in the presence of a base.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The base to be used in the above reaction may be either inorganic base or organic base. Examples of the organic base include triethylamine, diisopropylethylamine, pyridine, 4-(dimethylamino)pyridine and 2,6-lutidine. Examples of the inorganic base include alkali metal carbonates such as sodium carbonate and potassium carbonate; alkali metal hydroxides such as sodium hydroxide and potassium hydroxide; and alkali metal hydrides such as sodium hydride and potassium hydride. As the base, one or more may suitably be selected and mixed in an amount of from 0.5 to 100 equivalent amounts based on the compound of the formula (XII).

The above reaction can be carried out in the presence of a catalyst, as the case requires. The catalyst may, for example, be potassium iodide or tetra-n-butylammonium iodide.

The above reaction can be carried out at a reaction temperature of usually from 0° C. to 150° C. for a reaction time of usually from 1 minute to 48 hours.

The compound represented by the above formula (XII) can be produced in accordance with the following reaction [K].

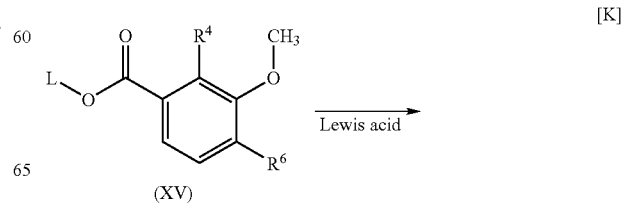

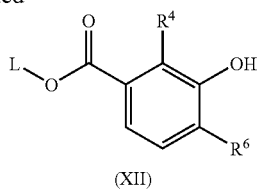

(XII)

wherein $R^4$, $R^6$ and L are as defined above.

Namely, the compound represented by the formula (XII) can be produced by reacting a compound represented by the formula (XV) with a Lewis acid such as $BBr_3$.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, and esters such as methyl acetate, ethyl acetate and propyl acetate. As the solvent, one or more types may suitably be selected.

The above reaction can be carried out at a reaction temperature of usually from 0° C. to 150° C. for a reaction time of usually from 1 minute to 48 hours.

The compound represented by the above formula (XV) can be produced in accordance with the following reaction [L].

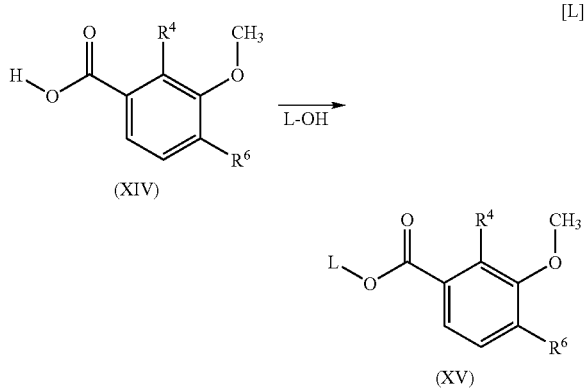

wherein $R^4$, $R^6$ and L are as defined above.

Namely, the compound represented by the formula (XV) can be produced by a reaction of introducing a protective group L into a compound represented by the formula (XVI).

The above reaction can be carried out in the presence of a solvent, as the case requires. Examples of the solvent include alcohols such as methanol and ethanol; aromatic hydrocarbons such as benzene, toluene and xylene; esters such as methyl acetate, ethyl acetate and propyl acetate; halogenated hydrocarbons such as methylene chloride, chloroform, dichloroethane and trichloroethane; and aprotic polar solvents such as acetonitrile, N,N-dimethylformamide; dimethylsulfoxide, sulfolane and dimethoxyethane. As the solvent, one or more may suitably be selected.

The above reaction can be carried out in the presence of an acid, as the case requires. Examples of the acid to be used for the above reaction include hydrochloric acid and sulfuric acid.

The above reaction can be carried out at a reaction temperature of usually from 0° C. to 150° C. for a reaction time of usually from 1 minute to 48 hours.

The compound represented by the above formula (XVI) can be produced in accordance with a known method. For example, among the compounds represented by the formula (XVI), a compound wherein $R^4$ is alkyl, and $R^6$ is alkylsulfonyl, as disclosed in WO93/13060, at page 4, and a compound wherein $R^4$ is halogen, and $R^6$ is alkylsulfonyl, as disclosed in JP-A-2-45448, at page 6, are known compounds, and they can be produced in accordance with a method disclosed in each publication or a method similar thereto.

Among the compounds represented by the above formula (XI), a compound wherein $R^5$ is $R^{5-a-2}$ can be produced in accordance with the following reaction [M].

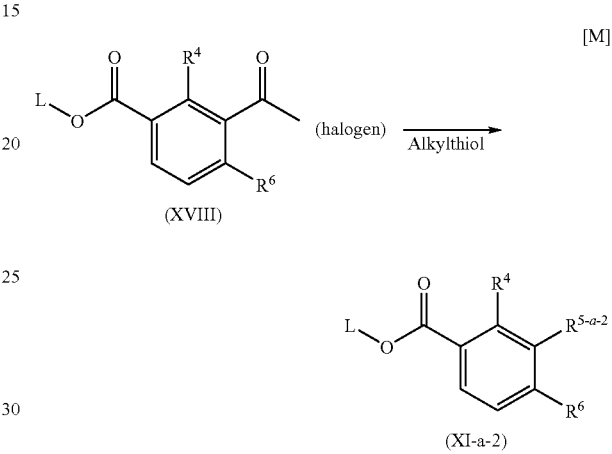

wherein $R^4$, $R^6$ and L are as defined above, and $R^{5-a-2}$ is alkylthiocarbonyl.

Namely, the compound represented by the formula (XI-a-2) can be produced by reacting a compound represented by the formula (XVIII) with alkylthiol.

The above reaction can be carried out in the presence of a solvent, as the case requires. The solvent may be any solvent so long as it is inert to the reaction. Examples thereof include ethers such as diethyl ether, dioxane and tetrahydrofuran; aromatic hydrocarbons such as benzene, toluene and xylene; esters such as methyl acetate, ethyl acetate and propyl acetate; and halogenated hydrocarbons such as methylene chloride, chloroform, dichloroethane and trichloroethane. As the solvent, one or more types may suitably be selected.

The above reaction can be carried out in the presence of a base, as the case requires. The base may be either inorganic base or organic base Examples of the organic base include triethylamine, diisopropylethylamine, pyridine, 4-(dimethylamino)pyridine and 2,6-lutidine. Examples of, the inorganic base include alkali metal carbonates such as potassium carbonate and sodium carbonate; alkali metal hydroxides such as sodium hydroxide and potassium hydroxide; and alkali metal hydrides such as sodium hydride and potassium hydride. As the base, one or more types may suitably be selected and mixed.

The above reaction can be carried out at a reaction temperature of usually from 0° C. to 150° C. for a reaction time of usually from 1 minute to 48 hours.

The compound represented by the above formula (XVIII) can be produced in accordance with the following reaction [N].

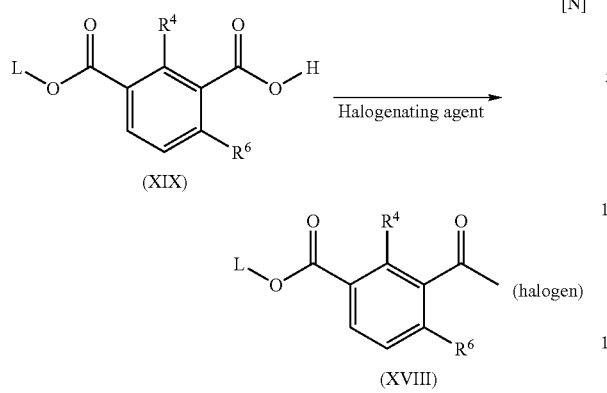

(XIX) → (XVIII)

wherein $R^4$, $R^6$ and L are as defined above.

Namely, the compound represented by the formula (XVIII) can be produced by reacting a compound represented by the formula (XIX) with a halogenating agent. This reaction can be carried out in the same manner as the above-described reaction [F].

The compound represented by the above formula (XIX) can be produced in accordance with the following reaction [O].

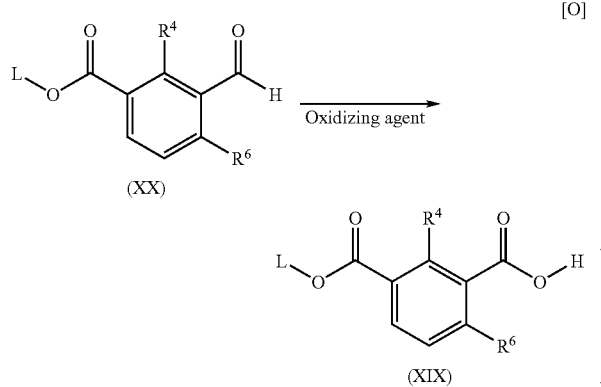

(XX) → (XIX)

wherein $R^4$, $R^6$ and L are as defined above.

Namely, the compound represented by the formula (XIX) can be produced by oxidizing a compound represented by the formula (XX).

The oxidizing agent in the above reaction may, for example, be potassium permanganate or chromium trioxide.

The above reaction can be carried out in the presence of a solvent, as the case requires. The solvent may be any solvent so long as it is inert to the reaction. Examples thereof include ketones such as acetone and methyl ethyl ketone; esters such as methyl acetate, ethyl acetate and propyl acetate; and ethers such as diethyl ether, dioxane and tetrahydrofuran. As the solvent, one or more types may suitably be selected.

The above reaction can be carried out at a reaction temperature of usually from 0° C. to 150° C. for a reaction time of usually from 1 minute to 48 hours.

The compound represented by the above formula (XX) can be produced in accordance with the following reaction [P].

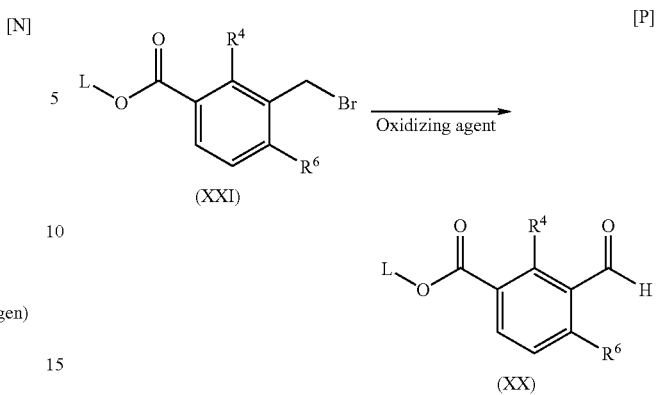

(XXI) → (XX)

wherein $R^4$, $R^6$ and L are as defined above.

Namely, the compound represented by the formula (XX) can be produced by reacting a compound represented by the formula (XXI) with an oxidizing agent in the presence of a solvent.

The oxidizing agent to be used for the above reaction may, for example, be N-methylmorpholine oxide.

The solvent to be used for the above reaction may be any solvent so long as it is inert to the reaction. Examples thereof include aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out at a reaction temperature of usually from 0° C. to 150° C. for a reaction time of usually from 1 minute to 48 hours.

The compounds represented by the above formula (XX) and the formula (XXI) can be produced by known methods. For example, among the compounds represented by the formulae (XX) and (XXI), a compound wherein $R^4$ is alkyl, and $R^6$ is alkylsulfonyl, as disclosed in JP-A-11-240872, at page 9, and a compound wherein $R^4$ is halogen, and $R^6$ is alkylsulfonyl, as disclosed in WO98/29392, at page 264, are known compounds, and they can be produced in accordance with a method disclosed in each publication or a method similar thereto.

Among the compounds represented by the above formula (XI), a compound wherein $R^5$ is $R^{5-a-3}$ can be produced in accordance with the following reaction [Q].

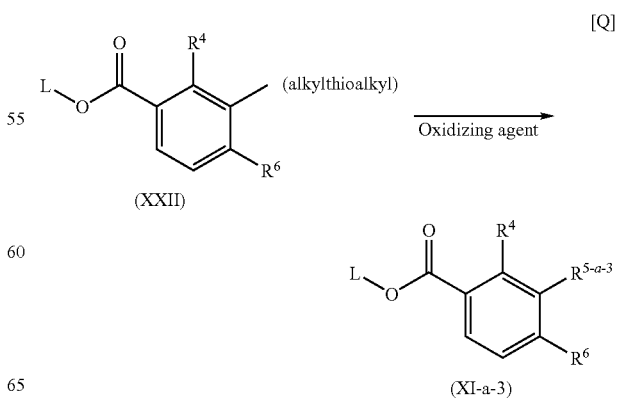

(XXII) → (XI-a-3)

wherein $R^4$, $R^6$ and L are as defined above, and $R^{5-a-3}$ is alkylsulfonylalkyl.

Namely, the compound represented by the formula (XI-a-3) can be produced by reacting a compound represented by the formula (XXII) with an oxidizing agent in the presence of a solvent.

The oxidizing agent to be used for the above reaction may, for example, be hydrogen peroxide, peracetic acid or m-chloroperbenzoic acid.

The solvent to be used for the above reaction may be any solvent so long as it is inert to the reaction. Examples thereof include halogenated hydrocarbons such as methylene chloride, chloroform, dichloroethane and trichloroethane; ketones such as acetone and dimethyl ethyl ketone; ethers such as diethyl ether, dioxane and tetrahydrofuran; and acetic acid. As the solvent, one or more types may suitably be selected.

The above reaction can be carried out at a reaction temperature of usually from 0° C. to 150° C. for a reaction time of usually from 1 minute to 48 hours.

The compound represented by the above formula (XXII) can be produced in accordance with the following reaction [R].

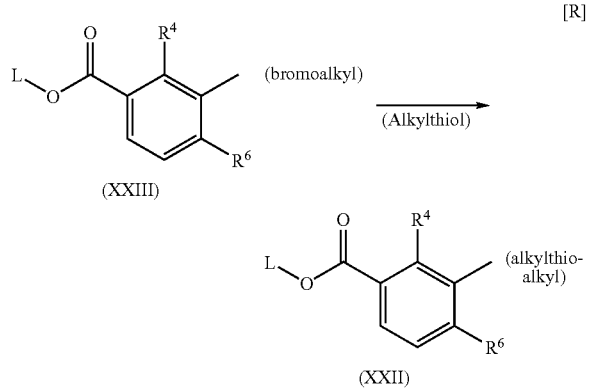

wherein $R^4$, $R^6$ and L are as defined above.

Namely, the compound represented by the above formula (XXII) can be produced by reacting a compound represented by the formula (XXIII) with an alkylthiol in the presence of a solvent.

The solvent to be used for the above reaction may be any solvent so long as it is inert to the reaction. Examples thereof include halogenated hydrocarbons such as methylene chloride, chloroform, dichloroethane and trichloroethane; ketones such as acetone and dimethyl ethyl ketone; ethers such as diethyl ether, dioxane and tetrahydrofuran; acetic acid; water; and N,N-dimethylformamide, dimethylsulfoxide, sulfolane and dimethoxyethane. As the solvent, one or more types may suitably be selected.

The above reaction can be carried out in the presence of a base, as the case requires. The base may be either inorganic base or organic base. Examples of the organic base include triethylamine, diisopropylethylamine, pyridine, 4-(dimethylamino)pyridine and 2,6-lutidine. Examples of the inorganic base include alkali metal carbonates such as sodium carbonate and potassium carbonate; alkali metal hydrogencarbonates such as sodium hydrogencarbonate and potassium hydrogencarbonate; alkaline earth metal carbonates such as calcium carbonate and magnesium carbonate; alkali metal hydroxides such as sodium hydroxide; and alkali metal hydrides such as sodium hydride and potassium hydride. As the base, one or more types may suitably be selected and mixed.

The above reaction can be carried out at a reaction temperature of usually from 0° C. to 150° C. for a reaction time of usually from 1 minute to 48 hours.

The compound represented by the above formula (XXIII) can be produced by a known method. For example, a compound wherein $R^4$ is alkyl and $R^6$ is alkylsulfonyl, as disclosed in JP-A-11-240872, at page 9, and a compound wherein $R^4$ is halogen and $R^6$ is alkylsulfonyl, as disclosed in WO98/29392, at page 264, are known compounds, and they can be produced in accordance with a method disclosed in each publication or a method similar thereto.

Among the compounds represented by the above formula (XI), a compound wherein $R^5$ is $R^{5-a-4}$ can be produced in accordance with the following reaction [S].

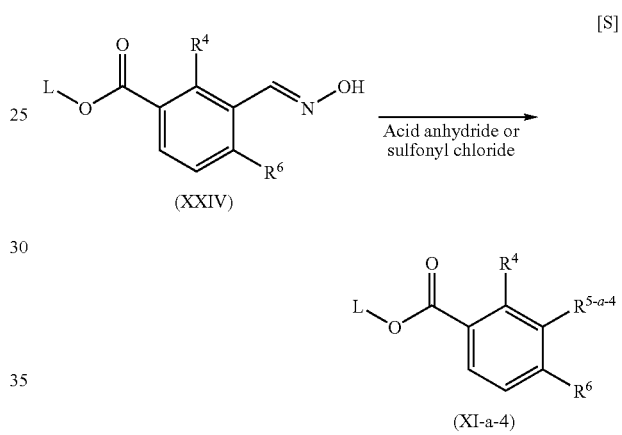

wherein $R^4$, $R^6$ and L are as defined above, and $R^{5-a-4}$ is cyano.

Namely, the compound represented by the formula (XI-a-4) can be produced by reacting a compound represented by the formula (XXIV) with an acid anhydride such as acetic anhydride or sulfonyl chloride such as methanesulfonyl chloride.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; ketones such as acetone and dimethyl ethyl ketone; ethers such as diethyl ether, dioxane and tetrahydrofuran; and pyridine. As the solvent, one or more types may suitably be selected.

The above reaction can be carried out in the presence of a base, as the case requires. Examples of the base include triethylamine, N,N-dimethylaminopyridine and diisopropylaminopyridine. As the base, one or more types may suitably be selected and mixed.

The above reaction can be carried out at a reaction temperature of usually from 0 to 150° C. for a reaction time of usually from 1 minute to 48 hours.

The compound represented by the above formula (XXIV) can be produced in accordance with the following reaction [T].

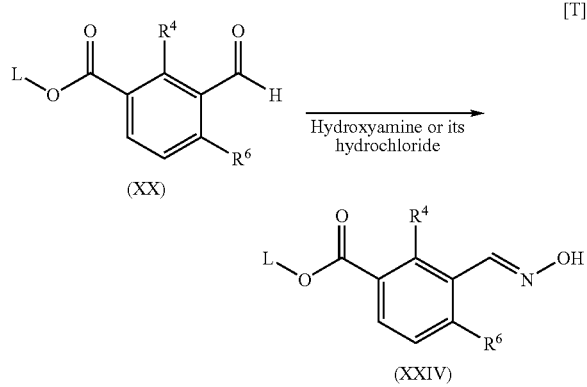

wherein $R^4$, $R^6$ and L are as defined above.

Namely, the compound represented by the formula (XXIV) can be produced by reacting a compound represented by the formula (XX) with hydroxyamine or hydroxyamine hydrochloride in the presence of a solvent.

The solvent to be used for the above reaction may be any solvent so long as it is inert to the reaction. Examples thereof include alcohols such as methanol and ethanol; halogenated hydrocarbons such as methylene chloride, chloroform, dichloroethane and trichloroethane; ketones such as acetone and dimethyl ethyl ketone; and ethers such as diethyl ether, dioxane and tetrahydrofuran. As the solvent, one or more types may suitably be selected.

The above reaction can be carried out in the presence of an acid or a base, as the case requires. Examples of the acid include p-toluenesulfonic acid. Examples of the base include sodium acetate.

The above reaction can be carried out at a reaction temperature of usually from 0° C. to 150° C. for a reaction time of usually from 1 minute to 48 hours.

Among the compounds represented by the above formula (XI), a compound wherein $R^5$ is $R^{5-a-5}$ can be produced in accordance with the following reaction [U].

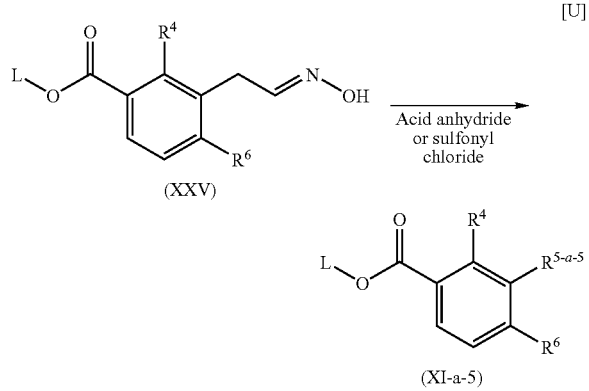

wherein $R^4$, $R^6$ and L are as defined above, and $R^{5-a-5}$ is cyanoalkyl.

Namely, the compound represented by the formula (XI-a-5) can be produced by reacting a compound represented by the formula (XXV) with an acid anhydride such as acetic anhydride or sulfonyl chloride such as methanesulfonyl chloride. This reaction can be carried out in the same manner as the above-described reaction [S].

The compound represented by the above formula (XXV) can be produced in accordance with the following reaction [V].

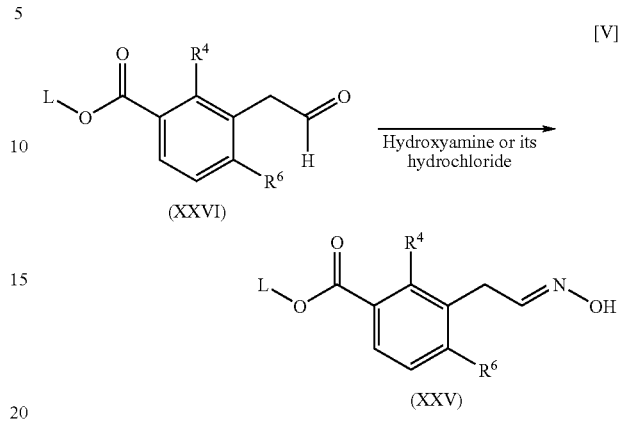

wherein $R^4$, $R^6$ and L are as defined above

Namely, the compound represented by the formula (XXV) can be produced by reacting a compound represented by the formula (XXVI) with hydroxyamine or hydroxyamine hydrochloride in the presence of a solvent. This reaction can be carried out in the same manner as the above-described reaction [T].

The compound represented by the above formula (XXVI) is can be produced in accordance with the following reaction [W].

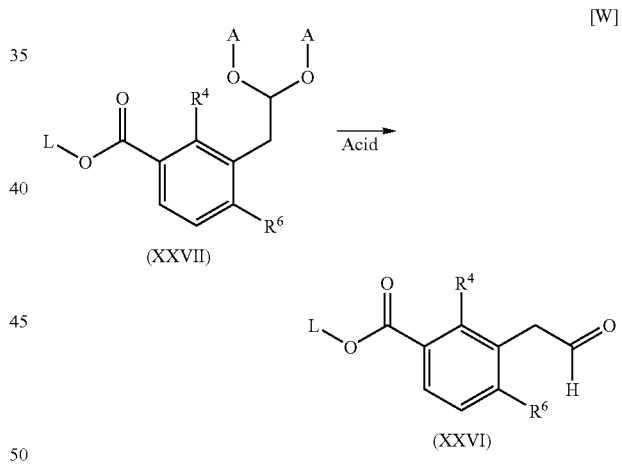

wherein $R^4$, $R^6$ and L are as defined above, and A is alkyl.

Namely, the compound represented by the formula (XXVI) can be produced by reacting a compound of the formula (XXVII) with an acid such as hydrochloric acid.

The above reaction can be carried out in the presence of a solvent, as the case requires. The solvent may be any solvent so long as it is inert to the reaction. Examples thereof include water; alcohols such a methanol and ethanol; and ethers such as diethyl ether, dioxane and tetrahydrofuran. As the solvent, one or more types may suitably be selected.

The above reaction can be carried out at a reaction temperature of usually from 0° C. to 150° C. for a reaction time of usually from 1 minute to 48 hours.

The compound represented by the above formula (XXVII) can be produced in accordance with the following reaction [X].

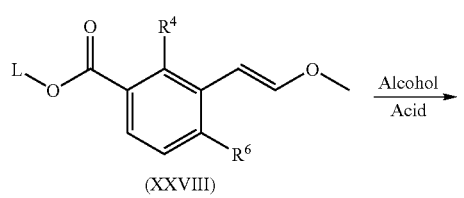

(XXVIII)

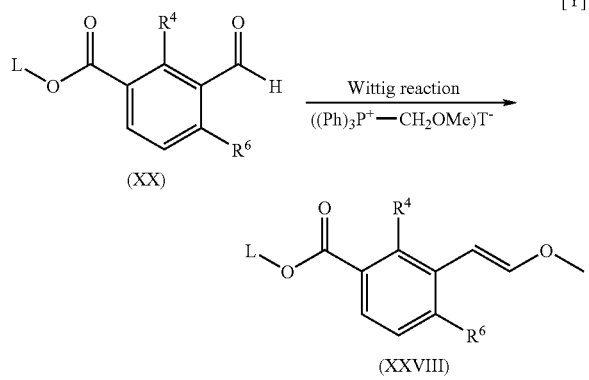

(XXVII)

wherein $R^4$, $R^6$, L and A are as defined above.

Namely, the compound represented by the formula (XXVII) can be produced by reacting a compound represented by the formula (XXVIII) with an alcohol in the presence of an acid.

The alcohol to be used for the above reaction may, for example, be methanol or ethanol. Further, the acid may, for example, be hydrochloric acid or toluenesulfonic acid.

The above reaction can be carried out at a reaction temperature of usually from 0° C. to 150° C. for a reaction time of usually from 1 minute to 48 hours.

The compound represented by the above formula (XXVIII) can be produced in accordance with the following reaction [Y].

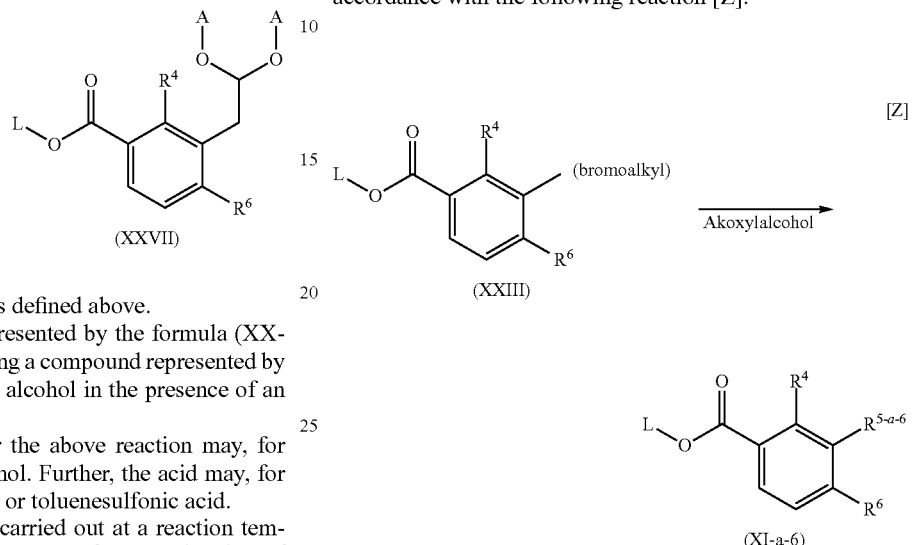

wherein $R^4$, $R^6$ and L are as defined above, T is halogen, Ph is phenyl, and Me is methyl.

Namely, the compound represented by the formula (XXVIII) can be produced by subjecting a compound represented by the formula (XX) to Wittig reaction in the presence of a solvent.

The solvent to be used for the above reaction may be any solvent so long as it is inert to the reaction. Examples thereof include ethers such as diethyl ether, dioxane and tetrahydrofuran; aromatic hydrocarbons such as benzene, toluene and xylene; and aprotic polar solvents such as acetonitrile, N,N-dimethylformamide, dimethylsulfoxide, sulfolane and dimethoxyethane.

The above reaction can be carried out in the presence of a base, as the case requires. Examples of the base include sodium hydride (NaH); alkali lithium agents such as n-butyllithium; and metal amides such as sodium amide ($NaNH_2$).

The above reaction can be carried out at a reaction temperature of usually from −80° C. to 150° C. for a reaction time of usually from 1 minute to 48 hours.

Among the compounds represented by the above formula (XI), a compound wherein $R^5$ is $R^{5-a-6}$ can be produced in accordance with the following reaction [Z].

wherein $R^4$, $R^6$ and L are as defined above, and $R^{5-a-5}$ is alkoxyalkoxyalkyl.

Namely, the compound represented by the formula (XI-a-6) can be produced by reacting a compound represented by the formula (XXIII) with an alkoxyalcohol.

The above reaction can be carried out in the presence of a solvent, as the case requires. The solvent may be any solvent so long as it is inert to the reaction, and examples thereof include alcohols such as methanol and ethanol; esters such as methyl acetate, ethyl acetate and propyl acetate; ethers such as diethyl ether, dioxane and tetrahydrofuran; and aprotic polar solvents such as acetonitrile, N,N-dimethylformamide, dimethylsulfoxide, sulfolane and dimethoxyethane. As the solvent, one or more may suitably be selected.

The above reaction can be carried out in the presence of a base, as the case requires. Examples of the base include alkali metal hydrides such as sodium hydride and potassium hydride.

The above reaction can be carried out at a reaction temperature of usually from 0° C. to 150° C. for a reaction time of usually from 1 minute to 48 hours.

The compound represented by the above formula (XXIII) can be produced by a known method. For example, a compound wherein $R^4$ is alkyl and $R^6$ is alkylsulfonyl, as disclosed in JP-A-11-240872, at page 9, and a compound wherein $R^4$ is halogen and $R^6$ is alkylsulfonyl, as disclosed in WO98/29392, at page 264, are known compounds, and they can be produced in accordance with a method disclosed in each publication or a method similar thereto.

Among the compounds represented by the above formula (XI), a compound wherein $R^5$ is $R^{5-a-7}$ can be prepared in accordance with the following reaction [AA].

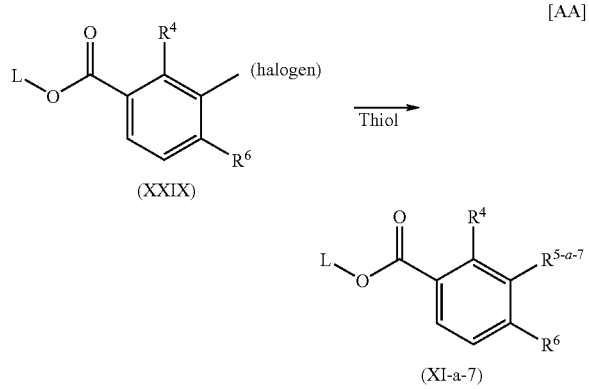

(XXIX) → (XI-a-7)

wherein $R^4$, $R^6$ and L are as defined above, and $R^{5-a-7}$ is alkylthio, alkoxyalkylthio, haloalkoxyalkylthio, alkoxyhaloalkylthio, haloalkoxyhaloalkylthio, alkylthioalkylthio, haloalkylthioalkylthio, alkylthiohaloalkylthio or haloalkylthiohaloalkylthio.

Namely, the compound represented by the formula (XI-a-7) can be produced by reacting a thiol corresponding to $R^{5-a-7}$ with a compound represented by the formula (XXIX).

The above reaction can be carried out in the presence of a solvent, as the case requires. The solvent may be any solvent so long as it is inert to the reaction, and examples thereof include alcohols such as methanol and ethanol; ethers such as diethyl ether, dioxane and tetrahydrofuran; aprotic polar solvents such as acetonitrile, N,N-dimethylformamide, dimethylsulfoxide, sulfolane and dimethoxyethane; and water. As the solvent, one or more types may suitably be selected.

The above reaction can be carried out in the presence of a base, as the case requires. Examples of the base include alkali metal hydrides such as sodium hydride and potassium hydride; alkali metal hydroxides such as sodium hydroxide and potassium hydroxide; and alkaline earth metal hydroxides such as calcium hydroxide.

The above reaction can be carried out at a reaction temperature of usually from 0° C. to 250° C. for a reaction time of usually from 1 minute to 48 hours.

The compound represented by the above formula (XXIX) can be produced by a known method. For example, a compound wherein $R^4$ is halogen and $R^6$ is alkylsulfonyl, as disclosed in European Patent Publication No. 0195247, at page 8, and a compound wherein $R^4$ is alkyl and $R^6$ is alkylsulfonyl, as disclosed in Pest Management Science (2002), 58(12), 1175 to 1186, are known compounds, and they can be produced in accordance with a method disclosed in the publication or a method similar thereto.

Among the compounds represented by the above formula (XI), a compound wherein $R^5$ is $R^{5-a-8}$ can be prepared in accordance with following reaction [AB].

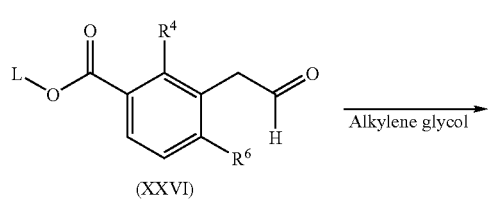

(XXVI)

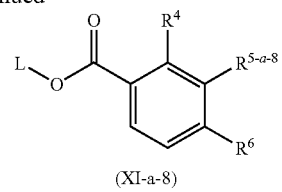

(XI-a-8)

wherein $R^4$, $R^6$ and L are as defined above, and $R^{5-a-8}$ is a heterocyclylalkyl containing two oxygen atoms.

Namely, the compound represented by the formula (XI-a-8) can be produced by reacting an alkylene glycol with a compound represented by the formula (XXVI) in the presence of a solvent and an acid catalyst.

The solvent to be used for the above reaction may be any solvent so long as it is inert to the reaction. Examples thereof include halogenated hydrocarbons such as methylene chloride, chloroform, dichloroethane and trichloroethane; aromatic hydrocarbons such as benzene, toluene and xylene; esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The acid catalyst to be used for the above reaction may, for example, be p-toluenesulfonic acid or pyridium p-toluenesulfonate.

In the above reaction, it is preferred to remove moisture generated by the reaction by azeotropy with the solvent or by using a drying agent.

The above reaction can be carried out at a reaction temperature of usually from 0° C. to 150° C. for a reaction time of usually from 1 minute to 48 hours.

Among the compounds represented by the above formula (II), a compound wherein $R^5$ is $R^{5-a-9}$ can be prepared in accordance with the following reaction [AC].

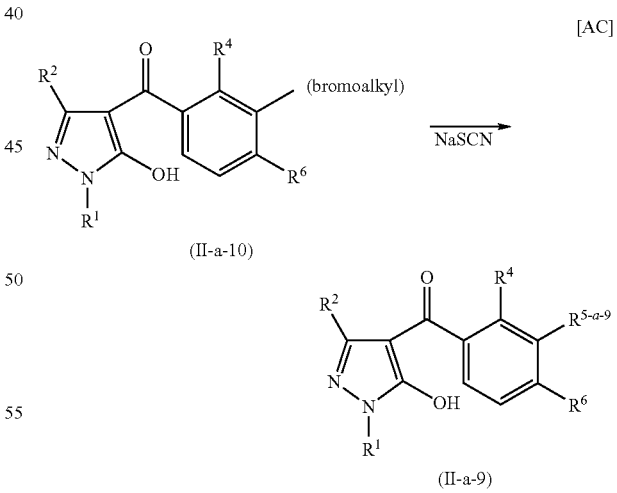

wherein $R^1$, $R^2$, $R^4$ and $R^6$ are as defined above, and $R^{5-a-9}$ is thiocyanatoalkyl.

Namely, the compound represented by the formula (II-a-9) can be produced by reacting NaSCN with a compound represented by the formula (II-a-10).

The above reaction can be carried out in the presence of a solvent, as the case requires. The solvent to be used for the above reaction may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; ethers such as diethyl ether, dioxane and tetrahydrofuran; and alcohols such as methanol, ethanol and propanol. As the solvent, one or more types may suitably be selected.

The above reaction can be carried out at a reaction temperature of usually from 0° C. to 150° C. for a reaction time of usually from 1 minute to 48 hours.

Among the compounds represented by the above formula (XI), a compound wherein $R^5$ is $R^{5-a-10}$ can be prepared in accordance with the following reaction [AD].

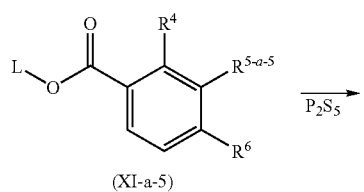

wherein $R^4$, $R^{5-a-5}$, $R^6$ and L are as defined above, and $R^{5-a-10}$ is amino(thiocarbonyl)alkyl which may be substituted by at least one substituent selected from alkyl, cyano, cyanoalkyl, (alkylthio)carbonylalkyl, alkyl(thiocarbonyl)alkyl, —C(O)OR$^7$ and —C(O)SR$^7$.

Namely, the compound represented by the formula (XI-a-10) can be produced by reacting $P_2S_5$ with a compound represented by the formula (XI-a-5) in the presence of a solvent.

The solvent to be used for the above reaction may be any solvent so long as it is inert to the reaction, and examples thereof include alcohols such as methanol, ethanol and propanol; halogenated hydrocarbons such as methylene chloride, chloroform, dichloroethane and trichloroethane; aromatic hydrocarbons such as benzene, toluene and xylene; esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out at a reaction temperature of usually from 0° C. to 250° C. for a reaction time of usually from 1 minute to 48 hours.

Among the compounds represented by the above formula (XI), a compound wherein $R^5$ is $R^{5-a-11}$ can be prepared in accordance with the following reaction [AE].

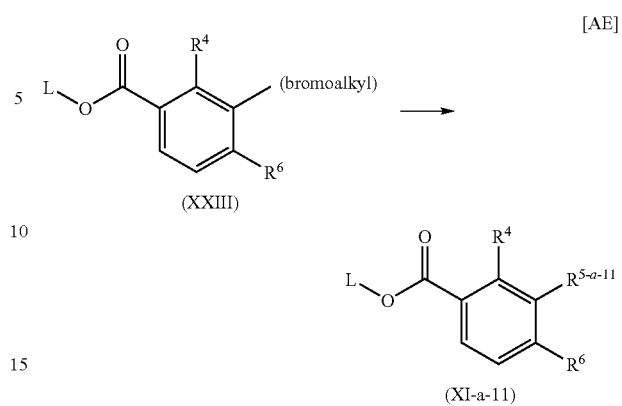

wherein $R^4$, $R^6$ and L are as defined above, and $R^{5-a-11}$ is aminoalkyl which may be substituted by at least one substituent selected from alkyl, cyano, cyanoalkyl, (alkylthio)carbonylalkyl, alkyl(thiocarbonyl)alkyl, —C(O)OR$^7$ and —C(O)SR$^7$.

Namely, the compound represented by the formula (XI-a-11) can be produced by reacting ammonia or an amine which may be substituted by at least one substituent selected from alkyl, cyano, cyanoalkyl, (alkylthio)carbonylalkyl, alkyl(thiocarbonyl)alkyl, —C(O)OR$^7$ and —C(O)SR$^7$, with a compound represented by the formula (XXIII).

The above reaction can be carried out in the presence of a solvent, as the case requires. The solvent to be used for the above reaction may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may is be either inorganic base or organic base. Examples of the inorganic base include alkali metal carbonates such as sodium carbonate and potassium carbonate; alkali metal hydrogencarbonates such as sodium hydrogencarbonate and potassium hydrogencarbonate; alkaline earth metal carbonates such as calcium carbonate and magnesium carbonate; sodium hydride (NaH); alkali lithium reagents such as n-butyllithium; and metal amides such as sodium amide (NaNH$_2$). Examples of the organic base include amines such as triethylamine, N,N-dimethylaminopyridine, diisopropylaminopyridine and DBU (diazabicycloundecene).

The above reaction can be carried out in the presence of a catalyst, as the case requires. The catalyst may, for example, be TBAI (tert-butylammonium iodide).

The above reaction can be carried out at a reaction temperature of usually from 0° C. to 150° C. for a reaction time of usually from 1 minute to 48 hours.

Among the compounds represented by the above formula (XI), a compound wherein $R^5$ is $R^{5-a-12}$ can be prepared in accordance with the following reaction [AF-1].

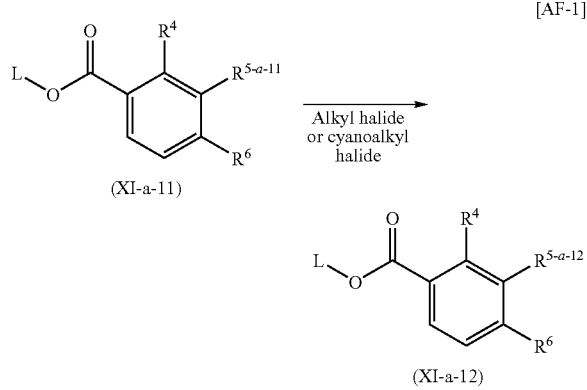

[AF-1]

(XI-a-11) → Alkyl halide or cyanoalkyl halide → (XI-a-12)

wherein $R^4$, $R^6$, $R^{5-a-11}$ and L are as defined above, and $R^{5-a-12}$ is one having the amino moiety of $R^{5-a-11}$ substituted by alkyl or cyanoalkyl.

Namely, the compound represented by the formula (XI-a-12) can be produced by reacting a compound represented by the formula (XI-a-11) with an alkyl halide or a cyanoalkyl halide.

The above reaction can be carried out in the presence of a solvent, as the case requires. The solvent may be any solvent so long as it is inert to the reaction, and examples thereof include alcohols such as methanol, ethanol and propanol; halogenated hydrocarbons such as methylene chloride, chloroform, dichloroethane and trichloroethane; aromatic hydrocarbons such as benzene, toluene and xylene; esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may be either inorganic base or organic base. Examples of the inorganic base include alkali metal carbonates such as sodium carbonate and potassium carbonate; alkali metal hydrogencarbonates such as sodium hydrogencarbonate and potassium hydrogencarbonate; and alkaline earth metal carbonates such as calcium carbonate and magnesium carbonate. Examples of the organic base include amines such as triethylamine, N,N-dimethylaminopyridine, diisopropylaminopyridine and DBU (diazabicycloundecene).

The above reaction can be carried out at a reaction temperature of usually from 0° C. to 150° C. for a reaction time of usually from 1 minute to 48 hours.

Among the compounds represented by the above formula (I), a compound wherein $R^5$ is $R^{5-a-13}$ can be prepared in accordance with the following reaction [AF-2].

[AF-2]

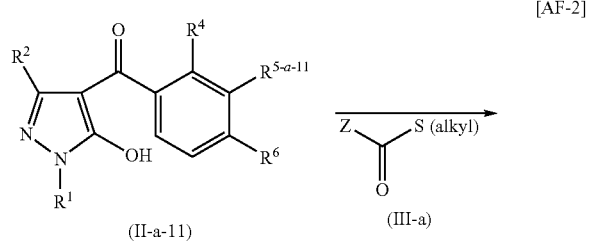

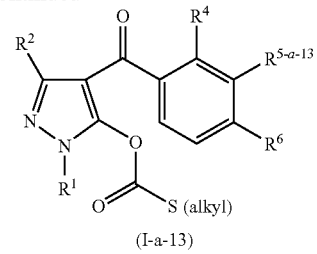

(I-a-13)

wherein $R^1$, $R^2$, $R^4$, $R^6 R^{5-a-11}$ and Z are as defined above, and $R^{5-a-13}$ is one having the amino moiety of $R^{5-a-11}$ substituted by (alkylthio)carbonyl.

Namely, the compound represented by the formula (I-a-13) can be produced by reacting a compound represented by the formula (II-a-11) with a compound represented by the formula (III-a). This reaction can be carried out in the same manner as the above-described reaction [A].

Among the compounds represented by the above formula (XI), a compound wherein $R^5$ is $R^{5-a-14}$ can be prepared in accordance with the following reaction [AG].

[AG]

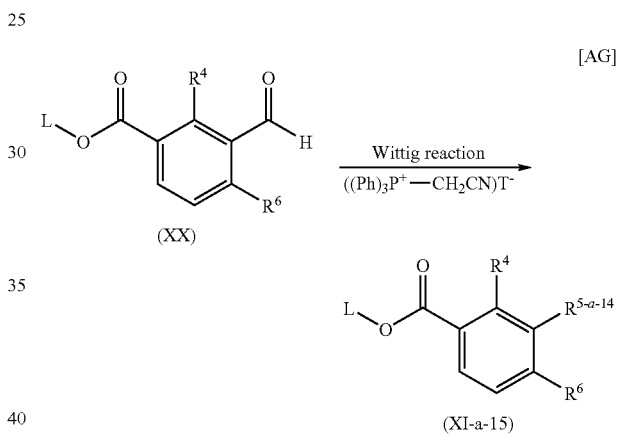

wherein $R^4$, $R^6$, L, T and Ph are as defined above, and $R^{5-a-14}$ is cyanoalkenyl.

Namely, the compound represented by the formula (XI-a-15) can be produced by subjecting a compound represented by the formula (XX) to Wittig reaction in the presence of a solvent. This reaction can be carried, out in the same manner as the above-described reaction [Y].

The compounds of the present invention have excellent herbicidal effects when used as an active ingredient of herbicides. The application range extends to agricultural fields such as paddy fields, crop plant fields, orchards and mulberry fields and non-agricultural fields such as forest land, farm roads, play grounds and factory sites. The application method may suitably be selected from soil application, foliar application, water application, etc.

The compounds of the present invention are capable of controlling a wide range of undesired plants such as grasses (or gramineae) such as barnyardgrass (*Echinochloa crusgalli* L.), early watergrass (*Echinochloa oryzicola* vasing), crabgrass (*Digitaria sanguinalis* L.), greenfoxtail (*Setaria viridis* L.), giant foxtail (*Setaria faberi* Herrm.), goosegrass (*Eleusine indica* L.), wild oat (*Avena fatua* L.), johnsongrass (*Sorghum halepense* L.), quackgrass (*Agropyron repens* L.), alexandergrass (*Brachiaria plantaginea*), paragrass (*Panicum purpurascens*), sprangletop (*Leptochloa chinensis*), red sprangletop (*Leptochloa panicea*), annual bluegrass (*Poa annua* L.), black grass (*Alopecurus myosuroides* Huds.) and cholorado bluestem (*Agropyron tsukushiense* (Honda) Ohwi), sedges (or Cyperaceae) such as rice flatsedge (*Cyperus iria* L.), purple nutsedge (*Cyperus rotundus* L.), yellow nutsedge (*Cyperus esculentus* L.), japanese bulrush (*Scirpus juncoides*), flatsedge (*Cyperus serotinus*), small-flower umbrellaplant (*Cyperus difformis*), slender spikerush (*Eleocharis acicularis*) and water chestnut (*Eleocharis kuroguwai*), alismataceae such as japanese ribbon waparo (*Sagittaria pygmaea*), arrow-head (*Sagittaria trifolia*) and narrowleaf waterplantain (*Alisma canaliculatum*), pontederiaceae such as monochoria (*Monochoria Vaginalis*) and *monochoria* species (*Monochoria korsakowii*), scrophulariaceae such as false pimpernel (*Lindernia pyxidaria*) and abunome (*Dopatrium junceum*), lythraceae such as toothcup (*Rotala india*) and red stem (*Ammannia multiflora*), and other broad leaves such as velvetleaf (*Abutilon theophrasti* MEDIC.), tall morningglory (*Ipombea purpurea* L.), common lambsquarters (*Chenopodium album* L.), prickly sida (*Sida spinosa* L.), common purslane (*Portulaca oleracea* L.), slender amaranth (*Amaranthus viridis* L.), redroot pigweed (*Amaranthus retroflexus* L.), sicklepod (*Cassia obtusifolia* L.), black nightshade (*Solanum nigrum* L.), pale smartweed (*Polygonum lapathifolium* L.), common chickweed (*Stellaria media* L.), long stem waterwort (*Elatine triandra* SCHK.), common cocklebur (*Xanthium strumarium* L.), flexuous bittercress (*Cardamine flexuosa* WITH.), henbit (*Lamium amplexicaule* L.), common ragweed (*Ambrosia elatior* L.), catchweed (*Galium spurium* L.), field bindweed (*Calystegia arvensis* L.), jimsonweed (*Datura stramonium*), thistle (*Breea setosa* (BIEB.)KITAM.) and threeseeded copperleaf (*Acalypha australis* L.). Therefore, they can be effectively used for selectively controlling noxious weeds or nonselectively controlling noxious weeds in cultivation of useful crops such as corn (*Zea mays* L.), soybean (*Glycine max* Merr.), cotton (*Gossypium* spp.), wheat (*Triticum* spp.), rice (*Oryza sativa* L.), barley (*Hordeum vulgare* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), japanese lawngrass (*Zoysia japonica* stend), peanut (*Arachis hypogaea* L.), flax (*Linum usitatissimum* L.), tobacco (*Nicotiana tabacum* L.), and coffee (*Coffea* spp.). Particularly, the compounds of the present invention are effectively used for selectively controlling noxious weeds in cultivation of corn, soybean, cotton, wheat, rice, rape, sunflower, sugar beet, sugar cane, japanese lawngrass, peanut, flax, tobacco, coffee, and the like, and among these, especially corn, soybean, wheat, rice and the like.

The compound of the present invention may be mixed with various agricultural additives and applied in the form of various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

The additives to be used for the formulation include, for example, a solid carrier such as diatomaceous earth, slaked lime, calcium carbonate, talc, white carbon, kaoline, bentonite, a mixture of kaolinite and sericite, clay, sodium carbonate, sodium bicarbonate, mirabilite, zeolite or starch; a solvent such as water, toluene, xylene, solvent naphtha, dioxane, acetone, isophorone, methyl isobutyl ketone, chlorobenzene, cyclohexane, dimethyl sulfoxide, N,N-dimethylformamide, dimethylacetamide, N-methyl-2-pyrrolidone or an alcohol; an anionic surfactant such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonate condensed with formaldehyde or an alkylnaphthalene sulfonate condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the compound of the present invention to such various additives may be from 0.1:99.9 to 95:5, preferably from 0.2:99.8 to 85:15.

The dose of the herbicide containing the compound of the present invention can not generally be defined, as it varies depending upon the weather conditions, the soil conditions, the type of the formulation, the type of the weeds to be controlled, the application season, etc. However, it is usually applied in an amount of the compound of the present invention of from 0.5 to 5,000 g, preferably from 1 to 1,000 g, more preferably from 10 to 500 g, per hectare. The present invention includes such a method for controlling undesired weeds, by such applications of the herbicide.

Further, the herbicide containing compound of the present invention may be mixed with or may be used in combination with other agricultural chemicals, fertilizers or phytotoxicity-reducing agents, whereby synergistic effects or activities may sometimes be obtained. Such other agricultural chemicals include, for example, a herbicide, a fungicide, an antibiotic, a plant hormone and an insecticide. Especially, with a mixed herbicidal composition having a compound of the present invention mixed with or used in combination with one, or more active compounds of other herbicides, the range of weeds to be controlled, the time of application of the composition, the herbicidal activities, etc. may be improved to preferred directions. The compound of the present invention and the active compounds of other herbicides may separately be formulated so that they may be mixed for use at the time of application, or they may be formulated together. The present invention includes such a mixed herbicidal composition.

The mixing ratio of the compound of the present invention to the active compounds of other herbicides can not generally be defined, since it varies depending upon the weather conditions, the soil conditions, the types of formulations, the application time, the application method, etc., but the other herbicides are mixed in an amount of from 0.001 to 10,000 parts by weight, preferably from 0.01 to 1,000 parts by weight per one type of the active compound, based on 1 part by weight of the compound of the present invention. Further, the dose for the application is such that the total amount of the active compounds is from 0.1 to 10,000 g, preferably from 0.2 to 5,000 g, more preferably from 10 to 3,000 g, per hectare. The present invention includes a method for controlling undesired weeds by application of such a mixed herbicidal composition.

Another herbicidally active compound includes, for example, the following compounds (common names including ones under application for approval by ISO). Even when not specifically mentioned here, in a case where such compounds have salts, alkyl esters, etc., they are, of course, all included.

(1) Those which are believed to exhibit herbicidal effects by disturbing hormone activities of plants, such as a phenoxy type such as 2,4-D, 2,4-DB, 2,4-DP, MCPA, MCPB, MCPP, naproanilide or clomeprop, an aromatic carboxylic acid type such as 2,3,6-TBA, dicamba, dichlobenil, picloram, triclopyr, clopyralid or aminopyralid, and others such as naptalam, benazolin, quinclorac, quinmerac, diflufenzopyr and thiazopyr.

(2) Those which are believed to exhibit herbicidal effects by inhibiting photosynthesis of plants, such as a urea type such as chlorotoluron, diuron, fluometuron, linuron, isoproturon, metobenzuron or tebuthiuron, a triazine type such as simazine, atrazine, atratone, simetryn, prometryn, dimethametryn, hexazinone, metribuzin, terbuthylazine, cyanazine, ametryn, cybutryne, triaziflam or propazine, a uracil type such as bromacil, lenacil or terbacil, an anilide type such as propanil or cypromid, a carbamate type such as swep, desmedipham or phenmedipham, a hydroxybenzonitrile type such as bromoxynil, bromoxynil-octanoate or ioxynil, and others such as pyridate, bentazone, amicarbazone and methazole.

(3) Quaternary ammonium salt type such as paraquat or diquat, which is believed to be converted to free radicals by itself to form active oxygen in the plant body.

(4) Those which are believed to exhibit herbicidal, effects by inhibiting chlorophyll biosynthesis of plants and abnormally accumulating a photosensitizing peroxide substance in the plant body, such as a diphenylether type such as nitrofen, chlomethoxyfen, bifenox, acifluorfen-sodium, fomesafen, oxyfluorfen, lactofen or ethoxyfen-ethyl, a cyclic imide type such as chlorphthalim, flumioxazin, flumiclorac-pentyl or fluthiacet-methyl, and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, metobenzuron, cinidon-ethyl, flupoxam, fluazolate, profluazol, pyrachlonil, flufenpyr-ethyl and bencarbazone.

(5) Those which are believed to exhibit herbicidal, effects characterized by bleaching activities by inhibiting chromogenesis of plants such as carotenoids, such as a pyridazinone type such as norflurazon, chloridazon or metflurazon, a pyrazole type such as pyrazolate, pyrazoxyfen, benzofenap, topramezone (BAS-670H) or pyrasulfotole, and others such as amitrol, fluridone, flurtamone, diflufenican, methoxyphenone, clomazone, sulcotrione, mesotrione, tembotrione, tefuryltrione (AVH-301), isoxaflutole, difenzoquat, isoxachlortole, benzobicyclon, picolinafen and beflubutamid.

(6) Those which exhibit strong herbicidal effects specifically to gramineous plants, such as an aryloxyphenoxypropionic acid type such as diclofop-methyl, flamprop-M-methyl, pyriphenop-sodium, fluazifop-butyl, haloxyfop-methyl, quizalofop-ethyl, cyhalofop-butyl, fenoxaprop-ethyl or metamifop-propyl, and a cyclohexanedione type such as alloxydim-sodium, clethodim, sethoxydim, tralkoxydim, butroxydim, teptaloxydim, caloxydim, clefoxydim or profoxydim.

(7) Those which are believed to exhibit herbicidal effects by inhibiting an amino acid biosynthesis of plants, such as a sulfonylurea type such as chlorimuron-ethyl, sulfometuron-methyl, primisulfuron-methyl, bensulfuron-methyl, chlorsulfuron, metsulfuron-methyl, cinosulfuron, pyrazosulfuron-ethyl, azimsulfuron, flazasulfuron, rimsulfuron, nicosulfuron, imazosulfuron, cyclosulfamuron, prosulfuron, flupyrsulfuron, triflusulfuron-methyl, halosulfuron-methyl, thifensulfuron-methyl, ethoxysulfuron, oxasulfuron, ethametsulfuron, iodosulfuron, sulfosulfuron, triasulfuron, tribenuron-methyl, tritosulfuron, foramsulfuron, trifloxysulfuron, mesosulfuron-methyl, orthosulfamuron, flucetosulfuron, amidosulfuron, TH-547, a compound disclosed in WO2005092104, a triazolopyrimidinesulfonamide type such as flumetsulam, metosulam, diclosulam, cloransulam-methyl, florasulam, metosulfam or penoxsulam, an imidazolinone type such as imazapyr, imazethapyr, imazaquin, imazamox, imazameth, imazamethabenz or imazapic, a pyrimidinylsalicylic acid type such as pyrithiobac-sodium, bispyribac-sodium, pyriminobac-methyl, pyribenzoxim, pyriftalid or pyrimisulfan (KUH-021), a sulfonylaminocarbonyltriazolinone type such as flucarbazone or procarbazone-sodium, and others such as glyphosate, glyphosate-sodium, glyphosate-potassium, glyphosate-ammonium, glyphosate-isopropylamine, sulfosate, glufosinate, glufosinate-ammonium and bilanafos.

(8) Those which are believed to exhibit herbicidal effects by inhibiting cell mitoses of plants, such as a dinitroaniline type such as trifluralin, oryzalin, nitralin, pendimethalin, ethalfluralin, benfluralin or prodiamine, an amide type such as bensulide, napronamide or pronamide, an organic phosphorus type such as amiprofos-methyl, butamifos, anilofos or piperophos, a phenylcarbamate type such as propham, chlorpropham or barban, a cumylamine type such as daimuron, cumyluron or bromobutide, and others such as asulam, dithiopyr and thiazopyr.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachloror propisochlor, a carbamate type such as molinate, dimepiperate or pyributicarb, and others such as etobenzanid, mefenacet, flufenacet, tridiphane, cafenstrole, fentrazamide, oxaziclomefone, indanofan, dimethenamid, benfuresate and pyroxasulfone (KIH-485).

(10) A thiocarbamate type such as EPTC, butylate, vernolate, pebulate, cycloate, prosulfocarb, esprocarb, thiobencarb, diallate or triallate, and others such as MSMA, DSMA, endothall, ethofumesate, sodium chlorate, pelargonic acid, fosamine, pinoxaden and HOK-201.

(11) Those which are believed to exhibit herbicidal effects by being parasitic on plants, such as *Xanthomonas campestris, Epicoccosurus nematosurus, Exserohilum monoseras* and *Drechsrela monoceras*.

Examples of preferred embodiments of the present invention are shown below, but the present invention is by no means restricted thereto.

(1) A benzoylpyrazole compound of the above formula (I), wherein $R^1$ is alkyl or cycloalkyl, $R^2$ is a hydrogen atom or alkyl, $R^3$ is alkyl; cycloalkyl; haloalkyl; alkoxyalkyl; alkenyl; or arylalkyl which may be substituted by $R^8$, $R^4$ is alkyl; haloalkyl; alkoxy; halogen; nitro; cyano; alkylthio; alkylsulfinyl; or alkylsulfonyl, $R^5$ is a hydrogen atom; alkyl; halogen; cyano; cyanoalkyl; haloalkyl; alkoxyalkyl; haloalkoxyalkyl; alkoxy; haloalkoxy; alkoxyalkoxy; haloalkoxyalkoxy; alkoxyhaloalkoxy; alkoxyalkoxyalkyl; alkylthio; alkoxyalkylthio; haloalkoxyalkylthio; alkylthioalkylthio; haloalkylthioalkylthio; alkylthioalkoxy; alkylsulfonyl; alkylsulfonylalkyl; alkoxycarbonylalkyl; alkoxycarbonylalkoxy; heterocyclyloxy; heterocyclylalkoxy; heterocyclylalkoxyalkyl; —OC(O)SR$^7$; —OC(O)OR$^7$; —C(O)OR$^7$; —C(O)SR$^7$; or 4,5-dihydroisoxazol-3-yl which may be substituted by $R^9$, $R^6$ is haloalkyl; halogen; nitro; cyano; alkylthio; alkylsulfinyl; or alkylsulfonyl, $R^7$ is alkyl; haloalkyl; alkoxyalkyl; alkenyl; haloalkenyl; alkynyl; or arylalkyl which may be substituted by $R^{10}$, and each of $R^8$, $R^9$ and $R^{10}$ which are independent of one another, is halogen; alkyl; or alkoxy, or its salt, a process for producing it, a herbicide containing it as an active ingredient, and a method for controlling undesired plants or inhibiting their growth, which comprises applying a herbicidally effective amount of it to the undesired plants or to a place where they grow.

(2) A benzoylpyrazole compound of the above formula (I), wherein $R^1$ is alkyl or cycloalkyl, $R^2$ is a hydrogen atom or alkyl, $R^3$ is alkyl; cycloalkyl; haloalkyl; alkoxyalkyl; or arylalkyl which may be substituted by $R^8$, $R^4$ is alkyl; haloalkyl; alkoxy; halogen; nitro; cyano; alkylthio; alkylsulfinyl; or alkylsulfony, $R^5$ is alkyl; haloalkyl; alkoxyalkyl; haloalkoxyalkyl; alkoxy; haloalkoxy; alkoxyalkoxy; haloalkoxyalkoxy; heterocyclyloxy; heterocyclylalkoxy; heterocyclylalkoxyalkyl; —OC(O)SR$^7$; —OC(O)OR$^7$; —C(O)OR$^7$; —C(O)SR$^7$; or 4,5-dihydroisoxazol-3-yl which may be substituted by $R^9$, $R^6$ is haloalkyl; halogen; nitro; cyano; alkylthio; alkylsulfinyl; or alkylsulfonyl, $R^7$ is alkyl; haloalkyl; alkoxyalkyl; alkenyl; haloalkenyl; alkynyl; or arylalkyl which may be substituted by $R^{10}$, and each of $R^8$, $R^9$ and $R^{10}$ which are independent of one another, is halogen; alkyl; or alkoxy, or its salt, a process for producing it, a herbicide containing it as an active ingredient, and a method for controlling undesired plants or inhibiting their growth, which comprises applying a herbicidally effective amount of it to the undesired plants or to a place where they grow.

(3) A benzoylpyrazole compound of the above formula (I) wherein $R^1$ is alkyl, $R^2$ is a hydrogen atom, $R^3$ is alkyl, $R^4$ is alkyl, $R^5$ is alkoxy; haloalkoxy; —C(O)OR$^7$; or 4,5-dihydroisoxazol-3-yl, and $R^5$ is alkylsulfonyl, or its salt, a process for producing it, a herbicide containing it as an active ingredient, and a method for controlling undesired plants or inhibiting their growth, which comprises applying a herbicidally effective amount of it to the undesired plants or to a place where they grow.

(4) A mixed herbicidal composition containing the benzoylpyrazole compound of the above formula (I) or its salt, and one or more types of active compounds of other herbicides, and a method for controlling undesired plants or inhibiting their growth, which comprises applying a herbicidally effective amount of such a composition to, the undesired plants or to a place where they grow.

Now, the present invention will be described in detail with reference to Examples. However, it should be understood that the present invention is by no means restricted to such specific Examples.

Preparation examples for compounds of the present invention are described below.

Preparation Example 1

Preparation of 5-(ethylthio)carbonyloxy-1-methylpyrazol-4-yl 3-(methoxycarbonyl)-2-methyl-4-(methylsulfonyl)phenyl ketone (Compound No. 1 as Described Hereinafter)

5-Hydroxy-1-methylpyrazol-4-yl 3-(methoxycarbonyl)-2-methyl-4-(methylsulfonyl)phenyl ketone (290 mg, 0.82 mmol) was dissolved in dry tetrahydrofuran (15 mL), and triethylamine (166 mg, 1.64 mmol) was added thereto. A solution (4 mL) of 96% S-ethyl chlorothiolformate (107 mg) dissolved in dry tetrahydrofuran was added thereto little by little under cooling with ice water. The reaction mixture was stirred for 90 minutes while the reaction temperature was allowed to warm to room temperature. The reaction solution was poured into ice water, followed by extraction with ethyl acetate. The extract was dried over anhydrous sodium sulfate, and the solvent was distilled off under reduced pressure. The residue was purified by silica gel column chromatography (n-hexane:ethyl acetate=6:4) to obtain the desired product as an amorphous solid (202 mg, 0.46 mmol) (yield: 56%).

Preparation Example 2

Preparation of 1-ethyl-5-(ethylthio)carbonyloxypyrazol-4-yl 3-(methoxycarbonyl)-2-methyl-4-(methylsulfonyl)phenyl ketone (Compound No. 2 as Described Hereinafter)

5-Hydroxy-1-ethylpyrazol-4-yl 3-(methoxycarbonyl)-2-methyl-4-(methylsulfonyl)phenyl ketone (510 mg, 1.39 mmol) was dissolved in dry tetrahydrofuran-(20 mL), and triethylamine (281 mg, 2.78 mmol) was added thereto. A solution (4 mL) of 96% S-ethyl chlorothiolformate (217 mg) dissolved in dry tetrahydrofuran was added thereto little by little under cooling with ice water. The reaction mixture was stirred for 90 minutes while the reaction temperature was allowed to warm to room temperature. The reaction mixture was poured into ice water, followed by extraction with ethyl acetate. The organic layer was dried over anhydrous sodium sulfate, and the solvent was distilled off under reduced pressure. The residue was purified by silica gel column chromatography (n-hexane:ethyl acetate=6:4) to obtain the desired product as an oil (417 mg, 0.92 mmol) (yield: 66%)

Preparation Example 3

Preparation of 5-(ethylthio)carbonyloxy-1-methylpyrazol-4-yl 3-(methoxy)-2-methyl-4-(methylsulfonyl)phenyl ketone (Compound No. 35 as Described Hereinafter)

(1) To a stirred mixture of 3-methoxy-2-methyl-4-(methylsulfonyl)benzoic acid (340 mg, 1.39 mmol) and 5-hydroxy-1-methylpyrazole hydrochloride (230 mg) in anhydrous methylene chloride (10 mL) were added DCC (dicyclohexylcarbodiimide) (315 mg) and triethylamine (260 mg) at room temperature, followed by stirring for 2 hours. The reaction mixture was subjected to filtration through Celite, the filtrate was concentrated, and the obtained residue was dissolved in 10 mL of anhydrous acetonitrile. Triethylamine (260 mg) and acetone cyanohydrin in a catalytic amount were added thereto, and the reaction solution was stirred overnight at room temperature. 150 mL of ethyl acetate was added, and the solution was washed once with a 1N hydrochloric acid aqueous solution and washed once with a saturated brine. The organic layer was dried over anhydrous sodium sulfate, and then the solvent was distilled off under reduced pressure. The obtained residue was purified by silica gel column chromatography (ethyl acetate:methanol=9:1) to obtain 5-hydroxy-1-methylpyrazol-4-yl 3-methoxy-2-methyl-4-(methylsulfonyl)phenyl ketone (115 mg).

$^1$H-NMR (400 MHz CDCl$_3$ δ ppm): 2.31 (s, 3H), 3.20 (s, 3H) 3.66 (s, 3H), 3.92 (s, 3H), 7.1 (br s, 1H), 7.29 (d, 1H, J=7.6 Hz), 7.30 (s, 1H), 7.85 (d, 1H, J=7.6 Hz).

(2) To a solution of 5-hydroxy-1-methylpyrazol-4-yl 3-methoxy-2-methyl-4-(methylsulfonyl)phenyl ketone (100 mg, 0.3 mmol) in dry tetrahydrofuran (5 mL) were added triethylamine (61 mg) and 96% S-ethyl chlorothiolformate (50 mg) at room temperature. After the reaction solution was stirred for 1 hour, 150 mL of ethyl acetate was added. The mixture was washed twice with a saturated brine, the organic layer was dried over anhydrous sodium sulfate, and the solvent was distilled off under reduced pressure. The residue was purified by silica gel column chromatography (n-hexane:ethyl acetate=2:1) to obtain the desired product as an oil.

Preparation Example 4

Preparation of 5-(ethylthio)carbonyloxy-1-methylpyrazol-4-yl 2-methyl-4-(methylsulfonyl)-3-(4,5-dihydroisoxazol-3-yl)phenyl ketone (Compound No. 39 as Described Hereinafter)

To a solution of 5-hydroxy-1-methylpyrazol-4-yl 3-(4,5-dihydroisoxazol-3-yl)-2-methyl-4-(methylsulfonyl)phenyl ketone (100 mg, 2.75×10$^{-4}$ mol) in anhydrous tetrahydrofuran (5 mL) were added triethylamine (55 mg) and 96% S-ethyl chlorothiolformate (45 mg) at room temperature. After the reaction solution was stirred for 1 hour, 150 mL of ethyl acetate was added, and the solution was washed twice with a saturated brine. The organic layer was dried over anhydrous sodium sulfate, and the solvent was distilled off under reduced pressure. The residue was purified by silica gel column chromatography (n-hexane:ethyl acetate=6:4) to obtain the desired product (82 mg) as an oil.

Preparation Example 5

Preparation of 5-(ethylthio)carbonyloxy-1-methylpyrazol-4-yl 3-(difluoromethoxy)-2-methyl-4-(methylsulfonyl)phenyl ketone (Compound No. 38 as Described Hereinafter)

(1) To a stirred mixture of 3-(difluoromethoxy)-2-methyl-4-(methylsulfonyl)benzoic acid (500 mg, 1.78 mmol) and 5-hydroxy-1-methylpyrazole hydrochloride (288 mg) in anhydrous acetonitrile (10 mL) were added 1-ethyl-3-(3-dimethylaminopropyl)carbodiimide hydrochloride (443 mg), triethylamine (360 mg) and dimethylaminopyridine (217 mg) at room temperature. After being stirred for 12 hours, the reaction mixture was concentrated under reduced pressure, and the residue was dissolved in 100 mL of methylene chloride. This solution was washed with 100 mL of water, and the organic layer was dried over anhydrous sodium sulfate, and the solvent was distilled off under reduced pressure. The residue was dissolved in 10 mL of anhydrous acetonitrile, and triethylamine (260 mg) and acetone cyanohydrin in a catalytic amount were added, followed by stirring overnight at room temperature. 150 mL of methylene chloride was added, followed by extraction with a 1N potassium carbonate aqueous solution, and the aqueous layer was acidified by 2N hydrochloric acid. The obtained acidic aqueous solution was extracted twice with methylene chloride (100 mL), the combined organic layer was dried over anhydrous sodium sulfate, and the solvent was distilled off under reduced pressure. The obtained crude product was purified by silica gel column chromatography (ethyl acetate:hexane=1:1 to 9:1) to obtain 5-hydroxy-1-methylpyrazol-4-yl 3-(difluoromethoxy)-2-methyl-4-(methylsulfonyl)phenyl ketone as an oil.

$^1$H-NMR (400 MHz acetone-d$_6$ δ ppm): 2.37 (s, 3H), 3.28 (s, 3H), 3.61 (s, 3H), 6.90 (d, 1H, J=75.2 Hz), 7.27 (s, 1H), 7.59 (d, 1H, J=8.4 Hz), 7.96 (d, 1H, J=8.4 Hz).

(2) To a solution of 5-hydroxy-1-methylpyrazol-4-yl 3-(difluoromethoxy)-2-methyl-4-(methylsulfonyl)phenyl ketone (89 mg) in dry tetrahydrofuran (5 mL) were added triethylamine (50 mg) and 96% S-ethyl chlorothiolformate (40 mg) at room temperature. After the reaction solution was stirred for 1 hour, 150 mL of ethyl acetate was added. The mixture was washed twice with a saturated brine, the organic layer was dried over anhydrous sodium sulfate, and the solvent was distilled off under reduced pressure. The residue was purified by silica gel column chromatography (n-hexane:ethyl acetate=2:1) to obtain the desired product as an oil.

Preparation Example 6

Preparation of 5-(ethylthio)carbonyloxy-1-methylpyrazol-4-yl 3-(2-methoxyethoxy)-2-methyl-4-(methylsulfonyl)phenyl ketone (Compound No. 55 as Described Hereinafter)

(1) To a stirred suspension of sodium hydride (60%, 22.0 mg, 5.32 mmol) in anhydrous N,N-dimethylformamide (10 mL) was added methyl 3-hydroxy-2-methyl-4-(methylsulfonyl)benzoate (1 g, 4.09 mmol) under nitrogen atmosphere at room temperature. After stirring for 30 minutes, 2-bromoethyl methyl ether (1.13 g, 8.18 mmol) and potassium iodide in a catalytic amount were added thereto, and the reaction solution was stirred at 60° C. for 12 hours. 200 mL of ethyl acetate was added to the reaction solution, and the solution was washed twice with a saturate brine. The organic layer was dried over anhydrous sodium sulfate and concentrated under reduced pressure. The residue was purified by silica gel column chromatography (n-hexane:ethyl acetate=1:2) to obtain methyl 3-(2-methoxyethoxy)-2-methyl-4-(methylsulfonyl)benzoate as an oil (680 mg).

$^1$H-NMR 400 MHz (CDCl$_3$ δ ppm) 2.53 (s, 3H), 3.26 (s, 3H), 3.46 (s, 3H), 3.78 (m, 2H), 3.91 (s, 3H), 4.19 (m, 2H), 7.71 (d, 1H, J=8.4 Hz), 7.84 (d, 1H, J=8.4 Hz).

(2) Methyl 3-(2-methoxyethoxy)-2-methyl-4-(methylsulfonyl)benzoate (680 mg, 2.25 mmol) was dissolved in methanol (10 mL), and an aqueous sodium hydroxide solution (2 mL) at a concentration of 20% was added thereto at room temperature. After stirring for 30 minutes, the solvent was removed under reduced pressure. 100 mL of 1N hydrochloric acid was added to the residue, followed by extraction with ethyl acetate (200 mL). The organic layer was washed twice with a saturated brine and dried over anhydrous sodium sulfate. The solvent was distilled off under reduced pressure to obtain 3-(2-methoxyethoxy)-2-methyl-4-(methylsulfonyl)benzoic acid (570 mg) as a white solid.

$^1$H-NMR 400 MHz (acetone-$d_6$ δ ppm); 2.56 (s, 3H), 3.31 (s, 3H), 3.41 (s, 3H), 3.80 (m, 2H), 4.21 (m, 2H), 7.81 (s, 2H).

(3) To a solution of 3-(2-methoxyethoxy)-2-methyl-4-(methylsulfonyl)benzoic acid (195 mg, 6.76 mmol) in chloroform (15 mL) were added oxalyl-chloride (0.5 mL) and DMF in a catalytic amount. The reaction mixture was stirred for 30 minutes at room temperature, and the solvent was distilled off under reduced pressure. The residue was dissolved in anhydrous THF (20 mL), and 5-hydroxy-1-methylpyrazole hydrochloride (136 mg, 1.01 mmol), triethylamine (136 mg) and N,N-dimethylaminopyridine (250 mg) were added, followed by reflux with heating for 1 hour. The reaction mixture was allowed to cool to room temperature, and diluted with ethyl acetate (200 mL). The mixture was washed twice with a saturated brine. The organic layer was dried over anhydrous sodium sulfate, and the solvent was distilled off under reduced pressure. The residue was dissolved in anhydrous acetonitrile (10 mL), and triethylamine (136 mg) and acetone cyanohydrin in a catalytic amount were added. The mixture was stirred for 12 hours at room temperature. The solvent was distilled off under reduced pressure to obtain crude 5-hydroxy-1-methylpyrazol-4-yl 3-(2-methoxyethoxy)-2-methyl-4-(methylsulfonyl)phenyl ketone.

$^1$H-NMR (400 MHz CDCl$_3$ δ ppm); 2.39 (s, 3H), 3.29 (s, 3H), 3.46 (s, 3H), 3.71 (s, 3H), 3.81 (m, 2H), 4.24 (m, 2H), 7.34 (s, 1H), 7.35 (d, 1H, J=7.6 Hz), 7.92 (d, 1H, J=7.6 Hz).

(4) The crude 5-hydroxy-1-methylpyrazol-4-yl 3-(2-methoxyethoxy)-2-methyl-4-(methylsulfonyl)phenyl ketone obtained in the above step (3) was dissolved in anhydrous THF (10 mL), and triethylamine (190 mg) and 96% S-ethyl chlorothiolformate (151 mg) were added, followed by stirring for 1 hour at room temperature. Ethyl acetate (200 mL) was added to the reaction mixture, and the mixture was washed twice with a saturated brine. The organic layer was dried over anhydrous sodium sulfate, and the solvent was distilled off under reduced pressure. The residue was purified by silica gel column chromatography (n-hexane:ethyl acetate=1:1) to obtain the desired product (250 mg).

Preparation Example 7

Preparation of 5-(ethylthio)carbonyloxy-1-ethylpyrazol-4-yl 3-(2-methoxyethoxy)-2-methyl-4-(methylsulfonyl)phenyl ketone (Compound No. 16 as Described Hereinafter)

(1) To a solution of 3-(2-methoxyethoxy)-2-methyl-4-(methylsulfonyl)benzoic acid (200 mg, 6.90×10$^{-4}$ mol) in chloroform (15 mL) were added oxalyl chloride (0.5 mL) and DMF in a catalytic amount. The reaction mixture was stirred at room temperature for 30 minutes, and the solvent was distilled off under reduced pressure. The residue was dissolved in anhydrous THF (20 mL), and 5-hydroxy-1-ethylpyrazole hydrochloride (134 mg, 9.01×10$^{-4}$ mol), triethylamine (139 mg) and N,N-dimethylaminopyridine (170 mg) were added. The mixture was heated at refluxed temperature for 1 hour. The reaction mixture was allowed to cool to room temperature, and then ethyl acetate (200 mL) was added. The mixture was washed twice with a saturated brine, and the organic layer was dried over anhydrous sodium sulfate. The solvent was distilled off under reduced pressure. The residue was dissolved in anhydrous acetonitrile (10 mL), and triethylamine (139 mg) and acetone cyanohydrin in a catalytic amount were added, followed by stirring for 12 hours at room temperature. The solvent was distilled off under reduced pressure to obtain crude 5-hydroxy-1-ethylpyrazol-4-yl 3-(2-methoxyethoxy)-2-methyl-4-(methylsulfonyl)phenyl ketone.

$^1$H-NMR (400 MHz CDCl$_3$ δ ppm); 1.40 (t, 3H, J=7.0 Hz), 2.39 (s, 3H), 3.25 (s, 3H), 3.42 (s, 3H), 3.76 (m, 2H), 4.02 (q, 2H, J=7.0 Hz), 4.20 (m, 2H), 7.28 (s, 1H), 7.31 (d, 1H, J=7.6 Hz), 7.87 (d, 1H, J=7.6 Hz).

(2) The crude 5-hydroxy-1-ethylpyrazol-4-yl 3-(2-methoxyethoxy)-2-methyl-4-(methylsulfonyl)phenyl ketone obtained in the above step (1) was dissolved in anhydrous THF (10 mL), and triethylamine (139 mg) and 96% S-ethyl chlorothiolformate (111 mg) were added, followed by stirring for 1 hour at room temperature. Ethyl acetate (200 mL) was added to the obtained reaction mixture, and the mixture was washed twice with a saturated brine. The organic layer was dried over anhydrous sodium sulfate, and the solvent was distilled off under reduced pressure. The residue was purified by silica gel column chromatography (n-hexane:ethyl acetate=1:1) to obtain the desired product (170 mg).

Preparation Example 8

Preparation of 5-(ethylthio)carbonyloxy-1-methylpyrazol-4-yl 3-(2,2-dimethoxyethoxy)-2-methyl-4-(methylsulfonyl)phenyl ketone (Compound No. 209 as Described Hereinafter)

(1) 3-Hydroxy-2-methyl-4-(methylsulfonyl)benzoic acid (300 mg, 1.30 mmol) was dissolved in N,N-dimethylformamide (10 mL), and potassium carbonate (360 mg, 2.72 mmol) and bromoacetaldehyde dimethyl acetal (660 mg, 3.90 mmol) were added at room temperature. The reaction mixture was heated at 80° C., followed by stirring for 32 hours. The reaction mixture was allowed to cool to room temperature, and 100 mL of water and a 0.5N sodium hydroxide aqueous solution (10 mL) were added. Then, extraction with ethyl acetate (200 mL) was carried out, and the organic layer was dried over anhydrous sodium sulfate. The solvent was distilled off under reduced pressure to obtain 2,2-dimethoxyethyl 3-(2,2-dimethoxyethoxy)-2-methyl-4-(methylsulfonyl)benzoate as an oil.

$^1$H-NMR 400 MHz (CDCl$_3$ δ ppm) 2.54 (s, 3H), 3.31 (s, 1H), 3.39 (s, 6H), 3.44 (s, 6H), 4.06 (d, 2H, J=5.4 Hz), 4.31 (d, 2H, J=5.4 Hz), 4.73 (t, 1H, J=5.4 Hz), 4.87 (t, 1H, J=5.4 Hz), 7.76 (d, 1H, J=8.4 Hz), 7.82 (d, 1H, J=8.4 Hz).

(2) The 2,2-dimethoxyethyl 3-(2,2-dimethoxyethoxy)-2-methyl-4-(methylsulfonyl)benzoate obtained in the above step (1) was dissolved in methanol (20 mL), and an aqueous sodium hydroxide solution (2 mL) at a concentration of 20% was added thereto at room temperature. After stirring for 30 minutes, 100 mL of 1N hydrochloric acid was added to the reaction solution, followed by extraction with ethyl acetate (200 mL). The organic layer was washed twice with a saturated brine and dried over anhydrous sodium sulfate. The solvent was distilled off under reduced pressure to obtain 3-(2,2-dimethoxyethoxy)-2-methyl-4-(methylsulfonyl)benzoic acid (390 mg) as a white solid.

$^1$H-NMR 400 MHz (acetone-$d_6$ δ ppm): 2.56 (s, 3H), 3.31 (s, 3H), 3.44 (s, 6H), 4.06 (d, 2H, J=5.2 Hz), 4.88 (t, 1H, J=5.2 Hz), 7.82 (br s, 2H).

(3) 3-(2,2-Dimethoxyethoxy)-2-methyl-4-(methylsulfonyl)benzoic acid (390 mg, 1.23 mmol) was dissolved in chloroform (15 mL), and oxalyl chloride (0.5 mL) and DMF in a catalytic amount were added thereto. The reaction mixture was stirred at room temperature for 30 minutes, and the solvent was distilled off under reduced pressure. The residue was dissolved in anhydrous THF (20 mL), and 5-hydroxy-1-methylpyrazole (132 mg, 1.35 mmol), triethylamine (250 mg)

and N,N-dimethylaminopyridine (300 mg) were added, followed by reflux with heating for 1 hour. The reaction mixture was allowed to cool to room temperature, and ethyl acetate (200 mL) was added. The mixture was washed twice with a saturated brine. The organic layer was dried over anhydrous sodium sulfate, and the solvent was distilled off under reduced pressure. The residue was dissolved in anhydrous acetonitrile (10 mL), and triethylamine (250 mg) and acetone cyanohydrin in a catalytic amount were added, followed by stirring for 12 hours at room temperature. The solvent was distilled off under reduced pressure to obtain crude 5-hydroxy-1-methylpyrazol-4-yl 3-(2,2-dimethoxyethoxy)-2-methyl-4-(methylsulfonyl)phenyl ketone.

$^1$H-NMR (400 MHz CDCl$_3$ δ ppm): 2.38 (s, 3H), 3.29 (s, 3H), 3.47 (s, 6H), 3.70 (s, 3H), 4.09 (d, 2H, J=5.2 Hz), 4.1 (br s, 1H), 4.83 (t, 1H, J=5.2 Hz), 7.32 (s, 1H), 7.35 (d, 1H, J=8.4 Hz), 7.91 (d, 1H, J=8.4 Hz).

(4) The crude 5-hydroxy-1-methylpyrazol-4-yl 3-(2,2-dimethoxyethoxy)-2-methyl-4-(methylsulfonyl)phenyl ketone obtained in the above step (3) was dissolved in anhydrous THF (10 mL), and triethylamine (250 mg) and, 96% S-ethyl chlorothiolformate (200 mg) were added, followed by stirring for 1 hour at room temperature. Ethyl acetate (200 mL) was added to the obtained reaction mixture, and the mixture was washed twice with a saturated brine. The organic layer was dried over anhydrous sodium sulfate, and the solvent was distilled off under reduced pressure. The residue was purified by silica gel column chromatography (n-hexane: ethyl acetate=1:1) to obtain the desired product (150 mg).

Now, typical examples of the compounds of the present invention represented by the above formula (I) are shown in Table 1, and their $^1$H-NMR spectrum data are shown in Table 2. Further, typical examples of the compounds represented by the formula (II) as intermediates for preparation of the compounds of the formula (I) are shown in Table 3, and their $^1$H-NMR spectrum data are shown in Table 4. These compounds can be prepared in accordance with the above Preparation Examples or the above various processes for production of the compounds of the present invention. In Tables 1 to 4, No. represents the Compound No. In Tables 1 and 3, Me represents a methyl group, Et an ethyl group, n-Pr a normal-propyl group, i-Pr an isopropyl group, c-Pr a cyclopropyl group, s-Bu a secondary butyl group, t-Bu a tertiary butyl group, Ph a phenyl group, and Bn a benzyl group, respectively.

TABLE 1

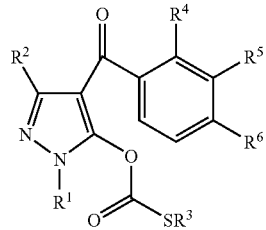

(I)

| No. | R$^1$ | R$^2$ | R$^3$ | R$^4$ | R$^5$ | R$^6$ |
|---|---|---|---|---|---|---|
| 1 | Me | H | Et | Me | CO$_2$Me | SO$_2$Me |
| 2 | Et | H | Et | Me | CO$_2$Me | SO$_2$Me |
| 3 | Me | H | Me | Me | CO$_2$Me | SO$_2$Me |
| 4 | Et | H | Me | Me | CO$_2$Me | SO$_2$Me |
| 5 | n-Pr | H | Et | Me | CO$_2$Me | SO$_2$Me |
| 6 | c-Pr | H | Et | Me | CO$_2$Me | SO$_2$Me |
| 7 | n-Pr | H | Me | Me | CO$_2$Me | SO$_2$Me |
| 8 | c-Pr | H | Me | Me | CO$_2$Me | SO$_2$Me |
| 9 | t-Bu | H | Et | Me | CO$_2$Me | SO$_2$Me |
| 10 | t-Bu | H | Me | Me | CO$_2$Me | SO$_2$Me |
| 11 | Me | Me | Et | Me | CO$_2$Me | SO$_2$Me |
| 12 | Et | H | Et | Me | CO$_2$(i-Pr) | SO$_2$Me |
| 13 | Me | H | Et | Me | CO$_2$Et | SO$_2$Me |
| 14 | Et | H | Et | Me | CO$_2$Me | NO$_2$ |
| 15 | Et | H | Et | SO$_2$Me | CO$_2$Me | CF$_3$ |
| 16 | Et | H | Et | Me | OCH$_2$CH$_2$OMe | SO$_2$Me |
| 17 | Et | H | Et | Cl | OCH$_2$CH$_2$OMe | SO$_2$Me |
| 18 | Et | H | Et | Me | CO$_2$Me | CN |
| 19 | Me | H | Et | Me | C(O)SMe | SO$_2$Me |
| 20 | Et | H | Et | Me | C(O)SMe | SO$_2$Me |
| 21 | Me | H | Me | Me | C(O)SEt | SO$_2$Me |
| 22 | Et | H | Me | Me | C(O)SEt | SO$_2$Me |
| 23 | Me | H | Et | Me | 2-(2-oxolanyl)ethoxy | SO$_2$Me |
| 24 | Me | H | Et | Me | 2-(2-(1,3-dioxolanyl))-ethoxy | SO$_2$Me |
| 25 | Et | H | Et | Me | CH$_2$OMe | SO$_2$Me |
| 26 | Et | H | Et | Me | 2-oxolanylmethoxymethyl | SO$_2$Me |
| 27 | Me | H | Et | Cl | CO$_2$Me | SO$_2$Me |
| 28 | Et | H | Et | Cl | CO$_2$Me | SO$_2$Et |
| 29 | Me | H | Me | Cl | CO$_2$Me | SO$_2$Me |
| 30 | Et | H | Me | Br | CO$_2$Me | SO$_2$Me |
| 31 | Me | H | Et | Cl | C(O)SMe | SO$_2$Me |
| 32 | Et | H | Et | Cl | C(O)SMe | SO$_2$Me |
| 33 | Me | H | Et | Cl | C(O)SEt | SO$_2$Me |
| 34 | Et | H | Et | Cl | C(O)SEt | SO$_2$Me |
| 35 | Me | H | Et | Me | OMe | SO$_2$Me |
| 36 | Me | H | Et | Me | OEt | SO$_2$Me |

TABLE 1-continued (I)

| No. | R¹ | R² | R³ | R⁴ | R⁵ | R⁶ |
|---|---|---|---|---|---|---|
| 37 | Me | H | Et | Me | O(i-Pr) | $SO_2Me$ |
| 38 | Me | H | Et | Me | $OCHF_2$ | $SO_2Me$ |
| 39 | Me | H | Et | Me | (4,5-dihydroisoxazol-3-yl) | $SO_2Me$ |
| 40 | Me | H | Me | Me | (4,5-dihydroisoxazol-3-yl) | $SO_2Me$ |
| 41 | Me | H | Et | Me | O(n-Pr) | $SO_2Et$ |
| 42 | Me | H | Et | Cl | $CH_2OMe$ | $SO_2Me$ |
| 43 | Me | H | Et | Me | $OCO_2Me$ | $SO_2Me$ |
| 44 | Et | H | Et | Me | $OCO_2Me$ | $SO_2Me$ |
| 45 | Me | H | Me | Me | $OCO_2Me$ | $SO_2Me$ |
| 46 | Et | H | Me | Me | $OCO_2Me$ | $SO_2Me$ |
| 47 | Me | H | Et | Me | OC(O)SMe | $SO_2Me$ |
| 48 | Et | H | Et | Me | OC(O)SMe | $SO_2Me$ |
| 49 | Me | H | Me | Me | OC(O)SMe | $SO_2Me$ |
| 50 | Et | H | Me | Me | OC(O)SMe | $SO_2Me$ |
| 51 | Me | H | Et | Me | OC(O)SEt | $SO_2Me$ |
| 52 | Et | H | Et | Me | OC(O)SEt | $SO_2Me$ |
| 53 | Me | H | Me | Me | OC(O)SEt | $SO_2Me$ |
| 54 | Et | H | Me | Me | OC(O)SEt | $SO_2Me$ |
| 55 | Me | H | Et | Me | $OCH_2CH_2OMe$ | $SO_2Me$ |
| 56 | Me | H | Me | Me | $OCH_2CH_2OMe$ | $SO_2Et$ |
| 57 | Me | H | Et | Cl | $OCH_2CH_2OMe$ | $SO_2Me$ |
| 58 | Et | H | Et | Me | OEt | $SO_2Me$ |
| 59 | Et | H | Et | Cl | $CO_2Et$ | $SO_2Me$ |
| 60 | Et | H | Et | Cl | $CO_2(n-Pr)$ | $SO_2Me$ |
| 61 | Et | H | Et | Me | $CO_2Et$ | $SO_2Me$ |
| 62 | Et | H | Me | Me | $CO_2Et$ | $SO_2Me$ |
| 63 | Me | H | Et | Me | $CH_2OMe$ | $SO_2Me$ |
| 64 | Me | H | Et | Me | $CH_2CO_2Me$ | $SO_2Me$ |
| 65 | Me | H | Et | Me | $OCH_2CO_2Et$ | $SO_2Me$ |
| 66 | Me | H | Et | Me | O(n-Pr) | $SO_2Me$ |
| 67 | Et | H | Et | Me | O(n-Pr) | $SO_2Me$ |
| 68 | Et | H | Et | $SO_2Me$ | H | $CF_3$ |
| 69 | Me | H | Et | Me | $CH_2OCH_2CF_3$ | $SO_2Me$ |
| 70 | Me | H | Et | Cl | $CH_2OCH_2CF_3$ | $SO_2Me$ |
| 71 | Et | H | Et | Me | Cl | $SO_2Me$ |
| 72 | Me | H | Et | Me | $CH_2SO_2Me$ | $SO_2Me$ |
| 73 | Me | H | Et | Me | $CH_2OEt$ | $SO_2Me$ |
| 74 | Me | H | Me | Cl | $CH_2OMe$ | $SO_2Me$ |
| 75 | Me | H | Et | Me | $CH_2CH_2OMe$ | $SO_2Me$ |
| 76 | Me | H | Et | Me | $CH_2OCH_2CH_2OMe$ | $SO_2Me$ |
| 77 | Me | H | Et | Me | $OCH_2CH_2OEt$ | $SO_2Me$ |
| 78 | Me | H | Et | Me | $OCH_2CH_2Cl$ | $SO_2Me$ |
| 79 | Me | H | Et | Me | $OCH_2CF_3$ | $SO_2Me$ |
| 80 | Me | H | Et | Me | $CH_2OCH_2OMe$ | $SO_2Me$ |
| 81 | Me | H | Et | Me | $OCH_2CH_2SMe$ | $SO_2Me$ |
| 82 | Me | H | Et | Me | CN | $SO_2Me$ |
| 83 | Me | H | Et | Me | $CH_2CN$ | $SO_2Me$ |
| 84 | Me | H | n-Pr | Me | $CO_2Me$ | $SO_2Me$ |
| 85 | Et | H | n-Pr | Me | $CO_2Me$ | $SO_2Me$ |
| 86 | Me | H | i-Pr | Me | $CO_2Me$ | $SO_2Me$ |
| 87 | Et | H | i-Pr | Me | $CO_2Me$ | $SO_2Me$ |
| 88 | Me | H | s-Bu | Me | $CO_2Me$ | $SO_2Me$ |
| 89 | Et | H | s-Bu | Me | $CO_2Me$ | $SO_2Me$ |
| 90 | Me | H | t-Bu | Me | $CO_2Me$ | $SO_2Me$ |
| 91 | Et | H | t-Bu | Me | $CO_2Me$ | $SO_2Me$ |
| 92 | Me | H | Bn | Me | $CO_2Me$ | $SO_2Me$ |
| 93 | Et | H | Bn | Me | $CO_2Me$ | $SO_2Me$ |
| 94 | Me | H | Et | Br | $CO_2Me$ | $SO_2Me$ |
| 95 | Et | H | Et | Cl | $CO_2Me$ | $SO_2Me$ |
| 96 | Me | H | Me | Br | $CO_2Me$ | $SO_2Me$ |
| 97 | Et | H | Me | Cl | $CO_2Me$ | $SO_2Me$ |
| 98 | Me | H | Allyl | Me | $CO_2Me$ | $SO_2Me$ |
| 99 | Et | H | Allyl | Me | $CO_2Me$ | $SO_2Me$ |
| 100 | Me | H | $CH_2CH(CH_3)=CH_2$ | Me | $CO_2Me$ | $SO_2Me$ |
| 101 | Et | H | $CH_2CH(CH_3)=CH_2$ | Me | $CO_2Me$ | $SO_2Me$ |

TABLE 1-continued

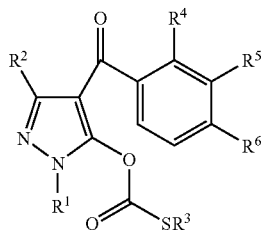

(I)

| No. | $R^1$ | $R^2$ | $R^3$ | $R^4$ | $R^5$ | $R^6$ |
|---|---|---|---|---|---|---|
| 102 | Me | H | Et | Cl | $OCH_2CH_2OCF_3$ | $SO_2Me$ |
| 103 | Et | H | Et | Cl | $OCH_2CH_2OCF_3$ | $SO_2Me$ |
| 104 | Me | H | Et | Me | $OCH_2CH_2OCF_3$ | $SO_2Me$ |
| 105 | Et | H | Et | Me | $OCH_2CH_2OCF_3$ | $SO_2Me$ |
| 106 | Me | H | Et | $CF_3$ | $OCH_2CH_2OCF_3$ | $SO_2Me$ |
| 107 | Et | H | Et | $CF_3$ | $OCH_2CH_2OCF_3$ | $SO_2Me$ |
| 108 | Me | H | Et | Br | $OCH_2CH_2OCF_3$ | $SO_2Me$ |
| 109 | Et | H | Et | Br | $OCH_2CH_2OCF_3$ | $SO_2Me$ |
| 110 | Me | H | Et | $SO_2Me$ | $OCH_2CH_2OCF_3$ | $CF_3$ |
| 111 | Et | H | Et | $SO_2Me$ | $OCH_2CH_2OCF_3$ | $CF_3$ |
| 112 | Me | H | Et | Cl | $OCH_2CH_2OCHClF$ | $SO_2Me$ |
| 113 | Et | H | Et | Cl | $OCH_2CH_2OCHClF$ | $SO_2Me$ |
| 114 | Me | H | Et | Me | $OCH_2CH_2OCHClF$ | $SO_2Me$ |
| 115 | Et | H | Et | Me | $OCH_2CH_2OCHClF$ | $SO_2Me$ |
| 116 | Me | H | Et | $CF_3$ | $OCH_2CH_2OCHClF$ | $SO_2Me$ |
| 117 | Et | H | Et | $CF_3$ | $OCH_2CH_2OCHClF$ | $SO_2Me$ |
| 118 | Me | H | Et | Br | $OCH_2CH_2OCHClF$ | $SO_2Me$ |
| 119 | Et | H | Et | Br | $OCH_2CH_2OCHClF$ | $SO_2Me$ |
| 120 | Me | H | Et | $SO_2Me$ | $OCH_2CH_2OCHClF$ | $CF_3$ |
| 121 | Et | H | Et | $SO_2Me$ | $OCH_2CH_2OCHClF$ | $CF_3$ |
| 122 | Me | H | Et | Cl | $OCH_2CHFOCF_3$ | $SO_2Me$ |
| 123 | Et | H | Et | Cl | $OCH_2CHFOCF_3$ | $SO_2Me$ |
| 124 | Me | H | Et | Me | $OCH_2CHFOCF_3$ | $SO_2Me$ |
| 125 | Me | H | Et | Cl | $OCH_2CHFOMe$ | $SO_2Me$ |
| 126 | Et | H | Et | Cl | $OCH_2CHFOMe$ | $SO_2Me$ |
| 127 | Me | H | Et | Me | $OCH_2CHFOMe$ | $SO_2Me$ |
| 128 | Et | H | Et | Me | $OCH_2CHFOMe$ | $SO_2Me$ |
| 129 | Me | H | Et | $CF_3$ | $OCH_2CHFOMe$ | $SO_2Me$ |
| 130 | Et | H | Et | $CF_3$ | $OCH_2CHFOMe$ | $SO_2Me$ |
| 131 | Me | H | Et | Br | $OCH_2CHFOMe$ | $SO_2Me$ |
| 132 | Et | H | Et | Br | $OCH_2CHFOMe$ | $SO_2Me$ |
| 133 | Me | H | Et | $SO_2Me$ | $OCH_2CHFOMe$ | $CF_3$ |
| 134 | Et | H | Et | $SO_2Me$ | $OCH_2CHFOMe$ | $CF_3$ |
| 135 | Me | H | Et | Cl | $OCHFCH_2OCF_3$ | $SO_2Me$ |
| 136 | Et | H | Et | Cl | $OCHFCH_2OCF_3$ | $SO_2Me$ |
| 137 | Me | H | Et | Cl | $OCH_2CH_2OCF_2Cl$ | $SO_2Me$ |
| 138 | Et | H | Et | Cl | $OCH_2CH_2OCF_2Cl$ | $SO_2Me$ |
| 139 | Me | H | Et | Me | $OCH_2CH_2OCF_2Cl$ | $SO_2Me$ |
| 140 | Et | H | Et | Me | $OCH_2CH_2OCF_2Cl$ | $SO_2Me$ |
| 141 | Me | H | Et | $CF_3$ | $OCH_2CH_2OCF_2Cl$ | $SO_2Me$ |
| 142 | Et | H | Et | $CF_3$ | $OCH_2CH_2OCF_2Cl$ | $SO_2Me$ |
| 143 | Me | H | Et | Br | $OCH_2CH_2OCF_2Cl$ | $SO_2Me$ |
| 144 | Et | H | Et | Br | $OCH_2CH_2OCF_2Cl$ | $SO_2Me$ |
| 145 | Me | H | Et | $SO_2Me$ | $OCH_2CH_2OCF_2Cl$ | $CF_3$ |
| 146 | Et | H | Et | $SO_2Me$ | $OCH_2CH_2OCF_2Cl$ | $CF_3$ |
| 147 | Me | H | Et | Cl | $SCH_2CH_2OCH_3$ | $SO_2Me$ |
| 148 | Et | H | Et | Cl | $SCH_2CH_2OCH_3$ | $SO_2Me$ |
| 149 | Me | H | Et | Me | $SCH_2CH_2OCH_3$ | $SO_2Me$ |
| 150 | Et | H | Et | Me | $SCH_2CH_2OCH_3$ | $SO_2Me$ |
| 151 | Me | H | Et | $CF_3$ | $SCH_2CH_2OCH_3$ | $SO_2Me$ |
| 152 | Et | H | Et | $CF_3$ | $SCH_2CH_2OCH_3$ | $SO_2Me$ |
| 153 | Me | H | Et | Br | $SCH_2CH_2OCH_3$ | $SO_2Me$ |
| 154 | Et | H | Et | Br | $SCH_2CH_2OCH_3$ | $SO_2Me$ |
| 155 | Me | H | Et | $SO_2Me$ | $SCH_2CH_2OCH_3$ | $CF_3$ |
| 156 | Et | H | Et | $SO_2Me$ | $SCH_2CH_2OCH_3$ | $CF_3$ |
| 157 | Me | H | Et | Cl | $SCH_2CH_2OCF_3$ | $SO_2Me$ |
| 158 | Et | H | Et | Cl | $SCH_2CH_2OCF_3$ | $SO_2Me$ |
| 159 | Me | H | Et | Me | $SCH_2CH_2OCF_3$ | $SO_2Me$ |
| 160 | Et | H | Et | Me | $SCH_2CH_2OCF_3$ | $SO_2Me$ |
| 161 | Me | H | Et | $CF_3$ | $SCH_2CH_2OCF_3$ | $SO_2Me$ |
| 162 | Et | H | Et | $CF_3$ | $SCH_2CH_2OCF_3$ | $SO_2Me$ |
| 163 | Me | H | Et | Br | $SCH_2CH_2OCF_3$ | $SO_2Me$ |
| 164 | Et | H | Et | Br | $SCH_2CH_2OCF_3$ | $SO_2Me$ |
| 165 | Me | H | Et | $SO_2Me$ | $SCH_2CH_2OCF_3$ | $CF_3$ |
| 166 | Et | H | Et | $SO_2Me$ | $SCH_2CH_2OCF_3$ | $CF_3$ |

TABLE 1-continued

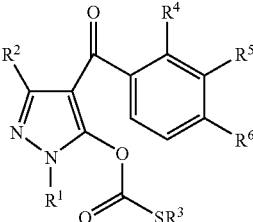

(I)

| No. | $R^1$ | $R^2$ | $R^3$ | $R^4$ | $R^5$ | $R^6$ |
|---|---|---|---|---|---|---|
| 167 | Me | H | Et | Cl | $SCH_2CH_2SCH_3$ | $SO_2Me$ |
| 168 | Et | H | Et | Cl | $SCH_2CH_2SCH_3$ | $SO_2Me$ |
| 169 | Me | H | Et | Me | $SCH_2CH_2SCH_3$ | $SO_2Me$ |
| 170 | Et | H | Et | Me | $SCH_2CH_2SCH_3$ | $SO_2Me$ |
| 171 | Me | H | Et | $CF_3$ | $SCH_2CH_2SCH_3$ | $SO_2Me$ |
| 172 | Et | H | Et | $CF_3$ | $SCH_2CH_2SCH_3$ | $SO_2Me$ |
| 173 | Me | H | Et | Br | $SCH_2CH_2SCH_3$ | $SO_2Me$ |
| 174 | Et | H | Et | Br | $SCH_2CH_2SCH_3$ | $SO_2Me$ |
| 175 | Me | H | Et | $SO_2Me$ | $SCH_2CH_2SCH_3$ | $CF_3$ |
| 176 | Et | H | Et | $SO_2Me$ | $SCH_2CH_2SCH_3$ | $CF_3$ |
| 177 | Me | H | Et | Cl | $SCH_2CH_2SCF_3$ | $SO_2Me$ |
| 178 | Et | H | Et | Cl | $SCH_2CH_2SCF_3$ | $SO_2Me$ |
| 179 | Me | H | Et | Me | $SCH_2CH_2SCF_3$ | $SO_2Me$ |
| 180 | Et | H | Et | Me | $SCH_2CH_2SCF_3$ | $SO_2Me$ |
| 181 | Me | H | Et | $CF_3$ | $SCH_2CH_2SCF_3$ | $SO_2Me$ |
| 182 | Et | H | Et | $CF_3$ | $SCH_2CH_2SCF_3$ | $SO_2Me$ |
| 183 | Me | H | Et | Br | $SCH_2CH_2SCF_3$ | $SO_2Me$ |
| 184 | Et | H | Et | Br | $SCH_2CH_2SCF_3$ | $SO_2Me$ |
| 185 | Me | H | Et | $SO_2Me$ | $SCH_2CH_2SCF_3$ | $CF_3$ |
| 186 | Et | H | Et | $SO_2Me$ | $SCH_2CH_2SCF_3$ | $CF_3$ |
| 187 | Me | H | Et | Cl | $OCH_2CH(CH_3)OCH_3$ | $SO_2Me$ |
| 188 | Et | H | Et | Cl | $OCH_2CH(CH_3)OCH_3$ | $SO_2Me$ |
| 189 | Me | H | Et | Me | $OCH_2CH(CH_3)OCH_3$ | $SO_2Me$ |
| 190 | Et | H | Et | Me | $OCH_2CH(CH_3)OCH_4$ | $SO_2Me$ |
| 191 | Me | H | Et | $CF_3$ | $OCH_2CH(CH_3)OCH_3$ | $SO_2Me$ |
| 192 | Et | H | Et | $CF_3$ | $OCH_2CH(CH_3)OCH_3$ | $SO_2Me$ |
| 193 | Me | H | Et | Br | $OCH_2CH(CH_3)OCH_3$ | $SO_2Me$ |
| 194 | Et | H | Et | Br | $OCH_2CH(CH_3)OCH_3$ | $SO_2Me$ |
| 195 | Me | H | Et | $SO_2Me$ | $OCH_2CH(CH_3)OCH_3$ | $CF_3$ |
| 196 | Et | H | Et | $SO_2Me$ | $OCH_2CH(CH_3)OCH_3$ | $CF_3$ |
| 197 | Me | H | Et | Cl | $OCH_2CF_2OCH_3$ | $SO_2Me$ |
| 198 | Et | H | Et | Cl | $OCH_2CF_2OCH_3$ | $SO_2Me$ |
| 199 | Me | H | Et | Me | $OCH_2CF_2OCH_3$ | $SO_2Me$ |
| 200 | Et | H | Et | Me | $OCH_2CF_2OCH_3$ | $SO_2Me$ |
| 201 | Me | H | Et | $CF_3$ | $OCH_2CF_2OCH_3$ | $SO_2Me$ |
| 202 | Et | H | Et | $CF_3$ | $OCH_2CF_2OCH_3$ | $SO_2Me$ |
| 203 | Me | H | Et | Br | $OCH_2CF_2OCH_3$ | $SO_2Me$ |
| 204 | Et | H | Et | Br | $OCH_2CF_2OCH_3$ | $SO_2Me$ |
| 205 | Me | H | Et | $SO_2Me$ | $OCH_2CF_2OCH_3$ | $CF_3$ |
| 206 | Et | H | Et | $SO_2Me$ | $OCH_2CF_2OCH_3$ | $CF_3$ |
| 207 | Me | H | i-Pr | Me | $OCH_2CH_2OCH_3$ | $SO_2Me$ |
| 208 | Et | H | i-Pr | Me | $OCH_2CH_2OCH_3$ | $SO_2Me$ |
| 209 | Me | H | Et | Me | $OCH_2CH(OCH_3)_2$ | $SO_2Me$ |
| 210 | Me | H | Et | Me | $CH_2N(Me)CH_2CN$ | $SO_2Me$ |
| 211 | Me | H | Et | Me | (tetrahydrofuran-2-yl)methoxy | $SO_2Me$ |
| 212 | Me | H | Et | Cl | SMe | $SO_2Me$ |
| 213 | Me | H | Et | Cl | Cl | $SO_2Me$ |
| 214 | Me | H | Et | Cl | OMe | $SO_2Me$ |
| 215 | Me | H | Et | Me | (tetrahydro-2H-pyran-2-yl)methoxy | $SO_2Me$ |
| 216 | Me | H | Et | Cl | $OCH_2CH_2OMe$ | $SO_2Me$ |
| 217 | Me | H | Et | Me | tetrahydrofuran-3-yloxy | $SO_2Me$ |
| 218 | Me | H | Et | Me | $OCH_2CH_2CH_2OMe$ | $SO_2Me$ |
| 219 | Me | H | n-Pr | Me | $OCH_2CH_2OMe$ | $SO_2Me$ |
| 220 | Et | H | s-Bu | Cl | C(O)OMe | $SO_2Me$ |
| 221 | Et | H | Et | Cl | 2-(1,3-dioxolan-2-yl)ethoxy | $SO_2Me$ |
| 222 | Me | H | Et | Me | propargyloxy | $SO_2Me$ |
| 223 | Me | H | Et | Me | (tetrahydrofuran-3-yloxy)methyl | $SO_2Me$ |
| 224 | Me | H | Et | Cl | $SO_2Me$ | $SO_2Me$ |
| 225 | Me | H | Et | Me | $(CH_2)_6Me$ | $SO_2Me$ |
| 226 | Me | H | Et | Me | $CH_2CH_2OMe$ | $SO_2Me$ |
| 227 | Et | H | Et | Cl | (1,3-dioxolan-2-yl)methoxy | $SO_2Me$ |
| 228 | Me | H | Et | Me | $CH_2N[C(O)SEt]CH_2CN$ | $SO_2Me$ |
| 229 | Me | H | Et | Me | CH=CHCN | $SO_2Me$ |
| 230 | Me | H | Et | Me | $CH_2CH_2CN$ | $SO_2Me$ |
| 231 | Me | H | Et | Me | $CH_2SCN$ | $SO_2Me$ |

TABLE 1-continued

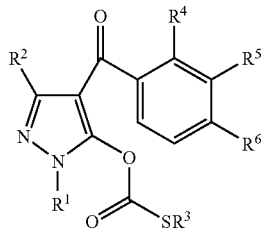

(I)

| No. | R¹ | R² | R³ | R⁴ | R⁵ | R⁶ |
|---|---|---|---|---|---|---|
| 232 | Me | H | Et | Me | CH₂C(S)NH₂ | SO₂Me |
| 233 | Me | H | Me | Me | OCH₂CH₂OMe | SO₂Me |
| 234 | Et | H | Me | Me | OCH₂CH₂OMe | SO₂Me |
| 235 | Et | H | n-Pr | Me | OCH₂CH₂OMe | SO₂Me |
| 236 | Me | H | Et | Me | OCH(CH₃)CH₂OMe | SO₂Me |
| 237 | Et | H | Et | Me | OCH₂CH(Et)OMe | SO₂Me |
| 238 | Me | H | Et | Me | (1,3-dioxolan-2-yl)methyl | SO₂Me |
| 239 | Me | H | s-Bu | Me | OCH₂CH₂OMe | SO₂Me |
| 240 | Me | H | Et | Me | CH₂O(i-Pr) | SO₂Me |
| 241 | Me | H | t-Bu | Me | OCH₂CH₂OMe | SO₂Me |
| 242 | Me | H | CH₂CO₂Me | Me | OCH₂CH₂OMe | SO₂Me |
| 243 | Et | H | c-Pr | Me | CO₂Me | SO₂Me |
| 244 | Et | H | c-Pr | Me | CO₂(i-Pr) | SO₂Me |
| 245 | Et | H | c-Pr | Me | OCH₂CH₂OMe | SO₂Me |
| 246 | Et | H | c-Pr | SO₂Me | CO₂Me | CN |
| 247 | Me | H | c-Pr | Me | C(O)SMe | SO₂Me |
| 248 | Me | H | c-Pr | Me | C(O)SEt | SO₂Me |
| 249 | Me | H | c-Pr | Me | 2-(2-oxolanyl)ethoxy | SO₂Me |
| 250 | Me | H | c-Pr | Me | 2-(2-(1,3-dioxolanyl))ethoxy | SO₂Me |
| 251 | Et | H | c-Pr | Me | CH₂OMe | SO₂Me |
| 252 | Et | H | c-Pr | Me | 2-oxolanylmethoxymethyl | SO₂Me |
| 253 | Me | H | c-Pr | Cl | CO₂Me | SO₂Me |
| 254 | Et | H | c-Pr | Cl | CO₂Me | SO₂Et |
| 255 | Me | H | c-Pr | Cl | C(O)SMe | SO₂Me |
| 256 | Me | H | c-Pr | Cl | C(O)SEt | SO₂Me |
| 257 | Me | H | c-Pr | Me | OMe | SO₂Me |
| 258 | Me | H | c-Pr | Me | OEt | SO₂Me |
| 259 | Me | H | c-Pr | Me | O(i-Pr) | SO₂Me |
| 260 | Me | H | c-Pr | Me | OCHF₂ | SO₂Me |
| 261 | Me | H | c-Pr | Me | (4,5-dihydroisoxazol-3-yl) | SO₂Me |
| 262 | Me | H | c-Pr | Me | O(n-Pr) | SO₂Et |
| 263 | Me | H | c-Pr | Cl | CH₂OMe | SO₂Me |
| 264 | Me | H | c-Pr | Me | OCO₂Me | SO₂Me |
| 265 | Me | H | c-Pr | Me | OC(O)SMe | SO₂Me |
| 266 | Me | H | c-Pr | Me | OC(O)SEt | SO₂Me |
| 267 | Me | H | c-Pr | Me | OCH₂CH₂OMe | SO₂Me |
| 268 | Et | H | c-Pr | Me | OEt | SO₂Me |
| 269 | Et | H | c-Pr | Cl | CO₂Et | SO₂Me |
| 270 | Et | H | c-Pr | Cl | CO₂(n-Pr) | SO₂Me |
| 271 | Et | H | c-Pr | Me | CO₂Et | SO₂Me |
| 272 | Me | H | c-Pr | CN | CO₂Me | SO₂Me |
| 273 | Et | H | c-Pr | CN | CO₂(i-Pr) | SO₂Me |
| 274 | Me | H | c-Pr | Me | CH₂CO₂Me | SO₂Me |
| 275 | Me | H | c-Pr | Me | OCH₂CO₂Et | SO₂Me |
| 276 | Me | H | c-Pr | Me | O(n-Pr) | SO₂Me |
| 277 | Et | H | c-Pr | SO₂Me | H | CF₃ |
| 278 | Me | H | c-Pr | Me | CH₂OCH₂CF₃ | SO₂Me |
| 279 | Me | H | c-Pr | Cl | CH₂OCH₂CF₃ | SO₂Me |
| 280 | Et | H | c-Pr | Me | Cl | SO₂Me |
| 281 | Me | H | c-Pr | Me | CH₂SO₂Me | SO₂Me |
| 282 | Me | H | c-Pr | Me | CH₂OEt | SO₂Me |
| 283 | Me | H | c-Pr | Cl | CH₂OMe | SO₂Me |
| 284 | Me | H | c-Pr | Me | CH₂CH₂OMe | SO₂Me |
| 285 | Me | H | c-Pr | Me | CH₂OCH₂CH₂OMe | SO₂Me |
| 286 | Me | H | c-Pr | Me | OCH₂CH₂OEt | SO₂Me |
| 287 | Me | H | c-Pr | Me | OCH₂CH₂Cl | SO₂Me |
| 288 | Me | H | c-Pr | Me | OCH₂CF₃ | SO₂Me |
| 289 | Me | H | c-Pr | Me | CH₂OCH₂OMe | SO₂Me |
| 290 | Me | H | c-Pr | Me | OCH₂CH₂SMe | SO₂Me |
| 291 | Me | H | c-Pr | Me | CN | SO₂Me |
| 292 | Me | H | c-Pr | Me | CH₂CN | SO₂Me |
| 293 | Me | H | c-Pr | Br | CO₂Me | SO₂Me |
| 294 | Et | H | c-Pr | Cl | CO₂Me | SO₂Me |
| 295 | Me | H | c-Pr | Br | CO₂Et | SO₂Me |
| 296 | Me | H | c-Pr | Cl | OCH₂CH₂OCF₃ | SO₂Me |

TABLE 1-continued

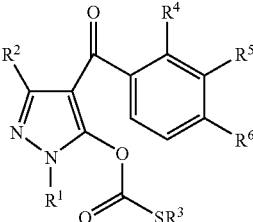

| No. | $R^1$ | $R^2$ | $R^3$ | $R^4$ | $R^5$ | $R^6$ |
|---|---|---|---|---|---|---|
| 297 | Et | H | c-Pr | Cl | $OCH_2CH_2OCF_3$ | $SO_2Me$ |
| 298 | Me | H | c-Pr | Me | $OCH_2CH_2OCF_3$ | $SO_2Me$ |
| 299 | Et | H | c-Pr | Me | $OCH_2CH_2OCF_3$ | $SO_2Me$ |
| 300 | Me | H | c-Pr | $CF_3$ | $OCH_2CH_2OCF_3$ | $SO_2Me$ |
| 301 | Et | H | c-Pr | $CF_3$ | $OCH_2CH_2OCF_3$ | $SO_2Me$ |
| 302 | Me | H | c-Pr | Br | $OCH_2CH_2OCF_3$ | $SO_2Me$ |
| 303 | Et | H | c-Pr | Br | $OCH_2CH_2OCF_3$ | $SO_2Me$ |
| 304 | Me | H | c-Pr | $SO_2Me$ | $OCH_2CH_2OCF_3$ | $CF_3$ |
| 305 | Et | H | c-Pr | $SO_2Me$ | $OCH_2CH_2OCF_3$ | $CF_3$ |
| 306 | Me | H | c-Pr | Cl | $OCH_2CH_2OCHClF$ | $SO_2Me$ |
| 307 | Et | H | c-Pr | Cl | $OCH_2CH_2OCHClF$ | $SO_2Me$ |
| 308 | Me | H | c-Pr | Me | $OCH_2CH_2OCHClF$ | $SO_2Me$ |
| 309 | Et | H | c-Pr | Me | $OCH_2CH_2OCHClF$ | $SO_2Me$ |
| 310 | Me | H | c-Pr | $CF_3$ | $OCH_2CH_2OCHClF$ | $SO_2Me$ |
| 311 | Et | H | c-Pr | $CF_3$ | $OCH_2CH_2OCHClF$ | $SO_2Me$ |
| 312 | Me | H | c-Pr | Br | $OCH_2CH_2OCHClF$ | $SO_2Me$ |
| 313 | Et | H | c-Pr | Br | $OCH_2CH_2OCHClF$ | $SO_2Me$ |
| 314 | Me | H | c-Pr | $SO_2Me$ | $OCH_2CH_2OCHClF$ | $CF_3$ |
| 315 | Et | H | c-Pr | $SO_2Me$ | $OCH_2CH_2OCHClF$ | $CF_3$ |
| 316 | Me | H | c-Pr | Cl | $OCH_2CHFOCF_3$ | $SO_2Me$ |
| 317 | Et | H | c-Pr | Cl | $OCH_2CHFOCF_3$ | $SO_2Me$ |
| 318 | Me | H | c-Pr | Me | $OCH_2CHFOCF_3$ | $SO_2Me$ |
| 319 | Me | H | c-Pr | Cl | $OCH_2CHFOMe$ | $SO_2Me$ |
| 320 | Et | H | c-Pr | Cl | $OCH_2CHFOMe$ | $SO_2Me$ |
| 321 | Me | H | c-Pr | Me | $OCH_2CHFOMe$ | $SO_2Me$ |
| 322 | Et | H | c-Pr | Me | $OCH_2CHFOMe$ | $SO_2Me$ |
| 323 | Me | H | c-Pr | $CF_3$ | $OCH_2CHFOMe$ | $SO_2Me$ |
| 324 | Et | H | c-Pr | $CF_3$ | $OCH_2CHFOMe$ | $SO_2Me$ |
| 325 | Me | H | c-Pr | Br | $OCH_2CHFOMe$ | $SO_2Me$ |
| 326 | Et | H | c-Pr | Br | $OCH_2CHFOMe$ | $SO_2Me$ |
| 327 | Me | H | c-Pr | $SO_2Me$ | $OCH_2CHFOMe$ | $CF_3$ |
| 328 | Et | H | c-Pr | $SO_2Me$ | $OCH_2CHFOMe$ | $CF_3$ |
| 329 | Me | H | c-Pr | Cl | $OCHFCH_2OCF_3$ | $SO_2Me$ |
| 330 | Et | H | c-Pr | Cl | $OCHFCH_2OCF_3$ | $SO_2Me$ |
| 331 | Me | H | c-Pr | Cl | $OCH_2CH_2OCF_2Cl$ | $SO_2Me$ |
| 332 | Et | H | c-Pr | Cl | $OCH_2CH_2OCF_2Cl$ | $SO_2Me$ |
| 333 | Me | H | c-Pr | Me | $OCH_2CH_2OCF_2Cl$ | $SO_2Me$ |
| 334 | Me | H | c-Pr | CN | $OCH_2CH_2OCF_3$ | $SO_2Me$ |
| 335 | Et | H | c-Pr | Me | $OCH_2CH_2OCF_2Cl$ | $SO_2Me$ |
| 336 | Me | H | c-Pr | $CF_3$ | $OCH_2CH_2OCF_2Cl$ | $SO_2Me$ |
| 337 | Et | H | c-Pr | $CF_3$ | $OCH_2CH_2OCF_2Cl$ | $SO_2Me$ |
| 338 | Me | H | c-Pr | Br | $OCH_2CH_2OCF_2Cl$ | $SO_2Me$ |
| 339 | Et | H | c-Pr | Br | $OCH_2CH_2OCF_2Cl$ | $SO_2Me$ |
| 340 | Me | H | c-Pr | $SO_2Me$ | $OCH_2CH_2OCF_2Cl$ | $CF_3$ |
| 341 | Et | H | c-Pr | $SO_2Me$ | $OCH_2CH_2OCF_2Cl$ | $CF_3$ |
| 342 | Me | H | c-Pr | Cl | $SCH_2CH_2OCH_3$ | $SO_2Me$ |
| 343 | Et | H | c-Pr | Cl | $SCH_2CH_2OCH_3$ | $SO_2Me$ |
| 344 | Me | H | c-Pr | Me | $SCH_2CH_2OCH_3$ | $SO_2Me$ |
| 345 | Et | H | c-Pr | Me | $SCH_2CH_2OCH_3$ | $SO_2Me$ |
| 346 | Me | H | c-Pr | $CF_3$ | $SCH_2CH_2OCH_3$ | $SO_2Me$ |
| 347 | Et | H | c-Pr | $CF_3$ | $SCH_2CH_2OCH_3$ | $SO_2Me$ |
| 348 | Me | H | c-Pr | Br | $SCH_2CH_2OCH_3$ | $SO_2Me$ |
| 349 | Et | H | c-Pr | Br | $SCH_2CH_2OCH_3$ | $SO_2Me$ |
| 350 | Me | H | c-Pr | $SO_2Me$ | $SCH_2CH_2OCH_3$ | $CF_3$ |
| 351 | Et | H | c-Pr | $SO_2Me$ | $SCH_2CH_2OCH_3$ | $CF_3$ |
| 352 | Me | H | c-Pr | Cl | $SCH_2CH_2OCF_3$ | $SO_2Me$ |
| 353 | Et | H | c-Pr | Cl | $SCH_2CH_2OCF_3$ | $SO_2Me$ |
| 354 | Me | H | c-Pr | Me | $SCH_2CH_2OCF_3$ | $SO_2Me$ |
| 355 | Et | H | c-Pr | Me | $SCH_2CH_2OCF_3$ | $SO_2Me$ |
| 356 | Me | H | c-Pr | $CF_3$ | $SCH_2CH_2OCF_3$ | $SO_2Me$ |
| 357 | Et | H | c-Pr | $CF_3$ | $SCH_2CH_2OCF_3$ | $SO_2Me$ |
| 358 | Me | H | c-Pr | Br | $SCH_2CH_2OCF_3$ | $SO_2Me$ |
| 359 | Et | H | c-Pr | Br | $SCH_2CH_2OCF_3$ | $SO_2Me$ |
| 360 | Me | H | c-Pr | $SO_2Me$ | $SCH_2CH_2OCF_3$ | $CF_3$ |
| 361 | Et | H | c-Pr | $SO_2Me$ | $SCH_2CH_2OCF_3$ | $CF_3$ |

TABLE 1-continued

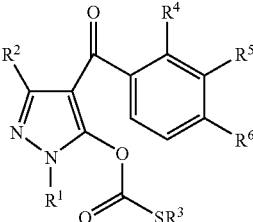

| No. | R$^1$ | R$^2$ | R$^3$ | R$^4$ | R$^5$ | R$^6$ |
|---|---|---|---|---|---|---|
| 362 | Me | H | c-Pr | Cl | SCH$_2$CH$_2$SCH$_3$ | SO$_2$Me |
| 363 | Et | H | c-Pr | Cl | SCH$_2$CH$_2$SCH$_3$ | SO$_2$Me |
| 364 | Me | H | c-Pr | Me | SCH$_2$CH$_2$SCH$_3$ | SO$_2$Me |
| 365 | Et | H | c-Pr | Me | SCH$_2$CH$_2$SCH$_3$ | SO$_2$Me |
| 366 | Me | H | c-Pr | CF$_3$ | SCH$_2$CH$_2$SCH$_3$ | SO$_2$Me |
| 367 | Et | H | c-Pr | CF$_3$ | SCH$_2$CH$_2$SCH$_3$ | SO$_2$Me |
| 368 | Me | H | c-Pr | Br | SCH$_2$CH$_2$SCH$_3$ | SO$_2$Me |
| 369 | Et | H | c-Pr | Br | SCH$_2$CH$_2$SCH$_3$ | SO$_2$Me |
| 370 | Me | H | c-Pr | SO$_2$Me | SCH$_2$CH$_2$SCH$_3$ | CF$_3$ |
| 371 | Et | H | c-Pr | SO$_2$Me | SCH$_2$CH$_2$SCH$_3$ | CF$_3$ |
| 372 | Me | H | c-Pr | Cl | SCH$_2$CH$_2$SCF$_3$ | SO$_2$Me |
| 373 | Et | H | c-Pr | Cl | SCH$_2$CH$_2$SCF$_3$ | SO$_2$Me |
| 374 | Me | H | c-Pr | Me | SCH$_2$CH$_2$SCF$_3$ | SO$_2$Me |
| 375 | Et | H | c-Pr | Me | SCH$_2$CH$_2$SCF$_3$ | SO$_2$Me |
| 376 | Me | H | c-Pr | CF$_3$ | SCH$_2$CH$_2$SCF$_3$ | SO$_2$Me |
| 377 | Et | H | c-Pr | CF$_3$ | SCH$_2$CH$_2$SCF$_3$ | SO$_2$Me |
| 378 | Me | H | c-Pr | Br | SCH$_2$CH$_2$SCF$_3$ | SO$_2$Me |
| 379 | Et | H | c-Pr | Br | SCH$_2$CH$_2$SCF$_3$ | SO$_2$Me |
| 380 | Me | H | c-Pr | SO$_2$Me | SCH$_2$CH$_2$SCF$_3$ | CF$_3$ |
| 381 | Et | H | c-Pr | SO$_2$Me | SCH$_2$CH$_2$SCF$_3$ | CF$_3$ |
| 382 | Me | H | c-Pr | Cl | OCH$_2$CH(CH$_3$)OCH$_3$ | SO$_2$Me |
| 383 | Et | H | c-Pr | Cl | OCH$_2$CH(CH$_3$)OCH$_3$ | SO$_2$Me |
| 384 | Me | H | c-Pr | Me | OCH$_2$CH(CH$_3$)OCH$_3$ | SO$_2$Me |
| 385 | Et | H | c-Pr | Me | OCH$_2$CH(CH$_3$)OCH$_3$ | SO$_2$Me |
| 386 | Me | H | c-Pr | CF$_3$ | OCH$_2$CH(CH$_3$)OCH$_3$ | SO$_2$Me |
| 387 | Et | H | c-Pr | CF$_3$ | OCH$_2$CH(CH$_3$)OCH$_3$ | SO$_2$Me |
| 388 | Me | H | c-Pr | Br | OCH$_2$CH(CH$_3$)OCH$_3$ | SO$_2$Me |
| 389 | Et | H | c-Pr | Br | OCH$_2$CH(CH$_3$)OCH$_3$ | SO$_2$Me |
| 390 | Me | H | c-Pr | SO$_2$Me | OCH$_2$CH(CH$_3$)OCH$_3$ | CF$_3$ |
| 391 | Et | H | c-Pr | SO$_2$Me | OCH$_2$CH(CH$_3$)OCH$_3$ | CF$_3$ |
| 392 | Me | H | c-Pr | Cl | OCH$_2$CF$_2$OCH$_3$ | SO$_2$Me |
| 393 | Et | H | c-Pr | Cl | OCH$_2$CF$_2$OCH$_3$ | SO$_2$Me |
| 394 | Me | H | c-Pr | Me | OCH$_2$CF$_2$OCH$_3$ | SO$_2$Me |
| 395 | Et | H | c-Pr | Me | OCH$_2$CF$_2$OCH$_3$ | SO$_2$Me |
| 396 | Me | H | c-Pr | CF$_3$ | OCH$_2$CF$_2$OCH$_3$ | SO$_2$Me |
| 397 | Et | H | c-Pr | CF$_3$ | OCH$_2$CF$_2$OCH$_3$ | SO$_2$Me |
| 398 | Me | H | c-Pr | Br | OCH$_2$CF$_2$OCH$_3$ | SO$_2$Me |
| 399 | Et | H | c-Pr | Br | OCH$_2$CF$_2$OCH$_3$ | SO$_2$Me |
| 400 | Me | H | c-Pr | SO$_2$Me | OCH$_2$CF$_2$OCH$_3$ | CF$_3$ |
| 401 | Et | H | c-Pr | SO$_2$Me | OCH$_2$CF$_2$OCH$_3$ | CF$_3$ |
| 402 | Me | H | c-Pr | Me | OCH$_2$CH$_2$OCH$_3$ | SO$_2$Me |
| 403 | Et | H | c-Pr | Me | OCH$_2$CH$_2$OCH$_3$ | SO$_2$Me |
| 404 | Me | H | c-Pr | Me | OCH$_2$CH(OCH$_3$)$_2$ | SO$_2$Me |
| 405 | Me | H | c-Pr | Me | CH$_2$N(Me)CH$_2$CN | SO$_2$Me |
| 406 | Me | H | c-Pr | Me | (tetrahydrofuran-2-yl)methoxy | SO$_2$Me |
| 407 | Me | H | c-Pr | Cl | SMe | SO$_2$Me |
| 408 | Me | H | c-Pr | Cl | Cl | SO$_2$Me |
| 409 | Me | H | c-Pr | Cl | OMe | SO$_2$Me |
| 410 | Me | H | c-Pr | Me | (tetrahydro-2H-pyran-2-yl)methoxy | SO$_2$Me |
| 411 | Me | H | c-Pr | Cl | OCH$_2$CH$_2$OMe | SO$_2$Me |
| 412 | Me | H | c-Pr | Me | tetrahydrofuran-3-yloxy | SO$_2$Me |
| 413 | Me | H | c-Pr | Me | OCH$_2$CH$_2$CH$_2$OMe | SO$_2$Me |
| 414 | Me | H | c-Pr | CN | OCH$_2$CH$_2$OMe | SO$_2$Me |
| 415 | Et | H | c-Pr | Cl | 2-(1,3-dioxolan-2-yl)ethoxy | SO$_2$Me |
| 416 | Me | H | c-Pr | Me | propargyloxy | SO$_2$Me |
| 417 | Me | H | c-Pr | Me | (tetrahydrofuran-3-yloxy)methyl | SO$_2$Me |
| 418 | Me | H | c-Pr | Cl | SO$_2$Me | SO$_2$Me |
| 419 | Me | H | c-Pr | Me | (CH$_2$)$_6$Me | SO$_2$Me |
| 420 | Me | H | c-Pr | Me | CH$_2$CH$_2$CH$_2$OMe | SO$_2$Me |
| 421 | Et | H | c-Pr | Cl | (1,3-dioxolan-2-yl)methoxy | SO$_2$Me |
| 422 | Me | H | c-Pr | Me | CH$_2$N[C(O)SEt]CH$_2$CN | SO$_2$Me |
| 423 | Me | H | c-Pr | Me | CH=CHCN | SO$_2$Me |
| 424 | Me | H | c-Pr | Me | CH$_2$CH$_2$CN | SO$_2$Me |
| 425 | Me | H | c-Pr | Me | CH$_2$SCN | SO$_2$Me |
| 426 | Me | H | c-Pr | Me | CH$_2$C(S)NH$_2$ | SO$_2$Me |

TABLE 1-continued (I)

| No. | R¹ | R² | R³ | R⁴ | R⁵ | R⁶ |
|---|---|---|---|---|---|---|
| 427 | Me | H | c-Pr | NO$_2$ | OCH$_2$CH$_2$OMe | SO$_2$Me |
| 428 | Et | H | c-Pr | NO$_2$ | OCH$_2$CH$_2$OMe | SO$_2$Me |
| 429 | Me | H | c-Pr | Me | OCH(CH$_3$)CH$_2$OMe | SO$_2$Me |
| 430 | Et | H | c-Pr | Me | OCH$_2$CH(Et)OMe | SO$_2$Me |
| 431 | Me | H | c-Pr | Me | (1,3-dioxolan-2-yl)methyl | SO$_2$Me |
| 432 | Me | H | c-Pr | Me | CH$_2$O(i-Pr) | SO$_2$Me |
| 433 | Et | H | s-Bu | Me | CO$_2$(i-Pr) | SO$_2$Me |
| 434 | Me | H | s-Bu | Cl | CO$_2$Et | SO$_2$Me |
| 435 | Et | H | s-Bu | Me | CO$_2$Me | CF$_3$ |
| 436 | Et | H | s-Bu | Me | OCH$_2$CH$_2$OMe | SO$_2$Me |
| 437 | Et | H | s-Bu | SO$_2$Me | CO$_2$Me | CN |
| 438 | Me | H | s-Bu | Me | C(O)SMe | SO$_2$Me |
| 439 | Me | H | s-Bu | Me | C(O)SEt | SO$_2$Me |
| 440 | Me | H | s-Bu | Me | 2-(2-oxolanyl)ethoxy | SO$_2$Me |
| 441 | Me | H | s-Bu | Me | 2-(2-(1,3-dioxolanyl)ethoxy | SO$_2$Me |
| 442 | Et | H | s-Bu | Me | CH$_2$OMe | SO$_2$Me |
| 443 | Et | H | s-Bu | Me | 2-oxolanylmethoxymethyl | SO$_2$Me |
| 444 | Me | H | s-Bu | Cl | CO$_2$Me | SO$_2$Me |
| 445 | Et | H | s-Bu | Cl | CO$_2$Me | SO$_2$Et |
| 446 | Me | H | s-Bu | Cl | C(O)SMe | SO$_2$Me |
| 447 | Me | H | s-Bu | Cl | C(O)SEt | SO$_2$Me |
| 448 | Me | H | s-Bu | Me | OMe | SO$_2$Me |
| 449 | Me | H | s-Bu | Me | OEt | SO$_2$Me |
| 450 | Me | H | s-Bu | Me | O(i-Pr) | SO$_2$Me |
| 451 | Me | H | s-Bu | Me | OCHF$_2$ | SO$_2$Me |
| 452 | Me | H | s-Bu | Me | (4,5-dihydroisoxazol-3-yl) | SO$_2$Me |
| 453 | Me | H | s-Bu | Me | O(n-Pr) | SO$_2$Et |
| 454 | Me | H | s-Bu | Cl | CH$_2$OMe | SO$_2$Me |
| 455 | Me | H | s-Bu | Me | OCO$_2$Me | SO$_2$Me |
| 456 | Me | H | s-Bu | Me | OC(O)SMe | SO$_2$Me |
| 457 | Me | H | s-Bu | Me | OC(O)SEt | SO$_2$Me |
| 458 | Et | H | s-Bu | Me | OEt | SO$_2$Me |
| 459 | Et | H | s-Bu | Cl | CO$_2$Et | SO$_2$Me |
| 460 | Et | H | s-Bu | Cl | CO$_2$(n-Pr) | SO$_2$Me |
| 461 | Et | H | s-Bu | Me | CO$_2$Et | SO$_2$Me |
| 462 | Me | H | s-Bu | Me | CH$_2$CO$_2$Me | SO$_2$Me |
| 463 | Me | H | s-Bu | Me | OCH$_2$CO$_2$Et | SO$_2$Me |
| 464 | Me | H | s-Bu | Me | O(n-Pr) | SO$_2$Me |
| 465 | Et | H | s-Bu | SO$_2$Me | H | CF$_3$ |
| 466 | Me | H | s-Bu | Me | CH$_2$OCH$_2$CF$_3$ | SO$_2$Me |
| 467 | Me | H | s-Bu | Cl | CH$_2$OCH$_2$CF$_3$ | SO$_2$Me |
| 468 | Et | H | s-Bu | Me | Cl | SO$_2$Me |
| 469 | Me | H | s-Bu | Me | CH$_2$SO$_2$Me | SO$_2$Me |
| 470 | Me | H | s-Bu | Me | CH$_2$OEt | SO$_2$Me |
| 471 | Me | H | s-Bu | Cl | CH$_2$OMe | SO$_2$Me |
| 472 | Me | H | s-Bu | Me | CH$_2$CH$_2$OMe | SO$_2$Me |
| 473 | Me | H | s-Bu | Me | CH$_2$OCH$_2$CH$_2$OMe | SO$_2$Me |
| 474 | Me | H | s-Bu | Me | OCH$_2$CH$_2$OEt | SO$_2$Me |
| 475 | Me | H | s-Bu | Me | OCH$_2$CH$_2$Cl | SO$_2$Me |
| 476 | Me | H | s-Bu | Me | OCH$_2$CF$_3$ | SO$_2$Me |
| 477 | Me | H | s-Bu | Me | CH$_2$OCH$_2$OMe | SO$_2$Me |
| 478 | Me | H | s-Bu | Me | OCH$_2$CH$_2$SMe | SO$_2$Me |
| 479 | Me | H | s-Bu | Me | CN | SO$_2$Me |
| 480 | Me | H | s-Bu | Me | CH$_2$CN | SO$_2$Me |
| 481 | Me | H | s-Bu | Br | CO$_2$Me | SO$_2$Me |
| 482 | Et | H | s-Bu | Cl | CO$_2$Me | SO$_2$Me |
| 483 | Me | H | s-Bu | CN | CO$_2$Me | SO$_2$Me |
| 484 | Me | H | s-Bu | Cl | OCH$_2$CH$_2$OCF$_3$ | SO$_2$Me |
| 485 | Et | H | s-Bu | Cl | OCH$_2$CH$_2$OCF$_3$ | SO$_2$Me |
| 486 | Me | H | s-Bu | Me | OCH$_2$CH$_2$OCF$_3$ | SO$_2$Me |
| 487 | Et | H | s-Bu | Me | OCH$_2$CH$_2$OCF$_3$ | SO$_2$Me |
| 488 | Me | H | s-Bu | CF$_3$ | OCH$_2$CH$_2$OCF$_3$ | SO$_2$Me |
| 489 | Et | H | s-Bu | CF$_3$ | OCH$_2$CH$_2$OCF$_3$ | SO$_2$Me |
| 490 | Me | H | s-Bu | Br | OCH$_2$CH$_2$OCF$_3$ | SO$_2$Me |
| 491 | Et | H | s-Bu | Br | OCH$_2$CH$_2$OCF$_3$ | SO$_2$Me |

TABLE 1-continued (I)

| No. | R¹ | R² | R³ | R⁴ | R⁵ | R⁶ |
|---|---|---|---|---|---|---|
| 492 | Me | H | s-Bu | SO₂Me | OCH₂CH₂OCF₃ | CF₃ |
| 493 | Et | H | s-Bu | SO₂Me | OCH₂CH₂OCF₃ | CF₃ |
| 494 | Me | H | s-Bu | Cl | OCH₂CH₂OCHClF | SO₂Me |
| 495 | Et | H | s-Bu | Cl | OCH₂CH₂OCHClF | SO₂Me |
| 496 | Me | H | s-Bu | Me | OCH₂CH₂OCHClF | SO₂Me |
| 497 | Et | H | s-Bu | Me | OCH₂CH₂OCHClF | SO₂Me |
| 498 | Me | H | s-Bu | CF₃ | OCH₂CH₂OCHClF | SO₂Me |
| 499 | Et | H | s-Bu | CF₃ | OCH₂CH₂OCHClF | SO₂Me |
| 500 | Me | H | s-Bu | Br | OCH₂CH₂OCHClF | SO₂Me |
| 501 | Et | H | s-Bu | Br | OCH₂CH₂OCHClF | SO₂Me |
| 502 | Me | H | s-Bu | SO₂Me | OCH₂CH₂OCHClF | CF₃ |
| 503 | Et | H | s-Bu | SO₂Me | OCH₂CH₂OCHClF | CF₃ |
| 504 | Me | H | s-Bu | Cl | OCH₂CHFOCF₃ | SO₂Me |
| 505 | Et | H | s-Bu | Cl | OCH₂CHFOCF₃ | SO₂Me |
| 506 | Me | H | s-Bu | Me | OCH₂CHFOCF₃ | SO₂Me |
| 507 | Me | H | s-Bu | Cl | OCH₂CHFOMe | SO₂Me |
| 508 | Et | H | s-Bu | Cl | OCH₂CHFOMe | SO₂Me |
| 509 | Me | H | s-Bu | Me | OCH₂CHFOMe | SO₂Me |
| 510 | Et | H | s-Bu | Me | OCH₂CHFOMe | SO₂Me |
| 511 | Me | H | s-Bu | CF₃ | OCH₂CHFOMe | SO₂Me |
| 512 | Et | H | s-Bu | CF₃ | OCH₂CHFOMe | SO₂Me |
| 513 | Me | H | s-Bu | Br | OCH₂CHFOMe | SO₂Me |
| 514 | Et | H | s-Bu | Br | OCH₂CHFOMe | SO₂Me |
| 515 | Me | H | s-Bu | SO₂Me | OCH₂CHFOMe | CF₃ |
| 516 | Et | H | s-Bu | SO₂Me | OCH₂CHFOMe | CF₃ |
| 517 | Me | H | s-Bu | Cl | OCHFCH₂OCF₃ | SO₂Me |
| 518 | Et | H | s-Bu | Cl | OCHFCH₂OCF₃ | SO₂Me |
| 519 | Me | H | s-Bu | Cl | OCH₂CH₂OCF₂Cl | SO₂Me |
| 520 | Et | H | s-Bu | Cl | OCH₂CH₂OCF₂Cl | SO₂Me |
| 521 | Me | H | s-Bu | Me | OCH₂CH₂OCF₂Cl | SO₂Me |
| 522 | Et | H | s-Bu | Me | OCH₂CH₂OCF₂Cl | SO₂Me |
| 523 | Me | H | s-Bu | CF₃ | OCH₂CH₂OCF₂Cl | SO₂Me |
| 524 | Et | H | s-Bu | CF₃ | OCH₂CH₂OCF₂Cl | SO₂Me |
| 525 | Me | H | s-Bu | Br | OCH₂CH₂OCF₂Cl | SO₂Me |
| 526 | Et | H | s-Bu | Br | OCH₂CH₂OCF₂Cl | SO₂Me |
| 527 | Me | H | s-Bu | SO₂Me | OCH₂CH₂OCF₂Cl | CF₃ |
| 528 | Et | H | s-Bu | SO₂Me | OCH₂CH₂OCF₂Cl | CF₃ |
| 529 | Me | H | s-Bu | Cl | SCH₂CH₂OCH₃ | SO₂Me |
| 530 | Et | H | s-Bu | Cl | SCH₂CH₂OCH₃ | SO₂Me |
| 531 | Me | H | s-Bu | Me | SCH₂CH₂OCH₃ | SO₂Me |
| 532 | Et | H | s-Bu | Me | SCH₂CH₂OCH₃ | SO₂Me |
| 533 | Me | H | s-Bu | CF₃ | SCH₂CH₂OCH₃ | SO₂Me |
| 534 | Et | H | s-Bu | CF₃ | SCH₂CH₂OCH₃ | SO₂Me |
| 535 | Me | H | s-Bu | Br | SCH₂CH₂OCH₃ | SO₂Me |
| 536 | Et | H | s-Bu | Br | SCH₂CH₂OCH₃ | SO₂Me |
| 537 | Me | H | s-Bu | SO₂Me | SCH₂CH₂OCH₃ | CF₃ |
| 538 | Et | H | s-Bu | SO₂Me | SCH₂CH₂OCH₃ | CF₃ |
| 539 | Me | H | s-Bu | Cl | SCH₂CH₂OCF₃ | SO₂Me |
| 540 | Et | H | s-Bu | Cl | SCH₂CH₂OCF₃ | SO₂Me |
| 541 | Me | H | s-Bu | Me | SCH₂CH₂OCF₃ | SO₂Me |
| 542 | Et | H | s-Bu | Me | SCH₂CH₂OCF₃ | SO₂Me |
| 543 | Me | H | s-Bu | CF₃ | SCH₂CH₂OCF₃ | SO₂Me |
| 544 | Et | H | s-Bu | CF₃ | SCH₂CH₂OCF₃ | SO₂Me |
| 545 | Me | H | s-Bu | Br | SCH₂CH₂OCF₃ | SO₂Me |
| 546 | Et | H | s-Bu | Br | SCH₂CH₂OCF₃ | SO₂Me |
| 547 | Me | H | s-Bu | SO₂Me | SCH₂CH₂OCF₃ | CF₃ |
| 548 | Et | H | s-Bu | SO₂Me | SCH₂CH₂OCF₃ | CF₃ |
| 549 | Me | H | s-Bu | Cl | SCH₂CH₂SCH₃ | SO₂Me |
| 550 | Et | H | s-Bu | Cl | SCH₂CH₂SCH₃ | SO₂Me |
| 551 | Me | H | s-Bu | Me | SCH₂CH₂SCH₃ | SO₂Me |
| 552 | Et | H | s-Bu | Me | SCH₂CH₂SCH₃ | SO₂Me |
| 553 | Me | H | s-Bu | CF₃ | SCH₂CH₂SCH₃ | SO₂Me |
| 554 | Et | H | s-Bu | CF₃ | SCH₂CH₂SCH₃ | SO₂Me |
| 555 | Me | H | s-Bu | Br | SCH₂CH₂SCH₃ | SO₂Me |
| 556 | Et | H | s-Bu | Br | SCH₂CH₂SCH₃ | SO₂Me |

TABLE 1-continued

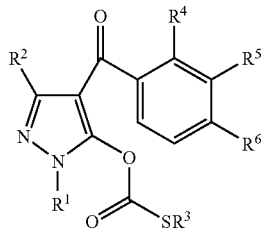

(I)

| No. | R$^1$ | R$^2$ | R$^3$ | R$^4$ | R$^5$ | R$^6$ |
|---|---|---|---|---|---|---|
| 557 | Me | H | s-Bu | SO$_2$Me | SCH$_2$CH$_2$SCH$_3$ | CF$_3$ |
| 558 | Et | H | s-Bu | SO$_2$Me | SCH$_2$CH$_2$SCH$_3$ | CF$_3$ |
| 559 | Me | H | s-Bu | Cl | SCH$_2$CH$_2$SCF$_3$ | SO$_2$Me |
| 560 | Et | H | s-Bu | Cl | SCH$_2$CH$_2$SCF$_3$ | SO$_2$Me |
| 561 | Me | H | s-Bu | Me | SCH$_2$CH$_2$SCF$_3$ | SO$_2$Me |
| 562 | Et | H | s-Bu | Me | SCH$_2$CH$_2$SCF$_3$ | SO$_2$Me |
| 563 | Me | H | s-Bu | CF$_3$ | SCH$_2$CH$_2$SCF$_3$ | SO$_2$Me |
| 564 | Et | H | s-Bu | CF$_3$ | SCH$_2$CH$_2$SCF$_3$ | SO$_2$Me |
| 565 | Me | H | s-Bu | Br | SCH$_2$CH$_2$SCF$_3$ | SO$_2$Me |
| 566 | Et | H | s-Bu | Br | SCH$_2$CH$_2$SCF$_3$ | SO$_2$Me |
| 567 | Me | H | s-Bu | SO$_2$Me | SCH$_2$CH$_2$SCF$_3$ | CF$_3$ |
| 568 | Et | H | s-Bu | SO$_2$Me | SCH$_2$CH$_2$SCF$_3$ | CF$_3$ |
| 569 | Me | H | s-Bu | Cl | OCH$_2$CH(CH$_3$)OCH$_3$ | SO$_2$Me |
| 570 | Et | H | s-Bu | Cl | OCH$_2$CH(CH$_3$)OCH$_3$ | SO$_2$Me |
| 571 | Me | H | s-Bu | Me | OCH$_2$CH(CH$_3$)OCH$_3$ | SO$_2$Me |
| 572 | Et | H | s-Bu | Me | OCH$_2$CH(CH$_3$)OCH$_3$ | SO$_2$Me |
| 573 | Me | H | s-Bu | CF$_3$ | OCH$_2$CH(CH$_3$)OCH$_3$ | SO$_2$Me |
| 574 | Et | H | s-Bu | CF$_3$ | OCH$_2$CH(CH$_3$)OCH$_3$ | SO$_2$Me |
| 575 | Me | H | s-Bu | Br | OCH$_2$CH(CH$_3$)OCH$_3$ | SO$_2$Me |
| 576 | Et | H | s-Bu | Br | OCH$_2$CH(CH$_3$)OCH$_3$ | SO$_2$Me |
| 577 | Me | H | s-Bu | SO$_2$Me | OCH$_2$CH(CH$_3$)OCH$_3$ | CF$_3$ |
| 578 | Et | H | s-Bu | SO$_2$Me | OCH$_2$CH(CH$_3$)OCH$_3$ | CF$_3$ |
| 579 | Me | H | s-Bu | Cl | OCH$_2$CF$_2$OCH$_3$ | SO$_2$Me |
| 580 | Et | H | s-Bu | Cl | OCH$_2$CF$_2$OCH$_3$ | SO$_2$Me |
| 581 | Me | H | s-Bu | Me | OCH$_2$CF$_2$OCH$_3$ | SO$_2$Me |
| 582 | Et | H | s-Bu | Me | OCH$_2$CF$_2$OCH$_3$ | SO$_2$Me |
| 583 | Me | H | s-Bu | CF$_3$ | OCH$_2$CF$_2$OCH$_3$ | SO$_2$Me |
| 584 | Et | H | s-Bu | CF$_3$ | OCH$_2$CF$_2$OCH$_3$ | SO$_2$Me |
| 585 | Me | H | s-Bu | Br | OCH$_2$CF$_2$OCH$_3$ | SO$_2$Me |
| 586 | Et | H | s-Bu | Br | OCH$_2$CF$_2$OCH$_3$ | SO$_2$Me |
| 587 | Me | H | s-Bu | SO$_2$Me | OCH$_2$CF$_2$OCH$_3$ | CF$_3$ |
| 588 | Et | H | s-Bu | SO$_2$Me | OCH$_2$CF$_2$OCH$_3$ | CF$_3$ |
| 589 | Me | H | s-Bu | Me | OCH$_2$CH$_2$OCH$_3$ | SO$_2$Me |
| 590 | Et | H | s-Bu | Me | OCH$_2$CH$_2$OCH$_3$ | SO$_2$Me |
| 591 | Me | H | s-Bu | Me | OCH$_2$CH(OCH$_3$)$_2$ | SO$_2$Me |
| 592 | Me | H | s-Bu | Me | CH$_2$N(Me)CH$_2$CN | SO$_2$Me |
| 593 | Me | H | s-Bu | Me | (tetrahydrofuran-2-yl)methoxy | SO$_2$Me |
| 594 | Me | H | s-Bu | Cl | SMe | SO$_2$Me |
| 595 | Me | H | s-Bu | Cl | Cl | SO$_2$Me |
| 596 | Me | H | s-Bu | Cl | OMe | SO$_2$Me |
| 597 | Me | H | s-Bu | Me | (tetrahydro-2H-pyran-2-yl)methoxy | SO$_2$Me |
| 598 | Me | H | s-Bu | Cl | OCH$_2$CH$_2$OMe | SO$_2$Me |
| 599 | Me | H | s-Bu | Me | tetrahydrofuran-3-yloxy | SO$_2$Me |
| 600 | Me | H | s-Bu | Me | OCH$_2$CH$_2$CH$_2$OMe | SO$_2$Me |
| 601 | Me | H | s-Bu | Me | OCH$_2$CH$_2$OMe | SO$_2$Me |
| 602 | Me | H | s-Bu | OCHF$_2$ | OCH$_2$CH$_2$OMe | SO$_2$Me |
| 603 | Et | H | s-Bu | Cl | 2-(1,3-dioxolan-2-yl)ethoxy | SO$_2$Me |
| 604 | Me | H | s-Bu | Me | propargyloxy | SO$_2$Me |
| 605 | Me | H | s-Bu | Me | (tetrahydrofuran-3-yloxy)methyl | SO$_2$Me |
| 606 | Me | H | s-Bu | Cl | SO$_2$Me | SO$_2$Me |
| 607 | Me | H | s-Bu | Me | (CH$_2$)$_6$Me | SO$_2$Me |
| 608 | Me | H | s-Bu | Me | CH$_2$CH$_2$CH$_2$OMe | SO$_2$Me |
| 609 | Et | H | s-Bu | Cl | (1,3-dioxolan-2-yl)methoxy | SO$_2$Me |
| 610 | Me | H | s-Bu | Me | CH$_2$N[C(O)SEt]CH$_2$CH$_2$CN | SO$_2$Me |
| 611 | Me | H | s-Bu | Me | CH=CHCN | SO$_2$Me |
| 612 | Me | H | s-Bu | Me | CH$_2$CH$_2$CN | SO$_2$Me |
| 613 | Me | H | s-Bu | Me | CH$_2$SCN | SO$_2$Me |
| 614 | Me | H | s-Bu | Me | CH$_2$C(S)NH$_2$ | SO$_2$Me |
| 615 | Me | H | s-Bu | Me | OCH$_2$CH$_2$OMe | SO$_2$Me |
| 616 | Et | H | s-Bu | Me | OCH$_2$CH$_2$OMe | SO$_2$Me |
| 617 | Me | H | s-Bu | Me | OCH(CH$_3$)CH$_2$OMe | SO$_2$Me |
| 618 | Et | H | s-Bu | Me | OCH$_2$CH(Et)OMe | SO$_2$Me |
| 619 | Me | H | s-Bu | Me | (1,3-dioxolan-2-yl)methyl | SO$_2$Me |
| 620 | Me | H | s-Bu | Me | CH$_2$O(i-Pr) | SO$_2$Me |
| 621 | Me | H | s-Bu | OCHF$_2$ | CH$_2$OMe | SO$_2$Me |

TABLE 1-continued (I)

$$\text{Structure: pyrazole with } R^1 \text{ on N, } R^2 \text{ on pyrazole, O-C(O)-SR}^3 \text{ group, and benzoyl with } R^4, R^5, R^6$$

| No. | $R^1$ | $R^2$ | $R^3$ | $R^4$ | $R^5$ | $R^6$ |
|---|---|---|---|---|---|---|
| 622 | Me | H | s-Bu | $CHF_2$ | $CH_2OMe$ | $SO_2Me$ |
| 623 | Et | H | t-Bu | Me | $CO_2$(i-Pr) | $SO_2Me$ |
| 624 | Me | H | t-Bu | Cl | $CO_2Et$ | $SO_2Me$ |
| 625 | Et | H | t-Bu | Me | $CO_2Me$ | $CF_3$ |
| 626 | Et | H | t-Bu | Me | $OCH_2CH_2OMe$ | $SO_2Me$ |
| 627 | Et | H | t-Bu | $SO_2Me$ | $CO_2Me$ | CN |
| 628 | Me | H | t-Bu | Me | C(O)SMe | $SO_2Me$ |
| 629 | Me | H | t-Bu | Me | C(O)SEt | $SO_2Me$ |
| 630 | Me | H | t-Bu | Me | 2-(2-oxolanyl)ethoxy | $SO_2Me$ |
| 631 | Me | H | t-Bu | Me | 2-(2-(1,3-dioxolanyl))ethoxy | $SO_2Me$ |
| 632 | Et | H | t-Bu | Me | $CH_2OMe$ | $SO_2Me$ |
| 633 | Et | H | t-Bu | Me | 2-oxolanylmethoxymethyl | $SO_2Me$ |
| 634 | Me | H | t-Bu | Cl | $CO_2Me$ | $SO_2Me$ |
| 635 | Et | H | t-Bu | Cl | $CO_2Me$ | $SO_2Et$ |
| 636 | Me | H | t-Bu | Cl | C(O)SMe | $SO_2Me$ |
| 637 | Me | H | t-Bu | Cl | C(O)SEt | $SO_2Me$ |
| 638 | Me | H | t-Bu | Me | OMe | $SO_2Me$ |
| 639 | Me | H | t-Bu | Me | OEt | $SO_2Me$ |
| 640 | Me | H | t-Bu | Me | O(i-Pr) | $SO_2Me$ |
| 641 | Me | H | t-Bu | Me | $OCHF_2$ | $SO_2Me$ |
| 642 | Me | H | t-Bu | Me | (4,5-dihydroisoxazol-3-yl | $SO_2Me$ |
| 643 | Me | H | t-Bu | Me | O(n-Pr) | $SO_2Et$ |
| 644 | Me | H | t-Bu | Cl | $CH_2OMe$ | $SO_2Me$ |
| 645 | Me | H | t-Bu | Me | $OCO_2Me$ | $SO_2Me$ |
| 646 | Me | H | t-Bu | Me | OC(O)SMe | $SO_2Me$ |
| 647 | Me | H | t-Bu | Me | OC(O)SEt | $SO_2Me$ |
| 648 | Me | H | t-Bu | Me | $OCH_2CH_2OMe$ | $SO_2Me$ |
| 649 | Et | H | t-Bu | Me | OEt | $SO_2Me$ |
| 650 | Et | H | t-Bu | Cl | $CO_2Et$ | $SO_2Me$ |
| 651 | Et | H | t-Bu | Cl | $CO_2$(n-Pr) | $SO_2Me$ |
| 652 | Et | H | t-Bu | Me | $CO_2Et$ | $SO_2Me$ |
| 653 | Me | H | t-Bu | Me | $CH_2CO_2Et$ | $SO_2Me$ |
| 654 | Me | H | t-Bu | Me | $OCH_2CO_2Et$ | $SO_2Me$ |
| 655 | Me | H | t-Bu | Me | O(n-Pr) | $SO_2Me$ |
| 656 | Et | H | t-Bu | $SO_2Me$ | H | $CF_3$ |
| 657 | Me | H | t-Bu | Me | $CH_2OCH_2CF_3$ | $SO_2Me$ |
| 658 | Me | H | t-Bu | Cl | $CH_2OCH_2CF_3$ | $SO_2Me$ |
| 659 | Et | H | t-Bu | Me | Cl | $SO_2Me$ |
| 660 | Me | H | t-Bu | Me | $CH_2SO_2Me$ | $SO_2Me$ |
| 661 | Me | H | t-Bu | Me | $CH_2OEt$ | $SO_2Me$ |
| 662 | Me | H | t-Bu | Cl | $CH_2OMe$ | $SO_2Me$ |
| 663 | Me | H | t-Bu | Me | $CH_2CH_2OMe$ | $SO_2Me$ |
| 664 | Me | H | t-Bu | Me | $CH_2OCH_2CH_2OMe$ | $SO_2Me$ |
| 665 | Me | H | t-Bu | Me | $OCH_2CH_2OEt$ | $SO_2Me$ |
| 666 | Me | H | t-Bu | Me | $OCH_2CH_2Cl$ | $SO_2Me$ |
| 667 | Me | H | t-Bu | Me | $OCH_2CF_3$ | $SO_2Me$ |
| 668 | Me | H | t-Bu | Me | $CH_2OCH_2OMe$ | $SO_2Me$ |
| 669 | Me | H | t-Bu | Me | $OCH_2CH_2SMe$ | $SO_2Me$ |
| 670 | Me | H | t-Bu | Me | CN | $SO_2Me$ |
| 671 | Me | H | t-Bu | Me | $CH_2CN$ | $SO_2Me$ |
| 672 | Me | H | t-Bu | Br | $CO_2Me$ | $SO_2Me$ |
| 673 | Et | H | t-Bu | Cl | $CO_2Me$ | $SO_2Me$ |
| 674 | Me | H | t-Bu | Br | $CO_2Me$ | $SO_2Me$ |
| 675 | Me | H | t-Bu | Cl | $OCH_2CH_2OCF_3$ | $SO_2Me$ |
| 676 | Et | H | t-Bu | Cl | $OCH_2CH_2OCF_3$ | $SO_2Me$ |
| 677 | Me | H | t-Bu | Me | $OCH_2CH_2OCF_3$ | $SO_2Me$ |
| 678 | Et | H | t-Bu | Me | $OCH_2CH_2OCF_3$ | $SO_2Me$ |
| 679 | Me | H | t-Bu | $CF_3$ | $OCH_2CH_2OCF_3$ | $SO_2Me$ |
| 680 | Et | H | t-Bu | $CF_3$ | $OCH_2CH_2OCF_3$ | $SO_2Me$ |
| 681 | Me | H | t-Bu | Br | $OCH_2CH_2OCF_3$ | $SO_2Me$ |
| 682 | Et | H | t-Bu | Br | $OCH_2CH_2OCF_3$ | $SO_2Me$ |
| 683 | Me | H | t-Bu | $SO_2Me$ | $OCH_2CH_2OCF_3$ | $CF_3$ |
| 684 | Et | H | t-Bu | $SO_2Me$ | $OCH_2CH_2OCF_3$ | $CF_3$ |
| 685 | Me | H | t-Bu | Cl | $OCH_2CH_2OCHClF$ | $SO_2Me$ |
| 686 | Et | H | t-Bu | Cl | $OCH_2CH_2OCHClF$ | $SO_2Me$ |

TABLE 1-continued

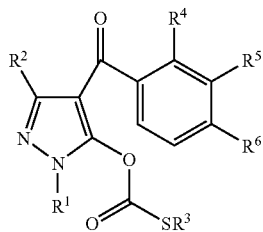

| No. | R¹ | R² | R³ | R⁴ | R⁵ | R⁶ |
|---|---|---|---|---|---|---|
| 687 | Me | H | t-Bu | Me | OCH$_2$CH$_2$OCHClF | SO$_2$Me |
| 688 | Et | H | t-Bu | Me | OCH$_2$CH$_2$OCHClF | SO$_2$Me |
| 689 | Me | H | t-Bu | CF$_3$ | OCH$_2$CH$_2$OCHClF | SO$_2$Me |
| 690 | Et | H | t-Bu | CF$_3$ | OCH$_2$CH$_2$OCHClF | SO$_2$Me |
| 691 | Me | H | t-Bu | Br | OCH$_2$CH$_2$OCHClF | SO$_2$Me |
| 692 | Et | H | t-Bu | Br | OCH$_2$CH$_2$OCHClF | SO$_2$Me |
| 693 | Me | H | t-Bu | SO$_2$Me | OCH$_2$CH$_2$OCHClF | CF$_3$ |
| 694 | Et | H | t-Bu | SO$_2$Me | OCH$_2$CH$_2$OCHClF | CF$_3$ |
| 695 | Me | H | t-Bu | Cl | OCH$_2$CHFOCF$_3$ | SO$_2$Me |
| 696 | Et | H | t-Bu | Cl | OCH$_2$CHFOCF$_3$ | SO$_2$Me |
| 697 | Me | H | t-Bu | Me | OCH$_2$CHFOCF$_3$ | SO$_2$Me |
| 698 | Me | H | t-Bu | Cl | OCH$_2$CHFOMe | SO$_2$Me |
| 699 | Et | H | t-Bu | Cl | OCH$_2$CHFOMe | SO$_2$Me |
| 700 | Me | H | t-Bu | Me | OCH$_2$CHFOMe | SO$_2$Me |
| 701 | Et | H | t-Bu | Me | OCH$_2$CHFOMe | SO$_2$Me |
| 702 | Me | H | t-Bu | CF$_3$ | OCH$_2$CHFOMe | SO$_2$Me |
| 703 | Et | H | t-Bu | CF$_3$ | OCH$_2$CHFOMe | SO$_2$Me |
| 704 | Me | H | t-Bu | Br | OCH$_2$CHFOMe | SO$_2$Me |
| 705 | Et | H | t-Bu | Br | OCH$_2$CHFOMe | SO$_2$Me |
| 706 | Me | H | t-Bu | SO$_2$Me | OCH$_2$CHFOMe | CF$_3$ |
| 707 | Et | H | t-Bu | SO$_2$Me | OCH$_2$CHFOMe | CF$_3$ |
| 708 | Me | H | t-Bu | Cl | OCHFCH$_2$OCF$_3$ | SO$_2$Me |
| 709 | Et | H | t-Bu | Cl | OCHFCH$_2$OCF$_3$ | SO$_2$Me |
| 710 | Me | H | t-Bu | Cl | OCH$_2$CH$_2$OCF$_2$Cl | SO$_2$Me |
| 711 | Et | H | t-Bu | Cl | OCH$_2$CH$_2$OCF$_2$Cl | SO$_2$Me |
| 712 | Me | H | t-Bu | Me | OCH$_2$CH$_2$OCF$_2$Cl | SO$_2$Me |
| 713 | Et | H | t-Bu | Me | OCH$_2$CH$_2$OCF$_2$Cl | SO$_2$Me |
| 714 | Me | H | t-Bu | CF$_3$ | OCH$_2$CH$_2$OCF$_2$Cl | SO$_2$Me |
| 715 | Et | H | t-Bu | CF$_3$ | OCH$_2$CH$_2$OCF$_2$Cl | SO$_2$Me |
| 716 | Me | H | t-Bu | Br | OCH$_2$CH$_2$OCF$_2$Cl | SO$_2$Me |
| 717 | Et | H | t-Bu | Br | OCH$_2$CH$_2$OCF$_2$Cl | SO$_2$Me |
| 718 | Me | H | t-Bu | SO$_2$Me | OCH$_2$CH$_2$OCF$_2$Cl | CF$_3$ |
| 719 | Et | H | t-Bu | SO$_2$Me | OCH$_2$CH$_2$OCF$_2$Cl | CF$_3$ |
| 720 | Me | H | t-Bu | Cl | SCH$_2$CH$_2$OCH$_3$ | SO$_2$Me |
| 721 | Et | H | t-Bu | Cl | SCH$_2$CH$_2$OCH$_3$ | SO$_2$Me |
| 722 | Me | H | t-Bu | Me | SCH$_2$CH$_2$OCH$_3$ | SO$_2$Me |
| 723 | Et | H | t-Bu | Me | SCH$_2$CH$_2$OCH$_3$ | SO$_2$Me |
| 724 | Me | H | t-Bu | CF$_3$ | SCH$_2$CH$_2$OCH$_3$ | SO$_2$Me |
| 725 | Et | H | t-Bu | CF$_3$ | SCH$_2$CH$_2$OCH$_3$ | SO$_2$Me |
| 726 | Me | H | t-Bu | Br | SCH$_2$CH$_2$OCH$_3$ | SO$_2$Me |
| 727 | Et | H | t-Bu | Br | SCH$_2$CH$_2$OCH$_3$ | SO$_2$Me |
| 728 | Me | H | t-Bu | SO$_2$Me | SCH$_2$CH$_2$OCH$_3$ | CF$_3$ |
| 729 | Et | H | t-Bu | SO$_2$Me | SCH$_2$CH$_2$OCH$_3$ | CF$_3$ |
| 730 | Me | H | t-Bu | Cl | SCH$_2$CH$_2$OCF$_3$ | SO$_2$Me |
| 731 | Et | H | t-Bu | Cl | SCH$_2$CH$_2$OCF$_3$ | SO$_2$Me |
| 732 | Me | H | t-Bu | Me | SCH$_2$CH$_2$OCF$_3$ | SO$_2$Me |
| 733 | Et | H | t-Bu | Me | SCH$_2$CH$_2$OCF$_3$ | SO$_2$Me |
| 734 | Me | H | t-Bu | CF$_3$ | SCH$_2$CH$_2$OCF$_3$ | SO$_2$Me |
| 735 | Et | H | t-Bu | CF$_3$ | SCH$_2$CH$_2$OCF$_3$ | SO$_2$Me |
| 736 | Me | H | t-Bu | Br | SCH$_2$CH$_2$OCF$_3$ | SO$_2$Me |
| 737 | Et | H | t-Bu | Br | SCH$_2$CH$_2$OCF$_3$ | SO$_2$Me |
| 738 | Me | H | t-Bu | SO$_2$Me | SCH$_2$CH$_2$OCF$_3$ | CF$_3$ |
| 739 | Et | H | t-Bu | SO$_2$Me | SCH$_2$CH$_2$OCF$_3$ | CF$_3$ |
| 740 | Me | H | t-Bu | Cl | SCH$_2$CH$_2$SCH$_3$ | SO$_2$Me |
| 741 | Et | H | t-Bu | Cl | SCH$_2$CH$_2$SCH$_3$ | SO$_2$Me |
| 742 | Me | H | t-Bu | Me | SCH$_2$CH$_2$SCH$_3$ | SO$_2$Me |
| 743 | Et | H | t-Bu | Me | SCH$_2$CH$_2$SCH$_3$ | SO$_2$Me |
| 744 | Me | H | t-Bu | CF$_3$ | SCH$_2$CH$_2$SCH$_3$ | SO$_2$Me |
| 745 | Et | H | t-Bu | CF$_3$ | SCH$_2$CH$_2$SCH$_3$ | SO$_2$Me |
| 746 | Me | H | t-Bu | Br | SCH$_2$CH$_2$SCH$_3$ | SO$_2$Me |
| 747 | Et | H | t-Bu | Br | SCH$_2$CH$_2$SCH$_3$ | SO$_2$Me |
| 748 | Me | H | t-Bu | SO$_2$Me | SCH$_2$CH$_2$SCH$_3$ | CF$_3$ |
| 749 | Et | H | t-Bu | SO$_2$Me | SCH$_2$CH$_2$SCH$_3$ | CF$_3$ |
| 750 | Me | H | t-Bu | Cl | SCH$_2$CH$_2$SCF$_3$ | SO$_2$Me |
| 751 | Et | H | t-Bu | Cl | SCH$_2$CH$_2$SCF$_3$ | SO$_2$Me |

TABLE 1-continued

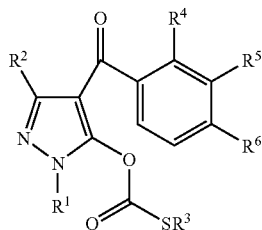
(I)

| No. | $R^1$ | $R^2$ | $R^3$ | $R^4$ | $R^5$ | $R^6$ |
|---|---|---|---|---|---|---|
| 752 | Me | H | t-Bu | Me | $SCH_2CH_2SCF_3$ | $SO_2Me$ |
| 753 | Et | H | t-Bu | Me | $SCH_2CH_2SCF_3$ | $SO_2Me$ |
| 754 | Me | H | t-Bu | $CF_3$ | $SCH_2CH_2SCF_3$ | $SO_2Me$ |
| 755 | Et | H | t-Bu | $CF_3$ | $SCH_2CH_2SCF_3$ | $SO_2Me$ |
| 756 | Me | H | t-Bu | Br | $SCH_2CH_2SCF_3$ | $SO_2Me$ |
| 757 | Et | H | t-Bu | Br | $SCH_2CH_2SCF_3$ | $SO_2Me$ |
| 758 | Me | H | t-Bu | $SO_2Me$ | $SCH_2CH_2SCF_3$ | $CF_3$ |
| 759 | Et | H | t-Bu | $SO_2Me$ | $SCH_2CH_2SCF_3$ | $CF_3$ |
| 760 | Me | H | t-Bu | Cl | $OCH_2CH(CH_3)OCH_3$ | $SO_2Me$ |
| 761 | Et | H | t-Bu | Cl | $OCH_2CH(CH_3)OCH_3$ | $SO_2Me$ |
| 762 | Me | H | t-Bu | Me | $OCH_2CH(CH_3)OCH_3$ | $SO_2Me$ |
| 763 | Et | H | t-Bu | Me | $OCH_2CH(CH_3)OCH_3$ | $SO_2Me$ |
| 764 | Me | H | t-Bu | $CF_3$ | $OCH_2CH(CH_3)OCH_3$ | $SO_2Me$ |
| 765 | Et | H | t-Bu | $CF_3$ | $OCH_2CH(CH_3)OCH_3$ | $SO_2Me$ |
| 766 | Me | H | t-Bu | Br | $OCH_2CH(CH_3)OCH_3$ | $SO_2Me$ |
| 767 | Et | H | t-Bu | Br | $OCH_2CH(CH_3)OCH_3$ | $SO_2Me$ |
| 768 | Me | H | t-Bu | $SO_2Me$ | $OCH_2CH(CH_3)OCH_3$ | $CF_3$ |
| 769 | Et | H | t-Bu | $SO_2Me$ | $OCH_2CH(CH_3)OCH_3$ | $CF_3$ |
| 770 | Me | H | t-Bu | Cl | $OCH_2CF_2OCH_3$ | $SO_2Me$ |
| 771 | Et | H | t-Bu | Cl | $OCH_2CF_2OCH_3$ | $SO_2Me$ |
| 772 | Me | H | t-Bu | Me | $OCH_2CF_2OCH_3$ | $SO_2Me$ |
| 773 | Et | H | t-Bu | Me | $OCH_2CF_2OCH_3$ | $SO_2Me$ |
| 774 | Me | H | t-Bu | $CF_3$ | $OCH_2CF_2OCH_3$ | $SO_2Me$ |
| 775 | Et | H | t-Bu | $CF_3$ | $OCH_2CF_2OCH_3$ | $SO_2Me$ |
| 776 | Me | H | t-Bu | Br | $OCH_2CF_2OCH_3$ | $SO_2Me$ |
| 777 | Et | H | t-Bu | Br | $OCH_2CF_2OCH_3$ | $SO_2Me$ |
| 778 | Me | H | t-Bu | $SO_2Me$ | $OCH_2CF_2OCH_3$ | $CF_3$ |
| 779 | Et | H | t-Bu | $SO_2Me$ | $OCH_2CF_2OCH_3$ | $CF_3$ |
| 780 | Et | H | t-Bu | CN | $OCH_2CF_2OCH_3$ | $SO_2Me$ |
| 781 | Et | H | t-Bu | Me | $OCH_2CF_2OCH_3$ | $SO_2Me$ |
| 782 | Me | H | t-Bu | Me | $OCH_2CH(OCH_3)_2$ | $SO_2Me$ |
| 783 | Me | H | t-Bu | Me | $CH_2N(Me)CH_2CN$ | $SO_2Me$ |
| 784 | Me | H | t-Bu | Me | (tetrahydrofuran-2-yl)methoxy | $SO_2Me$ |
| 785 | Me | H | t-Bu | Cl | SMe | $SO_2Me$ |
| 786 | Me | H | t-Bu | Cl | Cl | $SO_2Me$ |
| 787 | Me | H | t-Bu | Cl | OMe | $SO_2Me$ |
| 788 | Me | H | t-Bu | Me | (tetrahydro-2H-pyran-2-yl)methoxy | $SO_2Me$ |
| 789 | Me | H | t-Bu | Cl | $OCH_2CH_2OMe$ | $SO_2Me$ |
| 790 | Me | H | t-Bu | Me | tetrahydrofuran-3-yloxy | $SO_2Me$ |
| 791 | Me | H | t-Bu | Me | $OCH_2CH_2CH_2OMe$ | $SO_2Me$ |
| 792 | Me | H | t-Bu | Me | $OCH_2CH_2OMe$ | $SO_2Me$ |
| 793 | Et | H | t-Bu | Cl | (1,3-dioxolan-2-yl)ethoxy | $SO_2Me$ |
| 794 | Me | H | t-Bu | Me | propargyloxy | $SO_2Me$ |
| 795 | Me | H | t-Bu | Me | (tetrahydrofuran-3-yloxy)methyl | $SO_2Me$ |
| 796 | Me | H | t-Bu | Cl | $SO_2Me$ | $SO_2Me$ |
| 797 | Me | H | t-Bu | Me | $(CH_2)_6Me$ | $SO_2Me$ |
| 798 | Me | H | t-Bu | Me | $CH_2CH_2OMe$ | $SO_2Me$ |
| 799 | Et | H | t-Bu | Cl | (1,3-dioxolan-2-yl)methoxy | $SO_2Me$ |
| 800 | Me | H | t-Bu | Me | $CH_2N[C(O)SEt]CH_2CN$ | $SO_2Me$ |
| 801 | Me | H | t-Bu | Me | $CH=CHCN$ | $SO_2Me$ |
| 802 | Me | H | t-Bu | Me | $CH_2CH_2CN$ | $SO_2Me$ |
| 803 | Me | H | t-Bu | Me | $CH_2SCN$ | $SO_2Me$ |
| 804 | Me | H | t-Bu | Me | $CH_2C(S)NH_2$ | $SO_2Me$ |
| 805 | Me | H | t-Bu | Me | $OCH_2CH_2OMe$ | $SO_2Me$ |
| 806 | Et | H | t-Bu | Me | $OCH_2CH_2OMe$ | $SO_2Me$ |
| 807 | Me | H | t-Bu | Me | $OCH(CH_3)CH_2OMe$ | $SO_2Me$ |
| 808 | Et | H | t-Bu | Me | $OCH_2CH(Et)OMe$ | $SO_2Me$ |
| 809 | Me | H | t-Bu | Me | (1,3-dioxolan-2-yl)methyl | $SO_2Me$ |
| 810 | Me | H | t-Bu | Me | $CH_2O(i-Pr)$ | $SO_2Me$ |
| 811 | Me | Me | t-Bu | Me | $CO_2Me$ | $SO_2Me$ |
| 812 | Et | Me | t-Bu | Me | $CO_2Me$ | $SO_2Me$ |
| 813 | Et | Me | t-Bu | Me | $CO_2(i-Pr)$ | $SO_2Me$ |
| 814 | Me | Me | t-Bu | Cl | $CO_2Et$ | $SO_2Me$ |
| 815 | Et | Me | t-Bu | Me | $CO_2Me$ | $CF_3$ |
| 816 | Et | Me | t-Bu | Me | $OCH_2CH_2OMe$ | $SO_2Me$ |

TABLE 1-continued

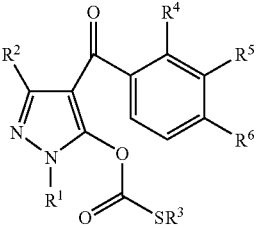

| No. | $R^1$ | $R^2$ | $R^3$ | $R^4$ | $R^5$ | $R^6$ |
|---|---|---|---|---|---|---|
| 817 | Et | Me | t-Bu | $SO_2Me$ | $CO_2Me$ | CN |
| 818 | Me | Me | t-Bu | Me | C(O)SMe | $SO_2Me$ |
| 819 | Me | Me | t-Bu | Me | C(O)SEt | $SO_2Me$ |
| 820 | Me | Me | t-Bu | Me | 2-(2-oxolanyl)ethoxy | $SO_2Me$ |
| 821 | Me | Me | t-Bu | Me | 2-(2-(1,3-dioxolanyl))ethoxy | $SO_2Me$ |
| 822 | Et | Me | t-Bu | Me | $CH_2OMe$ | $SO_2Me$ |
| 823 | Et | Me | t-Bu | Me | 2-oxolanylmethoxymethyl | $SO_2Me$ |
| 824 | Me | Me | t-Bu | Cl | $CO_2Me$ | $SO_2Me$ |
| 825 | Et | Me | t-Bu | Cl | $CO_2Me$ | $SO_2Et$ |
| 826 | Me | Me | t-Bu | Cl | C(O)SMe | $SO_2Me$ |
| 827 | Me | Me | t-Bu | Cl | C(O)SEt | $SO_2Me$ |
| 828 | Me | Me | t-Bu | Me | OMe | $SO_2Me$ |
| 829 | Me | Me | t-Bu | Me | OEt | $SO_2Me$ |
| 830 | Me | Me | t-Bu | Me | O(i-Pr) | $SO_2Me$ |
| 831 | Me | Me | t-Bu | Me | $OCHF_2$ | $SO_2Me$ |
| 832 | Me | Me | t-Bu | Me | (4,5-dihydroisoxazol-3-yl) | $SO_2Me$ |
| 833 | Me | Me | t-Bu | Me | O(n-Pr) | $SO_2Et$ |
| 834 | Me | Me | t-Bu | Cl | $CH_2OMe$ | $SO_2Me$ |
| 835 | Me | Me | t-Bu | Me | $OCO_2Me$ | $SO_2Me$ |
| 836 | Me | Me | t-Bu | Me | OC(O)SMe | $SO_2Me$ |
| 837 | Me | Me | t-Bu | Me | OC(O)SEt | $SO_2Me$ |
| 838 | Me | Me | t-Bu | Me | $OCH_2CH_2OMe$ | $SO_2Me$ |
| 839 | Et | Me | t-Bu | Me | OEt | $SO_2Me$ |
| 840 | Et | Me | t-Bu | Cl | $CO_2Et$ | $SO_2Me$ |
| 841 | Et | Me | t-Bu | Cl | $CO_2(n-Pr)$ | $SO_2Me$ |
| 842 | Et | Me | t-Bu | Me | $CO_2Et$ | $SO_2Me$ |
| 843 | Me | Me | t-Bu | Me | $CH_2CO_2Me$ | $SO_2Me$ |
| 844 | Me | Me | t-Bu | Me | $OCH_2CO_2Et$ | $SO_2Me$ |
| 845 | Me | Me | t-Bu | Me | O(n-Pr) | $SO_2Me$ |
| 846 | Et | Me | t-Bu | $SO_2Me$ | H | $CF_3$ |
| 847 | Me | Me | t-Bu | Me | $CH_2OCH_2CF_3$ | $SO_2Me$ |
| 848 | Me | Me | t-Bu | Cl | $CH_2OCH_2CF_3$ | $SO_2Me$ |
| 849 | Et | Me | t-Bu | Me | Cl | $SO_2Me$ |
| 850 | Me | Me | t-Bu | Me | $CH_2SO_2Me$ | $SO_2Me$ |
| 851 | Me | Me | t-Bu | Me | $CH_2OEt$ | $SO_2Me$ |
| 852 | Me | Me | t-Bu | Cl | $CH_2OMe$ | $SO_2Me$ |
| 853 | Me | Me | t-Bu | Me | $CH_2CH_2OMe$ | $SO_2Me$ |
| 854 | Me | Me | t-Bu | Me | $CH_2OCH_2CH_2OMe$ | $SO_2Me$ |
| 855 | Me | Me | t-Bu | Me | $OCH_2CH_2OEt$ | $SO_2Me$ |
| 856 | Me | Me | t-Bu | Me | $OCH_2CH_2Cl$ | $SO_2Me$ |
| 857 | Me | Me | t-Bu | Me | $OCH_2CF_3$ | $SO_2Me$ |
| 858 | Me | Me | t-Bu | Me | $CH_2OCH_2OMe$ | $SO_2Me$ |
| 859 | Me | Me | t-Bu | Me | $OCH_2CH_2SMe$ | $SO_2Me$ |
| 860 | Me | Me | t-Bu | Me | CN | $SO_2Me$ |
| 861 | Me | Me | t-Bu | Me | $CH_2CN$ | $SO_2Me$ |
| 862 | Me | Me | t-Bu | Br | $CO_2Me$ | $SO_2Me$ |
| 863 | Et | Me | t-Bu | Cl | $CO_2Me$ | $SO_2Me$ |
| 864 | Me | Me | t-Bu | Br | $CO_2Me$ | $SO_2Me$ |
| 865 | Me | Me | t-Bu | Cl | $OCH_2CH_2OCF_3$ | $SO_2Me$ |
| 866 | Et | Me | t-Bu | Cl | $OCH_2CH_2OCF_3$ | $SO_2Me$ |
| 867 | Me | Me | t-Bu | Me | $OCH_2CH_2OCF_3$ | $SO_2Me$ |
| 868 | Et | Me | t-Bu | Me | $OCH_2CH_2OCF_3$ | $SO_2Me$ |
| 869 | Me | Me | t-Bu | $CF_3$ | $OCH_2CH_2OCF_3$ | $SO_2Me$ |
| 870 | Et | Me | t-Bu | $CF_3$ | $OCH_2CH_2OCF_3$ | $SO_2Me$ |
| 871 | Me | Me | t-Bu | Br | $OCH_2CH_2OCF_3$ | $SO_2Me$ |
| 872 | Et | Me | t-Bu | Br | $OCH_2CH_2OCF_3$ | $SO_2Me$ |
| 873 | Me | Me | t-Bu | $SO_2Me$ | $OCH_2CH_2OCF_3$ | $CF_3$ |
| 874 | Et | Me | t-Bu | $SO_2Me$ | $OCH_2CH_2OCF_3$ | $CF_3$ |
| 875 | Me | Me | t-Bu | Cl | $OCH_2CH_2OCHClF$ | $SO_2Me$ |
| 876 | Et | Me | t-Bu | Cl | $OCH_2CH_2OCHClF$ | $SO_2Me$ |
| 877 | Me | Me | t-Bu | Me | $OCH_2CH_2OCHClF$ | $SO_2Me$ |
| 878 | Et | Me | t-Bu | Me | $OCH_2CH_2OCHClF$ | $SO_2Me$ |
| 879 | Me | Me | t-Bu | $CF_3$ | $OCH_2CH_2OCHClF$ | $SO_2Me$ |
| 880 | Et | Me | t-Bu | $CF_3$ | $OCH_2CH_2OCHClF$ | $SO_2Me$ |
| 881 | Me | Me | t-Bu | Br | $OCH_2CH_2OCHClF$ | $SO_2Me$ |

TABLE 1-continued (I)

| No. | R¹ | R² | R³ | R⁴ | R⁵ | R⁶ |
|---|---|---|---|---|---|---|
| 882 | Et | Me | t-Bu | Br | OCH₂CH₂OCHClF | SO₂Me |
| 883 | Me | Me | t-Bu | SO₂Me | OCH₂CH₂OCHClF | CF₃ |
| 884 | Et | Me | t-Bu | SO₂Me | OCH₂CH₂OCHClF | CF₃ |
| 885 | Me | Me | t-Bu | Cl | OCH₂CHFOCF₃ | SO₂Me |
| 886 | Et | Me | t-Bu | Cl | OCH₂CHFOCF₃ | SO₂Me |
| 887 | Me | Me | t-Bu | Me | OCH₂CHFOCF₃ | SO₂Me |
| 888 | Me | Me | t-Bu | Cl | OCH₂CHFOMe | SO₂Me |
| 889 | Et | Me | t-Bu | Cl | OCH₂CHFOMe | SO₂Me |
| 890 | Me | Me | t-Bu | Me | OCH₂CHFOMe | SO₂Me |
| 891 | Et | Me | t-Bu | Me | OCH₂CHFOMe | SO₂Me |
| 892 | Me | Me | t-Bu | CF₃ | OCH₂CHFOMe | SO₂Me |
| 893 | Et | Me | t-Bu | CF₃ | OCH₂CHFOMe | SO₂Me |
| 894 | Me | Me | t-Bu | Br | OCH₂CHFOMe | SO₂Me |
| 895 | Et | Me | t-Bu | Br | OCH₂CHFOMe | SO₂Me |
| 896 | Me | Me | t-Bu | SO₂Me | OCH₂CHFOMe | CF₃ |
| 897 | Et | Me | t-Bu | SO₂Me | OCH₂CHFOMe | CF₃ |
| 898 | Me | Me | t-Bu | Cl | OCHFCH₂OCF₃ | SO₂Me |
| 899 | Et | Me | t-Bu | Cl | OCHFCH₂OCF₃ | SO₂Me |
| 900 | Me | Me | t-Bu | Cl | OCH₂CH₂OCF₂Cl | SO₂Me |
| 901 | Et | Me | t-Bu | Cl | OCH₂CH₂OCF₂Cl | SO₂Me |
| 902 | Me | Me | t-Bu | Me | OCH₂CH₂OCF₂Cl | SO₂Me |
| 903 | Et | Me | t-Bu | Me | OCH₂CH₂OCF₂Cl | SO₂Me |
| 904 | Me | Me | t-Bu | CF₃ | OCH₂CH₂OCF₂Cl | SO₂Me |
| 905 | Et | Me | t-Bu | CF₃ | OCH₂CH₂OCF₂Cl | SO₂Me |
| 906 | Me | Me | t-Bu | Br | OCH₂CH₂OCF₂Cl | SO₂Me |
| 907 | Et | Me | t-Bu | Br | OCH₂CH₂OCF₂Cl | SO₂Me |
| 908 | Me | Me | t-Bu | SO₂Me | OCH₂CH₂OCF₂Cl | CF₃ |
| 909 | Et | Me | t-Bu | SO₂Me | OCH₂CH₂OCF₂Cl | CF₃ |
| 910 | Me | Me | t-Bu | Cl | SCH₂CH₂OCH₃ | SO₂Me |
| 911 | Et | Me | t-Bu | Cl | SCH₂CH₂OCH₃ | SO₂Me |
| 912 | Me | Me | t-Bu | Me | SCH₂CH₂OCH₃ | SO₂Me |
| 913 | Et | Me | t-Bu | Me | SCH₂CH₂OCH₃ | SO₂Me |
| 914 | Me | Me | t-Bu | CF₃ | SCH₂CH₂OCH₃ | SO₂Me |
| 915 | Et | Me | t-Bu | CF₃ | SCH₂CH₂OCH₃ | SO₂Me |
| 916 | Me | Me | t-Bu | Br | SCH₂CH₂OCH₃ | SO₂Me |
| 917 | Et | Me | t-Bu | Br | SCH₂CH₂OCH₃ | SO₂Me |
| 918 | Me | Me | t-Bu | SO₂Me | SCH₂CH₂OCH₃ | CF₃ |
| 919 | Et | Me | t-Bu | SO₂Me | SCH₂CH₂OCH₃ | CF₃ |
| 920 | Me | Me | t-Bu | Cl | SCH₂CH₂OCF₃ | SO₂Me |
| 921 | Et | Me | t-Bu | Cl | SCH₂CH₂OCF₃ | SO₂Me |
| 922 | Me | Me | t-Bu | Me | SCH₂CH₂OCF₃ | SO₂Me |
| 923 | Et | Me | t-Bu | Me | SCH₂CH₂OCF₃ | SO₂Me |
| 924 | Me | Me | t-Bu | CF₃ | SCH₂CH₂OCF₃ | SO₂Me |
| 925 | Et | Me | t-Bu | CF₃ | SCH₂CH₂OCF₃ | SO₂Me |
| 926 | Me | Me | t-Bu | Br | SCH₂CH₂OCF₃ | SO₂Me |
| 927 | Et | Me | t-Bu | Br | SCH₂CH₂OCF₃ | SO₂Me |
| 928 | Me | Me | t-Bu | SO₂Me | SCH₂CH₂OCF₃ | CF₃ |
| 929 | Et | Me | t-Bu | SO₂Me | SCH₂CH₂OCF₃ | CF₃ |
| 930 | Me | Me | t-Bu | Cl | SCH₂CH₂SCH₃ | SO₂Me |
| 931 | Et | Me | t-Bu | Cl | SCH₂CH₂SCH₃ | SO₂Me |
| 932 | Me | Me | t-Bu | Me | SCH₂CH₂SCH₃ | SO₂Me |
| 933 | Et | Me | t-Bu | Me | SCH₂CH₂SCH₃ | SO₂Me |
| 934 | Me | Me | t-Bu | CF₃ | SCH₂CH₂SCH₃ | SO₂Me |
| 935 | Et | Me | t-Bu | CF₃ | SCH₂CH₂SCH₃ | SO₂Me |
| 936 | Me | Me | t-Bu | Br | SCH₂CH₂SCH₃ | SO₂Me |
| 937 | Et | Me | t-Bu | Br | SCH₂CH₂SCH₃ | SO₂Me |
| 938 | Me | Me | t-Bu | SO₂Me | SCH₂CH₂SCH₃ | CF₃ |
| 939 | Et | Me | t-Bu | SO₂Me | SCH₂CH₂SCH₃ | CF₃ |
| 940 | Me | Me | t-Bu | Cl | SCH₂CH₂SCF₃ | SO₂Me |
| 941 | Et | Me | t-Bu | Cl | SCH₂CH₂SCF₃ | SO₂Me |
| 942 | Me | Me | t-Bu | Me | SCH₂CH₂SCF₃ | SO₂Me |
| 943 | Et | Me | t-Bu | Me | SCH₂CH₂SCF₃ | SO₂Me |
| 944 | Me | Me | t-Bu | CF₃ | SCH₂CH₂SCF₃ | SO₂Me |
| 945 | Et | Me | t-Bu | CF₃ | SCH₂CH₂SCF₃ | SO₂Me |
| 946 | Me | Me | t-Bu | Br | SCH₂CH₂SCF₃ | SO₂Me |

TABLE 1-continued (I)

| No. | R¹ | R² | R³ | R⁴ | R⁵ | R⁶ |
|---|---|---|---|---|---|---|
| 947 | Et | Me | t-Bu | Br | SCH$_2$CH$_2$SCF$_3$ | SO$_2$Me |
| 948 | Me | Me | t-Bu | SO$_2$Me | SCH$_2$CH$_2$SCF$_3$ | CF$_3$ |
| 949 | Et | Me | t-Bu | SO$_2$Me | SCH$_2$CH$_2$SCF$_3$ | CF$_3$ |
| 950 | Me | Me | t-Bu | Cl | OCH$_2$CH(CH$_3$)OCH$_3$ | SO$_2$Me |
| 951 | Et | Me | t-Bu | Cl | OCH$_2$CH(CH$_3$)OCH$_3$ | SO$_2$Me |
| 952 | Me | Me | t-Bu | Me | OCH$_2$CH(CH$_3$)OCH$_3$ | SO$_2$Me |
| 953 | Et | Me | t-Bu | Me | OCH$_2$CH(CH$_3$)OCH$_3$ | SO$_2$Me |
| 954 | Me | Me | t-Bu | CF$_3$ | OCH$_2$CH(CH$_3$)OCH$_3$ | SO$_2$Me |
| 955 | Et | Me | t-Bu | CF$_3$ | OCH$_2$CH(CH$_3$)OCH$_3$ | SO$_2$Me |
| 956 | Me | Me | t-Bu | Br | OCH$_2$CH(CH$_3$)OCH$_3$ | SO$_2$Me |
| 957 | Et | Me | t-Bu | Br | OCH$_2$CH(CH$_3$)OCH$_3$ | SO$_2$Me |
| 958 | Me | Me | t-Bu | SO$_2$Me | OCH$_2$CH(CH$_3$)OCH$_3$ | CF$_3$ |
| 959 | Et | Me | t-Bu | SO$_2$Me | OCH$_2$CH(CH$_3$)OCH$_3$ | CF$_3$ |
| 960 | Me | Me | t-Bu | Cl | OCH$_3$CF$_2$OCH$_3$ | SO$_2$Me |
| 961 | Et | Me | t-Bu | Cl | OCH$_3$CF$_2$OCH$_3$ | SO$_2$Me |
| 962 | Me | Me | t-Bu | Me | OCH$_3$CF$_2$OCH$_3$ | SO$_2$Me |
| 963 | Et | Me | t-Bu | Me | OCH$_3$CF$_2$OCH$_3$ | SO$_2$Me |
| 964 | Me | Me | t-Bu | CF$_3$ | OCH$_3$CF$_2$OCH$_3$ | SO$_2$Me |
| 965 | Et | Me | t-Bu | CF$_3$ | OCH$_3$CF$_2$OCH$_3$ | SO$_2$Me |
| 966 | Me | Me | t-Bu | Br | OCH$_3$CF$_2$OCH$_3$ | SO$_2$Me |
| 967 | Et | Me | t-Bu | Br | OCH$_3$CF$_2$OCH$_3$ | SO$_2$Me |
| 968 | Me | Me | t-Bu | SO$_2$Me | OCH$_3$CF$_2$OCH$_3$ | CF$_3$ |
| 969 | Et | Me | t-Bu | SO$_2$Me | OCH$_3$CF$_2$OCH$_3$ | CF$_3$ |
| 970 | Me | Me | t-Bu | Me | OCH$_3$CH$_2$OCH$_3$ | SO$_2$Me |
| 971 | Et | Me | t-Bu | Me | OCH$_3$CH$_2$OCH$_3$ | SO$_2$Me |
| 972 | Me | Me | t-Bu | Me | OCH$_2$CH(OCH$_3$)$_2$ | SO$_2$Me |
| 973 | Me | Me | t-Bu | Me | CH$_2$N(Me)CH$_2$CN | SO$_2$Me |
| 974 | Me | Me | t-Bu | Me | (tetrahydrofuran-2-yl)methoxy | SO$_2$Me |
| 975 | Me | Me | t-Bu | Cl | SMe | SO$_2$Me |
| 976 | Me | Me | t-Bu | Cl | Cl | SO$_2$Me |
| 977 | Me | Me | t-Bu | Cl | OMe | SO$_2$Me |
| 978 | Me | Me | t-Bu | Me | (tetrahydro-2H-pyran-2-yl)methoxy | SO$_2$Me |
| 979 | Me | Me | t-Bu | Cl | OCH$_2$CH$_2$OMe | SO$_2$Me |
| 980 | Me | Me | t-Bu | Me | Tetrahydrofuran-3-yloxy | SO$_2$Me |
| 981 | Me | Me | t-Bu | Me | OCH$_2$CH$_2$CH$_2$OMe | SO$_2$Me |
| 982 | Me | Me | t-Bu | Me | OCH$_2$CH$_2$OMe | SO$_2$Me |
| 983 | Et | Me | t-Bu | Cl | (1,3-dioxolan-2-yl)ethoxy | SO$_2$Me |
| 984 | Me | Me | t-Bu | Me | propargyloxy | SO$_2$Me |
| 985 | Me | Me | t-Bu | Me | (tetrahydrofuran-3-yloxy)methyl | SO$_2$Me |
| 986 | Me | Me | t-Bu | Cl | SO$_2$Me | SO$_2$Me |
| 987 | Me | Me | t-Bu | Me | (CH$_2$)$_6$Me | SO$_2$Me |
| 988 | Me | Me | t-Bu | Me | CH$_2$CH$_2$CH$_2$OMe | SO$_2$Me |
| 989 | Et | Me | t-Bu | Cl | (1,3-dioxolan-2-yl)methoxy | SO$_2$Me |
| 990 | Me | Me | t-Bu | Me | CH$_2$N[C(O)SEt]CH$_2$CN | SO$_2$Me |
| 991 | Me | Me | t-Bu | Me | CH=CHCN | SO$_2$Me |
| 992 | Me | Me | t-Bu | Me | CH$_2$CH$_2$CN | SO$_2$Me |
| 993 | Me | Me | t-Bu | Me | CH$_2$SCN | SO$_2$Me |
| 994 | Me | Me | t-Bu | Me | CH$_2$C(S)NH$_2$ | SO$_2$Me |
| 995 | Me | Me | t-Bu | Me | OCH$_2$CH$_2$OMe | SO$_2$Me |
| 996 | Et | Me | t-Bu | Me | OCH$_2$CH$_2$OMe | SO$_2$Me |
| 997 | Me | Me | t-Bu | Me | OCH(CH$_3$)CH$_2$OMe | SO$_2$Me |
| 998 | Et | Me | t-Bu | Me | OCH$_2$CH(Et)OMe | SO$_2$Me |
| 999 | Me | Me | t-Bu | Me | (1,3-dioxolan-2-yl)methyl | SO$_2$Me |
| 1000 | Me | Me | t-Bu | Me | CH$_2$O(i-Pr) | SO$_2$Me |
| 1001 | Me | H | CH(Et)$_2$ | Me | CO$_2$Me | SO$_2$Me |
| 1002 | Et | H | CH(Et)$_2$ | Me | CO$_2$Me | SO$_2$Me |
| 1003 | Et | H | CH(Et)$_2$ | Me | CO$_2$(i-Pr) | SO$_2$Me |
| 1004 | Me | H | CH(Et)$_2$ | Cl | CO$_2$Et | SO$_2$Me |
| 1005 | Et | H | CH(Et)$_2$ | Me | CO$_2$Me | CF$_3$ |
| 1006 | Et | H | CH(Et)$_2$ | Me | OCH$_2$CH$_2$OMe | SO$_2$Me |
| 1007 | Et | H | CH(Et)$_2$ | SO$_2$Me | CO$_2$Me | CN |
| 1008 | Me | H | CH(Et)$_2$ | Me | C(O)SMe | SO$_2$Me |
| 1009 | Me | H | CH(Et)$_2$ | Me | C(O)SEt | SO$_2$Me |
| 1010 | Me | H | CH(Et)$_2$ | Me | 2-(2-oxolanyl)ethoxy | SO$_2$Me |
| 1011 | Me | H | CH(Et)$_2$ | Me | 2-(2-(1,3-dioxolanyl))ethoxy | SO$_2$Me |

TABLE 1-continued

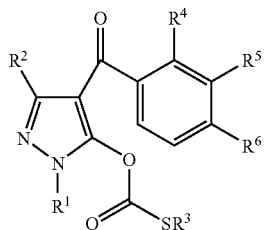

(I)

| No. | $R^1$ | $R^2$ | $R^3$ | $R^4$ | $R^5$ | $R^6$ |
|---|---|---|---|---|---|---|
| 1012 | Et | H | CH(Et)$_2$ | Me | CH$_2$OMe | SO$_2$Me |
| 1013 | Et | H | CH(Et)$_2$ | Me | 2-oxolanylmethoxymethyl | SO$_2$Me |
| 1014 | Me | H | CH(Et)$_2$ | Cl | CO$_2$Me | SO$_2$Me |
| 1015 | Et | H | CH(Et)$_2$ | Cl | CO$_2$Me | SO$_2$Et |
| 1016 | Me | H | CH(Et)$_2$ | Cl | C(O)SMe | SO$_2$Me |
| 1017 | Me | H | CH(Et)$_2$ | Cl | C(O)SEt | SO$_2$Me |
| 1018 | Me | H | CH(Et)$_2$ | Me | OMe | SO$_2$Me |
| 1019 | Me | H | CH(Et)$_2$ | Me | OEt | SO$_2$Me |
| 1020 | Me | H | CH(Et)$_2$ | Me | O(i-Pr) | SO$_2$Me |
| 1021 | Me | H | CH(Et)$_2$ | Me | OCHF$_2$ | SO$_2$Me |
| 1022 | Me | H | CH(Et)$_2$ | Me | (4,5-dihydroisoxazol-3-yl) | SO$_2$Me |
| 1023 | Me | H | CH(Et)$_2$ | Me | O(n-Pr) | SO$_2$Et |
| 1024 | Me | H | CH(Et)$_2$ | Cl | CH$_2$OMe | SO$_2$Me |
| 1025 | Me | H | CH(Et)$_2$ | Me | OCO$_2$Me | SO$_2$Me |
| 1026 | Me | H | CH(Et)$_2$ | Me | OC(O)SMe | SO$_2$Me |
| 1027 | Me | H | CH(Et)$_2$ | Me | OC(O)SEt | SO$_2$Me |
| 1028 | Me | H | CH(Et)$_2$ | Me | OCH$_2$CH$_2$OMe | SO$_2$Me |
| 1029 | Et | H | CH(Et)$_2$ | Me | OEt | SO$_2$Me |
| 1030 | Et | H | CH(Et)$_2$ | Cl | CO$_2$Et | SO$_2$Me |
| 1031 | Et | H | CH(Et)$_2$ | Cl | CO$_2$(n-Pr) | SO$_2$Me |
| 1032 | Et | H | CH(Et)$_2$ | Me | CO$_2$Et | SO$_2$Me |
| 1033 | Me | H | CH(Et)$_2$ | Me | CH$_2$CO$_2$Me | SO$_2$Me |
| 1034 | Me | H | CH(Et)$_2$ | Me | OCH$_2$CO$_2$Et | SO$_2$Me |
| 1035 | Me | H | CH(Et)$_2$ | Me | O(n-Pr) | SO$_2$Me |
| 1036 | Et | H | CH(Et)$_2$ | SO$_2$Me | H | CF$_3$ |
| 1037 | Me | H | CH(Et)$_2$ | Me | CH$_2$OCH$_2$CF$_3$ | SO$_2$Me |
| 1038 | Me | H | CH(Et)$_2$ | Cl | CH$_2$OCH$_2$CF$_3$ | SO$_2$Me |
| 1039 | Et | H | CH(Et)$_2$ | Me | Cl | SO$_2$Me |
| 1040 | Me | H | CH(Et)$_2$ | Me | CH$_2$SO$_2$Me | SO$_2$Me |
| 1041 | Me | H | CH(Et)$_2$ | Me | CH$_2$OEt | SO$_2$Me |
| 1042 | Me | H | CH(Et)$_2$ | Cl | CH$_2$OMe | SO$_2$Me |
| 1043 | Me | H | CH(Et)$_2$ | Me | CH$_2$CH$_2$OMe | SO$_2$Me |
| 1044 | Me | H | CH(Et)$_2$ | Me | CH$_2$OCH$_2$CH$_2$OMe | SO$_2$Me |
| 1045 | Me | H | CH(Et)$_2$ | Me | OCH$_2$CH$_2$OEt | SO$_2$Me |
| 1046 | Me | H | CH(Et)$_2$ | Me | OCH$_2$CH$_2$Cl | SO$_2$Me |
| 1047 | Me | H | CH(Et)$_2$ | Me | OCH$_2$CF$_3$ | SO$_2$Me |
| 1048 | Me | H | CH(Et)$_2$ | Me | CH$_2$OCH$_2$OMe | SO$_2$Me |
| 1049 | Me | H | CH(Et)$_2$ | Me | OCH$_2$CH$_2$SMe | SO$_2$Me |
| 1050 | Me | H | CH(Et)$_2$ | Me | CN | SO$_2$Me |
| 1051 | Me | H | CH(Et)$_2$ | Me | CH$_2$CN | SO$_2$Me |
| 1052 | Me | H | CH(Et)$_2$ | Br | CO$_2$Me | SO$_2$Me |
| 1053 | Et | H | CH(Et)$_2$ | Cl | CO$_2$Me | SO$_2$Me |
| 1054 | Me | H | CH(Et)$_2$ | Br | CO$_2$Me | SO$_2$Me |
| 1055 | Me | H | CH(Et)$_2$ | Cl | OCH$_2$CH$_2$OCF$_3$ | SO$_2$Me |
| 1056 | Et | H | CH(Et)$_2$ | Cl | OCH$_2$CH$_2$OCF$_3$ | SO$_2$Me |
| 1057 | Me | H | CH(Et)$_2$ | Me | OCH$_2$CH$_2$OCF$_3$ | SO$_2$Me |
| 1058 | Et | H | CH(Et)$_2$ | Me | OCH$_2$CH$_2$OCF$_3$ | SO$_2$Me |
| 1059 | Me | H | CH(Et)$_2$ | CF$_3$ | OCH$_2$CH$_2$OCF$_3$ | SO$_2$Me |
| 1060 | Et | H | CH(Et)$_2$ | CF$_3$ | OCH$_2$CH$_2$OCF$_3$ | SO$_2$Me |
| 1061 | Me | H | CH(Et)$_2$ | Br | OCH$_2$CH$_2$OCF$_3$ | SO$_2$Me |
| 1062 | Et | H | CH(Et)$_2$ | Br | OCH$_2$CH$_2$OCF$_3$ | SO$_2$Me |
| 1063 | Me | H | CH(Et)$_2$ | SO$_2$Me | OCH$_2$CH$_2$OCF$_3$ | CF$_3$ |
| 1064 | Et | H | CH(Et)$_2$ | SO$_2$Me | OCH$_2$CH$_2$OCF$_3$ | CF$_3$ |
| 1065 | Me | H | CH(Et)$_2$ | Cl | OCH$_2$CH$_2$OCHClF | SO$_2$Me |
| 1066 | Et | H | CH(Et)$_2$ | Cl | OCH$_2$CH$_2$OCHClF | SO$_2$Me |
| 1067 | Me | H | CH(Et)$_2$ | Me | OCH$_2$CH$_2$OCHClF | SO$_2$Me |
| 1068 | Et | H | CH(Et)$_2$ | Me | OCH$_2$CH$_2$OCHClF | SO$_2$Me |
| 1069 | Me | H | CH(Et)$_2$ | CF$_3$ | OCH$_2$CH$_2$OCHClF | SO$_2$Me |
| 1070 | Et | H | CH(Et)$_2$ | CF$_3$ | OCH$_2$CH$_2$OCHClF | SO$_2$Me |
| 1071 | Me | H | CH(Et)$_2$ | Br | OCH$_2$CH$_2$OCHClF | SO$_2$Me |
| 1072 | Et | H | CH(Et)$_2$ | Br | OCH$_2$CH$_2$OCHClF | SO$_2$Me |
| 1073 | Me | H | CH(Et)$_2$ | SO$_2$Me | OCH$_2$CH$_2$OCHClF | CF$_3$ |
| 1074 | Et | H | CH(Et)$_2$ | SO$_2$Me | OCH$_2$CH$_2$OCHClF | CF$_3$ |
| 1075 | Me | H | CH(Et)$_2$ | Cl | OCH$_2$CHFOCF$_3$ | SO$_2$Me |
| 1076 | Et | H | CH(Et)$_2$ | Cl | OCH$_2$CHFOCF$_3$ | SO$_2$Me |

TABLE 1-continued

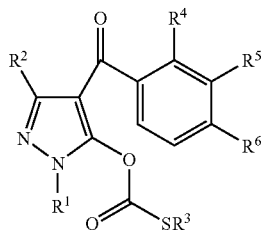

(I)

| No. | R$^1$ | R$^2$ | R$^3$ | R$^4$ | R$^5$ | R$^6$ |
|---|---|---|---|---|---|---|
| 1077 | Me | H | CH(Et)$_2$ | Me | OCH$_2$CHFOCF$_3$ | SO$_2$Me |
| 1078 | Me | H | CH(Et)$_2$ | Cl | OCH$_2$CHFOMe | SO$_2$Me |
| 1079 | Et | H | CH(Et)$_2$ | Cl | OCH$_2$CHFOMe | SO$_2$Me |
| 1080 | Me | H | CH(Et)$_2$ | Me | OCH$_2$CHFOMe | SO$_2$Me |
| 1081 | Et | H | CH(Et)$_2$ | Me | OCH$_2$CHFOMe | SO$_2$Me |
| 1082 | Me | H | CH(Et)$_2$ | CF$_3$ | OCH$_2$CHFOMe | SO$_2$Me |
| 1083 | Et | H | CH(Et)$_2$ | CF$_3$ | OCH$_2$CHFOMe | SO$_2$Me |
| 1084 | Me | H | CH(Et)$_2$ | Br | OCH$_2$CHFOMe | SO$_2$Me |
| 1085 | Et | H | CH(Et)$_2$ | Br | OCH$_2$CHFOMe | SO$_2$Me |
| 1086 | Me | H | CH(Et)$_2$ | SO$_2$Me | OCH$_2$CHFOMe | CF$_3$ |
| 1087 | Et | H | CH(Et)$_2$ | SO$_2$Me | OCH$_2$CHFOMe | CF$_3$ |
| 1088 | Me | H | CH(Et)$_2$ | Cl | OCHFCH$_2$OCF$_3$ | SO$_2$Me |
| 1089 | Et | H | CH(Et)$_2$ | Cl | OCHFCH$_2$OCF$_3$ | SO$_2$Me |
| 1090 | Me | H | CH(Et)$_2$ | Cl | OCH$_2$CH$_2$OCF$_2$Cl | SO$_2$Me |
| 1091 | Et | H | CH(Et)$_2$ | Cl | OCH$_2$CH$_2$OCF$_2$Cl | SO$_2$Me |
| 1092 | Me | H | CH(Et)$_2$ | Me | OCH$_2$CH$_2$OCF$_2$Cl | SO$_2$Me |
| 1093 | Et | H | CH(Et)$_2$ | Me | OCH$_2$CH$_2$OCF$_2$Cl | SO$_2$Me |
| 1094 | Me | H | CH(Et)$_2$ | CF$_3$ | OCH$_2$CH$_2$OCF$_2$Cl | SO$_2$Me |
| 1095 | Et | H | CH(Et)$_2$ | CF$_3$ | OCH$_2$CH$_2$OCF$_2$Cl | SO$_2$Me |
| 1096 | Me | H | CH(Et)$_2$ | Br | OCH$_2$CH$_2$OCF$_2$Cl | SO$_2$Me |
| 1097 | Et | H | CH(Et)$_2$ | Br | OCH$_2$CH$_2$OCF$_2$Cl | SO$_2$Me |
| 1098 | Me | H | CH(Et)$_2$ | SO$_2$Me | OCH$_2$CH$_2$OCF$_2$Cl | CF$_3$ |
| 1099 | Et | H | CH(Et)$_2$ | SO$_2$Me | OCH$_2$CH$_2$OCF$_2$Cl | CF$_3$ |
| 1100 | Me | H | CH(Et)$_2$ | Cl | SCH$_2$CH$_2$OCH$_3$ | SO$_2$Me |
| 1101 | Et | H | CH(Et)$_2$ | Cl | SCH$_2$CH$_2$OCH$_3$ | SO$_2$Me |
| 1102 | Me | H | CH(Et)$_2$ | Me | SCH$_2$CH$_2$OCH$_3$ | SO$_2$Me |
| 1103 | Et | H | CH(Et)$_2$ | Me | SCH$_2$CH$_2$OCH$_3$ | SO$_2$Me |
| 1104 | Me | H | CH(Et)$_2$ | CF$_3$ | SCH$_2$CH$_2$OCH$_3$ | SO$_2$Me |
| 1105 | Et | H | CH(Et)$_2$ | CF$_3$ | SCH$_2$CH$_2$OCH$_3$ | SO$_2$Me |
| 1106 | Me | H | CH(Et)$_2$ | Br | SCH$_2$CH$_2$OCH$_3$ | SO$_2$Me |
| 1107 | Et | H | CH(Et)$_2$ | Br | SCH$_2$CH$_2$OCH$_3$ | SO$_2$Me |
| 1108 | Me | H | CH(Et)$_2$ | SO$_2$Me | SCH$_2$CH$_2$OCH$_3$ | CF$_3$ |
| 1109 | Et | H | CH(Et)$_2$ | SO$_2$Me | SCH$_2$CH$_2$OCH$_3$ | CF$_3$ |
| 1110 | Me | H | CH(Et)$_2$ | Cl | SCH$_2$CH$_2$OCF$_3$ | SO$_2$Me |
| 1111 | Et | H | CH(Et)$_2$ | Cl | SCH$_2$CH$_2$OCF$_3$ | SO$_2$Me |
| 1112 | Me | H | CH(Et)$_2$ | Me | SCH$_2$CH$_2$OCF$_3$ | SO$_2$Me |
| 1113 | Et | H | CH(Et)$_2$ | Me | SCH$_2$CH$_2$OCF$_3$ | SO$_2$Me |
| 1114 | Me | H | CH(Et)$_2$ | CF$_3$ | SCH$_2$CH$_2$OCF$_3$ | SO$_2$Me |
| 1115 | Et | H | CH(Et)$_2$ | CF$_3$ | SCH$_2$CH$_2$OCF$_3$ | SO$_2$Me |
| 1116 | Me | H | CH(Et)$_2$ | Br | SCH$_2$CH$_2$OCF$_3$ | SO$_2$Me |
| 1117 | Et | H | CH(Et)$_2$ | Br | SCH$_2$CH$_2$OCF$_3$ | SO$_2$Me |
| 1118 | Me | H | CH(Et)$_2$ | SO$_2$Me | SCH$_2$CH$_2$OCF$_3$ | CF$_3$ |
| 1119 | Et | H | CH(Et)$_2$ | SO$_2$Me | SCH$_2$CH$_2$OCF$_3$ | CF$_3$ |
| 1120 | Me | H | CH(Et)$_2$ | Cl | SCH$_2$CH$_2$SCH$_3$ | SO$_2$Me |
| 1121 | Et | H | CH(Et)$_2$ | Cl | SCH$_2$CH$_2$SCH$_3$ | SO$_2$Me |
| 1122 | Me | H | CH(Et)$_2$ | Me | SCH$_2$CH$_2$SCH$_3$ | SO$_2$Me |
| 1123 | Et | H | CH(Et)$_2$ | Me | SCH$_2$CH$_2$SCH$_3$ | SO$_2$Me |
| 1124 | Me | H | CH(Et)$_2$ | CF$_3$ | SCH$_2$CH$_2$SCH$_3$ | SO$_2$Me |
| 1125 | Et | H | CH(Et)$_2$ | CF$_3$ | SCH$_2$CH$_2$SCH$_3$ | SO$_2$Me |
| 1126 | Me | H | CH(Et)$_2$ | Br | SCH$_2$CH$_2$SCH$_3$ | SO$_2$Me |
| 1127 | Et | H | CH(Et)$_2$ | Br | SCH$_2$CH$_2$SCH$_3$ | SO$_2$Me |
| 1128 | Me | H | CH(Et)$_2$ | SO$_2$Me | SCH$_2$CH$_2$SCH$_3$ | CF$_3$ |
| 1129 | Et | H | CH(Et)$_2$ | SO$_2$Me | SCH$_2$CH$_2$SCH$_3$ | CF$_3$ |
| 1130 | Me | H | CH(Et)$_2$ | Cl | SCH$_2$CH$_2$SCF$_3$ | SO$_2$Me |
| 1131 | Et | H | CH(Et)$_2$ | Cl | SCH$_2$CH$_2$SCF$_3$ | SO$_2$Me |
| 1132 | Me | H | CH(Et)$_2$ | Me | SCH$_2$CH$_2$SCF$_3$ | SO$_2$Me |
| 1133 | Et | H | CH(Et)$_2$ | Me | SCH$_2$CH$_2$SCF$_3$ | SO$_2$Me |
| 1134 | Me | H | CH(Et)$_2$ | CF$_3$ | SCH$_2$CH$_2$SCF$_3$ | SO$_2$Me |
| 1135 | Et | H | CH(Et)$_2$ | CF$_3$ | SCH$_2$CH$_2$SCF$_3$ | SO$_2$Me |
| 1136 | Me | H | CH(Et)$_2$ | Br | SCH$_2$CH$_2$SCF$_3$ | SO$_2$Me |
| 1137 | Et | H | CH(Et)$_2$ | Br | SCH$_2$CH$_2$SCF$_3$ | SO$_2$Me |
| 1138 | Me | H | CH(Et)$_2$ | SO$_2$Me | SCH$_2$CH$_2$SCF$_3$ | CF$_3$ |
| 1139 | Et | H | CH(Et)$_2$ | SO$_2$Me | SCH$_2$CH$_2$SCF$_3$ | CF$_3$ |
| 1140 | Me | H | CH(Et)$_2$ | Cl | OCH$_2$CH(CH$_3$)OCH$_3$ | SO$_2$Me |
| 1141 | Et | H | CH(Et)$_2$ | Cl | OCH$_2$CH(CH$_3$)OCH$_3$ | SO$_2$Me |

TABLE 1-continued (I)

| No. | R¹ | R² | R³ | R⁴ | R⁵ | R⁶ |
|---|---|---|---|---|---|---|
| 1142 | Me | H | CH(Et)₂ | Me | OCH₂CH(CH₃)OCH₃ | SO₂Me |
| 1143 | Et | H | CH(Et)₂ | Me | OCH₂CH(CH₃)OCH₃ | SO₂Me |
| 1144 | Me | H | CH(Et)₂ | CF₃ | OCH₂CH(CH₃)OCH₃ | SO₂Me |
| 1145 | Et | H | CH(Et)₂ | CF₃ | OCH₂CH(CH₃)OCH₃ | SO₂Me |
| 1146 | Me | H | CH(Et)₂ | Br | OCH₂CH(CH₃)OCH₃ | SO₂Me |
| 1147 | Et | H | CH(Et)₂ | Br | OCH₂CH(CH₃)OCH₃ | SO₂Me |
| 1148 | Me | H | CH(Et)₂ | SO₂Me | OCH₂CH(CH₃)OCH₃ | CF₃ |
| 1149 | Et | H | CH(Et)₂ | SO₂Me | OCH₂CH(CH₃)OCH₃ | CF₃ |
| 1150 | Me | H | CH(Et)₂ | Cl | OCH₂CF₂OCH₃ | SO₂Me |
| 1151 | Et | H | CH(Et)₂ | Cl | OCH₂CF₂OCH₃ | SO₂Me |
| 1152 | Me | H | CH(Et)₂ | Me | OCH₂CF₂OCH₃ | SO₂Me |
| 1153 | Et | H | CH(Et)₂ | Me | OCH₂CF₂OCH₃ | SO₂Me |
| 1154 | Me | H | CH(Et)₂ | CF₃ | OCH₂CF₂OCH₃ | SO₂Me |
| 1155 | Et | H | CH(Et)₂ | CF₃ | OCH₂CF₂OCH₃ | SO₂Me |
| 1156 | Me | H | CH(Et)₂ | Br | OCH₂CF₂OCH₃ | SO₂Me |
| 1157 | Et | H | CH(Et)₂ | Br | OCH₂CF₂OCH₃ | SO₂Me |
| 1158 | Me | H | CH(Et)₂ | SO₂Me | OCH₂CF₂OCH₃ | CF₃ |
| 1159 | Et | H | CH(Et)₂ | SO₂Me | OCH₂CF₂OCH₃ | CF₃ |
| 1160 | Me | H | CH(Et)₂ | CN | OCH₂CH₂OCH₃ | SO₂Me |
| 1161 | Et | H | CH(Et)₂ | Me | OCH₂CH₂OCH₃ | SO₂Me |
| 1162 | Me | H | CH(Et)₂ | Me | OCH₂CH(OCH₃)₂ | SO₂Me |
| 1163 | Me | H | CH(Et)₂ | Me | CH₂N(Me)CH₂CN | SO₂Me |
| 1164 | Me | H | CH(Et)₂ | Me | (tetrahydrofuran-2-yl)methoxy | SO₂Me |
| 1165 | Me | H | CH(Et)₂ | Cl | SMe | SO₂Me |
| 1166 | Me | H | CH(Et)₂ | Cl | Cl | SO₂Me |
| 1167 | Me | H | CH(Et)₂ | Cl | OMe | SO₂Me |
| 1168 | Me | H | CH(Et)₂ | Me | (tetrahydro-2H-pyran-2-yl)methoxy | SO₂Me |
| 1169 | Me | H | CH(Et)₂ | Cl | OCH₂CH₂OMe | SO₂Me |
| 1170 | Me | H | CH(Et)₂ | Me | tetrahydrofuran-3-yloxy | SO₂Me |
| 1171 | Me | H | CH(Et)₂ | Me | OCH₂CH₂CH₂OMe | SO₂Me |
| 1172 | Me | H | CH(Et)₂ | NO₂ | OCH₂OMe | SO₂Me |
| 1173 | Et | H | CH(Et)₂ | Cl | (1,3-dioxolan-2-yl)ethoxy | SO₂Me |
| 1174 | Me | H | CH(Et)₂ | Me | propargyloxy | SO₂Me |
| 1175 | Me | H | CH(Et)₂ | Me | (tetrahydrofuran-3-yloxy)methyl | SO₂Me |
| 1176 | Me | H | CH(Et)₂ | Cl | SO₂Me | SO₂Me |
| 1177 | Me | H | CH(Et)₂ | Me | (CH₂)₆Me | SO₂Me |
| 1178 | Me | H | CH(Et)₂ | Me | CH₂CH₂CH₂OMe | SO₂Me |
| 1179 | Et | H | CH(Et)₂ | Cl | (1,3-dioxolan-2-yl)methoxy | SO₂Me |
| 1180 | Me | H | CH(Et)₂ | Me | CH₂N[C(O)SEt]CH₂CN | SO₂Me |
| 1181 | Me | H | CH(Et)₂ | Me | CH=CHCN | SO₂Me |
| 1182 | Me | H | CH(Et)₂ | Me | CH₂CH₂CN | SO₂Me |
| 1183 | Me | H | CH(Et)₂ | Me | CH₂SCN | SO₂Me |
| 1184 | Me | H | CH(Et)₂ | Me | CH₂C(S)NH₂ | SO₂Me |
| 1185 | Me | H | CH(Et)₂ | Me | OCH₂CH₂OMe | SO₂Me |
| 1186 | Et | H | CH(Et)₂ | Me | OCH₂CH₂OMe | SO₂Me |
| 1187 | Me | H | CH(Et)₂ | Me | OCH(CH₃)CH₂OMe | SO₂Me |
| 1188 | Et | H | CH(Et)₂ | Me | OCH₂CH(Et)OMe | SO₂Me |
| 1189 | Me | H | CH(Et)₂ | Me | (1,3-dioxolan-2-yl)methyl | SO₂Me |
| 1190 | Me | H | CH(Et)₂ | Me | CH₂O(i-Pr) | SO₂Me |
| 1191 | i-Pr | H | Et | Me | CO₂Me | SO₂Me |
| 1192 | t-Bu | H | Et | Me | CO₂Me | SO₂Me |
| 1193 | t-Bu | H | Me | Me | CO₂(i-Pr) | SO₂Me |
| 1194 | i-Pr | H | Me | Cl | CO₂Et | SO₂Me |
| 1195 | t-Bu | H | Et | Me | CO₂Me | CF₃ |
| 1196 | t-Bu | H | Et | Me | OCH₂CH₂OMe | SO₂Me |
| 1197 | t-Bu | H | Me | SO₂Me | CO₂Me | CN |
| 1198 | i-Pr | H | Me | Me | C(O)SMe | SO₂Me |
| 1199 | i-Pr | H | Et | Me | C(O)SEt | SO₂Me |
| 1200 | i-Pr | H | Me | Me | 2-(2-oxolanyl)ethoxy | SO₂Me |
| 1201 | i-Pr | H | Et | Me | 2-(2-(1,3-dioxolanyl))ethoxy | SO₂Me |
| 1202 | t-Bu | H | Et | Me | CH₂OMe | SO₂Me |
| 1203 | t-Bu | H | Et | Me | 2-oxolanylmethoxymethyl | SO₂Me |
| 1204 | i-Pr | H | Et | Cl | CO₂Me | SO₂Me |
| 1205 | t-Bu | H | Et | Cl | CO₂Me | SO₂Et |
| 1206 | i-Pr | H | Et | Cl | C(O)SMe | SO₂Me |

TABLE 1-continued

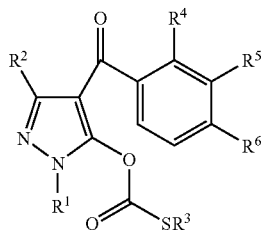

(I)

| No. | $R^1$ | $R^2$ | $R^3$ | $R^4$ | $R^5$ | $R^6$ |
|---|---|---|---|---|---|---|
| 1207 | i-Pr | H | Et | Cl | C(O)SEt | $SO_2Me$ |
| 1208 | i-Pr | H | Et | Me | OMe | $SO_2Me$ |
| 1209 | i-Pr | H | Et | Me | OEt | $SO_2Me$ |
| 1210 | i-Pr | H | Et | Me | O(i-Pr) | $SO_2Me$ |
| 1211 | i-Pr | H | Me | Me | $OCHF_2$ | $SO_2Me$ |
| 1212 | i-Pr | H | Me | Me | (4,5-dihydroisoxazol-3-yl) | $SO_2Me$ |
| 1213 | i-Pr | H | Et | Me | O(n-Pr) | $SO_2Et$ |
| 1214 | i-Pr | H | Et | Cl | $CH_2OMe$ | $SO_2Me$ |
| 1215 | i-Pr | H | Et | Me | $OCO_2Me$ | $SO_2Me$ |
| 1216 | i-Pr | H | Et | Me | OC(O)SMe | $SO_2Me$ |
| 1217 | i-Pr | H | Et | Me | OC(O)SEt | $SO_2Me$ |
| 1218 | i-Pr | H | Et | Me | $OCH_2CH_2OMe$ | $SO_2Me$ |
| 1219 | t-Bu | H | Et | Me | OEt | $SO_2Me$ |
| 1220 | t-Bu | H | Me | Cl | $CO_2Et$ | $SO_2Me$ |
| 1221 | t-Bu | H | Me | Cl | $CO_2(n-Pr)$ | $SO_2Me$ |
| 1222 | t-Bu | H | Et | Me | $CO_2Et$ | $SO_2Me$ |
| 1223 | i-Pr | H | Et | Me | $CH_2CO_2Me$ | $SO_2Me$ |
| 1224 | i-Pr | H | Me | Me | $OCH_2CO_2Et$ | $SO_2Me$ |
| 1225 | i-Pr | H | Me | Me | O(n-Pr) | $SO_2Me$ |
| 1226 | t-Bu | H | Et | $SO_2Me$ | H | $CF_3$ |
| 1227 | i-Pr | H | Me | Me | $CH_2OCH_2CF_3$ | $SO_2Me$ |
| 1228 | i-Pr | H | Et | Cl | $CH_2OCH_2CF_3$ | $SO_2Me$ |
| 1229 | t-Bu | H | Et | Me | Cl | $SO_2Me$ |
| 1230 | i-Pr | H | Et | Me | $CH_2SO_2Me$ | $SO_2Me$ |
| 1231 | i-Pr | H | Et | Me | $CH_2OEt$ | $SO_2Me$ |
| 1232 | i-Pr | H | Et | CN | $CH_2OMe$ | $SO_2Me$ |
| 1233 | i-Pr | H | Et | Me | $CH_2CH_2OMe$ | $SO_2Me$ |
| 1234 | i-Pr | H | Et | Me | $CH_2OCH_2CH_2OMe$ | $SO_2Me$ |
| 1235 | i-Pr | H | Et | Me | $OCH_2CH_2OEt$ | $SO_2Me$ |
| 1236 | i-Pr | H | Et | Me | $OCH_2CH_2Cl$ | $SO_2Me$ |
| 1237 | i-Pr | H | Et | Me | $OCH_2CF_3$ | $SO_2Me$ |
| 1238 | i-Pr | H | Me | Me | $CH_2OCH_2OMe$ | $SO_2Me$ |
| 1239 | i-Pr | H | Me | Me | $OCH_2CH_2SMe$ | $SO_2Me$ |
| 1240 | i-Pr | H | Et | Me | CN | $SO_2Me$ |
| 1241 | i-Pr | H | Et | Me | $CH_2CN$ | $SO_2Me$ |
| 1242 | i-Pr | H | Et | Br | $CO_2Me$ | $SO_2Me$ |
| 1243 | t-Bu | H | Et | Cl | $CO_2Me$ | $SO_2Me$ |
| 1244 | i-Pr | H | Et | Br | $CO_2Me$ | $SO_2Me$ |
| 1245 | i-Pr | H | Et | Cl | $OCH_2CH_2OCF_3$ | $SO_2Me$ |
| 1246 | t-Bu | H | Et | Cl | $OCH_2CH_2OCF_3$ | $SO_2Me$ |
| 1247 | i-Pr | H | Me | Me | $OCH_2CH_2OCF_3$ | $SO_2Me$ |
| 1248 | t-Bu | H | Me | Me | $OCH_2CH_2OCF_3$ | $SO_2Me$ |
| 1249 | i-Pr | H | Et | $CF_3$ | $OCH_2CH_2OCF_3$ | $SO_2Me$ |
| 1250 | t-Bu | H | Et | $CF_3$ | $OCH_2CH_2OCF_3$ | $SO_2Me$ |
| 1251 | i-Pr | H | Me | Br | $OCH_2CH_2OCF_3$ | $SO_2Me$ |
| 1252 | t-Bu | H | Me | Br | $OCH_2CH_2OCF_3$ | $SO_2Me$ |
| 1253 | i-Pr | H | Et | $SO_2Me$ | $OCH_2CH_2OCF_3$ | $CF_3$ |
| 1254 | t-Bu | H | Et | $SO_2Me$ | $OCH_2CH_2OCF_3$ | $CF_3$ |
| 1255 | i-Pr | H | Et | Cl | $OCH_2CH_2OCHClF$ | $SO_2Me$ |
| 1256 | t-Bu | H | Et | Cl | $OCH_2CH_2OCHClF$ | $SO_2Me$ |
| 1257 | i-Pr | H | Et | Me | $OCH_2CH_2OCHClF$ | $SO_2Me$ |
| 1258 | t-Bu | H | Et | Me | $OCH_2CH_2OCHClF$ | $SO_2Me$ |
| 1259 | i-Pr | H | Et | $CF_3$ | $OCH_2CH_2OCHClF$ | $SO_2Me$ |
| 1260 | t-Bu | H | Et | $CF_3$ | $OCH_2CH_2OCHClF$ | $SO_2Me$ |
| 1261 | i-Pr | H | Et | Br | $OCH_2CH_2OCHClF$ | $SO_2Me$ |
| 1262 | t-Bu | H | Et | Br | $OCH_2CH_2OCHClF$ | $SO_2Me$ |
| 1263 | i-Pr | H | Et | $SO_2Me$ | $OCH_2CH_2OCHClF$ | $CF_3$ |
| 1264 | t-Bu | H | Et | $SO_2Me$ | $OCH_2CH_2OCHClF$ | $CF_3$ |
| 1265 | i-Pr | H | Me | Cl | $OCH_2CHFOCF_3$ | $SO_2Me$ |
| 1266 | t-Bu | H | Me | Cl | $OCH_2CHFOCF_3$ | $SO_2Me$ |
| 1267 | i-Pr | H | Et | Me | $OCH_2CHFOCF_3$ | $SO_2Me$ |
| 1268 | i-Pr | H | Et | Cl | $OCH_2CHFOMe$ | $SO_2Me$ |
| 1269 | t-Bu | H | Et | Cl | $OCH_2CHFOMe$ | $SO_2Me$ |
| 1270 | i-Pr | H | Et | Me | $OCH_2CHFOMe$ | $SO_2Me$ |
| 1271 | t-Bu | H | Et | Me | $OCH_2CHFOMe$ | $SO_2Me$ |

TABLE 1-continued

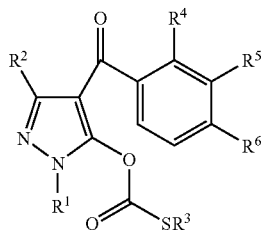

(I)

| No. | $R^1$ | $R^2$ | $R^3$ | $R^4$ | $R^5$ | $R^6$ |
|---|---|---|---|---|---|---|
| 1272 | i-Pr | H | Et | $CF_3$ | $OCH_2CHFOMe$ | $SO_2Me$ |
| 1273 | t-Bu | H | Et | $CF_3$ | $OCH_2CHFOMe$ | $SO_2Me$ |
| 1274 | i-Pr | H | Me | Br | $OCH_2CHFOMe$ | $SO_2Me$ |
| 1275 | t-Bu | H | Me | Br | $OCH_2CHFOMe$ | $SO_2Me$ |
| 1276 | i-Pr | H | Et | $SO_2Me$ | $OCH_2CHFOMe$ | $CF_3$ |
| 1277 | t-Bu | H | Et | $SO_2Me$ | $OCH_2CHFOMe$ | $CF_3$ |
| 1278 | i-Pr | H | Me | Cl | $OCHFCH_2OCF_3$ | $SO_2Me$ |
| 1279 | t-Bu | H | Me | Cl | $OCHFCH_2OCF_3$ | $SO_2Me$ |
| 1280 | i-Pr | H | Et | Cl | $OCH_2CH_2OCF_2Cl$ | $SO_2Me$ |
| 1281 | t-Bu | H | Me | Cl | $OCH_2CH_2OCF_2Cl$ | $SO_2Me$ |
| 1282 | i-Pr | H | Et | Me | $OCH_2CH_2OCF_2Cl$ | $SO_2Me$ |
| 1283 | t-Bu | H | Et | Me | $OCH_2CH_2OCF_2Cl$ | $SO_2Me$ |
| 1284 | i-Pr | H | Et | $CF_3$ | $OCH_2CH_2OCF_2Cl$ | $SO_2Me$ |
| 1285 | t-Bu | H | Et | $CF_3$ | $OCH_2CH_2OCF_2Cl$ | $SO_2Me$ |
| 1286 | i-Pr | H | Et | Br | $OCH_2CH_2OCF_2Cl$ | $SO_2Me$ |
| 1287 | t-Bu | H | Et | Br | $OCH_2CH_2OCF_2Cl$ | $SO_2Me$ |
| 1288 | i-Pr | H | Et | $SO_2Me$ | $OCH_2CH_2OCF_2Cl$ | $CF_3$ |
| 1289 | t-Bu | H | Et | $SO_2Me$ | $OCH_2CH_2OCF_2Cl$ | $CF_3$ |
| 1290 | i-Pr | H | Et | Cl | $SCH_2CH_2OCH_3$ | $SO_2Me$ |
| 1291 | t-Bu | H | Et | Cl | $SCH_2CH_2OCH_3$ | $SO_2Me$ |
| 1292 | i-Pr | H | Me | Me | $SCH_2CH_2OCH_3$ | $SO_2Me$ |
| 1293 | t-Bu | H | Me | Me | $SCH_2CH_2OCH_3$ | $SO_2Me$ |
| 1294 | i-Pr | H | Et | $CF_3$ | $SCH_2CH_2OCH_3$ | $SO_2Me$ |
| 1295 | t-Bu | H | Et | $CF_3$ | $SCH_2CH_2OCH_3$ | $SO_2Me$ |
| 1296 | i-Pr | H | Et | Br | $SCH_2CH_2OCH_3$ | $SO_2Me$ |
| 1297 | t-Bu | H | Et | Br | $SCH_2CH_2OCH_3$ | $SO_2Me$ |
| 1298 | i-Pr | H | Et | $SO_2Me$ | $SCH_2CH_2OCH_3$ | $CF_3$ |
| 1299 | t-Bu | H | Et | $SO_2Me$ | $SCH_2CH_2OCH_3$ | $CF_3$ |
| 1300 | i-Pr | H | Et | Cl | $SCH_2CH_2OCF_3$ | $SO_2Me$ |
| 1301 | t-Bu | H | Me | Cl | $SCH_2CH_2OCF_3$ | $SO_2Me$ |
| 1302 | i-Pr | H | Me | Me | $SCH_2CH_2OCF_3$ | $SO_2Me$ |
| 1303 | t-Bu | H | Et | Me | $SCH_2CH_2OCF_3$ | $SO_2Me$ |
| 1304 | i-Pr | H | Et | $CF_3$ | $SCH_2CH_2OCF_3$ | $SO_2Me$ |
| 1305 | t-Bu | H | Me | $CF_3$ | $SCH_2CH_2OCF_3$ | $SO_2Me$ |
| 1306 | i-Pr | H | Me | Br | $SCH_2CH_2OCF_3$ | $SO_2Me$ |
| 1307 | t-Bu | H | Et | Br | $SCH_2CH_2OCF_3$ | $SO_2Me$ |
| 1308 | i-Pr | H | Me | $SO_2Me$ | $SCH_2CH_2OCF_3$ | $CF_3$ |
| 1309 | t-Bu | H | Et | $SO_2Me$ | $SCH_2CH_2OCF_3$ | $CF_3$ |
| 1310 | i-Pr | H | Et | Cl | $SCH_2CH_2SCH_3$ | $SO_2Me$ |
| 1311 | t-Bu | H | Et | Cl | $SCH_2CH_2SCH_3$ | $SO_2Me$ |
| 1312 | i-Pr | H | Et | Me | $SCH_2CH_2SCH_3$ | $SO_2Me$ |
| 1313 | t-Bu | H | Et | Me | $SCH_2CH_2SCH_3$ | $SO_2Me$ |
| 1314 | i-Pr | H | Et | $CF_3$ | $SCH_2CH_2SCH_3$ | $SO_2Me$ |
| 1315 | t-Bu | H | Et | $CF_3$ | $SCH_2CH_2SCH_3$ | $SO_2Me$ |
| 1316 | i-Pr | H | Et | Br | $SCH_2CH_2SCH_3$ | $SO_2Me$ |
| 1317 | t-Bu | H | Et | Br | $SCH_2CH_2SCH_3$ | $SO_2Me$ |
| 1318 | i-Pr | H | Et | $SO_2Me$ | $SCH_2CH_2SCH_3$ | $CF_3$ |
| 1319 | t-Bu | H | Et | $SO_2Me$ | $SCH_2CH_2SCH_3$ | $CF_3$ |
| 1320 | i-Pr | H | Me | Cl | $SCH_2CH_2SCF_3$ | $SO_2Me$ |
| 1321 | t-Bu | H | Me | Cl | $SCH_2CH_2SCF_3$ | $SO_2Me$ |
| 1322 | i-Pr | H | Et | Me | $SCH_2CH_2SCF_3$ | $SO_2Me$ |
| 1323 | t-Bu | H | Et | Me | $SCH_2CH_2SCF_3$ | $SO_2Me$ |
| 1324 | i-Pr | H | Et | $CF_3$ | $SCH_2CH_2SCF_3$ | $SO_2Me$ |
| 1325 | t-Bu | H | Et | $CF_3$ | $SCH_2CH_2SCF_3$ | $SO_2Me$ |
| 1326 | i-Pr | H | Et | Br | $SCH_2CH_2SCF_3$ | $SO_2Me$ |
| 1327 | t-Bu | H | Et | Br | $SCH_2CH_2SCF_3$ | $SO_2Me$ |
| 1328 | i-Pr | H | Me | $SO_2Me$ | $SCH_2CH_2SCF_3$ | $CF_3$ |
| 1329 | t-Bu | H | Me | $SO_2Me$ | $SCH_2CH_2SCF_3$ | $CF_3$ |
| 1330 | i-Pr | H | Et | Cl | $OCH_2CH(CH_3)OCH_3$ | $SO_2Me$ |
| 1331 | t-Bu | H | Et | Cl | $OCH_2CH(CH_3)OCH_3$ | $SO_2Me$ |
| 1332 | i-Pr | H | Me | Me | $OCH_2CH(CH_3)OCH_3$ | $SO_2Me$ |
| 1333 | t-Bu | H | Me | Me | $OCH_2CH(CH_3)OCH_3$ | $SO_2Me$ |
| 1334 | i-Pr | H | Et | $CF_3$ | $OCH_2CH(CH_3)OCH_3$ | $SO_2Me$ |
| 1335 | t-Bu | H | Me | $CF_3$ | $OCH_2CH(CH_3)OCH_3$ | $SO_2Me$ |
| 1336 | i-Pr | H | Et | Br | $OCH_2CH(CH_3)OCH_3$ | $SO_2Me$ |

TABLE 1-continued

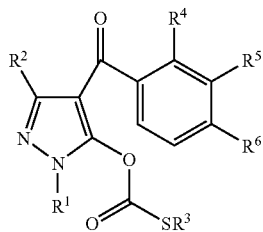

(I)

| No. | R¹ | R² | R³ | R⁴ | R⁵ | R⁶ |
|---|---|---|---|---|---|---|
| 1337 | t-Bu | H | Et | Br | OCH₂CH(CH₃)OCH₃ | SO₂Me |
| 1338 | i-Pr | H | Et | SO₂Me | OCH₂CH(CH₃)OCH₃ | CF₃ |
| 1339 | t-Bu | H | Et | SO₂Me | OCH₂CH(CH₃)OCH₃ | CF₃ |
| 1340 | i-Pr | H | Et | Cl | OCH₂CF₂OCH₃ | SO₂Me |
| 1341 | t-Bu | H | Et | Cl | OCH₂CF₂OCH₃ | SO₂Me |
| 1342 | i-Pr | H | Et | Me | OCH₂CF₂OCH₃ | SO₂Me |
| 1343 | t-Bu | H | Et | Me | OCH₂CF₂OCH₃ | SO₂Me |
| 1344 | i-Pr | H | Et | CF₃ | OCH₂CF₂OCH₃ | SO₂Me |
| 1345 | t-Bu | H | Et | CF₃ | OCH₂CF₂OCH₃ | SO₂Me |
| 1346 | i-Pr | H | Me | Br | OCH₂CF₂OCH₃ | SO₂Me |
| 1347 | t-Bu | H | Me | Br | OCH₂CF₂OCH₃ | SO₂Me |
| 1348 | i-Pr | H | Et | SO₂Me | OCH₂CF₂OCH₃ | CF₃ |
| 1349 | t-Bu | H | Et | SO₂Me | OCH₂CF₂OCH₃ | CF₃ |
| 1350 | i-Pr | H | Et | Me | OCH₂CH₂OCH₃ | SO₂Me |
| 1351 | t-Bu | H | Et | Me | OCH₂CH₂OCH₃ | SO₂Me |
| 1352 | i-Pr | H | Et | Me | OCH₂CH(OCH₃)₂ | SO₂Me |
| 1353 | i-Pr | H | Et | Me | CH₂NMeCH₂CN | SO₂Me |
| 1354 | i-Pr | H | Et | Me | (tetrahydrofuran-2-yl)methoxy | SO₂Me |
| 1355 | i-Pr | H | Me | Cl | SMe | SO₂Me |
| 1356 | i-Pr | H | Me | Cl | Cl | SO₂Me |
| 1357 | i-Pr | H | Et | Cl | OMe | SO₂Me |
| 1358 | i-Pr | H | Et | Me | (tetrahydro-2H-pyran-2-yl)methoxy | SO₂Me |
| 1359 | i-Pr | H | Me | Cl | OCH₂CH₂OMe | SO₂Me |
| 1360 | i-Pr | H | Me | Me | Tetrahydrofuran-3-yloxy | SO₂Me |
| 1361 | i-Pr | H | Et | Me | OCH₂CH₂CH₂OMe | SO₂Me |
| 1362 | i-Pr | H | Me | Me | OCH₂CH₂OMe | SO₂Me |
| 1363 | t-Bu | H | Et | Cl | (1,3-dioxolan-2-yl)ethoxy | SO₂Me |
| 1364 | i-Pr | H | Et | Me | propargyloxy | SO₂Me |
| 1365 | i-Pr | H | Et | Me | (tetrahydrofuran-3-yloxy)methyl | SO₂Me |
| 1366 | i-Pr | H | Et | Cl | SO₂Me | SO₂Me |
| 1367 | i-Pr | H | Et | Me | (CH₂)₆Me | SO₂Me |
| 1368 | i-Pr | H | Et | Me | CH₂CH₂CH₂OMe | SO₂Me |
| 1369 | t-Bu | H | Et | Cl | (1,3-dioxolan-2-yl)methoxy | SO₂Me |
| 1370 | i-Pr | H | Et | Me | CH₂N[C(O)SEt]CH₂CN | SO₂Me |
| 1371 | i-Pr | H | Et | Me | CH=CHCN | SO₂Me |
| 1372 | i-Pr | H | Et | Me | CH₂CH₂CN | SO₂Me |
| 1373 | i-Pr | H | Me | Me | CH₂SCN | SO₂Me |
| 1374 | i-Pr | H | Me | Me | CH₂C(S)NH₂ | SO₂Me |
| 1375 | i-Pr | H | Et | Me | OCH₂CH₂OMe | SO₂Me |
| 1376 | t-Bu | H | Et | Me | OCH₂CH₂OMe | SO₂Me |
| 1377 | i-Pr | H | Et | Me | OCH(CH₃)CH₂OMe | SO₂Me |
| 1378 | t-Bu | H | Et | Me | OCH₂CH(Et)OMe | SO₂Me |
| 1379 | i-Pr | H | Et | Me | (1,3-dioxolan-2-yl)methyl | SO₂Me |
| 1380 | i-Pr | H | Et | Me | CH₂O(i-Pr) | SO₂Me |
| 1381 | Et | H | i-Pr | Me | CO₂(i-Pr) | SO₂Me |
| 1382 | Me | H | i-Pr | Cl | CO₂Et | SO₂Me |
| 1383 | Et | H | i-Pr | Me | CO₂Me | CF₃ |
| 1384 | Et | H | i-Pr | SO₂Me | CO₂Me | CN |
| 1385 | Me | H | i-Pr | Me | C(O)SMe | SO₂Me |
| 1386 | Me | H | i-Pr | Me | C(O)SEt | SO₂Me |
| 1387 | Me | H | i-Pr | Me | 2-(2-oxolanyl)ethoxy | SO₂Me |
| 1388 | Me | H | i-Pr | Me | 2-(2-(1,3-dioxolanyl))ethoxy | SO₂Me |
| 1389 | Et | H | i-Pr | Me | CH₂OMe | SO₂Me |
| 1390 | Et | H | i-Pr | Me | 2-oxolanylmethoxymethyl | SO₂Me |
| 1391 | Me | H | i-Pr | Cl | CO₂Me | SO₂Me |
| 1392 | Et | H | i-Pr | Cl | CO₂Me | SO₂Et |
| 1393 | Me | H | i-Pr | Cl | C(O)SMe | SO₂Me |
| 1394 | Me | H | i-Pr | Cl | C(O)SEt | SO₂Me |
| 1395 | Me | H | i-Pr | Me | OMe | SO₂Me |
| 1396 | Me | H | i-Pr | Me | OEt | SO₂Me |
| 1397 | Me | H | i-Pr | Me | O(i-Pr) | SO₂Me |
| 1398 | Me | H | i-Pr | Me | OCHF₂ | SO₂Me |
| 1399 | Me | H | i-Pr | Me | (4,5-dihydroisoxazol-3-yl) | SO₂Me |
| 1400 | Me | H | i-Pr | Me | O(n-Pr) | SO₂Et |
| 1401 | Me | H | i-Pr | Cl | CH₂OMe | SO₂Me |

TABLE 1-continued

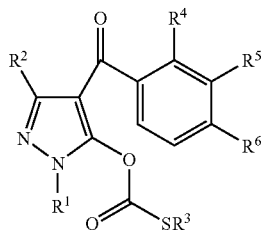

(I)

| No. | R$^1$ | R$^2$ | R$^3$ | R$^4$ | R$^5$ | R$^6$ |
|---|---|---|---|---|---|---|
| 1402 | Me | H | i-Pr | Me | OCO$_2$Me | SO$_2$Me |
| 1403 | Me | H | i-Pr | Me | OC(O)SMe | SO$_2$Me |
| 1404 | Me | H | i-Pr | Me | OC(O)SEt | SO$_2$Me |
| 1405 | Et | H | i-Pr | Me | OEt | SO$_2$Me |
| 1406 | Et | H | i-Pr | Cl | CO$_2$Et | SO$_2$Me |
| 1407 | Et | H | i-Pr | Cl | CO$_2$(n-Pr) | SO$_2$Me |
| 1408 | Et | H | i-Pr | Me | CO$_2$Et | SO$_2$Me |
| 1409 | Me | H | i-Pr | Me | CH$_2$CO$_2$Me | SO$_2$Me |
| 1410 | Me | H | i-Pr | Me | OCH$_2$CO$_2$Et | SO$_2$Me |
| 1411 | Me | H | i-Pr | Me | O(n-Pr) | SO$_2$Me |
| 1412 | Et | H | i-Pr | SO$_2$Me | H | CF$_3$ |
| 1413 | Me | H | i-Pr | Me | CH$_2$OCH$_2$CF$_3$ | SO$_2$Me |
| 1414 | Me | H | i-Pr | Cl | CH$_2$OCH$_2$CF$_3$ | SO$_2$Me |
| 1415 | Et | H | i-Pr | Me | Cl | SO$_2$Me |
| 1416 | Me | H | i-Pr | Me | CH$_2$SO$_2$Me | SO$_2$Me |
| 1417 | Me | H | i-Pr | Me | CH$_2$OEt | SO$_2$Me |
| 1418 | Me | H | i-Pr | Cl | CH$_2$OMe | SO$_2$Me |
| 1419 | Me | H | i-Pr | Me | CH$_2$CH$_2$OMe | SO$_2$Me |
| 1420 | Me | H | i-Pr | Me | CH$_2$OCH$_2$CH$_2$OMe | SO$_2$Me |
| 1421 | Me | H | i-Pr | Me | OCH$_2$CH$_2$OEt | SO$_2$Me |
| 1422 | Me | H | i-Pr | Me | OCH$_2$CH$_2$Cl | SO$_2$Me |
| 1423 | Me | H | i-Pr | Me | OCH$_2$CF$_3$ | SO$_2$Me |
| 1424 | Me | H | i-Pr | Me | CH$_2$OCH$_2$OMe | SO$_2$Me |
| 1425 | Me | H | i-Pr | Me | OCH$_2$CH$_2$SMe | SO$_2$Me |
| 1426 | Me | H | i-Pr | Me | CN | SO$_2$Me |
| 1427 | Me | H | i-Pr | Me | CH$_2$CN | SO$_2$Me |
| 1428 | Me | H | i-Pr | Br | CO$_2$Me | SO$_2$Me |
| 1429 | Et | H | i-Pr | Cl | CO$_2$Me | SO$_2$Me |
| 1430 | Me | H | i-Pr | Br | CO$_2$Me | SO$_2$Me |
| 1431 | Me | H | i-Pr | Cl | OCH$_2$CH$_2$OCF$_3$ | SO$_2$Me |
| 1432 | Et | H | i-Pr | Cl | OCH$_2$CH$_2$OCF$_3$ | SO$_2$Me |
| 1433 | Me | H | i-Pr | Me | OCH$_2$CH$_2$OCF$_3$ | SO$_2$Me |
| 1434 | Et | H | i-Pr | Me | OCH$_2$CH$_2$OCF$_3$ | SO$_2$Me |
| 1435 | Me | H | i-Pr | CF$_3$ | OCH$_2$CH$_2$OCF$_3$ | SO$_2$Me |
| 1436 | Et | H | i-Pr | CF$_3$ | OCH$_2$CH$_2$OCF$_3$ | SO$_2$Me |
| 1437 | Me | H | i-Pr | Br | OCH$_2$CH$_2$OCF$_3$ | SO$_2$Me |
| 1438 | Et | H | i-Pr | Br | OCH$_2$CH$_2$OCF$_3$ | SO$_2$Me |
| 1439 | Me | H | i-Pr | SO$_2$Me | OCH$_2$CH$_2$OCF$_3$ | CF$_3$ |
| 1440 | Et | H | i-Pr | SO$_2$Me | OCH$_2$CH$_2$OCF$_3$ | CF$_3$ |
| 1441 | Me | H | i-Pr | Cl | OCH$_2$CH$_2$OCHClF | SO$_2$Me |
| 1442 | Et | H | i-Pr | Cl | OCH$_2$CH$_2$OCHClF | SO$_2$Me |
| 1443 | Me | H | i-Pr | Me | OCH$_2$CH$_2$OCHClF | SO$_2$Me |
| 1444 | Et | H | i-Pr | Me | OCH$_2$CH$_2$OCHClF | SO$_2$Me |
| 1445 | Me | H | i-Pr | CF$_3$ | OCH$_2$CH$_2$OCHClF | SO$_2$Me |
| 1446 | Et | H | i-Pr | CF$_3$ | OCH$_2$CH$_2$OCHClF | SO$_2$Me |
| 1447 | Me | H | i-Pr | Br | OCH$_2$CH$_2$OCHClF | SO$_2$Me |
| 1448 | Et | H | i-Pr | Br | OCH$_2$CH$_2$OCHClF | SO$_2$Me |
| 1449 | Me | H | i-Pr | SO$_2$Me | OCH$_2$CH$_2$OCHClF | CF$_3$ |
| 1450 | Et | H | i-Pr | SO$_2$Me | OCH$_2$CH$_2$OCHClF | CF$_3$ |
| 1451 | Me | H | i-Pr | Cl | OCH$_2$CHFOCF$_3$ | SO$_2$Me |
| 1452 | Et | H | i-Pr | Cl | OCH$_2$CHFOCF$_3$ | SO$_2$Me |
| 1453 | Me | H | i-Pr | Me | OCH$_2$CHFOCF$_3$ | SO$_2$Me |
| 1454 | Me | H | i-Pr | Cl | OCH$_2$CHFOMe | SO$_2$Me |
| 1455 | Et | H | i-Pr | Cl | OCH$_2$CHFOMe | SO$_2$Me |
| 1456 | Me | H | i-Pr | Me | OCH$_2$CHFOMe | SO$_2$Me |
| 1457 | Et | H | i-Pr | Me | OCH$_2$CHFOMe | SO$_2$Me |
| 1458 | Me | H | i-Pr | CF$_3$ | OCH$_2$CHFOMe | SO$_2$Me |
| 1459 | Et | H | i-Pr | CF$_3$ | OCH$_2$CHFOMe | SO$_2$Me |
| 1460 | Me | H | i-Pr | Br | OCH$_2$CHFOMe | SO$_2$Me |
| 1461 | Et | H | i-Pr | Br | OCH$_2$CHFOMe | SO$_2$Me |
| 1462 | Me | H | i-Pr | SO$_2$Me | OCH$_2$CHFOMe | CF$_3$ |
| 1463 | Et | H | i-Pr | SO$_2$Me | OCH$_2$CHFOMe | CF$_3$ |
| 1464 | Me | H | i-Pr | Cl | OCHFCH$_2$OCF$_3$ | SO$_2$Me |
| 1465 | Et | H | i-Pr | Cl | OCHFCH$_2$OCF$_3$ | SO$_2$Me |
| 1466 | Me | H | i-Pr | Cl | OCH$_2$CH$_2$OCF$_2$Cl | SO$_2$Me |

TABLE 1-continued

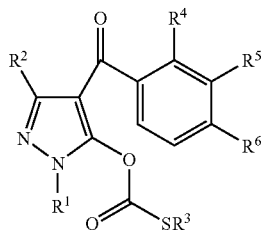

(I)

| No. | $R^1$ | $R^2$ | $R^3$ | $R^4$ | $R^5$ | $R^6$ |
|---|---|---|---|---|---|---|
| 1467 | Et | H | i-Pr | Cl | $OCH_2CH_2OCF_2Cl$ | $SO_2Me$ |
| 1468 | Me | H | i-Pr | Me | $OCH_2CH_2OCF_2Cl$ | $SO_2Me$ |
| 1469 | Et | H | i-Pr | Me | $OCH_2CH_2OCF_2Cl$ | $SO_2Me$ |
| 1470 | Me | H | i-Pr | $CF_3$ | $OCH_2CH_2OCF_2Cl$ | $SO_2Me$ |
| 1471 | Et | H | i-Pr | $CF_3$ | $OCH_2CH_2OCF_2Cl$ | $SO_2Me$ |
| 1472 | Me | H | i-Pr | Br | $OCH_2CH_2OCF_2Cl$ | $SO_2Me$ |
| 1473 | Et | H | i-Pr | Br | $OCH_2CH_2OCF_2Cl$ | $SO_2Me$ |
| 1474 | Me | H | i-Pr | $SO_2Me$ | $OCH_2CH_2OCF_2Cl$ | $CF_3$ |
| 1475 | Et | H | i-Pr | $SO_2Me$ | $OCH_2CH_2OCF_2Cl$ | $CF_3$ |
| 1476 | Me | H | i-Pr | Cl | $SCH_2CH_2OCH_3$ | $SO_2Me$ |
| 1477 | Et | H | i-Pr | Cl | $SCH_2CH_2OCH_3$ | $SO_2Me$ |
| 1478 | Me | H | i-Pr | Me | $SCH_2CH_2OCH_3$ | $SO_2Me$ |
| 1479 | Et | H | i-Pr | Me | $SCH_2CH_2OCH_3$ | $SO_2Me$ |
| 1480 | Me | H | i-Pr | $CF_3$ | $SCH_2CH_2OCH_3$ | $SO_2Me$ |
| 1481 | Et | H | i-Pr | $CF_3$ | $SCH_2CH_2OCH_3$ | $SO_2Me$ |
| 1482 | Me | H | i-Pr | Br | $SCH_2CH_2OCH_3$ | $SO_2Me$ |
| 1483 | Et | H | i-Pr | Br | $SCH_2CH_2OCH_3$ | $SO_2Me$ |
| 1484 | Me | H | i-Pr | $SO_2Me$ | $SCH_2CH_2OCH_3$ | $CF_3$ |
| 1485 | Et | H | i-Pr | $SO_2Me$ | $SCH_2CH_2OCH_3$ | $CF_3$ |
| 1486 | Me | H | i-Pr | Cl | $SCH_2CH_2OCF_3$ | $SO_2Me$ |
| 1487 | Et | H | i-Pr | Cl | $SCH_2CH_2OCF_3$ | $SO_2Me$ |
| 1488 | Me | H | i-Pr | Me | $SCH_2CH_2OCF_3$ | $SO_2Me$ |
| 1489 | Et | H | i-Pr | Me | $SCH_2CH_2OCF_3$ | $SO_2Me$ |
| 1490 | Me | H | i-Pr | $CF_3$ | $SCH_2CH_2OCF_3$ | $SO_2Me$ |
| 1491 | Et | H | i-Pr | $CF_3$ | $SCH_2CH_2OCF_3$ | $SO_2Me$ |
| 1492 | Me | H | i-Pr | Br | $SCH_2CH_2OCF_3$ | $SO_2Me$ |
| 1493 | Et | H | i-Pr | Br | $SCH_2CH_2OCF_3$ | $SO_2Et$ |
| 1494 | Me | H | i-Pr | $SO_2Me$ | $SCH_2CH_2OCF_3$ | $CF_3$ |
| 1495 | Et | H | i-Pr | $SO_2Me$ | $SCH_2CH_2OCF_3$ | $CF_3$ |
| 1496 | Me | H | i-Pr | Cl | $SCH_2CH_2SCH_3$ | $SO_2Me$ |
| 1497 | Et | H | i-Pr | Cl | $SCH_2CH_2SCH_3$ | $SO_2Me$ |
| 1498 | Me | H | i-Pr | Me | $SCH_2CH_2SCH_3$ | $SO_2Me$ |
| 1499 | Et | H | i-Pr | Me | $SCH_2CH_2SCH_3$ | $SO_2Me$ |
| 1500 | Me | H | i-Pr | $CF_3$ | $SCH_2CH_2SCH_3$ | $SO_2Me$ |
| 1501 | Et | H | i-Pr | $CF_3$ | $SCH_2CH_2SCH_3$ | $SO_2Me$ |
| 1502 | Me | H | i-Pr | Br | $SCH_2CH_2SCH_3$ | $SO_2Me$ |
| 1503 | Et | H | i-Pr | Br | $SCH_2CH_2SCH_3$ | $SO_2Me$ |
| 1504 | Me | H | i-Pr | $SO_2Me$ | $SCH_2CH_2SCH_3$ | $CF_3$ |
| 1505 | Et | H | i-Pr | $SO_2Me$ | $SCH_2CH_2SCH_3$ | $CF_3$ |
| 1506 | Me | H | i-Pr | Cl | $SCH_2CH_2SCF_3$ | $SO_2Me$ |
| 1507 | Et | H | i-Pr | Cl | $SCH_2CH_2SCF_3$ | $SO_2Me$ |
| 1508 | Me | H | i-Pr | Me | $SCH_2CH_2SCF_3$ | $SO_2Me$ |
| 1509 | Et | H | i-Pr | Me | $SCH_2CH_2SCF_3$ | $SO_2Me$ |
| 1510 | Me | H | i-Pr | $CF_3$ | $SCH_2CH_2SCF_3$ | $SO_2Me$ |
| 1511 | Et | H | i-Pr | $CF_3$ | $SCH_2CH_2SCF_3$ | $SO_2Me$ |
| 1512 | Me | H | i-Pr | Br | $SCH_2CH_2SCF_3$ | $SO_2Me$ |
| 1513 | Et | H | i-Pr | Br | $SCH_2CH_2SCF_3$ | $SO_2Me$ |
| 1514 | Me | H | i-Pr | $SO_2Me$ | $SCH_2CH_2SCF_3$ | $CF_3$ |
| 1515 | Et | H | i-Pr | $SO_2Me$ | $SCH_2CH_2SCF_3$ | $CF_3$ |
| 1516 | Me | H | i-Pr | Cl | $OCH_2CH(CH_3)OCH_3$ | $SO_2Me$ |
| 1517 | Et | H | i-Pr | Cl | $OCH_2CH(CH_3)OCH_3$ | $SO_2Me$ |
| 1517 | Me | H | i-Pr | Me | $OCH_2CH(CH_3)OCH_3$ | $SO_2Me$ |
| 1518 | Et | H | i-Pr | Me | $OCH_2CH(CH_3)OCH_3$ | $SO_2Me$ |
| 1519 | Me | H | i-Pr | $CF_3$ | $OCH_2CH(CH_3)OCH_3$ | $SO_2Me$ |
| 1520 | Et | H | i-Pr | $CF_3$ | $OCH_2CH(CH_3)OCH_3$ | $SO_2Me$ |
| 1521 | Me | H | i-Pr | Br | $OCH_2CH(CH_3)OCH_3$ | $SO_2Me$ |
| 1522 | Et | H | i-Pr | Br | $OCH_2CH(CH_3)OCH_3$ | $SO_2Me$ |
| 1523 | Me | H | i-Pr | $SO_2Me$ | $OCH_2CH(CH_3)OCH_3$ | $CF_3$ |
| 1524 | Et | H | i-Pr | $SO_2Me$ | $OCH_2CH(CH_3)OCH_3$ | $CF_3$ |
| 1525 | Me | H | i-Pr | Cl | $OCH_2CF_2OCH_3$ | $SO_2Me$ |
| 1526 | Et | H | i-Pr | Cl | $OCH_2CF_2OCH_3$ | $SO_2Me$ |
| 1527 | Me | H | i-Pr | Me | $OCH_2CF_2OCH_3$ | $SO_2Me$ |
| 1528 | Et | H | i-Pr | Me | $OCH_2CF_2OCH_3$ | $SO_2Me$ |
| 1529 | Me | H | i-Pr | $CF_3$ | $OCH_2CF_2OCH_3$ | $SO_2Me$ |
| 1530 | Et | H | i-Pr | $CF_3$ | $OCH_2CF_2OCH_3$ | $SO_2Me$ |

TABLE 1-continued

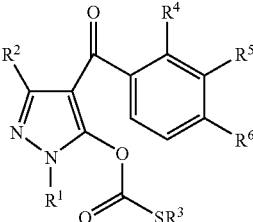

(I)

| No. | R¹ | R² | R³ | R⁴ | R⁵ | R⁶ |
|---|---|---|---|---|---|---|
| 1531 | Me | H | i-Pr | Br | OCH₂CF₂OCH₃ | SO₂Me |
| 1532 | Et | H | i-Pr | Br | OCH₂CF₂OCH₃ | SO₂Me |
| 1533 | Me | H | i-Pr | SO₂Me | OCH₂CF₂OCH₃ | CF₃ |
| 1534 | Et | H | i-Pr | SO₂Me | OCH₂CF₂OCH₃ | CF₃ |
| 1535 | Me | H | i-Pr | Me | OCH₂CH₂OCH₃ | SO₂Me |
| 1536 | Et | H | i-Pr | Me | OCH₂CH₂OCH₃ | SO₂Me |
| 1537 | Me | H | i-Pr | Me | OCH₂CH(OCH₃)₂ | SO₂Me |
| 1538 | Me | H | i-Pr | Me | CH₂N(Me)CH₂CN | SO₂Me |
| 1539 | Me | H | i-Pr | Me | (tetrahydrofuran-2-yl)methoxy | SO₂Me |
| 1540 | Me | H | i-Pr | Cl | SMe | SO₂Me |
| 1541 | Me | H | i-Pr | Cl | Cl | SO₂Me |
| 1542 | Me | H | i-Pr | Cl | OMe | SO₂Me |
| 1543 | Me | H | i-Pr | Me | (tetrahydro-2H-pyran-2-yl)methoxy | SO₂Me |
| 1544 | Me | H | i-Pr | Cl | OCH₂CH₂OMe | SO₂Me |
| 1545 | Me | H | i-Pr | Me | tetrahydrofuran-3-yloxy | SO₂Me |
| 1546 | Me | H | i-Pr | Me | OCH₂CH₂CH₂OMe | SO₂Me |
| 1547 | Me | H | i-Pr | Me | OCH₂CH₂OMe | SO₂Me |
| 1548 | Et | H | i-Pr | Cl | (1,3-dioxolan-2-yl)ethoxy | SO₂Me |
| 1549 | Me | H | i-Pr | Me | propargyloxy | SO₂Me |
| 1550 | Me | H | i-Pr | Me | (tetrahydrofuran-3-yloxy)methyl | SO₂Me |
| 1551 | Me | H | i-Pr | Cl | SO₂Me | SO₂Me |
| 1552 | Me | H | i-Pr | Me | (CH₂)₆Me | SO₂Me |
| 1553 | Me | H | i-Pr | Me | CH₂CH₂CH₂OMe | SO₂Me |
| 1554 | Et | H | i-Pr | Cl | (1,3-dioxolan-2-yl)methoxy | SO₂Me |
| 1555 | Me | H | i-Pr | Me | CH₂N[C(O)SEt]CH₂CN | SO₂Me |
| 1556 | Me | H | i-Pr | Me | CHCHCN | SO₂Me |
| 1557 | Me | H | i-Pr | Me | CH₂CH₂CN | SO₂Me |
| 1558 | Me | H | i-Pr | Me | CH₂SCN | SO₂Me |
| 1559 | Me | H | i-Pr | Me | CH₂C(S)NH₂ | SO₂Me |
| 1560 | Me | H | i-Pr | Me | OCH₂CH₂OMe | SO₂Me |
| 1561 | Et | H | i-Pr | Me | OCH₂CH₂OMe | SO₂Me |
| 1562 | Me | H | i-Pr | Me | OCH(CH₃)CH₂OMe | SO₂Me |
| 1563 | Et | H | i-Pr | Me | OCH₂CH(Et)OMe | SO₂Me |
| 1564 | Me | H | i-Pr | Me | (1,3-dioxolan-2-yl)methyl | SO₂Me |
| 1565 | Me | H | i-Pr | Me | CH₂O(i-Pr) | SO₂Me |
| 1567 | Me | Me | Et | Me | CO₂Me | SO₂Me |
| 1568 | Et | Me | Et | Me | CO₂Me | SO₂Me |
| 1569 | Me | Me | Me | Me | CO₂Me | SO₂Me |
| 1570 | Et | Me | Me | Me | CO₂Me | SO₂Me |
| 1571 | n-Pr | Me | Et | Me | CO₂Me | SO₂Me |
| 1572 | c-Pr | Me | Et | Me | CO₂Me | SO₂Me |
| 1573 | n-Pr | Me | Me | Me | CO₂Me | SO₂Me |
| 1574 | c-Pr | Me | Me | Me | CO₂Me | SO₂Me |
| 1575 | t-Bu | Me | Et | Me | CO₂Me | SO₂Me |
| 1576 | t-Bu | Me | Me | Me | CO₂Me | SO₂Me |
| 1577 | Et | Me | Et | Me | CO₂(i-Pr) | SO₂Me |
| 1578 | Me | Me | Et | Me | CO₂Et | SO₂Me |
| 1579 | Et | Me | Et | Me | CO₂Me | NO₂ |
| 1580 | Et | Me | Et | SO₂Me | CO₂Me | CF₃ |
| 1581 | Et | Me | Et | Me | OCH₂CH₂OMe | SO₂Me |
| 1582 | Et | Me | Et | Cl | OCH₂CH₂OMe | SO₂Me |
| 1583 | Et | Me | Et | Me | CO₂Me | CN |
| 1584 | Me | Me | Et | Me | C(O)SMe | SO₂Me |
| 1585 | Et | Me | Et | Me | C(O)SMe | SO₂Me |
| 1586 | Me | Me | Me | Me | C(O)SEt | SO₂Me |
| 1587 | Et | Me | Me | Me | C(O)SEt | SO₂Me |
| 1588 | Me | Me | Et | Me | 2-(2-oxolanyl)ethoxy | SO₂Me |
| 1589 | Me | Me | Et | Me | 2-(2-(1,3-dioxolanyl))ethoxy | SO₂Me |
| 1590 | Et | Me | Et | Me | CH₂OMe | SO₂Me |
| 1591 | Et | Me | Et | Me | 2-oxolanylmethoxymethyl | SO₂Me |
| 1592 | Me | Me | Et | Cl | CO₂Me | SO₂Et |
| 1593 | Et | Me | Et | Cl | CO₂Me | SO₂Me |
| 1594 | Me | Me | Me | Cl | CO₂Me | SO₂Me |
| 1595 | Et | Me | Me | Br | CO₂Me | SO₂Me |
| 1596 | Me | Me | Et | Cl | C(O)SMe | SO₂Me |

TABLE 1-continued (I)

| No. | R¹ | R² | R³ | R⁴ | R⁵ | R⁶ |
|---|---|---|---|---|---|---|
| 1597 | Et | Me | Et | Cl | C(O)SMe | SO₂Me |
| 1598 | Me | Me | Et | Cl | C(O)SEt | SO₂Me |
| 1599 | Et | Me | Et | Cl | C(O)SEt | SO₂Me |
| 1600 | Me | Me | Et | Me | OMe | SO₂Me |
| 1601 | Me | Me | Et | Me | OEt | SO₂Me |
| 1602 | Me | Me | Et | Me | O(i-Pr) | SO₂Me |
| 1603 | Me | Me | Et | Me | OCHF₂ | SO₂Me |
| 1604 | Me | Me | Et | Me | (4,5-dihydroisoxazol-3-yl) | SO₂Me |
| 1605 | Me | Me | Me | Me | (4,5-dihydroisoxazol-3-yl) | SO₂Me |
| 1606 | Me | Me | Et | Me | O(n-Pr) | SO₂Et |
| 1607 | Me | Me | Et | Cl | CH₂OMe | SO₂Me |
| 1608 | Me | Me | Et | Me | OCO₂Me | SO₂Me |
| 1609 | Et | Me | Et | Me | OCO₂Me | SO₂Me |
| 1610 | Me | Me | Me | Me | OCO₂Me | SO₂Me |
| 1611 | Et | Me | Me | Me | OCO₂Me | SO₂Me |
| 1612 | Me | Me | Et | Me | OC(O)SMe | SO₂Me |
| 1613 | Et | Me | Et | Me | OC(O)SMe | SO₂Me |
| 1614 | Me | Me | Me | Me | OC(O)SMe | SO₂Me |
| 1615 | Et | Me | Me | Me | OC(O)SMe | SO₂Me |
| 1616 | Me | Me | Et | Me | OC(O)SEt | SO₂Me |
| 1617 | Et | Me | Et | Me | OC(O)SEt | SO₂Me |
| 1618 | Me | Me | Me | Me | OC(O)SEt | SO₂Me |
| 1619 | Et | Me | Me | Me | OC(O)SEt | SO₂Me |
| 1620 | Me | Me | Et | Me | OCH₂CH₂OMe | SO₂Me |
| 1621 | Me | Me | Me | Me | OCH₂CH₂OMe | SO₂Et |
| 1622 | Me | Me | Et | Cl | OCH₂CH₂OMe | SO₂Me |
| 1623 | Et | Me | Et | Me | OEt | SO₂Me |
| 1624 | Et | Me | Et | Cl | CO₂Et | SO₂Me |
| 1625 | Et | Me | Et | Cl | CO₂(n-Pr) | SO₂Me |
| 1626 | Et | Me | Et | Me | CO₂Et | SO₂Me |
| 1627 | Et | Me | Me | Me | CO₂Et | SO₂Me |
| 1628 | Me | Me | Et | Me | CH₂OMe | SO₂Me |
| 1629 | Me | Me | Et | Me | CH₂CO₂Me | SO₂Me |
| 1630 | Me | Me | Et | Me | OCH₂CO₂Et | SO₂Me |
| 1631 | Me | Me | Et | Me | O(n-Pr) | SO₂Me |
| 1632 | Et | Me | Et | Me | O(n-Pr) | SO₂Me |
| 1633 | Et | Me | Et | SO₂Me | H | CF₃ |
| 1634 | Me | Me | Et | Me | CH₂OCH₂CF₃ | SO₂Me |
| 1635 | Me | Me | Et | Cl | CH₂OCH₂CF₃ | SO₂Me |
| 1636 | Et | Me | Et | Me | Cl | SO₂Me |
| 1637 | Me | Me | Et | Me | CH₂SO₂Me | SO₂Me |
| 1638 | Me | Me | Et | Me | CH₂OEt | SO₂Me |
| 1639 | Me | Me | Me | Cl | CH₂OMe | SO₂Me |
| 1640 | Me | Me | Et | Me | CH₂CH₂OMe | SO₂Me |
| 1641 | Me | Me | Et | Me | CH₂OCH₂CH₂OMe | SO₂Me |
| 1642 | Me | Me | Et | Me | OCH₂CH₂OEt | SO₂Me |
| 1643 | Me | Me | Et | Me | OCH₂CH₂Cl | SO₂Me |
| 1644 | Me | Me | Et | Me | OCH₂CF₃ | SO₂Me |
| 1645 | Me | Me | Et | Me | CH₂OCH₂OMe | SO₂Me |
| 1646 | Me | Me | Et | Me | OCH₂CH₂SMe | SO₂Me |
| 1647 | Me | Me | Et | Me | CN | SO₂Me |
| 1648 | Me | Me | Et | Me | CH₂CN | SO₂Me |
| 1649 | Me | Me | n-Pr | Me | CO₂Me | SO₂Me |
| 1650 | Et | Me | n-Pr | Me | CO₂Me | SO₂Me |
| 1651 | Me | Me | i-Pr | Me | CO₂Me | SO₂Me |
| 1652 | Et | Me | i-Pr | Me | CO₂Me | SO₂Me |
| 1653 | Me | Me | s-Bu | Me | CO₂Me | SO₂Me |
| 1654 | Et | Me | s-Bu | Me | CO₂Me | SO₂Me |
| 1655 | Me | Me | Bn | Me | CO₂Me | SO₂Me |
| 1656 | Et | Me | Bn | Me | CO₂Me | SO₂Me |
| 1657 | Me | Me | Et | Br | CO₂Me | SO₂Me |
| 1658 | Et | Me | Et | Cl | CO₂Me | SO₂Me |
| 1659 | Me | Me | Me | Br | CO₂Me | SO₂Me |
| 1660 | Et | Me | Me | Cl | CO₂Me | SO₂Me |
| 1661 | Me | Me | Allyl | Me | CO₂Me | SO₂Me |

TABLE 1-continued

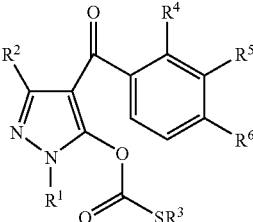

| No. | R$^1$ | R$^2$ | R$^3$ | R$^4$ | R$^5$ | R$^6$ |
|---|---|---|---|---|---|---|
| 1662 | Et | Me | Allyl | Me | CO$_2$Me | SO$_2$Me |
| 1663 | Me | Me | CH$_2$CH(CH$_3$)=CH$_2$ | Me | CO$_2$Me | SO$_2$Me |
| 1664 | Et | Me | CH$_2$CH(CH$_3$)=CH$_2$ | Me | CO$_2$Me | SO$_2$Me |
| 1665 | Me | Me | Et | Cl | OCH$_2$CH$_2$OCF$_3$ | SO$_2$Me |
| 1666 | Et | Me | Et | Cl | OCH$_2$CH$_2$OCF$_3$ | SO$_2$Me |
| 1667 | Me | Me | Et | Me | OCH$_2$CH$_2$OCF$_3$ | SO$_2$Me |
| 1668 | Et | Me | Et | Me | OCH$_2$CH$_2$OCF$_3$ | SO$_2$Me |
| 1669 | Me | Me | Et | CF$_3$ | OCH$_2$CH$_2$OCF$_3$ | SO$_2$Me |
| 1670 | Et | Me | Et | CF$_3$ | OCH$_2$CH$_2$OCF$_3$ | SO$_2$Me |
| 1671 | Me | Me | Et | Br | OCH$_2$CH$_2$OCF$_3$ | SO$_2$Me |
| 1672 | Et | Me | Et | Br | OCH$_2$CH$_2$OCF$_3$ | SO$_2$Me |
| 1673 | Me | Me | Et | SO$_2$Me | OCH$_2$CH$_2$OCF$_3$ | SO$_2$Me |
| 1674 | Et | Me | Et | SO$_2$Me | OCH$_2$CH$_2$OCF$_3$ | SO$_2$Me |
| 1675 | Me | Me | Et | Cl | OCH$_2$CH$_2$OCHClF | SO$_2$Me |
| 1676 | Et | Me | Et | Cl | OCH$_2$CH$_2$OCHClF | SO$_2$Me |
| 1677 | Me | Me | Et | Me | OCH$_2$CH$_2$OCHClF | SO$_2$Me |
| 1678 | Et | Me | Et | Me | OCH$_2$CH$_2$OCHClF | SO$_2$Me |
| 1679 | Me | Me | Et | CF$_3$ | OCH$_2$CH$_2$OCHClF | SO$_2$Me |
| 1680 | Et | Me | Et | CF$_3$ | OCH$_2$CH$_2$OCHClF | SO$_2$Me |
| 1681 | Me | Me | Et | Br | OCH$_2$CH$_2$OCHClF | SO$_2$Me |
| 1682 | Et | Me | Et | Br | OCH$_2$CH$_2$OCHClF | SO$_2$Me |
| 1683 | Me | Me | Et | SO$_2$Me | OCH$_2$CH$_2$OCHClF | CF$_3$ |
| 1684 | Et | Me | Et | SO$_2$Me | OCH$_2$CH$_2$OCHClF | CF$_3$ |
| 1685 | Me | Me | Et | Cl | OCH$_2$CHFOCF$_3$ | SO$_2$Me |
| 1686 | Et | Me | Et | Cl | OCH$_2$CHFOCF$_3$ | SO$_2$Me |
| 1687 | Me | Me | Et | Me | OCH$_2$CHFOCF$_3$ | SO$_2$Me |
| 1688 | Me | Me | Et | Cl | OCH$_2$CHFOMe | SO$_2$Me |
| 1689 | Et | Me | Et | Cl | OCH$_2$CHFOMe | SO$_2$Me |
| 1690 | Me | Me | Et | Me | OCH$_2$CHFOMe | SO$_2$Me |
| 1691 | Et | Me | Et | Me | OCH$_2$CHFOMe | SO$_2$Me |
| 1692 | Me | Me | Et | CF$_3$ | OCH$_2$CHFOMe | SO$_2$Me |
| 1693 | Et | Me | Et | CF$_3$ | OCH$_2$CHFOMe | SO$_2$Me |
| 1694 | Me | Me | Et | Br | OCH$_2$CHFOMe | SO$_2$Me |
| 1695 | Et | Me | Et | Br | OCH$_2$CHFOMe | SO$_2$Me |
| 1696 | Me | Me | Et | SO$_2$Me | OCH$_2$CHFOMe | CF$_3$ |
| 1697 | Et | Me | Et | SO$_2$Me | OCH$_2$CHFOMe | CF$_3$ |
| 1698 | Me | Me | Et | Cl | OCHFCH$_2$OCF$_3$ | SO$_2$Me |
| 1699 | Et | Me | Et | Cl | OCHFCH$_2$OCF$_3$ | SO$_2$Me |
| 1700 | Me | Me | Et | Cl | OCH$_2$CH$_2$OCF$_2$Cl | SO$_2$Me |
| 1701 | Et | Me | Et | Cl | OCH$_2$CH$_2$OCF$_2$Cl | SO$_2$Me |
| 1702 | Me | Me | Et | Me | OCH$_2$CH$_2$OCF$_2$Cl | SO$_2$Me |
| 1703 | Et | Me | Et | Me | OCH$_2$CH$_2$OCF$_2$Cl | SO$_2$Me |
| 1704 | Me | Me | Et | CF$_3$ | OCH$_2$CH$_2$OCF$_2$Cl | SO$_2$Me |
| 1705 | Et | Me | Et | CF$_3$ | OCH$_2$CH$_2$OCF$_2$Cl | SO$_2$Me |
| 1706 | Me | Me | Et | Br | OCH$_2$CH$_2$OCF$_2$Cl | SO$_2$Me |
| 1707 | Et | Me | Et | Br | OCH$_2$CH$_2$OCF$_2$Cl | SO$_2$Me |
| 1708 | Me | Me | Et | SO$_2$Me | OCH$_2$CH$_2$OCF$_2$Cl | CF$_3$ |
| 1709 | Et | Me | Et | SO$_2$Me | OCH$_2$CH$_2$OCF$_2$Cl | CF$_3$ |
| 1710 | Me | Me | Et | Cl | SCH$_2$CH$_2$OCH$_3$ | SO$_2$Me |
| 1711 | Et | Me | Et | Cl | SCH$_2$CH$_2$OCH$_3$ | SO$_2$Me |
| 1712 | Me | Me | Et | Me | SCH$_2$CH$_2$OCH$_3$ | SO$_2$Me |
| 1713 | Et | Me | Et | Me | SCH$_2$CH$_2$OCH$_3$ | SO$_2$Me |
| 1714 | Me | Me | Et | CF$_3$ | SCH$_2$CH$_2$OCH$_3$ | SO$_2$Me |
| 1715 | Et | Me | Et | CF$_3$ | SCH$_2$CH$_2$OCH$_3$ | SO$_2$Me |
| 1716 | Me | Me | Et | Br | SCH$_2$CH$_2$OCH$_3$ | SO$_2$Me |
| 1717 | Et | Me | Et | Br | SCH$_2$CH$_2$OCH$_3$ | SO$_2$Me |
| 1718 | Me | Me | Et | SO$_2$Me | SCH$_2$CH$_2$OCH$_3$ | CF$_3$ |
| 1719 | Et | Me | Et | SO$_2$Me | SCH$_2$CH$_2$OCH$_3$ | CF$_3$ |
| 1720 | Me | Me | Et | Cl | SCH$_2$CH$_2$OCF$_3$ | SO$_2$Me |
| 1721 | Et | Me | Et | Cl | SCH$_2$CH$_2$OCF$_3$ | SO$_2$Me |
| 1722 | Me | Me | Et | Me | SCH$_2$CH$_2$OCF$_3$ | SO$_2$Me |
| 1723 | Et | Me | Et | Me | SCH$_2$CH$_2$OCF$_3$ | SO$_2$Me |
| 1724 | Me | Me | Et | CF$_3$ | SCH$_2$CH$_2$OCF$_3$ | SO$_2$Me |
| 1725 | Et | Me | Et | CF$_3$ | SCH$_2$CH$_2$OCF$_3$ | SO$_2$Me |
| 1726 | Me | Me | Et | Br | SCH$_2$CH$_2$OCF$_3$ | SO$_2$Me |

TABLE 1-continued

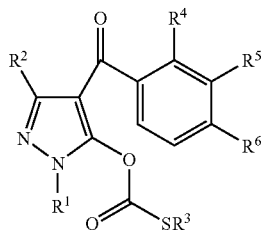

| No. | R¹ | R² | R³ | R⁴ | R⁵ | R⁶ |
|---|---|---|---|---|---|---|
| 1727 | Et | Me | Et | Br | $SCH_2CH_2OCF_3$ | $SO_2Me$ |
| 1728 | Me | Me | Et | $SO_2Me$ | $SCH_2CH_2OCF_3$ | $CF_3$ |
| 1729 | Et | Me | Et | $SO_2Me$ | $SCH_2CH_2OCF_3$ | $CF_3$ |
| 1730 | Me | Me | Et | Cl | $SCH_2CH_2SCH_3$ | $SO_2Me$ |
| 1731 | Et | Me | Et | Cl | $SCH_2CH_2SCH_3$ | $SO_2Me$ |
| 1732 | Me | Me | Et | Me | $SCH_2CH_2SCH_3$ | $SO_2Me$ |
| 1733 | Et | Me | Et | Me | $SCH_2CH_2SCH_3$ | $SO_2Me$ |
| 1734 | Me | Me | Et | $CF_3$ | $SCH_2CH_2SCH_3$ | $SO_2Me$ |
| 1735 | Et | Me | Et | $CF_3$ | $SCH_2CH_2SCH_3$ | $SO_2Me$ |
| 1736 | Me | Me | Et | Br | $SCH_2CH_2SCH_3$ | $SO_2Me$ |
| 1737 | Et | Me | Et | Br | $SCH_2CH_2SCH_3$ | $SO_2Me$ |
| 1738 | Me | Me | Et | $SO_2Me$ | $SCH_2CH_2SCH_3$ | $CF_3$ |
| 1739 | Et | Me | Et | $SO_2Me$ | $SCH_2CH_2SCH_3$ | $CF_3$ |
| 1740 | Me | Me | Et | Cl | $SCH_2CH_2SCF_3$ | $SO_2Me$ |
| 1741 | Et | Me | Et | Cl | $SCH_2CH_2SCF_3$ | $SO_2Me$ |
| 1742 | Me | Me | Et | Me | $SCH_2CH_2SCF_3$ | $SO_2Me$ |
| 1743 | Et | Me | Et | Me | $SCH_2CH_2SCF_3$ | $SO_2Me$ |
| 1744 | Me | Me | Et | $CF_3$ | $SCH_2CH_2SCF_3$ | $SO_2Me$ |
| 1745 | Et | Me | Et | $CF_3$ | $SCH_2CH_2SCF_3$ | $SO_2Me$ |
| 1746 | Me | Me | Et | Br | $SCH_2CH_2SCF_3$ | $SO_2Me$ |
| 1747 | Et | Me | Et | Br | $SCH_2CH_2SCF_3$ | $SO_2Me$ |
| 1748 | Me | Me | Et | $SO_2Me$ | $SCH_2CH_2SCF_3$ | $CF_3$ |
| 1749 | Et | Me | Et | $SO_2Me$ | $SCH_2CH_2SCF_3$ | $CF_3$ |
| 1750 | Me | Me | Et | Cl | $OCH_2CH(CH_3)OCH_3$ | $SO_2Me$ |
| 1751 | Et | Me | Et | Cl | $OCH_2CH(CH_3)OCH_3$ | $SO_2Me$ |
| 1752 | Me | Me | Et | Me | $OCH_2CH(CH_3)OCH_3$ | $SO_2Me$ |
| 1753 | Et | Me | Et | Me | $OCH_2CH(CH_3)OCH_3$ | $SO_2Me$ |
| 1754 | Me | Me | Et | $CF_3$ | $OCH_2CH(CH_3)OCH_3$ | $SO_2Me$ |
| 1755 | Et | Me | Et | $CF_3$ | $OCH_2CH(CH_3)OCH_3$ | $SO_2Me$ |
| 1756 | Me | Me | Et | Br | $OCH_2CH(CH_3)OCH_3$ | $SO_2Me$ |
| 1757 | Et | Me | Et | Br | $OCH_2CH(CH_3)OCH_3$ | $SO_2Me$ |
| 1758 | Me | Me | Et | $SO_2Me$ | $OCH_2CH(CH_3)OCH_3$ | $CF_3$ |
| 1759 | Et | Me | Et | $SO_2Me$ | $OCH_2CH(CH_3)OCH_3$ | $CF_3$ |
| 1760 | Me | Me | Et | Cl | $OCH_2CF_2OCH_3$ | $SO_2Me$ |
| 1761 | Et | Me | Et | Cl | $OCH_2CF_2OCH_3$ | $SO_2Me$ |
| 1762 | Me | Me | Et | Me | $OCH_2CF_2OCH_3$ | $SO_2Me$ |
| 1763 | Et | Me | Et | Me | $OCH_2CF_2OCH_3$ | $SO_2Me$ |
| 1764 | Me | Me | Et | $CF_3$ | $OCH_2CF_2OCH_3$ | $SO_2Me$ |
| 1765 | Et | Me | Et | $CF_3$ | $OCH_2CF_2OCH_3$ | $SO_2Me$ |
| 1766 | Me | Me | Et | Br | $OCH_2CF_2OCH_3$ | $SO_2Me$ |
| 1767 | Et | Me | Et | Br | $OCH_2CF_2OCH_3$ | $SO_2Me$ |
| 1768 | Me | Me | Et | $SO_2Me$ | $OCH_2CF_2OCH_3$ | $CF_3$ |
| 1769 | Et | Me | Et | $SO_2Me$ | $OCH_2CF_2OCH_3$ | $CF_3$ |
| 1770 | Me | Me | i-Pr | Me | $OCH_2CH_2OCH_3$ | $SO_2Me$ |
| 1771 | Et | Me | i-Pr | Me | $OCH_2CH_2OCH_3$ | $SO_2Me$ |
| 1772 | Me | Me | Et | Me | $OCH_2CH(OCH_3)_2$ | $SO_2Me$ |
| 1773 | Me | Me | Et | Me | $CH_2N(Me)CH_2CN$ | $SO_2Me$ |
| 1774 | Me | Me | Et | Me | (tetrahydrofuran-2-yl)methoxy | $SO_2Me$ |
| 1775 | Me | Me | Et | Cl | SMe | $SO_2Me$ |
| 1776 | Me | Me | Et | Cl | Cl | $SO_2Me$ |
| 1777 | Me | Me | Et | Cl | OMe | $SO_2Me$ |
| 1778 | Me | Me | Et | Me | (tetrahydro-2H-pyran-2-yl)methoxy | $SO_2Me$ |
| 1779 | Me | Me | Et | CN | $OCH_2CH_2OMe$ | $SO_2Me$ |
| 1780 | Me | Me | Et | Me | tetrahydrofuran-3-yloxy | $SO_2Me$ |
| 1781 | Me | Me | Et | Me | $OCH_2CH_2CH_2OMe$ | $SO_2Me$ |
| 1782 | Me | Me | n-Pr | Me | $OCH_2CH_2OMe$ | $SO_2Me$ |
| 1783 | Et | Me | s-Bu | Cl | C(O)OMe | $SO_2Me$ |
| 1784 | Et | Me | Et | Cl | 2-(1,3-dioxolan-2-yl)ethoxy | $SO_2Me$ |
| 1785 | Me | Me | Et | Me | propargyloxy | $SO_2Me$ |
| 1786 | Me | Me | Et | Me | (tetrahydrofuran-3-yloxy)methyl | $SO_2Me$ |
| 1787 | Me | Me | Et | Cl | $SO_2Me$ | $SO_2Me$ |
| 1788 | Me | Me | Et | Me | $(CH_2)_6Me$ | $SO_2Me$ |
| 1789 | Me | Me | Et | Me | $CH_2CH_2CH_2OMe$ | $SO_2Me$ |
| 1790 | Et | Me | Et | Cl | (1,3-dioxolan-2-yl)methoxy | $SO_2Me$ |
| 1791 | Me | Me | Et | Me | $CH_2N[C(O)SEt]CH_2CN$ | $SO_2Me$ |

TABLE 1-continued

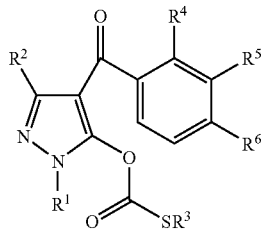

(I)

| No. | R¹ | R² | R³ | R⁴ | R⁵ | R⁶ |
|---|---|---|---|---|---|---|
| 1792 | Me | Me | Et | Me | CH=CHCN | $SO_2Me$ |
| 1793 | Me | Me | Et | Me | $CH_2CH_2CN$ | $SO_2Me$ |
| 1794 | Me | Me | Et | Me | $CH_2SCN$ | $SO_2Me$ |
| 1795 | Me | Me | Et | Me | $CH_2C(S)NH_2$ | $SO_2Me$ |
| 1796 | Me | Me | Me | Me | $OCH_2CH_2OMe$ | $SO_2Me$ |
| 1797 | Et | Me | Me | Me | $OCH_2CH_2OMe$ | $SO_2Me$ |
| 1798 | Et | Me | n-Pr | Me | $OCH_2CH_2OMe$ | $SO_2Me$ |
| 1799 | Me | Me | Et | Me | $OCH(CH_3)CH_2OMe$ | $SO_2Me$ |
| 1800 | Et | Me | Et | Me | $OCH_2CH(Et)OMe$ | $SO_2Me$ |
| 1801 | Me | Me | Et | Me | (1,3-dioxolan-2-yl)methyl | $SO_2Me$ |
| 1802 | Me | Me | s-Bu | Me | $OCH_2CH_2OMe$ | $SO_2Me$ |
| 1803 | Me | Me | Et | Me | $CH_2O(i-Pr)$ | $SO_2Me$ |
| 1804 | Me | H | $CH_2CF_3$ | Cl | $CO_2Et$ | $SO_2Me$ |
| 1805 | Et | H | $CH_2CF_3$ | Me | $CO_2Me$ | $CF_3$ |
| 1806 | Et | H | $CH_2CF_3$ | $SO_2Me$ | $CO_2Me$ | CN |
| 1807 | Me | H | $CH_2CF_3$ | Me | C(O)SMe | $SO_2Me$ |
| 1808 | Me | H | $CH_2CF_3$ | Me | C(O)SEt | $SO_2Me$ |
| 1809 | Me | H | $CH_2CF_3$ | Me | 2-(2-oxolanyl)ethoxy | $SO_2Me$ |
| 1810 | Me | H | $CH_2CF_3$ | Me | 2-(2-(1,3-dioxolanyl))ethoxy | $SO_2Me$ |
| 1811 | Et | H | $CH_2CF_3$ | Me | $CH_2OMe$ | $SO_2Me$ |
| 1812 | Et | H | $CH_2CF_3$ | Me | 2-oxolanylmethoxymethyl | $SO_2Me$ |
| 1813 | Me | H | $CH_2CF_3$ | Cl | $CO_2Me$ | $SO_2Me$ |
| 1814 | Et | H | $CH_2CF_3$ | Cl | $CO_2Me$ | $SO_2Et$ |
| 1815 | Me | H | $CH_2CF_3$ | Cl | C(O)SMe | $SO_2Me$ |
| 1816 | Me | H | $CH_2CF_3$ | Cl | C(O)SEt | $SO_2Me$ |
| 1817 | Me | H | $CH_2CF_3$ | Me | OMe | $SO_2Me$ |
| 1818 | Me | H | $CH_2CF_3$ | Me | OEt | $SO_2Me$ |
| 1819 | Me | H | $CH_2CF_3$ | Me | O(i-Pr) | $SO_2Me$ |
| 1820 | Me | H | $CH_2CF_3$ | Me | $OCHF_2$ | $SO_2Me$ |
| 1821 | Me | H | $CH_2CF_3$ | Me | (4,5-dihydroisoxazol-3-yl) | $SO_2Me$ |
| 1822 | Me | H | $CH_2CF_3$ | Me | O(n-Pr) | $SO_2Et$ |
| 1823 | Me | H | $CH_2CF_3$ | Cl | $CH_2OMe$ | $SO_2Me$ |
| 1824 | Me | H | $CH_2CF_3$ | Me | $OCO_2Me$ | $SO_2Me$ |
| 1825 | Me | H | $CH_2CF_3$ | Me | OC(O)SMe | $SO_2Me$ |
| 1826 | Me | H | $CH_2CF_3$ | Me | OC(O)SEt | $SO_2Me$ |
| 1827 | Et | H | $CH_2CF_3$ | Me | OEt | $SO_2Me$ |
| 1828 | Et | H | $CH_2CF_3$ | Cl | $CO_2Et$ | $SO_2Me$ |
| 1829 | Et | H | $CH_2CF_3$ | Cl | $CO_2(n-Pr)$ | $SO_2Me$ |
| 1830 | Et | H | $CH_2CF_3$ | Me | $CO_2Et$ | $SO_2Me$ |
| 1831 | Me | H | $CH_2CF_3$ | Me | $CH_2CO_2Me$ | $SO_2Me$ |
| 1832 | Me | H | $CH_2CF_3$ | Me | $OCH_2CO_2Et$ | $SO_2Me$ |
| 1833 | Me | H | $CH_2CF_3$ | Me | O(n-Pr) | $SO_2Me$ |
| 1834 | Et | H | $CH_2CF_3$ | $SO_2Me$ | H | $CF_3$ |
| 1835 | Me | H | $CH_2CF_3$ | Me | $CH_2OCH_2CF_3$ | $SO_2Me$ |
| 1836 | Me | H | $CH_2CF_3$ | Cl | $CH_2OCH_2CF_3$ | $SO_2Me$ |
| 1837 | Et | H | $CH_2CF_3$ | Me | Cl | $SO_2Me$ |
| 1838 | Me | H | $CH_2CF_3$ | Me | $CH_2SO_2Me$ | $SO_2Me$ |
| 1839 | Me | H | $CH_2CF_3$ | Me | $CH_2OEt$ | $SO_2Me$ |
| 1840 | Me | H | $CH_2CF_3$ | Cl | $CH_2OMe$ | $SO_2Me$ |
| 1841 | Me | H | $CH_2CF_3$ | Me | $CH_2CH_2OMe$ | $SO_2Me$ |
| 1842 | Me | H | $CH_2CF_3$ | Me | $CH_2OCH_2CH_2OMe$ | $SO_2Me$ |
| 1843 | Me | H | $CH_2CF_3$ | Me | $OCH_2CH_2OEt$ | $SO_2Me$ |
| 1844 | Me | H | $CH_2CF_3$ | Me | $OCH_2CH_2Cl$ | $SO_2Me$ |
| 1845 | Me | H | $CH_2CF_3$ | Me | $OCH_2CF_3$ | $SO_2Me$ |
| 1846 | Me | H | $CH_2CF_3$ | Me | $CH_2OCH_2OMe$ | $SO_2Me$ |
| 1847 | Me | H | $CH_2CF_3$ | Me | $OCH_2CH_2SMe$ | $SO_2Me$ |
| 1848 | Me | H | $CH_2CF_3$ | Me | CN | $SO_2Me$ |
| 1849 | Me | H | $CH_2CF_3$ | Me | $CH_2CN$ | $SO_2Me$ |
| 1850 | Me | H | $CH_2CF_3$ | Br | $CO_2Me$ | $SO_2Me$ |
| 1851 | Et | H | $CH_2CF_3$ | Cl | $CO_2Me$ | $SO_2Me$ |
| 1852 | Me | H | $CH_2CF_3$ | CN | $CO_2Me$ | $SO_2Me$ |
| 1853 | Me | H | $CH_2CF_3$ | Cl | $OCH_2CH_2OCF_3$ | $SO_2Me$ |
| 1854 | Et | H | $CH_2CF_3$ | Cl | $OCH_2CH_2OCF_3$ | $SO_2Me$ |
| 1855 | Me | H | $CH_2CF_3$ | Me | $OCH_2CH_2OCF_3$ | $SO_2Me$ |
| 1856 | Et | H | $CH_2CF_3$ | Me | $OCH_2CH_2OCF_3$ | $SO_2Me$ |

TABLE 1-continued (I)

[Structure: pyrazole ring with R¹ on N, R² on position 3, carbonyl linking to benzene ring bearing R⁴, R⁵, R⁶; pyrazole 5-position has O-C(=O)-SR³ group]

| No. | R¹ | R² | R³ | R⁴ | R⁵ | R⁶ |
|---|---|---|---|---|---|---|
| 1857 | Me | H | CH₂CF₃ | CF₃ | OCH₂CH₂OCF₃ | SO₂Me |
| 1858 | Et | H | CH₂CF₃ | CF₃ | OCH₂CH₂OCF₃ | SO₂Me |
| 1859 | Me | H | CH₂CF₃ | Br | OCH₂CH₂OCF₃ | SO₂Me |
| 1860 | Et | H | CH₂CF₃ | Br | OCH₂CH₂OCF₃ | SO₂Me |
| 1861 | Me | H | CH₂CF₃ | SO₂Me | OCH₂CH₂OCF₃ | CF₃ |
| 1862 | Et | H | CH₂CF₃ | SO₂Me | OCH₂CH₂OCF₃ | CF₃ |
| 1863 | Me | H | CH₂CF₃ | Cl | OCH₂CH₂OCHClF | SO₂Me |
| 1864 | Et | H | CH₂CF₃ | Cl | OCH₂CH₂OCHClF | SO₂Me |
| 1865 | Me | H | CH₂CF₃ | Me | OCH₂CH₂OCHClF | SO₂Me |
| 1866 | Et | H | CH₂CF₃ | Me | OCH₂CH₂OCHClF | SO₂Me |
| 1867 | Me | H | CH₂CF₃ | CF₃ | OCH₂CH₂OCHClF | SO₂Me |
| 1868 | Et | H | CH₂CF₃ | CF₃ | OCH₂CH₂OCHClF | SO₂Me |
| 1869 | Me | H | CH₂CF₃ | Br | OCH₂CH₂OCHClF | SO₂Me |
| 1870 | Et | H | CH₂CF₃ | Br | OCH₂CH₂OCHClF | SO₂Me |
| 1871 | Me | H | CH₂CF₃ | SO₂Me | OCH₂CH₂OCHClF | CF₃ |
| 1872 | Et | H | CH₂CF₃ | SO₂Me | OCH₂CH₂OCHClF | CF₃ |
| 1873 | Me | H | CH₂CF₃ | Cl | OCH₂CHFOCF₃ | CF₃ |
| 1874 | Et | H | CH₂CF₃ | Cl | OCH₂CHFOCF₃ | CF₃ |
| 1875 | Me | H | CH₂CF₃ | Me | OCH₂CHFOCF₃ | SO₂Me |
| 1876 | Me | H | CH₂CF₃ | Cl | OCH₂CHFOMe | SO₂Me |
| 1877 | Et | H | CH₂CF₃ | Cl | OCH₂CHFOMe | SO₂Me |
| 1878 | Me | H | CH₂CF₃ | Me | OCH₂CHFOMe | SO₂Me |
| 1879 | Et | H | CH₂CF₃ | Me | OCH₂CHFOMe | SO₂Me |
| 1880 | Me | H | CH₂CF₃ | CF₃ | OCH₂CHFOMe | SO₂Me |
| 1881 | Et | H | CH₂CF₃ | CF₃ | OCH₂CHFOMe | SO₂Me |
| 1882 | Me | H | CH₂CF₃ | Br | OCH₂CHFOMe | SO₂Me |
| 1883 | Et | H | CH₂CF₃ | Br | OCH₂CHFOMe | SO₂Me |
| 1884 | Me | H | CH₂CF₃ | SO₂Me | OCH₂CHFOMe | CF₃ |
| 1885 | Et | H | CH₂CF₃ | SO₂Me | OCH₂CHFOMe | CF₃ |
| 1886 | Me | H | CH₂CF₃ | Cl | OCHFCH₂OCF₃ | SO₂Me |
| 1887 | Et | H | CH₂CF₃ | Cl | OCHFCH₂OCF₃ | SO₂Me |
| 1888 | Me | H | CH₂CF₃ | Cl | OCH₂CH₂OCF₂Cl | SO₂Me |
| 1889 | Et | H | CH₂CF₃ | Cl | OCH₂CH₂OCF₂Cl | SO₂Me |
| 1890 | Me | H | CH₂CF₃ | Me | OCH₂CH₂OCF₂Cl | SO₂Me |
| 1891 | Et | H | CH₂CF₃ | Me | OCH₂CH₂OCF₂Cl | SO₂Me |
| 1892 | Me | H | CH₂CF₃ | CF₃ | OCH₂CH₂OCF₂Cl | SO₂Me |
| 1893 | Et | H | CH₂CF₃ | CF₃ | OCH₂CH₂OCF₂Cl | SO₂Me |
| 1894 | Me | H | CH₂CF₃ | Br | OCH₂CH₂OCF₂Cl | SO₂Me |
| 1895 | Et | H | CH₂CF₃ | Br | OCH₂CH₂OCF₂Cl | SO₂Me |
| 1896 | Me | H | CH₂CF₃ | SO₂Me | OCH₂CH₂OCF₂Cl | CF₃ |
| 1897 | Et | H | CH₂CF₃ | SO₂Me | OCH₂CH₂OCF₂Cl | CF₃ |
| 1898 | Me | H | CH₂CF₃ | Cl | SCH₂CH₂OCH₃ | SO₂Me |
| 1899 | Et | H | CH₂CF₃ | Cl | SCH₂CH₂OCH₃ | SO₂Me |
| 1900 | Me | H | CH₂CF₃ | Me | SCH₂CH₂OCH₃ | SO₂Me |
| 1901 | Et | H | CH₂CF₃ | Me | SCH₂CH₂OCH₃ | SO₂Me |
| 1902 | Me | H | CH₂CF₃ | CF₃ | SCH₂CH₂OCH₃ | SO₂Me |
| 1903 | Et | H | CH₂CF₃ | CF₃ | SCH₂CH₂OCH₃ | SO₂Me |
| 1904 | Me | H | CH₂CF₃ | Br | SCH₂CH₂OCH₃ | SO₂Me |
| 1905 | Et | H | CH₂CF₃ | Br | SCH₂CH₂OCH₃ | SO₂Me |
| 1906 | Me | H | CH₂CF₃ | SO₂Me | SCH₂CH₂OCH₃ | CF₃ |
| 1907 | Et | H | CH₂CF₃ | SO₂Me | SCH₂CH₂OCH₃ | CF₃ |
| 1908 | Me | H | CH₂CF₃ | Cl | SCH₂CH₂OCF₃ | SO₂Me |
| 1909 | Et | H | CH₂CF₃ | Cl | SCH₂CH₂OCF₃ | SO₂Me |
| 1910 | Me | H | CH₂CF₃ | Me | SCH₂CH₂OCF₃ | SO₂Me |
| 1911 | Et | H | CH₂CF₃ | Me | SCH₂CH₂OCF₃ | SO₂Me |
| 1912 | Me | H | CH₂CF₃ | CF₃ | SCH₂CH₂OCF₃ | SO₂Me |
| 1913 | Et | H | CH₂CF₃ | CF₃ | SCH₂CH₂OCF₃ | SO₂Me |
| 1914 | Me | H | CH₂CF₃ | Br | SCH₂CH₂OCF₃ | SO₂Me |
| 1915 | Et | H | CH₂CF₃ | Br | SCH₂CH₂OCF₃ | SO₂Me |
| 1916 | Me | H | CH₂CF₃ | SO₂Me | SCH₂CH₂OCF₃ | CF₃ |
| 1917 | Et | H | CH₂CF₃ | SO₂Me | SCH₂CH₂OCF₃ | CF₃ |
| 1918 | Me | H | CH₂CF₃ | Cl | SCH₂CH₂SCH₃ | SO₂Me |
| 1919 | Et | H | CH₂CF₃ | Cl | SCH₂CH₂SCH₃ | SO₂Me |
| 1920 | Me | H | CH₂CF₃ | Me | SCH₂CH₂SCH₃ | SO₂Me |
| 1921 | Et | H | CH₂CF₃ | Me | SCH₂CH₂SCH₃ | SO₂Me |

TABLE 1-continued

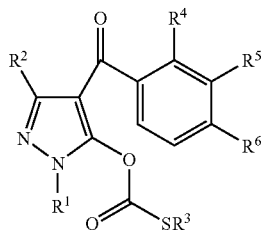

| No. | R$^1$ | R$^2$ | R$^3$ | R$^4$ | R$^5$ | R$^6$ |
|---|---|---|---|---|---|---|
| 1922 | Me | H | CH$_2$CF$_3$ | CF$_3$ | SCH$_2$CH$_2$SCH$_3$ | SO$_2$Me |
| 1923 | Et | H | CH$_2$CF$_3$ | CF$_3$ | SCH$_2$CH$_2$SCH$_3$ | SO$_2$Me |
| 1924 | Me | H | CH$_2$CF$_3$ | Br | SCH$_2$CH$_2$SCH$_3$ | SO$_2$Me |
| 1925 | Et | H | CH$_2$CF$_3$ | Br | SCH$_2$CH$_2$SCH$_3$ | SO$_2$Me |
| 1926 | Me | H | CH$_2$CF$_3$ | SO$_2$Me | SCH$_2$CH$_2$SCH$_3$ | CF$_3$ |
| 1927 | Et | H | CH$_2$CF$_3$ | SO$_2$Me | SCH$_2$CH$_2$SCH$_3$ | CF$_3$ |
| 1928 | Me | H | CH$_2$CF$_3$ | Cl | SCH$_2$CH$_2$SCF$_3$ | SO$_2$Me |
| 1929 | Et | H | CH$_2$CF$_3$ | Cl | SCH$_2$CH$_2$SCF$_3$ | SO$_2$Me |
| 1930 | Me | H | CH$_2$CF$_3$ | Me | SCH$_2$CH$_2$SCF$_3$ | SO$_2$Me |
| 1931 | Et | H | CH$_2$CF$_3$ | Me | SCH$_2$CH$_2$SCF$_3$ | SO$_2$Me |
| 1932 | Me | H | CH$_2$CF$_3$ | CF$_3$ | SCH$_2$CH$_2$SCF$_3$ | SO$_2$Me |
| 1933 | Et | H | CH$_2$CF$_3$ | CF$_3$ | SCH$_2$CH$_2$SCF$_3$ | SO$_2$Me |
| 1934 | Me | H | CH$_2$CF$_3$ | Br | SCH$_2$CH$_2$SCF$_3$ | SO$_2$Me |
| 1935 | Et | H | CH$_2$CF$_3$ | Br | SCH$_2$CH$_2$SCF$_3$ | SO$_2$Me |
| 1936 | Me | H | CH$_2$CF$_3$ | SO$_2$Me | SCH$_2$CH$_2$SCF$_3$ | CF$_3$ |
| 1937 | Et | H | CH$_2$CF$_3$ | SO$_2$Me | SCH$_2$CH$_2$SCF$_3$ | CF$_3$ |
| 1938 | Me | H | CH$_2$CF$_3$ | Cl | OCH$_2$CH(CH$_3$)OCH$_3$ | SO$_2$Me |
| 1939 | Et | H | CH$_2$CF$_3$ | Cl | OCH$_2$CH(CH$_3$)OCH$_3$ | SO$_2$Me |
| 1940 | Me | H | CH$_2$CF$_3$ | Me | OCH$_2$CH(CH$_3$)OCH$_3$ | SO$_2$Me |
| 1941 | Et | H | CH$_2$CF$_3$ | Me | OCH$_2$CH(CH$_3$)OCH$_3$ | SO$_2$Me |
| 1942 | Me | H | CH$_2$CF$_3$ | CF$_3$ | OCH$_2$CH(CH$_3$)OCH$_3$ | SO$_2$Me |
| 1943 | Et | H | CH$_2$CF$_3$ | CF$_3$ | OCH$_2$CH(CH$_3$)OCH$_3$ | SO$_2$Me |
| 1944 | Me | H | CH$_2$CF$_3$ | Br | OCH$_2$CH(CH$_3$)OCH$_3$ | SO$_2$Me |
| 1945 | Et | H | CH$_2$CF$_3$ | Br | OCH$_2$CH(CH$_3$)OCH$_3$ | SO$_2$Me |
| 1946 | Me | H | CH$_2$CF$_3$ | SO$_2$Me | OCH$_2$CH(CH$_3$)OCH$_3$ | CF$_3$ |
| 1947 | Et | H | CH$_2$CF$_3$ | SO$_2$Me | OCH$_2$CH(CH$_3$)OCH$_3$ | CF$_3$ |
| 1948 | Me | H | CH$_2$CF$_3$ | Cl | OCH$_2$CF$_2$OCH$_3$ | SO$_2$Me |
| 1949 | Et | H | CH$_2$CF$_3$ | Cl | OCH$_2$CF$_2$OCH$_3$ | SO$_2$Me |
| 1950 | Me | H | CH$_2$CF$_3$ | Me | OCH$_2$CF$_2$OCH$_3$ | SO$_2$Me |
| 1951 | Et | H | CH$_2$CF$_3$ | Me | OCH$_2$CF$_2$OCH$_3$ | SO$_2$Me |
| 1952 | Me | H | CH$_2$CF$_3$ | CF$_3$ | OCH$_2$CF$_2$OCH$_3$ | SO$_2$Me |
| 1953 | Et | H | CH$_2$CF$_3$ | CF$_3$ | OCH$_2$CF$_2$OCH$_3$ | SO$_2$Me |
| 1954 | Me | H | CH$_2$CF$_3$ | Br | OCH$_2$CF$_2$OCH$_3$ | SO$_2$Me |
| 1955 | Et | H | CH$_2$CF$_3$ | Br | OCH$_2$CF$_2$OCH$_3$ | SO$_2$Me |
| 1956 | Me | H | CH$_2$CF$_3$ | SO$_2$Me | OCH$_2$CF$_2$OCH$_3$ | CF$_3$ |
| 1957 | Et | H | CH$_2$CF$_3$ | SO$_2$Me | OCH$_2$CF$_2$OCH$_3$ | CF$_3$ |
| 1958 | Me | H | CH$_2$CF$_3$ | Me | OCH$_2$CH$_2$OCH$_3$ | SO$_2$Me |
| 1959 | Et | H | CH$_2$CF$_3$ | Me | OCH$_2$CH$_2$OCH$_3$ | SO$_2$Me |
| 1960 | Me | H | CH$_2$CF$_3$ | Me | OCH$_2$(OCH$_3$)$_2$ | SO$_2$Me |
| 1961 | Me | H | CH$_2$CF$_3$ | Me | CH$_2$N(Me)CH$_2$CN | SO$_2$Me |
| 1962 | Me | H | CH$_2$CF$_3$ | Me | (tetrahydrofuran-2-yl)methoxy | SO$_2$Me |
| 1963 | Me | H | CH$_2$CF$_3$ | Cl | SMe | SO$_2$Me |
| 1964 | Me | H | CH$_2$CF$_3$ | Cl | Cl | SO$_2$Me |
| 1965 | Me | H | CH$_2$CF$_3$ | Cl | OMe | SO$_2$Me |
| 1966 | Me | H | CH$_2$CF$_3$ | Me | (tetrahydro-2H-pyran-2-yl)methoxy | SO$_2$Me |
| 1967 | Me | H | CH$_2$CF$_3$ | Cl | OCH$_2$CH$_2$OMe | SO$_2$Me |
| 1968 | Me | H | CH$_2$CF$_3$ | Me | tetrahydrofuran-3-yloxy | SO$_2$Me |
| 1969 | Me | H | CH$_2$CF$_3$ | Me | OCH$_2$CH$_2$CH$_2$OMe | SO$_2$Me |
| 1970 | Me | H | CH$_2$CF$_3$ | Me | OCH$_2$CH$_2$OMe | SO$_2$Me |
| 1971 | Et | H | CH$_2$CF$_3$ | Cl | 2-(1,3-dioxolan-2-yl)ethoxy | SO$_2$Me |
| 1972 | Me | H | CH$_2$CF$_3$ | Me | propargyloxy | SO$_2$Me |
| 1973 | Me | H | CH$_2$CF$_3$ | Me | (tetrahydrofuran-3-yloxy)methyl | SO$_2$Me |
| 1974 | Me | H | CH$_2$CF$_3$ | Cl | SO$_2$Me | SO$_2$Me |
| 1975 | Me | H | CH$_2$CF$_3$ | Me | (CH$_2$)$_6$Me | SO$_2$Me |
| 1976 | Me | H | CH$_2$CF$_3$ | Me | CH$_2$CH$_2$CH$_2$OMe | SO$_2$Me |
| 1977 | Et | H | CH$_2$CF$_3$ | Cl | (1,3-dioxolan-2-yl)methoxy | SO$_2$Me |
| 1978 | Me | H | CH$_2$CF$_3$ | Me | CH$_2$N[C(O)SEt]CH$_2$CN | SO$_2$Me |
| 1979 | Me | H | CH$_2$CF$_3$ | Me | CH=CHCN | SO$_2$Me |
| 1980 | Me | H | CH$_2$CF$_3$ | Me | CH$_2$CH$_2$CN | SO$_2$Me |
| 1981 | Me | H | CH$_2$CF$_3$ | Me | CH$_2$SCN | SO$_2$Me |
| 1982 | Me | H | CH$_2$CF$_3$ | Me | CH$_2$C(S)NH$_2$ | SO$_2$Me |
| 1983 | Me | H | CH$_2$CF$_3$ | CN | OCH$_2$CH$_2$OMe | SO$_2$Me |
| 1984 | Et | H | CH$_2$CF$_3$ | Me | OCH$_2$CH$_2$OMe | SO$_2$Me |
| 1985 | Me | H | CH$_2$CF$_3$ | Me | OCH(CH$_3$)CH$_2$OMe | SO$_2$Me |
| 1986 | Et | H | CH$_2$CF$_3$ | Me | OCH$_2$CH(Et)OMe | SO$_2$Me |

TABLE 1-continued

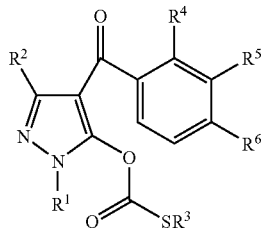

(I)

| No. | $R^1$ | $R^2$ | $R^3$ | $R^4$ | $R^5$ | $R^6$ |
|---|---|---|---|---|---|---|
| 1987 | Me | H | $CH_2CF_3$ | Me | (1,3-dioxolan-2-yl)methyl | $SO_2Me$ |
| 1988 | Me | H | $CH_2CF_3$ | Me | $CH_2O(i\text{-}Pr)$ | $SO_2Me$ |
| 1989 | Me | H | $CH_2CHF_2$ | Cl | $CO_2Et$ | $SO_2Me$ |
| 1990 | Et | H | $CH_2CHF_2$ | Me | $CO_2Me$ | $CF_3$ |
| 1991 | Et | H | $CH_2CHF_2$ | $SO_2Me$ | $CO_2Me$ | CN |
| 1992 | Me | H | $CH_2CHF_2$ | Me | C(O)SMe | $SO_2Me$ |
| 1993 | Me | H | $CH_2CHF_2$ | Me | C(O)SEt | $SO_2Me$ |
| 1994 | Me | H | $CH_2CHF_2$ | Me | 2-(2-oxolanyl)ethoxy | $SO_2Me$ |
| 1995 | Me | H | $CH_2CHF_2$ | Me | 2-(2-(1,3-dioxolanyl))ethoxy | $SO_2Me$ |
| 1996 | Et | H | $CH_2CHF_2$ | Me | $CH_2OMe$ | $SO_2Me$ |
| 1997 | Et | H | $CH_2CHF_2$ | Me | 2-oxolanylmethoxymethyl | $SO_2Me$ |
| 1998 | Me | H | $CH_2CHF_2$ | Cl | $CO_2Me$ | $SO_2Me$ |
| 1999 | Et | H | $CH_2CHF_2$ | Cl | $CO_2Me$ | $SO_2Et$ |
| 2000 | Me | H | $CH_2CHF_2$ | Cl | C(O)SMe | $SO_2Me$ |
| 2001 | Me | H | $CH_2CHF_2$ | Cl | C(O)SEt | $SO_2Me$ |
| 2002 | Me | H | $CH_2CHF_2$ | Me | OMe | $SO_2Me$ |
| 2003 | Me | H | $CH_2CHF_2$ | Me | OEt | $SO_2Me$ |
| 2004 | Me | H | $CH_2CHF_2$ | Me | O(i-Pr) | $SO_2Me$ |
| 2005 | Me | H | $CH_2CHF_2$ | Me | $OCHF_2$ | $SO_2Me$ |
| 2006 | Me | H | $CH_2CHF_2$ | Me | (4,5-dihydroisoxazol-3-yl) | $SO_2Me$ |
| 2007 | Me | H | $CH_2CHF_2$ | Me | O(n-Pr) | $SO_2Et$ |
| 2008 | Me | H | $CH_2CHF_2$ | Cl | $CH_2OMe$ | $SO_2Me$ |
| 2009 | Me | H | $CH_2CHF_2$ | Me | $OCO_2Me$ | $SO_2Me$ |
| 2010 | Me | H | $CH_2CHF_2$ | Me | OC(O)SMe | $SO_2Me$ |
| 2011 | Me | H | $CH_2CHF_2$ | Me | OC(O)SEt | $SO_2Me$ |
| 2012 | Et | H | $CH_2CHF_2$ | Me | OEt | $SO_2Me$ |
| 2013 | Et | H | $CH_2CHF_2$ | Cl | $CO_2Et$ | $SO_2Me$ |
| 2014 | Et | H | $CH_2CHF_2$ | Cl | $CO_2(n\text{-}Pr)$ | $SO_2Me$ |
| 2015 | Et | H | $CH_2CHF_2$ | Me | $CO_2Et$ | $SO_2Me$ |
| 2016 | Me | H | $CH_2CHF_2$ | Me | $CH_2CO_2Me$ | $SO_2Me$ |
| 2017 | Me | H | $CH_2CHF_2$ | Me | $OCH_2CO_2Et$ | $SO_2Me$ |
| 2018 | Me | H | $CH_2CHF_2$ | Me | O(n-Pr) | $SO_2Me$ |
| 2019 | Et | H | $CH_2CHF_2$ | $SO_2Me$ | H | $CF_3$ |
| 2020 | Me | H | $CH_2CHF_2$ | Me | $CH_2OCH_2CF_3$ | $SO_2Me$ |
| 2021 | Me | H | $CH_2CHF_2$ | Cl | $CH_2OCH_2CF_3$ | $SO_2Me$ |
| 2022 | Et | H | $CH_2CHF_2$ | Me | Cl | $SO_2Me$ |
| 2023 | Me | H | $CH_2CHF_2$ | Me | $CH_2SO_2Me$ | $SO_2Me$ |
| 2024 | Me | H | $CH_2CHF_2$ | Me | $CH_2OEt$ | $SO_2Me$ |
| 2025 | Me | H | $CH_2CHF_2$ | Cl | $CH_2OMe$ | $SO_2Me$ |
| 2026 | Me | H | $CH_2CHF_2$ | Me | $CH_2CH_2OMe$ | $SO_2Me$ |
| 2027 | Me | H | $CH_2CHF_2$ | Me | $CH_2OCH_2CH_2OMe$ | $SO_2Me$ |
| 2028 | Me | H | $CH_2CHF_2$ | Me | $OCH_2CH_2OEt$ | $SO_2Me$ |
| 2029 | Me | H | $CH_2CHF_2$ | Me | $OCH_2CH_2Cl$ | $SO_2Me$ |
| 2030 | Me | H | $CH_2CHF_2$ | Me | $OCH_2CF_3$ | $SO_2Me$ |
| 2031 | Me | H | $CH_2CHF_2$ | Me | $CH_2OCH_2OMe$ | $SO_2Me$ |
| 2032 | Me | H | $CH_2CHF_2$ | Me | $OCH_2CH_2SMe$ | $SO_2Me$ |
| 2033 | Me | H | $CH_2CHF_2$ | Me | CN | $SO_2Me$ |
| 2034 | Me | H | $CH_2CHF_2$ | Me | $CH_2CN$ | $SO_2Me$ |
| 2035 | Me | H | $CH_2CHF_2$ | Br | $CO_2Me$ | $SO_2Me$ |
| 2036 | Et | H | $CH_2CHF_2$ | Cl | $CO_2Me$ | $SO_2Me$ |
| 2037 | Me | H | $CH_2CHF_2$ | CN | $CO_2Me$ | $SO_2Me$ |
| 2038 | Me | H | $CH_2CHF_2$ | Cl | $OCH_2CH_2OCF_3$ | $SO_2Me$ |
| 2039 | Et | H | $CH_2CHF_2$ | Cl | $OCH_2CH_2OCF_3$ | $SO_2Me$ |
| 2040 | Me | H | $CH_2CHF_2$ | Me | $OCH_2CH_2OCF_3$ | $SO_2Me$ |
| 2041 | Et | H | $CH_2CHF_2$ | Me | $OCH_2CH_2OCF_3$ | $SO_2Me$ |
| 2042 | Me | H | $CH_2CHF_2$ | $CF_3$ | $OCH_2CH_2OCF_3$ | $SO_2Me$ |
| 2043 | Et | H | $CH_2CHF_2$ | $CF_3$ | $OCH_2CH_2OCF_3$ | $SO_2Me$ |
| 2044 | Me | H | $CH_2CHF_2$ | Br | $OCH_2CH_2OCF_3$ | $SO_2Me$ |
| 2045 | Et | H | $CH_2CHF_2$ | Br | $OCH_2CH_2OCF_3$ | $SO_2Me$ |
| 2046 | Me | H | $CH_2CHF_2$ | $SO_2Me$ | $OCH_2CH_2OCF_3$ | $CF_3$ |
| 2047 | Et | H | $CH_2CHF_2$ | $SO_2Me$ | $OCH_2CH_2OCF_3$ | $CF_3$ |
| 2048 | Me | H | $CH_2CHF_2$ | Cl | $OCH_2CH_2OCHClF$ | $SO_2Me$ |
| 2049 | Et | H | $CH_2CHF_2$ | Cl | $OCH_2CH_2OCHClF$ | $SO_2Me$ |
| 2050 | Me | H | $CH_2CHF_2$ | Me | $OCH_2CH_2OCHClF$ | $SO_2Me$ |
| 2051 | Et | H | $CH_2CHF_2$ | Me | $OCH_2CH_2OCHClF$ | $SO_2Me$ |

TABLE 1-continued

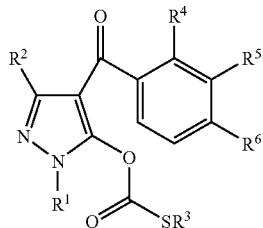

(I)

| No. | R¹ | R² | R³ | R⁴ | R⁵ | R⁶ |
|---|---|---|---|---|---|---|
| 2052 | Me | H | $CH_2CHF_2$ | $CF_3$ | $OCH_2CH_2OCHClF$ | $SO_2Me$ |
| 2053 | Et | H | $CH_2CHF_2$ | $CF_3$ | $OCH_2CH_2OCHClF$ | $SO_2Me$ |
| 2054 | Me | H | $CH_2CHF_2$ | Br | $OCH_2CH_2OCHClF$ | $SO_2Me$ |
| 2055 | Et | H | $CH_2CHF_2$ | Br | $OCH_2CH_2OCHClF$ | $SO_2Me$ |
| 2056 | Me | H | $CH_2CHF_2$ | $SO_2Me$ | $OCH_2CH_2OCHClF$ | $CF_3$ |
| 2057 | Et | H | $CH_2CHF_2$ | $SO_2Me$ | $OCH_2CH_2OCHClF$ | $CF_3$ |
| 2058 | Me | H | $CH_2CHF_2$ | Cl | $OCH_2CHFOCF_3$ | $SO_2Me$ |
| 2059 | Et | H | $CH_2CHF_2$ | Cl | $OCH_2CHFOCF_3$ | $SO_2Me$ |
| 2060 | Me | H | $CH_2CHF_2$ | Me | $OCH_2CHFOCF_3$ | $SO_2Me$ |
| 2061 | Me | H | $CH_2CHF_2$ | Cl | $OCH_2CHFOMe$ | $SO_2Me$ |
| 2062 | Et | H | $CH_2CHF_2$ | Cl | $OCH_2CHFOMe$ | $SO_2Me$ |
| 2063 | Me | H | $CH_2CHF_2$ | Me | $OCH_2CHFOMe$ | $SO_2Me$ |
| 2064 | Et | H | $CH_2CHF_2$ | Me | $OCH_2CHFOMe$ | $SO_2Me$ |
| 2065 | Me | H | $CH_2CHF_2$ | $CF_3$ | $OCH_2CHFOMe$ | $SO_2Me$ |
| 2066 | Et | H | $CH_2CHF_2$ | $CF_3$ | $OCH_2CHFOMe$ | $SO_2Me$ |
| 2067 | Me | H | $CH_2CHF_2$ | Br | $OCH_2CHFOMe$ | $SO_2Me$ |
| 2068 | Et | H | $CH_2CHF_2$ | Br | $OCH_2CHFOMe$ | $SO_2Me$ |
| 2069 | Me | H | $CH_2CHF_2$ | $SO_2Me$ | $OCH_2CHFOMe$ | $CF_3$ |
| 2070 | Et | H | $CH_2CHF_2$ | $SO_2Me$ | $OCH_2CHFOMe$ | $CF_3$ |
| 2071 | Me | H | $CH_2CHF_2$ | Cl | $OCHFCH_2OCF_3$ | $SO_2Me$ |
| 2072 | Et | H | $CH_2CHF_2$ | Cl | $OCHFCH_2OCF_3$ | $SO_2Me$ |
| 2073 | Me | H | $CH_2CHF_2$ | Cl | $OCH_2CH_2OCF_2Cl$ | $SO_2Me$ |
| 2074 | Et | H | $CH_2CHF_2$ | Cl | $OCH_2CH_2OCF_2Cl$ | $SO_2Me$ |
| 2075 | Me | H | $CH_2CHF_2$ | Me | $OCH_2CH_2OCF_2Cl$ | $SO_2Me$ |
| 2076 | Et | H | $CH_2CHF_2$ | Me | $OCH_2CH_2OCF_2Cl$ | $SO_2Me$ |
| 2077 | Me | H | $CH_2CHF_2$ | $CF_3$ | $OCH_2CH_2OCF_2Cl$ | $SO_2Me$ |
| 2078 | Et | H | $CH_2CHF_2$ | $CF_3$ | $OCH_2CH_2OCF_2Cl$ | $SO_2Me$ |
| 2079 | Me | H | $CH_2CHF_2$ | Br | $OCH_2CH_2OCF_2Cl$ | $SO_2Me$ |
| 2080 | Et | H | $CH_2CHF_2$ | Br | $OCH_2CH_2OCF_2Cl$ | $SO_2Me$ |
| 2081 | Me | H | $CH_2CHF_2$ | $SO_2Me$ | $OCH_2CH_2OCF_2Cl$ | $CF_3$ |
| 2082 | Et | H | $CH_2CHF_2$ | $SO_2Me$ | $OCH_2CH_2OCF_2Cl$ | $CF_3$ |
| 2083 | Me | H | $CH_2CHF_2$ | Cl | $SCH_2CH_2OCH_3$ | $SO_2Me$ |
| 2084 | Et | H | $CH_2CHF_2$ | Cl | $SCH_2CH_2OCH_3$ | $SO_2Me$ |
| 2085 | Me | H | $CH_2CHF_2$ | Me | $SCH_2CH_2OCH_3$ | $SO_2Me$ |
| 2086 | Et | H | $CH_2CHF_2$ | Me | $SCH_2CH_2OCH_3$ | $SO_2Me$ |
| 2087 | Me | H | $CH_2CHF_2$ | $CF_3$ | $SCH_2CH_2OCH_3$ | $SO_2Me$ |
| 2088 | Et | H | $CH_2CHF_2$ | $CF_3$ | $SCH_2CH_2OCH_3$ | $SO_2Me$ |
| 2089 | Me | H | $CH_2CHF_2$ | Br | $SCH_2CH_2OCH_3$ | $SO_2Me$ |
| 2090 | Et | H | $CH_2CHF_2$ | Br | $SCH_2CH_2OCH_3$ | $SO_2Me$ |
| 2091 | Me | H | $CH_2CHF_2$ | $SO_2Me$ | $SCH_2CH_2OCH_3$ | $CF_3$ |
| 2092 | Et | H | $CH_2CHF_2$ | $SO_2Me$ | $SCH_2CH_2OCH_3$ | $CF_3$ |
| 2093 | Me | H | $CH_2CHF_2$ | Cl | $SCH_2CH_2OCF_3$ | $SO_2Me$ |
| 2094 | Et | H | $CH_2CHF_2$ | Cl | $SCH_2CH_2OCF_3$ | $SO_2Me$ |
| 2095 | Me | H | $CH_2CHF_2$ | Me | $SCH_2CH_2OCF_3$ | $SO_2Me$ |
| 2096 | Et | H | $CH_2CHF_2$ | Me | $SCH_2CH_2OCF_3$ | $SO_2Me$ |
| 2097 | Me | H | $CH_2CHF_2$ | $CF_3$ | $SCH_2CH_2OCF_3$ | $SO_2Me$ |
| 2098 | Et | H | $CH_2CHF_2$ | $CF_3$ | $SCH_2CH_2OCF_3$ | $SO_2Me$ |
| 2099 | Me | H | $CH_2CHF_2$ | Br | $SCH_2CH_2OCF_3$ | $SO_2Me$ |
| 2100 | Et | H | $CH_2CHF_2$ | Br | $SCH_2CH_2OCF_3$ | $SO_2Me$ |
| 2101 | Me | H | $CH_2CHF_2$ | $SO_2Me$ | $SCH_2CH_2OCF_3$ | $CF_3$ |
| 2102 | Et | H | $CH_2CHF_2$ | $SO_2Me$ | $SCH_2CH_2OCF_3$ | $CF_3$ |
| 2103 | Me | H | $CH_2CHF_2$ | Cl | $SCH_2CH_2SCH_3$ | $SO_2Me$ |
| 2104 | Et | H | $CH_2CHF_2$ | Cl | $SCH_2CH_2SCH_3$ | $SO_2Me$ |
| 2105 | Me | H | $CH_2CHF_2$ | Me | $SCH_2CH_2SCH_3$ | $SO_2Me$ |
| 2106 | Et | H | $CH_2CHF_2$ | Me | $SCH_2CH_2SCH_3$ | $SO_2Me$ |
| 2107 | Me | H | $CH_2CHF_2$ | $CF_3$ | $SCH_2CH_2SCH_3$ | $SO_2Me$ |
| 2108 | Et | H | $CH_2CHF_2$ | $CF_3$ | $SCH_2CH_2SCH_3$ | $SO_2Me$ |
| 2109 | Me | H | $CH_2CHF_2$ | Br | $SCH_2CH_2SCH_3$ | $SO_2Me$ |
| 2110 | Et | H | $CH_2CHF_2$ | Br | $SCH_2CH_2SCH_3$ | $SO_2Me$ |
| 2111 | Me | H | $CH_2CHF_2$ | $SO_2Me$ | $SCH_2CH_2SCH_3$ | $CF_3$ |
| 2112 | Et | H | $CH_2CHF_2$ | $SO_2Me$ | $SCH_2CH_2SCH_3$ | $CF_3$ |
| 2113 | Me | H | $CH_2CHF_2$ | Cl | $SCH_2CH_2SCF_3$ | $SO_2Me$ |
| 2114 | Et | H | $CH_2CHF_2$ | Cl | $SCH_2CH_2SCF_3$ | $SO_2Me$ |
| 2115 | Me | H | $CH_2CHF_2$ | Me | $SCH_2CH_2SCF_3$ | $SO_2Me$ |
| 2116 | Et | H | $CH_2CHF_2$ | Me | $SCH_2CH_2SCF_3$ | $SO_2Me$ |

TABLE 1-continued

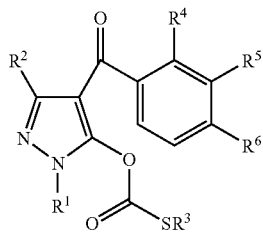

(I)

| No. | R¹ | R² | R³ | R⁴ | R⁵ | R⁶ |
|---|---|---|---|---|---|---|
| 2117 | Me | H | CH₂CHF₂ | CF₃ | SCH₂CH₂SCF₃ | SO₂Me |
| 2118 | Et | H | CH₂CHF₂ | CF₃ | SCH₂CH₂SCF₃ | SO₂Me |
| 2119 | Me | H | CH₂CHF₂ | Br | SCH₂CH₂SCF₃ | SO₂Me |
| 2120 | Et | H | CH₂CHF₂ | Br | SCH₂CH₂SCF₃ | SO₂Me |
| 2121 | Me | H | CH₂CHF₂ | SO₂Me | SCH₂CH₂SCF₃ | CF₃ |
| 2122 | Et | H | CH₂CHF₂ | SO₂Me | SCH₂CH₂SCF₃ | CF₃ |
| 2123 | Me | H | CH₂CHF₂ | Cl | OCH₂CH(CH₃)OCH₃ | SO₂Me |
| 2124 | Et | H | CH₂CHF₂ | Cl | OCH₂CH(CH₃)OCH₃ | SO₂Me |
| 2125 | Me | H | CH₂CHF₂ | Me | OCH₂CH(CH₃)OCH₃ | SO₂Me |
| 2126 | Et | H | CH₂CHF₂ | Me | OCH₂CH(CH₃)OCH₃ | SO₂Me |
| 2127 | Me | H | CH₂CHF₂ | CF₃ | OCH₂CH(CH₃)OCH₃ | SO₂Me |
| 2128 | Et | H | CH₂CHF₂ | CF₃ | OCH₂CH(CH₃)OCH₃ | SO₂Me |
| 2129 | Me | H | CH₂CHF₂ | Br | OCH₂CH(CH₃)OCH₃ | SO₂Me |
| 2130 | Et | H | CH₂CHF₂ | Br | OCH₂CH(CH₃)OCH₃ | SO₂Me |
| 2131 | Me | H | CH₂CHF₂ | SO₂Me | OCH₂CH(CH₃)OCH₃ | CF₃ |
| 2132 | Et | H | CH₂CHF₂ | SO₂Me | OCH₂CH(CH₃)OCH₃ | CF₃ |
| 2133 | Me | H | CH₂CHF₂ | Cl | OCH₂CF₂OCH₃ | SO₂Me |
| 2134 | Et | H | CH₂CHF₂ | Cl | OCH₂CF₂OCH₃ | SO₂Me |
| 2135 | Me | H | CH₂CHF₂ | Me | OCH₂CF₂OCH₃ | SO₂Me |
| 2136 | Et | H | CH₂CHF₂ | Me | OCH₂CF₂OCH₃ | SO₂Me |
| 2137 | Me | H | CH₂CHF₂ | CF₃ | OCH₂CF₂OCH₃ | SO₂Me |
| 2138 | Et | H | CH₂CHF₂ | CF₃ | OCH₂CF₂OCH₃ | SO₂Me |
| 2139 | Me | H | CH₂CHF₂ | Br | OCH₂CF₂OCH₃ | SO₂Me |
| 2140 | Et | H | CH₂CHF₂ | Br | OCH₂CF₂OCH₃ | SO₂Me |
| 2141 | Me | H | CH₂CHF₂ | SO₂Me | OCH₂CF₂OCH₃ | CF₃ |
| 2142 | Et | H | CH₂CHF₂ | SO₂Me | OCH₂CF₂OCH₃ | CF₃ |
| 2143 | Me | H | CH₂CHF₂ | Me | OCH₂CH₂OCH₃ | SO₂Me |
| 2144 | Et | H | CH₂CHF₂ | Me | OCH₂CH₂OCH₃ | SO₂Me |
| 2145 | Me | H | CH₂CHF₂ | Me | OCH₂CH(OCH₃)₂ | SO₂Me |
| 2146 | Me | H | CH₂CHF₂ | Me | CH₂N(Me)CH₂CN | SO₂Me |
| 2147 | Me | H | CH₂CHF₂ | Me | (tetrahydrofuran-2-yl)methoxy | SO₂Me |
| 2148 | Me | H | CH₂CHF₂ | Cl | SMe | SO₂Me |
| 2149 | Me | H | CH₂CHF₂ | Cl | Cl | SO₂Me |
| 2150 | Me | H | CH₂CHF₂ | Cl | OMe | SO₂Me |
| 2151 | Me | H | CH₂CHF₂ | Me | (tetrahydro-2H-pyran-2-yl)methoxy | SO₂Me |
| 2152 | Me | H | CH₂CHF₂ | Cl | OCH₂CH₂OMe | SO₂Me |
| 2153 | Me | H | CH₂CHF₂ | Me | tetrahydrofuran-3-yloxy | SO₂Me |
| 2154 | Me | H | CH₂CHF₂ | Me | OCH₂CH₂CH₂OMe | SO₂Me |
| 2155 | Me | H | CH₂CHF₂ | CN | OCH₂CH₂OMe | SO₂Me |
| 2156 | Et | H | CH₂CHF₂ | Cl | 2-(1,3-dioxolan-2-yl)ethoxy | SO₂Me |
| 2157 | Me | H | CH₂CHF₂ | Me | propargyloxy | SO₂Me |
| 2158 | Me | H | CH₂CHF₂ | Me | (tetrahydrofuran-3-yloxy)methyl | SO₂Me |
| 2159 | Me | H | CH₂CHF₂ | Cl | SO₂Me | SO₂Me |
| 2160 | Me | H | CH₂CHF₂ | Me | (CH₂)₆Me | SO₂Me |
| 2161 | Me | H | CH₂CHF₂ | Me | CH₂CH₂CH₂OMe | SO₂Me |
| 2162 | Et | H | CH₂CHF₂ | Cl | (1,3-dioxolan-2-yl)methoxy | SO₂Me |
| 2163 | Me | H | CH₂CHF₂ | Me | CH₂N[C(O)SEt]CH₂CN | SO₂Me |
| 2164 | Me | H | CH₂CHF₂ | Me | CH=CHCN | SO₂Me |
| 2165 | Me | H | CH₂CHF₂ | Me | CH₂CH₂CN | SO₂Me |
| 2166 | Me | H | CH₂CHF₂ | Me | CH₂SCN | SO₂Me |
| 2167 | Me | H | CH₂CHF₂ | Me | CH₂C(S)NH₂ | SO₂Me |
| 2168 | Me | H | CH₂CHF₂ | NO₂ | OCH₂CH₂OMe | SO₂Me |
| 2169 | Et | H | CH₂CHF₂ | Me | OCH₂CH₂OMe | SO₂Me |
| 2170 | Me | H | CH₂CHF₂ | Me | OCH(CH₃)CH₂OMe | SO₂Me |
| 2171 | Et | H | CH₂CHF₂ | Me | OCH₂CH(Et)OMe | SO₂Me |
| 2172 | Me | H | CH₂CHF₂ | Me | (1,3-dioxolan-2-yl)methyl | SO₂Me |
| 2173 | Me | H | CH₂CHF₂ | Me | CH₂O(i-Pr) | SO₂Me |

TABLE 2

$^1$H-NMR δ ppm (solvent: CDCl$_3$, measuring instrument: JEOL-GSX(400 MHz) or VARIAN MERCURY plus(300 MHz)/ the same applies hereinafter)

| No. | |
|---|---|
| 1 | 1.29 (t, 3H), 2.24 (s, 3H), 2.85 (q, 2H), 3.13 (s, 3H), 3.68 (s, 3H), 3.93 (s, 3H), 7.45 (d, 1H), 7.68 (s, 1H), 7.91 (d, 1H). |
| 2 | 1.31 (t, 3H), 1.41 (t, 3H), 2.27 (s, 3H), 2.88 (q, 2H), 3.21 (s, 3H), 3.96 (s, 3H), 4.03 (q, 2H), 7.48 (d, 1H), 7.70 (s, 1H), 7.93 (d, 1H). |
| 3 | 2.26 (s, 3H), 2.36 (s, 3H), 3.16 (s, 3H), 3.70 (s, 3H), 3.97 (s, 3H), 7.46 (d, 1H, J = 8.4 Hz), 7.73 (s, 1H), 7.94 (d, 1H, 8.4 Hz). |
| 4 | 1.42 (t, 3H, J = 7.3 Hz), 2.27 (s, 3H), 2.37 (s, 3H), 3.17 (s, 3H), 3.97 (s, 3H), 4.01 (q, 2H, J = 7.3 Hz), 7.47 (d, 1H, J = 7.8 Hz), 7.74 (s, 1H), 7.94 (d, 1H, J = 7.8 Hz). |
| 16 | 1.33 (t, 3H, J = 7.3 Hz), 1.42 (t, 3H, J = 7.3 Hz), 2.30 (s, 3H), 2.89 (q, 2H, J = 7.3 Hz), 3.27 (s, 3H), 3.45 (s, 3H), 3.79 (m, 2H), 4.01 (q, 2H, J = 7.3 Hz), 7.21 (d, 1H, J = 7.8 Hz), 7.65 (s, 1H), 7.86 (d, 1H, J = 7.8 Hz). |
| 27 | 1.32 (t, 3H, J = 7.4 Hz), 2.89 (q, 2H, J = 7.4 Hz), 3.18 (s, 3H), 3.71 (s, 3H), 3.99 (s, 3H), 7.52 (d, 1H, J = 8.2 Hz), 7.75 (s, 1H), 8.01 (d, 1H, J = 8.4 Hz). |
| 29 | 2.38 (s, 3H), 3.18 (s, 3H), 3.71 (s, 3H), 3.99 (s, 3H), 7.52 (d, 1H, J = 8.4 Hz), 7.76 (s, 1H), 8.02 (d, 1H, J = 8.0 Hz). |
| 31 | 1.32 (t, 3H, J = 7.4 Hz), 2.59 (s, 3H), 2.89 (q, 2H, J = 7.4 Hz), 3.16 (s, 3H), 3.71 (s, 3H), 7.52 (d, 1H, J = 7.8 Hz), 7.78 (s, 1H), 8.04 (d, 1H, J = 7.8 Hz). |
| 35 | 1.32 (t, 3H, J = 7.3 Hz), 2.27 (s, 3H), 2.89 (q, 2H, J = 7.3 Hz), 3.23 (s, 3H), 3.72 (s, 3H), 3.95 (s, 3H), 7.19 (d, 1H, J = 7.6 Hz), 7.67 (s, 1H), 7.85 (d, 1H, J = 7.6 Hz). |
| 36 | 1.33 (t, 3H, J = 7.2 Hz), 1.47 (t, 3H, J = 7.2 Hz), 2.26 (s, 3H), 2.88 (q, 2H, J = 7.2 Hz), 3.25 (s, 3H), 3.72 (s, 3H), 4.12 (q, 2H, J = 7.2 Hz), 7.18 (d, 1H, J = 7.9 Hz), 7.69 (s, 1H), 7.85 (d, 1H, J = 7.9 Hz). |
| 37 | 1.33 (m, 9H), 2.24 (s, 3H), 2.91 (q, 2H, J = 7.5 Hz), 3.21 (s, 3H), 3.72 (s, 3H), 4.82 (qq, 1H, J = 6.0, 6.0 Hz), 7.15 (d, 1H, J = 8.0 Hz), 7.63 (s, 1H), 7.90 (d, 1H, J = 8.0 Hz). |
| 38 | 1.33 (t, 3H, J = 7.4 Hz), 2.33 (s, 3H), 2.89 (q, 2H, J = 7.4 Hz), 3.21 (s, 3H), 3.72 (s, 3H), 6.75 (t, 1H, J = 75.2 Hz), 7.35 (d, 1H, J = 8.4 Hz), 7.67 (s, 1H), 7.96 (d, 1H, J = 8.4 Hz). |
| 39 | 1.32 (t, 3H, J = 7.5 Hz), 2.25 (s, 3H), 2.89 (q, 2H, J = 7.5 Hz), 3.18 (s, 3H), 3.3 (br s, 3H), 3.72 (s, 3H), 4.57 (t, 2H, J = 10 Hz), 7.50 (d, 1H, J = 8.4 Hz), 7.70 (s, 1H), 8.04 (d, 1H, J = 8.4 Hz). |
| 40 | 2.15 (s, 3H), 2.37 (s, 3H), 3.18 (s, 3H), 3.3 (br s, 2H), 3.72 (s, 3H), 4.57 (t, 2H, J = 10.2 Hz), 7.49 (d, 1H, J = 8.0 Hz), 7.73 (s, 1H), 8.04 (d, 1H, J = 8.0 Hz). |
| 42 | 1.31 (t, 3H, J = 7.4 Hz), 2.87 (q, 2H, J = 7.4 Hz), 3.25 (s, 3H), 3.49 (s, 3H), 3.70 (s, 3H), 5.09 (s, 2H), 7.42 (d, 1H, J = 8.0 Hz), 7.70 (s, 1H), 8.11 (d, 1H, J = 8.0 Hz). |
| 55 | 1.33 (t, 3H, J = 7.4 Hz), 2.29 (s, 3H), 2.89 (q, 2H, J = 7.4 Hz), 3.28 (s, 3H), 3.45 (s, 3H), 3.72 (s, 3H), 3.79 (m, 2H), 4.23 (m, 2H), 7.20 (d, 1H, J = 8.0 Hz), 7.66 (s, 1H), 7.86 (d, 1H, J = 8.0 Hz). |
| 58 | 1.33 (t, 3H, J = 7.4 Hz), 1.42 (t, 3H, J = 7.4 Hz), 1.47 (t, 3H, J = 6.8 Hz), 2.26 (s, 3H), 2.89 (q, 2H, J = 7.4 Hz), 3.25 (s, 3H), 4.02 (q, 2H, J = 7.4 Hz), 4.12 (q, 2H, J = 6.8 Hz), 7.19 (d, 1H, J = 8.0 Hz), 7.66 (s, 1H), 7.85 (d, 1H, J = 8.0 Hz). |
| 59 | 1.32 (t, 3H, J = 7.6 Hz), 1.40 (t, 3H, J = 7.2 Hz), 1.43 (t, 3H, J = 7.2 Hz), 2.90 (q, 2H, J = 7.6 Hz), 4.01 (q, 2H, J = 7.3 Hz), 4.47 (q, 2H, J = 7.2 Hz), 7.52 (d, 1H, J = 8.4 Hz), 7.74 (s, 1H), 8.01 (d, 1H, J = 8.4 Hz). |
| 60 | 1.00 (t, 3H, J = 7.6 Hz), 1.33 (t, 3H, J = 7.4 Hz), 1.43 (t, 3H, J = 7.2 Hz), 1.80 (qt, 2H, J = 6.9, 6.9 Hz), 2.90 (q, 2H, J = 7.3 Hz), 3.19 (s, 3H), 4.01 (q, 2H, J = 7.3 Hz), 4.37 (t, 2H, J = 6.8 Hz), 7.52 (d, 1H, J = 8.4 Hz), 7.74 (s, 1H), 8.01 (d, 1H, J = 8.4 Hz). |
| 61 | 1.31 (t, 3H, J = 7.2 Hz), 1.39 (t, 3H, J = 7.2 Hz), 1.42 (t, 3H, J = 7.4 Hz), 2.29 (s, 3H), 2.89 (q, 2H, J = 7.4 Hz), 3.17 (s, 3H), 4.01 (q, 2H, J = 7.2 Hz), 4.44 (d, 2H, J = 7.2 Hz), 7.47 (d, 1H, J = 7.6 Hz), 7.71 (s, 1H), 7.93 (d, 7.6 Hz). |
| 62 | 1.39 (t, 3H, J = 7.4 Hz), 1.42 (t, 3H, J = 7.4 Hz), 2.28 (s, 3H), 2.37 (s, 3H), 3.17 (s, 3H), 4.01 (q, 2H, J = 7.4 Hz), 4.44 (q, 2H, J = 7.1 Hz), 7.47 (d, 1H, J = 8.4 Hz), 7.74 (s, 1H), 7.94 (d, 1H, J = 8.4 Hz). |
| 63 | 1.31 (t, 3H, J = 7.4 Hz), 2.37 (s, 3H), 2.87 (q, 2H, J = 7.4 Hz), 3.19 (s, 3H), 3.48 (s, 3H), 3.71 (s, 3H), 4.93 (s, 2H), 7.37 (d, 1H, J = 8.2 Hz), 7.64 (s, 1H), 8.03 (d, 1H, J = 8.2 Hz) |
| 64 | 1.35 (t, 3H, J = 7.5 Hz), 2.24 (s, 3H), 2.91 (q, 2H, J = 7.5 Hz), 3.15 (s, 3H), 3.734 (s, 3H), 3.736 (s, 3H), 4.40 (s, 2H), 7.39 (d, 1H, J = 8.1 Hz), 7.65 (s, 1H), 8.05 (d, 1H, J = 8.1 Hz). |
| 65 | 1.31 (t, 3H, J = 7.2 Hz), 1.34 (t, 3H, J = 7.4 Hz), 2.27 (s, 3H), 2.89 (q, 2H, J = 7.3 Hz), 3.35 (s, 3H), 3.19 (s, 3H), 4.29 (q, 2H, J = 7.2 Hz), 4.65 (s, 2H), 7.26 (d, 1H, J = 8.0 Hz), 7.67 (s, 1H), 7.87 (d, 1H, J = 8.0 Hz) |
| 66 | 1.06 (t, 3H, J = 7.6 Hz), 1.32 (t, 3H, J = 7.6 Hz), 1.89 (qt, 2H, J = 6.9, 7.1 Hz), 2.25 (s, 3H), 2.32 (q, 2H, J = 7.3 Hz), 3.33 (s, 3H), 3.71 (s, 3H), 4.03 (t, 2H, J = 6.7 Hz), 7.17 (d, 1H, J = 8.0 Hz), 7.66 (s, 1H), 7.85 (d, 1H, J = 8.0 Hz). |
| 67 | 1.06 (t, 3H, J = 7.2 Hz), 1.34 (t, 3H, J = 7.2 Hz), 1.42 (t, 3H, J = 7.0 Hz), 1.89 (qt, 2H, J = 6.9, 6.9 Hz), 2.26 (s, 3H), 2.89 (q, 2H, J = 7.2 Hz), 3.24 (s, 3H), 3.9-4.0 (m, 4H), 7.19 (d, 1H, J = 8.0 Hz), 7.66 (s, 1H), 7.86 (d, 1H, J = 8.0 Hz). |
| 68 | 1.31 (t, 3H, J = 7.2 Hz), 1.43 (t, 3H, J = 7.4 Hz), 2.87 (q, 2H, J = 7.4 Hz), 3.28 (s, 3H), 3.99 (q, 2H, J = 7.2 Hz), 7.58 (d, 1H, J = 7.6 Hz), 7.69 (s, 1H), 7.93 (d, 1H, J = 7.6 Hz), 8.37 (br s, 1H). |
| 69 | 1.30 (t, 3H, J = 7.2 Hz), 2.38 (s, 3H), 2.86 (q, 2H, J = 7.2 Hz), 3.16 (s, 3H), 3.72 (s, 3H), 4.00 (q, 2H, J = 8.8 Hz), 5.21 (s, 1H), 7.42 (d, 1H, J = 8.2 Hz), 7.67 (s, 1H), 8.05 (d, 1H, J = 8.2 Hz). |
| 70 | 1.32 (t, 3H, J = 7.6 Hz), 2.87 (q, 2H, J = 7.6 Hz), 3.22 (s, 3H), 3.71 (s, 3H), 4.02 (q, 2H, J = 8.8 Hz), 5.35 (s, 2H), 7.48 (d, 1H, J = 8.4 Hz), 7.72 (s, 1H), 8.14 (d, 1H, J = 8.4 Hz). |
| 71 | 1.27 (t, 3H, J = 7.2 Hz), 1.37 (t, 3H, J = 7.2 Hz), 2.33 (s, 3H), 2.83 (q, 2H, J = 7.2 Hz), 3.25 (s, 3H), 3.96 (q, 2H, J = 7.2 Hz), 7.30 (d, 1H, J = 7.8 Hz), 7.65 (s, 1H), 8.03 (d, 1H, J = 7.8 Hz). |
| 72 | 1.33 (t, 3H, J = 7.2 Hz), 2.49 (s, 3H), 2.90 (q, 2H, J = 7.2 Hz), 3.01 (s, 3H), 3.29 (s, 3H), 3.71 (s, 3H), 7.44 (d, 1H, J = 8.0 Hz), 7.63 (s, 1H), 8.02 (d, 1H, J = 8.0 Hz). |
| 73 | 1.24 (t, 3H, J = 6.8 Hz), 1.31 (t, 3H, J = 7.2 Hz), 2.37 (s, 3H), 2.86 (q, 2H, J = 7.2 Hz), 3.29 (s, 3H), 3.67 (q, 2H, J = 6.8 Hz), 3.71 (s, 3H), 4.97 (s, 2H), 7.37 (d, 1H, J = 8.0 Hz), 7.65 (s, 1H), 8.03 (d, 1H, J = 8.0 Hz). |
| 74 | 2.36 (s, 3H), 3.26 (s, 3H), 3.49 (s, 3H), 3.71 (s, 3H), 5.09 (s, 2H), 7.42 (d, 1H, J = 8.0 Hz), 7.71 (s, 1H), 8.12 (d, 1H, J = 8.0 Hz). |
| 75 | 1.33 (t, 3H, J = 7.2 Hz), 2.33 (s, 3H), 2.88 (q, 2H, J = 7.2 Hz), 3.15 (s, 3H), 3.33 (s, 1H), 3.41 (t, 2H, J = 7.4 Hz), 3.63 (t, 2H, J = 7.4 Hz), 3.71 (s, 3H), 7.27 (d, 1H, J = 8.4 Hz), 7.64 (s, 1H), 8.00 (d, 1H, J = 8.4 Hz). |
| 76 | 1.32 (t, 3H, J = 7.2 Hz), 2.38 (s, 3H), 2.88 (q, 2H, J = 7.2 Hz), 3.24 (s, 3H), 3.33 (s, 3H), 3.56 (m, 2H), 3.71 (s, 3H), 3.76 (m, 2H), 5.04 (s, 2H), 7.37 (d, 1H, J = 7.6 Hz), 7.64 (s, 1H), 8.03 (d, 1H, J = 7.6 Hz). |
| 77 | 1.23 (t, 3H, J = 6.8 Hz), 1.33 (t, 3H, J = 7.2 Hz), 2.30 (s, 3H), 2.88 (q, 2H, J = 7.2 Hz), 3.28 (s, 3H), 3.60 (q, 2H, J = 6.8 Hz), 3.71 (s, 3H), 3.82 (m, 2H), 4.24 (m, 2H), 7.18 (d, 1H, J = 7.8 Hz), 7.66 (s, 1H), 7.85 (d, 1H, J = 7.8 Hz). |
| 78 | 1.34 (t, 3H, J = 7.2 Hz), 2.31 (s, 3H), 2.89 (q, 2H, J = 7.2 Hz), 3.26 (s, 3H), 3.72 (s, 3H), 3.91 (t, 2H, J = 5.2 Hz), 4.33 (t, 2H, J = 5.2 Hz), 7.23 (d, 1H, J = 8.0 Hz), 7.67 (s, 1H), 7.87 (d, 1H, J = 8.0 Hz). |
| 79 | 1.35 (t, 3H, J = 7.2 Hz), 2.30 (s, 3H), 2.89 (q, 2H, J = 7.2 Hz), 3.26 (s, 3H), 3.72 (s, 3H), 4.49 (q, 2H, J = 8.4 Hz), 7.30 (d, 1H, J = 8.0 Hz), 7.67 (s, 1H), 7.90 (d, 1H, J = 8.0 Hz). |

TABLE 2-continued

¹H-NMR δ ppm (solvent: CDCl₃, measuring instrument: JEOL-GSX(400 MHz) or VARIAN MERCURY plus(300 MHz)/ the same applies hereinafter)

| No. | |
|---|---|
| 81 | 1.34 (t, 3H, J = 7.2 Hz), 2.19 (s, 3H), 2.29 (s, 3H), 2.89 (q, 2H, J = 7.2 Hz), 2.96 (t, 2H, J = 6.6 Hz), 3.27 (s, 3H), 3.72 (s, 3H), 4.23 (t, 2H, J = 6.6 Hz), 7.20 (d, 1H, J = 8.4 Hz), 7.67 (s, 1H), 7.87 (d, 1H, J = 8.4 Hz). |
| 82 | 1.34 (t, 3H, J = 7.4 Hz), 2.61 (s, 3H), 2.90 (q, 2H, J = 7.5 Hz), 3.32 (s, 3H), 3.74 (s, 3H), 7.67 (d, 1H, J = 8.1 Hz), 7.72 (s, 1H), 8.12 (d, 1H, J = 8.1 Hz). |
| 83 | 1.34 (t, 3H, J = 7.4 Hz), 2.44 (s, 3H), 2.91 (q, 2H, J = 7.3 Hz), 3.22 (s, 3H), 3.74 (s, 3H), 4.44 (s, 2H), 7.48 (d, 1H, J = 8.1 Hz), 7.69 (s, 1H), 8.10 (d, 1H, J = 8.1 Hz). |
| 84 | 0.99 (t, 3H, J = 7.4 Hz), 1.65 (qt, 2H, J = 7.4, 7.4 Hz), 2.27 (s, 3H), 2.85 (t, 2H, J = 7.2 Hz), 3.16 (s, 3H), 3.71 (s, 3H), 3.97 (s, 3H), 7.47 (d, 1H, J = 8.0 Hz), 7.69 (s, 1H), 7.94 (d, 1H, J = 8.0 Hz) |
| 85 | 0.99 (t, 3H, J = 7.4 Hz), 1.42 (t, 3H, J = 7.2 Hz), 1.67 (qt, 2H, J = 7.4, 7.4 Hz), 2.28 (s, 3H), 2.86 (t, 2H, J = 7.4 Hz), 3.16 (s, 3H), 3.96 (s, 3H), 4.02 (quartet, 2H, J = 7.3 Hz), 7.44 (d, 1H, J = 8.0 Hz), 7.69 (s, 1H), 7.94 (d, 1H, J = 8.0 Hz) |
| 86 | 1.34 (d, 6H, J = 4.8 Hz), 2.28 (s, 3H), 3.16 (s, 3H), 3.50 (quintet, 1H, J = 6.8 Hz), 3.71 (s, 3H), 3.97 (s, 3H), 7.48 (d, 1H, J = 8.0 Hz), 7.69 (s, 1H), 7.94 (d, 1H, J = 8.0 Hz) |
| 87 | 1.34 (d, 6H, J = 4.8 Hz), 1.42 (t, 3H, J = 7.4 Hz), 2.28 (s, 3H), 3.16 (s, 3H), 3.51 (quintet, 1H, J = 6.9 Hz), 3.97 (s, 3H), 4.02 (quartet, 2H, J = 7.3 Hz), 7.48 (d, 1H, J = 8.0 Hz), 7.69 (s, 1H), 7.94 (d, 1H, J = 8.0 Hz) |
| 88 | 0.98 (t, 3H, J = 7.4 Hz), 1.36 (d, 6H, J = 6.8 Hz), 1.61-1.70 (m, 2H), 2.73 (m, 2H), 3.16 (s, 3H), 3.36 (qt, 1H, J = 6.8, 6.8 Hz), 3.71 (s, 3H), 3.96 (s, 3H), 7.48 (d, 1H, J = 7.6 Hz), 7.65 (s, 1H), 7.94 (d, 1H, J = 7.6 Hz) |
| 89 | 0.98 (t, 3H), 1.33 (d, 3H), 1.42 (t, 3H), 1.61-1.69 (m, 2H), 2.28 (s, 3H), 3.16 (s, 3H), 3.35 (m, 1H), 3.96 (s, 3H), 4.04 (q, 2H), 7.49 (d, 1H), 7.64 (s, 1H), 7.93 (d, 1H). |
| 90 | 1.47 (s, 9H), 2.29 (s, 3H), 3.17 (s, 3H), 3.71 (s, 3H), 3.96 (s, 3H), 7.48 (d, 1H, J = 8.0 Hz), 7.67 (s, 1H), 7.94 (d, 1H, J = 8.0 Hz) |
| 91 | 1.42 (t, 3H, J = 7.2 Hz), 1.47 (s, 9H), 2.29 (s, 3H), 3.17 (s, 3H), 3.96 (s, 3H), 4.02 (quartet, 2H, J = 7.3 Hz), 7.49 (d, 1H, J = 8.0 Hz), 7.67 (s, 1H), 7.94 (d, 1H, J = 8.0 Hz) |
| 92 | 2.29 (s, 3H), 3.14 (s, 3H), 3.68 (s, 3H), 3.98 (s, 3H), 4.130 (s, 2H), 7.26-7.33 (m, 5H), 7.47 (d, 1H, J = 8.0 Hz), 7.71 (s, 1H), 7.93 (d, 1H, J = 8.0 Hz) |
| 93 | 1.38 (t, 3H, J = 7.2 Hz), 2.29 (s, 3H), 3.15 (s, 3H), 3.95-4.00 (m, 5H), 4.10 (s, 2H), 7.25-7.34 (m, 5H), 7.43 (d, 1H, J = 8.0 Hz), 7.71 (s, 1H), 7.93 (d, 1H, J = 8.0 Hz) |
| 95 | 1.31 (t, 3H, J = 7.4 Hz), 1.40 (t, 3H, J = 7.4 Hz), 2.88 (q, 2H, J = 7.4 Hz), 3.17 (s, 3H), 3.97 (s, 3H), 3.98 (q, 2H, J = 7.4 Hz), 7.52 (d, 1H, J = 8.0 Hz), 7.73 (s, 1H), 7.97 (d, 1H, J = 8.0 Hz). |
| 97 | 1.42 (t, 3H, J = 7.4 Hz), 2.38 (s, 3H), 3.18 (s, 3H), 4.00 (s, 3H), 4.03 (q, 2H, J = 7.4 Hz), 7.52 (d, 1H, J = 8.0 Hz), 7.75 (s, 1H), 8.00 (d, 1H, J = 8.0 Hz). |
| 99 | 1.41 (t, 3H, J = 7.4 Hz), 2.27 (s, 3H), 3.16 (s, 3H), 3.53 (d, 2H, J = 7.6 Hz), 3.98 (s, 3H), 4.02 (q, 2H, J = 7.4 Hz), 5.19 (d, 1H, 10.9 Hz), 5.30 (d, 1H, J = 18.5 Hz), 5.8-5.9 (m, 1H), 7.48 (d, 1H, J = 8.0 Hz), 7.71 (s, 1H), 7.94 (d, 1H, J = 8.0 Hz) |
| 101 | 1.37 (t, 3H, J = 7.4 Hz), 1.75 (s, 3H), 2.23 (s, 3H), 3.11 (s, 3H), 3.50 (s, 2H), 3.74 (s, 3H), 3.93 (q, 2H, J = 7.4 Hz), 4.86 (s, 1H), 4.96 (s, 1H), 7.44 (d, 1H, J = 8.0 Hz), 7.63 (s, 1H), 7.89 (d, 1H, J = 8.0 Hz). |
| 189 | 1.27 (d, 3H, J = 6.4 Hz), 1.33 (t, 3H, J = 7.8 Hz), 2.29 (s, 3H), 2.89 (q, 2H, J = 7.8 Hz), 3.27 (s, 3H), 3.45 (s, 3H), 3.71 (s, 3H), 3.80 (m, 1H), 4.07 (m, 2H), 7.19 (d, 1H, J = 8.0 Hz), 7.65 (s, 1H), 7.86 (d, 1H, J = 8.0 Hz). |
| 207 | 1.37 (d, 6H, J = 7.0 Hz), 2.29 (s, 3H), 3.27 (s, 3H), 3.45 (s, 3H), 3.50 (tt, 1H, J = 7.0, 7.0 Hz), 3.71 (s, 3H), 3.79 (m, 2H), 4.24 (m, 2H), 7.20 (d, 1H, J = 7.6 Hz), 7.66 (s, 1H), 7.86 (d, 1H, J = 7.6 Hz). |
| 208 | 1.36 (d, 6H, J = 6.8 Hz), 1.42 (t, 3H, J = 7.2 Hz), 2.29 (s, 3H), 3.27 (s, 3H), 3.44 (s, 3H), 3.51 (tt, 1H, J = 6.8, 6.8 Hz), 3.79 (m, 2H), 4.00 (q, 2H, J = 7.2 Hz), 4.23 (m, 2H), 7.20 (d, 1H, J = 8.2 Hz), 7.64 (s, 1H), 7.85 (d, 1H, J = 8.2 Hz). |
| 209 | 1.33 (t, 3H, J = 7.4 Hz), 2.28 (s, 3H), 2.88 (q, 2H, J = 7.4 Hz), 3.27 (s, 3H), 3.47 (s, 6H), 3.71 (s, 3H), 4.09 (d, 2H, J = 5.4 Hz), 4.83 (t, 1H, J = 5.4 Hz), 7.20 (d, 1H, J = 8.2 Hz), 7.66 (s, 1H), 7.86 (d, 1H, J = 8.2 Hz). |
| 210 | 1.34 (t, 3H, J = 7.5 Hz), 2.39 (s, 6H), 2.89 (q, 2H, J = 7.5 Hz), 3.26 (s, 3H), 3.63 (s, 2H), 3.73 (s, 3H), 4.21 (s, 2H), 7.38 (d, 1H, J = 8.1 Hz), 7.67 (s, 1H), 8.08 (d, 1H, J = 8.1 Hz). |
| 211 | 1.33 (t, 3H, J = 7.6 Hz), 1.69 (m, 2H), 1.93 (m, 2H), 2.30 (s, 3H), 2.89 (q, 2H, J = 7.6 Hz), 3.28 (s, 3H), 3.17 (s, 3H), 3.85 (dt, 1H, J = 8.4, 6.8 Hz), 3.94 (dt, 1H, J = 8.4, 6.8 Hz), 4.07 (m, 2H), 4.37 (m, 1H), 7.20 (d, 1H, J = 7.6 Hz), 7.66 (s, 1H), 7.86 (d, 1H, J = 7.6 Hz). |
| 212 | 1.32 (t, 3H, J = 7.4 Hz), 2.32 (s, 3H), 2.48 (s, 3H), 2.88 (q, 2H, J = 7.2 Hz), 3.70 (s, 3H), 7.11 (d, 1H, J = 8.4 Hz), 7.16 (d, 1H, J = 8.4 Hz), 7.67 (s, 1H). |
| 213 | 1.33 (t, 3H, J = 7.6 Hz), 2.50 (s, 3H), 2.90 (q, 2H, J = 7.6 Hz), 3.71 (s, 3H), 7.06 (d, 1H, J = 8.4 Hz), 7.24 (d, 1H, J = 8.4 Hz), 7.68 (s, 1H) |
| 214 | 1.32 (t, 3H, J = 7.4 Hz), 2.88 (q, 2H, J = 7.4 Hz), 3.26 (s, 3H), 3.71 (s, 3H), 4.10 (s, 3H), 7.21 (d, 1H, J = 8.0 Hz), 7.73 (s, 1H), 7.92 (d, 1H, J = 8.0 Hz). |
| 215 | 1.33 (t, 3H, J = 7.4 Hz), 1.5-1.9 (m, 6H), 2.29 (s, 3H), 2.89 (q, 2H, J = 7.4 Hz), 3.27 (s, 3H), 3.52 (m, 1H), 3.71 (s, 3H), 3.81 (m, 1H), 3.9-4.1 (m, 3H), 7.18 (d, 1H, J = 8.4 Hz), 7.65 (s, 1H), 7.85 (d, 1H, J = 8.4 Hz). |
| 216 | 1.33 (t, 3H, J = 7.2 Hz), 2.87 (q, 2H, J = 7.2 Hz), 3.31 (s, 3H), 3.46 (s, 3H), 3.70 (s, 3H), 3.83 (m, 2H), 4.44 (m, 2H), 7.22 (d, 1H, J = 8.0 Hz), 7.72 (s, 1H), 7.94 (d, 1H, J = 8.0 Hz). |
| 217 | 1.34 (t, 3H, J = 7.2 Hz), 2.12 (m, 1H), 2.40 (m, 1H), 2.90 (q, 2H, J = 7.2 Hz), 3.21 (s, 3H), 3.72 (s, 3H), 3.8-3.9 (m, 3H), 4.1-4.2 (m, 2H), 5.16 (m, 1H), 7.19 (d, 1H, J = 8.4 Hz), 7.67 (s, 1H), 7.93 (d, 1H, J = 8.4 Hz). |
| 218 | 1.33 (t, 3H, J = 7.4 Hz), 2.13 (tt, 2H, J = 6.4, 6.4 Hz), 2.26 (s, 3H), 2.88 (q, 2H, J = 7.4 Hz), 3.23 (s, 3H), 3.35 (s, 3H), 3.59 (t, 2H, J = 6.4 Hz), 3.71 (s, 3H), 4.16 (t, 2H, J = 6.4 Hz), 7.18 (d, 1H, J = 8.0 Hz), 7.67 (s, 1H), 7.85 (d, 1H, J = 8.0 Hz). |
| 219 | 0.99 (t, 3H, J = 7.4 Hz), 1.68 (qt, 2H, J = 7.4, 7.4 Hz), 2.30 (s, 3H), 2.86 (t, 3H, J = 7.4 Hz), 3.27 (s, 3H), 3.45 (s, 3H), 3.71 (s, 3H), 3.79 (m, 2H), 4.23 (m, 2H), 7.19 (d, 1H, J = 8.0 Hz), 7.64 (s, 1H), 7.86 (d, 1H, J = 8.0 Hz). |
| 220 | 0.98 (t, 3H, J = 7.4 Hz), 1.36 (d, 3H, J = 7.4 Hz), 1.43 (t, 3H, J = 7.4 Hz), 1.6-1.7 (m, 2H), 3.15 (s, 3H), 3.3-3.4 (m, 1H), 4.00 (s, 3H), 4.0-4.1 (m, 2H), 7.54 (d, 1H, J = 8.2 Hz), 7.72 (s, 1H), 8.01 (d, 1H, J = 8.2 Hz). |
| 221 | 1.33 (t, 3H, J = 7.4 Hz), 1.42 (t, 3H, J = 7.4 Hz), 2.3-2.3 (m, 2H), 2.88 (q, 2H, J = 7.4 Hz), 3.28 (s, 3H), 3.8-3.9 (m, 2H), 3.9-4.1 (m, 4H), 4.43 (t, 2H, J = 5.4 Hz), 5.14 (t, 1H, J = 5.4 Hz), 7.22 (d, 1H, J = 8.2 Hz), 7.72 (s, 1H), 7.92 (d, 1H, J = 8.2 Hz). |
| 222 | 1.33 (t, 3H, J = 7.4 Hz), 2.33 (s, 3H), 2.62 (t, 1H, J = 2.4 Hz), 3.28 (s, 3H), 3.72 (s, 3H), 4.76 (d, 2H, J = 2.4 Hz), 7.23 (d, 1H, J = 7.2 Hz), 7.66 (s, 1H), 7.86 (d, 1H, J = 7.2 Hz). |
| 223 | 1.32 (t, 3H, J = 7.2 Hz), 2.07 (m, 2H), 2.37 (s, 3H), 2.87 (q, 2H, J = 7.2 Hz), 3.19 (s, 3H), 3.71 (s, 3H), 3.75-3.95 (m, 4H), 4.31 (m, 1H), 4.97 (d, 2H, J = 10.4 Hz), 5.02 (d, 2H, J = 10.4 Hz), 7.38 (d, 1H, J = 8.0 Hz), 7.65 (s, 1H), 8.03 (d, 1H, J = 8.0 Hz). |
| 224 | 1.28 (t, 3H, J = 7.6 Hz), 2.48 (3H, s), 2.81 (q, 2H, J = 7.6 Hz), 3.41 (s, 3H), 3.65 (s, 3H), 7.38 (d, 1H, J = 8.4 Hz), 7.70 (s, 1H), 8.12 (d, 2H, J = 8.4 Hz) |
| 225 | 0.87 (t, 3H, J = 6.9 Hz), 1.25-1.57 (m, 10H), 1.32 (t, 3H, J = 7.6 Hz), 2.29 (s, 3H), 2.87 (q, 2H, J = 7.6 Hz), 3.01 (m, 1H), 3.09 (s, 3H), 3.71 (s, 3H), 7.23 (d, 1H, J = 7.6 Hz), 7.66 (s, 1H), 7.97 (d, 1H, J = 7.6 Hz). |

TABLE 2-continued $^1$H-NMR δ ppm (solvent: CDCl$_3$, measuring instrument: JEOL-GSX(400 MHz) or VARIAN MERCURY plus(300 MHz)/ the same applies hereinafter)

| No. | |
|---|---|
| 226 | 1.32 (t, 3H, J = 7.6 Hz), 1.97 (m, 2H), 2.31 (s, 3H), 2.86 (q, 2H, J = 7.6 Hz), 3.11 (s, 3H), 3.12 (m, 2H), 3.36 (s, 3H), 3.50 (t, 2H, J = 6.2 Hz), 3.70 (s, 3H), 7.24 (d, 1H, J = 8.4 Hz), 7.67 (s, 1H), 7.97 (d, 1H, J = 8.4 Hz). |
| 227 | 1.32 (t, 3H, J = 7.4 Hz), 1.42 (t, 3H, J = 7.4 Hz), 2.88 (q, 2H, J = 7.4 Hz), 3.31 (s, 3H), 3.9-4.1 (m, 6H), 4.29 (d, 2H, J = 5.4 Hz), 5.47 (t, 1H, J = 5.4 Hz), 7.25 (d, 1H, J = 8.2 Hz), 7.74 (s, 1H), 7.94 (d, 1H, J = 8.2 Hz). |
| 228 | 1.31-1.44 (m, 6H), 2.33 (s, 3H), 2.96-3.05 (m, 4H), 3.14 (s, 3H), 3.74 (s, 3H), 4.37 (s, 2H), 5.21 (s, 2H), 7.50 (d, 1H, J = 8.1 Hz), 7.62 (s, 1H), 8.10 (d, 1H, J = 8.1 Hz). |
| 229 | 1.34 (t, 3H, J = 7.5 Hz), 2.30 (s, 3H), 2.89 (q, 2H, J = 7.5 Hz), 3.06 (s, 3H), 3.74 (s, 3H), 5.68 (d, 1H, J = 17.1 Hz), 7.47 (d, 1H, J = 8.1 Hz), 7.70 (s, 1H), 8.00 (d, 1H, J = 17.1 Hz), 8.05 (d, 1H, J = 8.1 Hz). |
| 230 | 1.36 (t, 3H, J = 7.5 Hz), 2.38 (s, 3H), 2.76 (t, 2H, J = 7.8 Hz), 2.92 (q, 2H, J = 7.5 Hz), 3.14 (s, 3H), 3.43 (q, 2H, J = 7.8 Hz), 3.74 (s, 3H), 7.37 (d, 1H, J = 8.1 Hz), 7.66 (s, 1H), 8.01 (d, 1H, J = 8.1 Hz). |
| 231 | 1.36 (t, 3H, J = 7.5 Hz), 2.49 (s, 3H), 2.92 (q, 2H, J = 7.5 Hz), 3.22 (s, 3H), 3.74 (s, 3H), 4.86 (s, 2H), 7.46 (d, 1H, J = 8.1 Hz), 7.66 (s, 1H), 8.03 (d, 1H, J = 8.1 Hz). |
| 232 | 1.37 (t, 3H, J = 7.5 Hz), 2.40 (s, 3H), 2.96 (q, 2H, J = 7.5 Hz), 3.19 (s, 3H), 3.74 (s, 3H), 4.63 (s, 2H), 7.34 (br, 1H), 7.40 (d, 1H, J = 8.1 Hz), 7.49 (br, 1H), 7.62 (s, 1H), 8.06 (d, 1H, J = 8.1 Hz). |
| 233 | 2.29 (s, 3H), 2.38 (s, 3H), 3.28 (s, 3H), 3.45 (s, 3H), 3.71 (s, 3H), 3.79 (m, 2H), 4.23 (m, 2H), 7.19 (d, 1H, J = 7.6 Hz), 7.66 (s, 1H), 7.86 (d, 1H, 7.6 Hz). |
| 234 | 1.42 (t, 3H, J = 7.4 Hz), 2.30 (s, 3H), 2.38 (s, 3H), 3.28 (s, 3H), 3.45 (s, 3H), 3.79 (m, 2H), 4.01 (q, 2H, J = 7.6 Hz), 4.23 (m, 2H), 7.22 (d, 1H, J = 8.4 Hz), 7.65 (s, 1H), 7.86 (d, 1H, J = 8.4 Hz). |
| 235 | 0.99 (t, 3H, J = 7.4 Hz), 1.42 (t, 3H, J = 7.4 Hz), 1.68 (qt, 2H, J = 7.4, 7.4 Hz), 2.29 (s, 3H), 2.86 (t, 2H, J = 7.4 Hz), 3.27 (s, 3H), 3.45 (s, 3H), 3.79 (m, 2H), 4.01 (q, 2H, J = 7.4 Hz), 4.23 (m, 2H), 7.20 (d, 1H, J = 8.4 Hz), 7.63 (s, 1H), 7.85 (d, 1H, J = 8.4 Hz). |
| 236 | 1.23 (d, 3H, J = 7.4 Hz), 1.37 (t, 3H, J = 7.4 Hz), 2.29 (s, 3H), 2.90-2.96 (m, 2H), 3.23 (s, 3H), 3.35 (s, 3H), 3.51-3.53 (m, 1H), 3.70-3.75 (m, 1H), 3.73 (s, 3H), 4.85-4.90 (m, 1H), 7.18 (d, 1H, J = 8.2 Hz), 7.60 (s, 1H), 7.89 (d, 1H, J = 8.2 Hz). |
| 238 | 1.33 (t, 3H, J = 7.1 Hz), 2.37 (s, 3H), 2.90 (q, 2H, J = 7.1 Hz), 3.19 (s, 3H), 3.66 (d, 2H, J = 6.0 Hz), 3.71 (s, 3H), 3.78-3.86 (m, 2H), 3.95-4.00 (m, 2H), 5.17 (t, 1H, J = 6.0 Hz), 7.31 (d, 1H, J = 9.4 Hz), 7.66 (s, 1H), 8.01 (d, 1H, J = 9.4 Hz). |
| 239 | 1.01 (t, 3H, J = 6.8 Hz), 1.39 (d, 3H, J = 7.4 Hz), 1.61-1.75 (m, 2H), 2.32 (s, 3H), 3.30 (s, 3H), 3.39 (m, 1H), 3.48 (s, 3H), 3.74 (s, 3H), 3.77-3.83 (m, 2H), 4.25-4.27 (m, 2H), 7.23 (d, 1H, J = 8.2 Hz), 7.66 (s, 1H), 7.89 (d, 1H, J = 8.2 Hz). |
| 240 | 1.24 (d, 6H), J = 6.4 Hz), 1.31 (t, 3H, J = 7.2 Hz), 1.42 (t, 3H, J = 7.2 Hz), 2.37 (s, 3H), 2.88 (q, 2H, J = 7.2 Hz), 3.23 (s, 3H), 3.80 (m, 1H), 4.01 (q, 2H, J = 7.2 Hz), 4.97 (s, 2H), 7.38 (d, 1H, J = 8.0 Hz), 7.64 (s, 1H), 8.02 (d, 1H, J = 8.0 Hz). |
| 241 | 1.47 (s, 9H), 2.29 (s, 3H), 3.23 (s, 3H), 3.45 (s, 3H), 3.67 (s, 3H), 3.79 (m, 2H), 4.24 (m, 2H), 7.18 (d, 1H, J = 8.0 Hz), 7.68 (s, 1H), 7.85 (d, 1H, J = 8.0 Hz). |
| 242 | 2.29 (s, 3H), 3.27 (s, 3H), 3.44 (s, 3H), 3.72 (s, 2H), 3.73 (s, 3H), 3.78 (s, 3H), 3.79 (m, 2H), 4.23 (m, 2H), 7.20 (d, 1H, J = 8.4 Hz), 7.61 (s, 1H), 7.87 (d, 1H, J = 8.4 Hz). |

TABLE 3

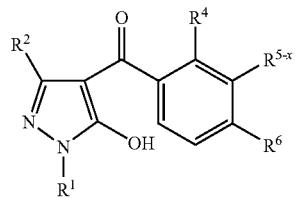

(II-x)

| No. | R$^1$ | R$^2$ | R$^4$ | R$^{5-x}$ | R$^6$ |
|---|---|---|---|---|---|
| 2-1 | Me | H | Me | CO$_2$Me | SO$_2$Me |
| 2-2 | Et | H | Me | CO$_2$Me | SO$_2$Me |
| 2-3 | Et | H | Me | CO$_2$(i-Pr) | SO$_2$Me |
| 2-4 | Me | H | Cl | CO$_2$Et | SO$_2$Me |
| 2-5 | Et | H | Me | CO$_2$Me | CF$_3$ |
| 2-6 | Et | H | Me | OCH$_2$CH$_2$OMe | SO$_2$Me |
| 2-7 | Et | H | SO$_2$Me | CO$_2$Me | CN |
| 2-8 | Me | H | Me | C(O)SMe | SO$_2$Me |
| 2-9 | Me | H | Me | C(O)SEt | SO$_2$Me |
| 2-10 | Me | H | Me | 2-(2-oxolanyl)ethoxy | SO$_2$Me |
| 2-11 | Me | H | Me | 2-(2-(1,3-dioxolanyl))ethoxy | SO$_2$Me |
| 2-12 | Et | H | Me | CH$_2$OMe | SO$_2$Me |
| 2-13 | Et | H | Me | 2-oxolanylmethoxymethyl | SO$_2$Me |
| 2-14 | Me | H | Cl | CO$_2$Me | SO$_2$Me |
| 2-15 | Et | H | Cl | CO$_2$Me | SO$_2$Et |
| 2-16 | Me | H | Cl | C(O)SMe | SO$_2$Me |
| 2-17 | Me | H | Cl | C(O)SEt | SO$_2$Me |
| 2-18 | Me | H | Me | OMe | SO$_2$Me |
| 2-19 | Me | H | Me | OEt | SO$_2$Me |
| 2-20 | Me | H | Me | O(i-Pr) | SO$_2$Me |
| 2-21 | Me | H | Me | OCHF$_2$ | SO$_2$Me |
| 2-22 | Me | H | Me | (4,5-dihydroisoxazol-3-yl)) | SO$_2$Me |
| 2-23 | Me | H | Me | O(n-Pr) | SO$_2$Et |
| 2-24 | Me | H | Cl | CH$_2$OMe | SO$_2$Me |
| 2-25 | Me | H | Me | OCO$_2$Me | SO$_2$Me |
| 2-26 | Me | H | Me | OC(O)SMe | SO$_2$Me |
| 2-27 | Me | H | Me | OC(O)SEt | SO$_2$Me |
| 2-28 | Me | H | Me | OCH$_2$CH$_2$OMe | SO$_2$Me |
| 2-29 | Me | H | Me | OEt | SO$_2$Me |
| 2-30 | Et | H | Cl | CO$_2$Et | SO$_2$Me |
| 2-31 | Et | H | Cl | CO$_2$(n-Pr) | SO$_2$Me |
| 2-32 | Et | H | Me | CO$_2$Et | SO$_2$Me |
| 2-33 | Me | H | Me | CH$_2$CO$_2$Me | SO$_2$Me |
| 2-34 | Me | H | Me | OCH$_2$CO$_2$Et | SO$_2$Me |
| 2-35 | Me | H | Me | O(n-Pr) | SO$_2$Me |
| 2-36 | Et | H | SO$_2$Me | H | CF$_3$ |
| 2-37 | Me | H | Me | CH$_2$OCH$_2$CF$_3$ | SO$_2$Me |
| 2-38 | Me | H | Cl | CH$_2$OCH$_2$CF$_3$ | SO$_2$Me |
| 2-39 | Et | H | Me | Cl | SO$_2$Me |
| 2-40 | Me | H | Me | CH$_2$SO$_2$Me | SO$_2$Me |
| 2-41 | Me | H | Me | CH$_2$OEt | SO$_2$Me |
| 2-42 | Me | H | Cl | CH$_2$OMe | SO$_2$Me |
| 2-43 | Me | H | Me | CH$_2$CH$_2$OMe | SO$_2$Me |
| 2-44 | Me | H | Me | CH$_2$OCH$_2$CH$_2$OMe | SO$_2$Me |
| 2-45 | Me | H | Me | OCH$_2$CH$_2$OEt | SO$_2$Me |
| 2-46 | Me | H | Me | OCH$_2$CH$_2$Cl | SO$_2$Me |
| 2-47 | Me | H | Me | OCH$_2$CF$_3$ | SO$_2$Me |
| 2-48 | Me | H | Me | CH$_2$OCH$_2$OMe | SO$_2$Me |
| 2-49 | Me | H | Me | OCH$_2$CH$_2$SMe | SO$_2$Me |
| 2-50 | Me | H | Me | CN | SO$_2$Me |
| 2-51 | Me | H | Me | CH$_2$CN | SO$_2$Me |
| 2-52 | Me | H | Br | CO$_2$Me | SO$_2$Me |
| 2-53 | Et | H | Cl | CO$_2$Me | SO$_2$Me |
| 2-54 | Me | H | Br | CO$_2$Me | SO$_2$Me |
| 2-55 | Me | H | Cl | OCH$_2$CH$_2$OCF$_3$ | SO$_2$Me |
| 2-56 | Et | H | Cl | OCH$_2$CH$_2$OCF$_3$ | SO$_2$Me |
| 2-57 | Me | H | Me | OCH$_2$CH$_2$OCF$_3$ | SO$_2$Me |
| 2-58 | Et | H | Me | OCH$_2$CH$_2$OCF$_3$ | SO$_2$Me |
| 2-59 | Me | H | CF$_3$ | OCH$_2$CH$_2$OCF$_3$ | SO$_2$Me |
| 2-60 | Et | H | CF$_3$ | OCH$_2$CH$_2$OCF$_3$ | SO$_2$Me |
| 2-61 | Me | H | Br | OCH$_2$CH$_2$OCF$_3$ | SO$_2$Me |

TABLE 3-continued (II-x)

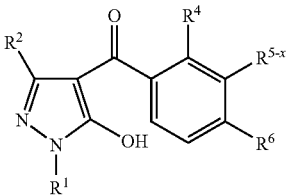

| No. | R¹ | R² | R⁴ | R⁵⁻ˣ | R⁶ |
|---|---|---|---|---|---|
| 2-62 | Et | H | Br | OCH₂CH₂OCF₃ | SO₂Me |
| 2-63 | Me | H | SO₂Me | OCH₂CH₂OCF₃ | CF₃ |
| 2-64 | Et | H | SO₂Me | OCH₂CH₂OCF₃ | CF₃ |
| 2-65 | Me | H | Cl | OCH₂CH₂OCHClF | SO₂Me |
| 2-66 | Et | H | Cl | OCH₂CH₂OCHClF | SO₂Me |
| 2-67 | Me | H | Me | OCH₂CH₂OCHClF | SO₂Me |
| 2-68 | Et | H | Me | OCH₂CH₂OCHClF | SO₂Me |
| 2-69 | Me | H | CF₃ | OCH₂CH₂OCHClF | SO₂Me |
| 2-70 | Et | H | CF₃ | OCH₂CH₂OCHClF | SO₂Me |
| 2-71 | Me | H | Br | OCH₂CH₂OCHClF | SO₂Me |
| 2-72 | Et | H | Br | OCH₂CH₂OCHClF | SO₂Me |
| 2-73 | Me | H | SO₂Me | OCH₂CH₂OCHClF | CF₃ |
| 2-74 | Et | H | SO₂Me | OCH₂CH₂OCHClF | CF₃ |
| 2-75 | Me | H | Cl | OCH₂CHFOCF₃ | SO₂Me |
| 2-76 | Et | H | Cl | OCH₂CHFOCF₃ | SO₂Me |
| 2-77 | Me | H | Me | OCH₂CHFOCF₃ | SO₂Me |
| 2-78 | Me | H | Cl | OCH₂CHFOMe | SO₂Me |
| 2-79 | Et | H | Cl | OCH₂CHFOMe | SO₂Me |
| 2-80 | Me | H | Me | OCH₂CHFOMe | SO₂Me |
| 2-81 | Et | H | Me | OCH₂CHFOMe | SO₂Me |
| 2-82 | Me | H | CF₃ | OCH₂CHFOMe | SO₂Me |
| 2-83 | Et | H | CF₃ | OCH₂CHFOMe | SO₂Me |
| 2-84 | Me | H | Br | OCH₂CHFOMe | SO₂Me |
| 2-85 | Et | H | Br | OCH₂CHFOMe | SO₂Me |
| 2-86 | Me | H | SO₂Me | OCH₂CHFOMe | CF₃ |
| 2-87 | Et | H | SO₂Me | OCH₂CHFOMe | CF₃ |
| 2-88 | Me | H | Cl | OCHFCH₂OCF₃ | SO₂Me |
| 2-89 | Et | H | Cl | OCHFCH₂OCF₃ | SO₂Me |
| 2-90 | Me | H | Cl | OCH₂CH₂OCF₂Cl | SO₂Me |
| 2-91 | Et | H | Cl | OCH₂CH₂OCF₂Cl | SO₂Me |
| 2-92 | Me | H | Me | OCH₂CH₂OCF₂Cl | SO₂Me |
| 2-93 | Et | H | Me | OCH₂CH₂OCF₂Cl | SO₂Me |
| 2-94 | Me | H | CF₃ | OCH₂CH₂OCF₂Cl | SO₂Me |
| 2-95 | Et | H | CF₃ | OCH₂CH₂OCF₂Cl | SO₂Me |
| 2-96 | Me | H | Br | OCH₂CH₂OCF₂Cl | SO₂Me |
| 2-97 | Et | H | Br | OCH₂CH₂OCF₂Cl | SO₂Me |
| 2-98 | Me | H | SO₂Me | OCH₂CH₂OCF₂Cl | CF₃ |
| 2-99 | Et | H | SO₂Me | OCH₂CH₂OCF₂Cl | CF₃ |
| 2-100 | Me | H | Cl | SCH₂CH₂OCH₃ | SO₂Me |
| 2-101 | Et | H | Cl | SCH₂CH₂OCH₃ | SO₂Me |
| 2-102 | Me | H | Me | SCH₂CH₂OCH₃ | SO₂Me |
| 2-103 | Et | H | Me | SCH₂CH₂OCH₃ | SO₂Me |
| 2-104 | Me | H | CF₃ | SCH₂CH₂OCH₃ | SO₂Me |
| 2-105 | Et | H | CF₃ | SCH₂CH₂OCH₃ | SO₂Me |
| 2-106 | Me | H | Br | SCH₂CH₂OCH₃ | SO₂Me |
| 2-107 | Et | H | Br | SCH₂CH₂OCH₃ | SO₂Me |
| 2-108 | Me | H | SO₂Me | SCH₂CH₂OCH₃ | CF₃ |
| 2-109 | Et | H | SO₂Me | SCH₂CH₂OCH₃ | CF₃ |
| 2-110 | Me | H | Cl | SCH₂CH₂OCF₃ | SO₂Me |
| 2-111 | Et | H | Cl | SCH₂CH₂OCF₃ | SO₂Me |
| 2-112 | Me | H | Me | SCH₂CH₂OCF₃ | SO₂Me |
| 2-113 | Et | H | Me | SCH₂CH₂OCF₃ | SO₂Me |
| 2-114 | Me | H | CF₃ | SCH₂CH₂OCF₃ | SO₂Me |
| 2-115 | Et | H | CF₃ | SCH₂CH₂OCF₃ | SO₂Me |
| 2-116 | Me | H | Br | SCH₂CH₂OCF₃ | SO₂Me |
| 2-117 | Et | H | Br | SCH₂CH₂OCF₃ | SO₂Me |
| 2-118 | Me | H | SO₂Me | SCH₂CH₂OCF₃ | CF₃ |
| 2-119 | Et | H | SO₂Me | SCH₂CH₂OCF₃ | CF₃ |
| 2-120 | Me | H | Cl | SCH₂CH₂SCH₃ | SO₂Me |
| 2-121 | Et | H | Cl | SCH₂CH₂SCH₃ | SO₂Me |
| 2-122 | Me | H | Me | SCH₂CH₂SCH₃ | SO₂Me |
| 2-123 | Et | H | Me | SCH₂CH₂SCH₃ | SO₂Me |
| 2-124 | Me | H | CF₃ | SCH₂CH₂SCH₃ | SO₂Me |
| 2-125 | Et | H | CF₃ | SCH₂CH₂SCH₃ | SO₂Me |
| 2-126 | Me | H | Br | SCH₂CH₂SCH₃ | SO₂Me |
| 2-127 | Et | H | Br | SCH₂CH₂SCH₃ | SO₂Me |

TABLE 3-continued (II-x)

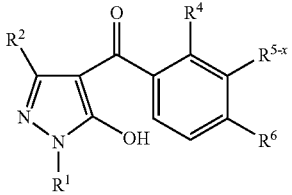

| No. | R¹ | R² | R⁴ | R⁵⁻ˣ | R⁶ |
|---|---|---|---|---|---|
| 2-128 | Me | H | SO₂Me | SCH₂CH₂SCH₃ | CF₃ |
| 2-129 | Et | H | SO₂Me | SCH₂CH₂SCH₃ | CF₃ |
| 2-130 | Me | H | Cl | SCH₂CH₂SCF₃ | SO₂Me |
| 2-131 | Et | H | Cl | SCH₂CH₂SCF₃ | SO₂Me |
| 2-132 | Me | H | Me | SCH₂CH₂SCF₃ | SO₂Me |
| 2-133 | Et | H | Me | SCH₂CH₂SCF₃ | SO₂Me |
| 2-134 | Me | H | CF₃ | SCH₂CH₂SCF₃ | SO₂Me |
| 2-135 | Et | H | CF₃ | SCH₂CH₂SCF₃ | SO₂Me |
| 2-136 | Me | H | Br | SCH₂CH₂SCF₃ | SO₂Me |
| 2-137 | Et | H | Br | SCH₂CH₂SCF₃ | SO₂Me |
| 2-138 | Me | H | SO₂Me | SCH₂CH₂SCF₃ | CF₃ |
| 2-139 | Et | H | SO₂Me | SCH₂CH₂SCF₃ | CF₃ |
| 2-140 | Me | H | Cl | OCH₂CH(CH₃)OCH₃ | SO₂Me |
| 2-141 | Et | H | Cl | OCH₂CH(CH₃)OCH₃ | SO₂Me |
| 2-142 | Me | H | Me | OCH₂CH(CH₃)OCH₃ | SO₂Me |
| 2-143 | Et | H | Me | OCH₂CH(CH₃)OCH₃ | SO₂Me |
| 2-144 | Me | H | CF₃ | OCH₂CH(CH₃)OCH₃ | SO₂Me |
| 2-145 | Et | H | CF₃ | OCH₂CH(CH₃)OCH₃ | SO₂Me |
| 2-146 | Me | H | Br | OCH₂CH(CH₃)OCH₃ | SO₂Me |
| 2-147 | Et | H | Br | OCH₂CH(CH₃)OCH₃ | SO₂Me |
| 2-148 | Me | H | SO₂Me | OCH₂CH(CH₃)OCH₃ | CF₃ |
| 2-149 | Et | H | SO₂Me | OCH₂CH(CH₃)OCH₃ | CF₃ |
| 2-150 | Me | H | Cl | OCH₂CF₂OCH₃ | SO₂Me |
| 2-151 | Et | H | Cl | OCH₂CF₂OCH₃ | SO₂Me |
| 2-152 | Me | H | Me | OCH₂CF₂OCH₃ | SO₂Me |
| 2-153 | Et | H | Me | OCH₂CF₂OCH₃ | SO₂Me |
| 2-154 | Me | H | CF₃ | OCH₂CF₂OCH₃ | SO₂Me |
| 2-155 | Et | H | CF₃ | OCH₂CF₂OCH₃ | SO₂Me |
| 2-156 | Me | H | Br | OCH₂CF₂OCH₃ | SO₂Me |
| 2-157 | Et | H | Br | OCH₂CF₂OCH₃ | SO₂Me |
| 2-158 | Me | H | SO₂Me | OCH₂CF₂OCH₃ | CF₃ |
| 2-159 | Et | H | SO₂Me | OCH₂CF₂OCH₃ | CF₃ |
| 2-160 | Me | H | Me | OCH₂CH₂OCH₃ | SO₂Me |
| 2-161 | Et | H | Me | OCH₂CH₂OCH₃ | SO₂Me |
| 2-162 | Me | H | Me | OCH₂CH(OCH₃)₂ | SO₂Me |
| 2-163 | Me | H | Me | CH₂N(Me)CH₂CN | SO₂Me |
| 2-164 | Me | H | Me | (tetrahydrofuran-2-yl)methoxy | SO₂Me |
| 2-165 | Me | H | Cl | SMe | SO₂Me |
| 2-166 | Me | H | Cl | Cl | SO₂Me |
| 2-167 | Me | H | Cl | OMe | SO₂Me |
| 2-168 | Me | H | Me | (tetrahydro-2H-pyran-2-yl)methoxy | SO₂Me |
| 2-169 | Me | H | Cl | OCH₂CH₂OMe | SO₂Me |
| 2-170 | Me | H | Me | Tetrahydrofuran-3-yloxy | SO₂Me |
| 2-171 | Me | H | Me | OCH₂CH₂CH₂OMe | SO₂Me |
| 2-172 | Me | H | Me | OCH₂CH₂OMe | SO₂Me |
| 2-173 | Et | H | Cl | (1,3-dioxolan-2-yl)ethoxy | SO₂Me |
| 2-174 | Me | H | Me | propargyloxy | SO₂Me |
| 2-175 | Me | H | Me | tetrahydrofuran-3-yloxy)methyl | SO₂Me |
| 2-176 | Me | H | Cl | SO₂Me | SO₂Me |
| 2-177 | Me | H | Me | (CH₂)₆Me | SO₂Me |
| 2-178 | Me | H | Me | CH₂CH₂CH₂OMe | SO₂Me |
| 2-179 | Et | H | Cl | (1,3-dioxolan-2-yl)methoxy | SO₂Me |
| 2-180 | Me | H | Me | CH₂N[C(O)SEt]CH₂CN | SO₂Me |
| 2-181 | Me | H | Me | CHCHCN | SO₂Me |
| 2-182 | Me | H | Me | CH₂CH₂CN | SO₂Me |
| 2-183 | Me | H | Me | CH₂SCN | SO₂Me |
| 2-184 | Me | H | Me | CH₂C(S)NH₂ | SO₂Me |
| 2-185 | Me | H | Me | OCH₂CH₂OMe | SO₂Me |
| 2-186 | Et | H | Me | OCH₂CH₂OMe | SO₂Me |
| 2-187 | Me | H | Me | OCH(CH₃)CH₂OMe | SO₂Me |

TABLE 3-continued

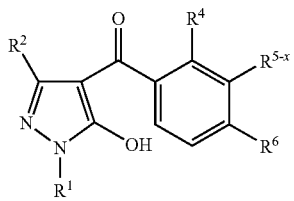

(II-x)

| No. | R¹ | R² | R⁴ | R⁵⁻ˣ | R⁶ |
|---|---|---|---|---|---|
| 2-188 | Me | H | Me | OCH₂CH(Et)OMe | SO₂Me |
| 2-189 | Me | H | Me | (1,3-dioxolan-2-yl) methyl | SO₂Me |
| 2-190 | Me | H | Me | CH₂O(i-Pr) | SO₂Me |

TABLE 4

¹H-NMR δ ppm (solvent: CDCl₃ unless otherwise specified, measuring instrument: JEOL-GSX (400 MHz) or VARIAN MERCURY plus (300 MHz)/ the same applies hereinafter)

| No. | |
|---|---|
| 2-1 | 2.32 (s, 3H), 3.13 (s, 3H), 3.61 (s, 3H), 3.93 (s, 3H), 7.28 (s, 1H), 7.56 (d, 1H, J = 7.8 Hz), 7.93 (d, 1H, J = 7.8 Hz), 8.44 (br.s, 1H). |
| 2-2 | 1.46 (t, 3H), 2.38 (s, 3H), 3.18 (s, 3H), 3.98 (s, 3H), 4.07 (q, 2H), 7.32 (d, 1H, J = 7.8 Hz), 7.61 (s, 1H), 7.98 (d, 1H, J = 7.8 Hz). |
| 2-19 | 1.48 (t, 3H, J = 7.2 Hz), 2.36 (s, 3H), 3.34 (s, 3H), 3.71 (s, 3H), 4.10 (q, 2H, J = 7.2 Hz), 6.98 (br s, 1H), 7.37 (m, 2H), 7.90 (d, 1H, J = 7.2 Hz). |
| 2-20 | 1.34 (d, 6H, J = 6.4 Hz), 2.33 (s, 3H), 3.22 (s, 3H), 3.70 (s, 3H), 4.82 (qq, 1H, J = 6.4, 6.4 Hz), 6.90 (br s. 1H), 7.29 (d, 1H, J = 7.6 Hz), 7.33 (s, 1H), 7.94 (d, 1H, J = 7.6 Hz). |
| 2-21 | 2.43 (s, 3H), 2.23 (s, 3H), 3.71 (s, 3H), 5.30 (br s, 1H), 6.75 (t, 1H, J = 74.8 Hz), 7.33 (s, 1H), 7.50 (d, 1H, J = 8.0 Hz), 8.00 (d, 1H, J = 8.0 Hz). |
| 2-29 | 1.44 (t, 3H, J = 7.2 Hz), 1.48 (t, 3H, J = 7.2 Hz), 2.36 (s, 3H), 3.27 (s, 3H), 4.06 (q, 2H, J = 7.2 Hz), 4.13 (q, 2H, J = 7.2 Hz), 5.2 (br s, 1H), 7.33 (d, 1H, J = 8.0 Hz), 7.34 (s, 1H), 7.90 (d, 1H, J = 8.0 Hz) |
| 2-30 | (Acetone-d₆) 1.30 (br s, 3H), 1.37 (t, 3H, J = 7.0 Hz), 3.25 (s, 3H), 3.95 (br s, 2H), 4.43 (q, 2H, J = 7.0 Hz), 7.27 (br s, 1H), 7.75 (br s, 1H), 8.07 (br s, 1H). |
| 2-31 | (Acetone-d₆) 1.18 (t, 3H, J = 7.4 Hz), 1.34 (br s, 3H), 1.80 (m, 2H), 3.25 (s, 3H), 3.98 (br s, 2H), 4.33 (t, 2H, J = 5.6 Hz), 7.32 (br s, 1H), 7.81 (br s, 1H), 8.08 (br s, 1H). |
| 2-33 | 2.33 (s, 3H), 3.16 (s, 3H), 3.73 (s, 2H), 3.76 (s, 3H), 4.42 (s, 2H), 7.20-7.60 (br s, 1H), 7.34 (s, 1H), 7.52 (d, 1H, J = 8.1 Hz), 8.10 (d, 1H, J = 8.1 Hz). |
| 2-34 | 1.27 (t, 3H, J = 7.6 Hz), 2.32 (s, 3H), 3.32 (s, 3H), 3.66 (s, 3H), 4.25 (q, 2H, J = 7.6 Hz), 4.61 (s, 2H), 7.30 (s, 1H), 7.35 (d, 1H, J = 8.0 Hz), 7.88 (d, 1H, J = 8.0 Hz). |
| 2-40 | (Acetone-d₆) 2.51 (s, 3H), 3.12 (s, 3H), 3.23 (s, 3H), 3.29 (s, 3H), 5.4 (br s, 2H), 6.8 (br s, 1H), 7.42 (d, 1H, J = 8.0 Hz), 8.00 (d, 1H, J = 8.0 Hz). |
| 2-50 | 2.72 (s, 3H), 3.34 (s, 3H), 3.74 (s, 3H), 5.10-5.60 (br s, 1H), 7.32 (s, 1H), 7.81 (d, 1H, J = 8.1 Hz), 8.16 (d, 1H, J = 8.1 Hz). |
| 2-51 | 2.53 (s, 3H), 3.24 (s, 3H), 3.74 (s, 3H), 4.47 (s, 2H), 6.70-7.20 (br s, 1H), 7.33 (s, 1H), 7.60 (d, 1H, J = 8.1 Hz), 8.14 (d, 1H, J = 8.1 Hz). |
| 2-53 | 1.42 (t, 3H, J = 7.3 Hz), 3.20 (s, 3H), 4.04 (s, 3H), 4.09 (q, 2H, J = 7.3 Hz), 7.34 (s, 1H), 7.64 (d, 1H, J = 7.8 Hz), 8.07 (d, 1H, J = 7.8 Hz). |
| 2-142 | 1.23 (d, 3H, J = 6.4 Hz), 2.34 (s, 3H), 3.24 (s, 3H), 3.41 (s, 3H), 3.65 (s, 3H), 3.77 (m, 2H), 3.99 (dd, 1H, J = 9.2, 4.0 Hz), 4.05 (dd, 1H, J = 9.2, 6.4 Hz), 7.28 (s, 1H), 7.29 (d, 1H, J = 8.4 Hz), 7.86 (d, 1H, J = 8.4 Hz). |
| 2-161 | 1.40 (t, 3H, J = 7.0 Hz), 2.39 (s, 3H), 3.23 (s, 3H), 3.43 (s, 3H), 3.76 (m, 2H), 4.21 (q, 1H, J = 7.0 Hz), 4.19 (m, 2H), 7.29 (s, 1H), 7.31 (d, 1H, J = 8.0 Hz), 7.83 (d, 1H, J = 8.0 Hz). |
| 2-163 | 2.41 (s, 3H), 2.48 (s, 3H), 3.27 (s, 3H), 3.63 (s, 2H), 3.72 (s, 3H), 4.23 (s, 2H), 7.29 (s, 1H), 7.51 (d, 1H, J = 8.1 Hz), 8.12 (d, 1H, J = 8.1 Hz). |
| 2-166 | 2.55 (s, 3H), 3.45 (s, 3H), 7.29-7.33 (m, 2H), 7.35 (d, 1H, J = 8.4 Hz). |
| 2-173 | 1.43 (t, 3H, J = 7.3 Hz), 2.28 (m, 2H), 3.29 (s, 3H), 3.86 (m, 2H), 3.96 (m, 2H), 4.08 (m, 2H), 4.39 (m, 2H), 5.13 (t, 1H, J = 5.5 Hz), 7.32 (s, 1H), 7.33 (d, 1H, J = 7.8 Hz), 7.96 (d, 1H, J = 7.8 Hz). |
| 2-176 | 2.49 (s, 3H), 3.54 (s, 3H), 3.57 (s, 3H), 7.40 (s, 1H), 7.63 (d, 1H, J = 7.6 Hz), 8.06 (d, 1H, J = 7.6 Hz). |
| 2-179 | 1.42 (t, 3H, J = 7.3 Hz), 3.35 (s, 3H), 3.95 (m, 2H), 4.04-4.12 (m, 4H), 4.29 (m, 2H), 5.46 (t, 1H, J = 5.5 Hz), 7.32 (s, 1H), 7.36 (d, 1H, J = 7.8 Hz), 7.98 (d, 1H, J = 7.8 Hz). |
| 2-183 | 2.58 (s, 3H), 2.80-3.20 (br s, 1H), 3.25 (s, 3H), 3.73 (s, 3H), 4.89 (s, 2H), 7.33 (s, 1H), 7.58 (d, 1H, J = 8.1 Hz), 8.07 (d, 1H, J = 8.1 Hz). |
| 2-184 | 2.50 (s, 3H), 3.20 (s, 3H), 3.72 (s, 3H), 4.66 (s, 2H), 7.32 (s, 1H), 7.40-7.50 (br s, 1H), 7.52 (d, 1H, J = 8.1 Hz), 8.11 (d, 1H, J = 8.1 Hz). |
| 2-187 | 1.25 (t, 3H, J = 7.3 Hz), 2.35 (s, 3H), 3.25 (s, 3H), 3.34 (s, 3H), 3.53 (m, 1H), 3.70 (s, 3H), 3.74 (m, 1H), 4.88 (m, 1H), 7.24 (s, 1H), 7.31 (d, 1H, J = 7.8 Hz), 7.85 (d, 1H, J = 7.8 Hz). |
| 2-189 | 2.41 (s, 3H), 3.14 (s, 3H), 3.61 (d, 2H, J = 5.2 Hz), 3.65 (s, 3H), 3.77-3.82 (m, 2H), 3.88-3.96 (m, 2H), 5.12 (t, 1H, J = 4.8 Hz), 5.45 (br s, 1H), 7.24 (s, 1H), 7.37 (d, 1H, J = 8.0 Hz), 8.01 (d, 1H, J = 8.0 Hz). |
| 2-190 | 1.25 (d, 6H, J = 6.4 Hz), 1.44 (t, 3H, J = 7.4 Hz), 2.47 (s, 3H), 3.25 (s, 3H), 3.83 (m, 1H), 4.06 (q, 2H, J = 7.4 Hz), 4.7 (br s, 1H), 5.00 (s, 2H), 7.31 (s, 1H), 7.50 (d, 1H, J = 8.4 Hz), 8.07 (d, 1H, J = 8.4 Hz). |

Now, Test Examples will be described.

Test Example 1

Upland field soil was put into a 1/170,000 hectare pot, and seeds of various plants were sown. When the respective plants reached predetermined leaf stage ((1) barnyardgrass (*Echinochloa crus-galli* L.); 0.8 to 2.5 leaf stage, (2) crabgrass (*Digitaria sanguinalis* L.): 0.5 to 3.0 leaf stage, (3) greenfoxtail (*Setaria viridis* L.): 1.0 to 3.0 leaf stage, (4) redroot pigweed (*Amaranthus retroflexus* L.): cotyledon stage to 2.0 leaf stage, (5) prickly *sida* (*Sida spinosa* L.): cotyledon stage to 1.1 leaf stage, (6) velvetleaf (*Abutilon theophrasti* MEDIC.): cotyledon stage to 1.5 leaf stage, (7) rice (*Oryza*

*sativa* L.): 1.0 to 2.5 leaf stage, (8) wheat (*Triticum* spp.): 1.7 to 3.4 leaf stage, (9) corn (*Zea mays* L.): 2.0 to 3.5 leaf stage, and (10) soybean (*Glycine max* Merr.): primary leaf stage to 0.3 leaf stage), wettable powders or emulsifiable concentrates of the compounds of the present invention prepared in accordance with a conventional preparation method, were weighed so that the active ingredients became the prescribed amounts, and diluted with water in an amount corresponding to 500 liter per 1 hectare. 0.1 vol % of an agricultural spreader was further added to the respective diluted liquids, followed by foliar treatment with a small sprayer.

On the 17th to 23rd day after application, the state of growth of the respective plants was visually observed, and the herbicidal effect was evaluated in accordance with a growth inhibition rate (%) of 0 (equivalent to the non-treated area) to 100% (complete kill). The results are shown in Table 5.

TABLE 5

| | | Growth inhibition rate (%) | | | | | | | | | |
|---|---|---|---|---|---|---|---|---|---|---|---|
| No. | Amount of active ingredient (g/ha) | Barnyardgrass | Crabgrass | Greenfoxtail | redroot pigweed | Prickly sida | Velvetleaf | Rice | Wheat | Corn | Soybean | Date of observation |
| 1 | 31 | 90 | 80 | 100 | 100 | 70 | 100 | 80 | 0 | 10 | — | 20 |
| 2 | 31 | 95 | 90 | 100 | 95 | 95 | 95 | 95 | 30 | 10 | — | 20 |
| 3 | 31 | 95 | 95 | 100 | 90 | 90 | 95 | 100 | 50 | 60 | 95 | 22 |
| 4 | 31 | 95 | 95 | 100 | — | 80 | 95 | 100 | 50 | 5 | 95 | 23 |
| 16 | 31 | 100 | 100 | 100 | — | 40 | 100 | 90 | 0 | 0 | 95 | 21 |
| 27 | 31 | 100 | 80 | 100 | 95 | 70 | 80 | 80 | 10 | 40 | 90 | 22 |
| 29 | 31 | 80 | 50 | 50 | 70 | 60 | 65 | 40 | 0 | 10 | 60 | 20 |
| 31 | 31 | 100 | 30 | 80 | 70 | 70 | 60 | 60 | 0 | 60 | 50 | 22 |
| 35 | 31 | 90 | 80 | 100 | 90 | 40 | 80 | 80 | 0 | 0 | 90 | 21 |
| 36 | 31 | 100 | 98 | 100 | 100 | 100 | 100 | 70 | 50 | 10 | — | 21 |
| 37 | 31 | 95 | 80 | 100 | 100 | — | 95 | 70 | 0 | 0 | 70 | 21 |
| 38 | 31 | 80 | 0 | 30 | 20 | 40 | 60 | 40 | 0 | 0 | 70 | 21 |
| 39 | 31 | 95 | 90 | 95 | 80 | — | 90 | 95 | 40 | 0 | 95 | 21 |
| 40 | 31 | 95 | 80 | 95 | 90 | 70 | 90 | 70 | 0 | 10 | 90 | 23 |
| 42 | 31 | 100 | 98 | 95 | 100 | 90 | 95 | 90 | 0 | 0 | 95 | 22 |
| 55 | 31 | 100 | 100 | 100 | 95 | — | 100 | 60 | 10 | 40 | 95 | 20 |
| 58 | 31 | 95 | 98 | 100 | 90 | 70 | 100 | 80 | 40 | 0 | 98 | 20 |
| 59 | 31 | 90 | 80 | 70 | 80 | 80 | 75 | 50 | 10 | 0 | 70 | 21 |
| 60 | 31 | 95 | 90 | 60 | 80 | 70 | 70 | 70 | 0 | 0 | 50 | 21 |
| 61 | 31 | 98 | 98 | 100 | 100 | 95 | 95 | 90 | 60 | 50 | 80 | 21 |
| 62 | 31 | 100 | 100 | 100 | 100 | — | 95 | 80 | 50 | 10 | 90 | 20 |
| 63 | 31 | 95 | 98 | 100 | 95 | — | 95 | 90 | 10 | 0 | 95 | 20 |
| 64 | 31 | 100 | — | 65 | 80 | 60 | 85 | 70 | 0 | 0 | — | 20 |
| 65 | 31 | 20 | 10 | 10 | 30 | 30 | 50 | 0 | 0 | 0 | 10 | 20 |
| 66 | 31 | 95 | 98 | 100 | 95 | 75 | 95 | 60 | 10 | 0 | 98 | 21 |
| 67 | 31 | 95 | 98 | 100 | 95 | 60 | 90 | 60 | 10 | 10 | 90 | 21 |
| 68 | 31 | 95 | 40 | 60 | 75 | 70 | 80 | 60 | 0 | 10 | 70 | 21 |
| 69 | 31 | 95 | 98 | 95 | 85 | 70 | 95 | 80 | 0 | 50 | 98 | 21 |
| 70 | 31 | 100 | 100 | 100 | 100 | 70 | 80 | 70 | 0 | 30 | 80 | 22 |
| 71 | 31 | 70 | 40 | 60 | 70 | 60 | 60 | 60 | 10 | 0 | 60 | 22 |
| 72 | 31 | 80 | 50 | 70 | 60 | 60 | 60 | 50 | 0 | 10 | 70 | 22 |
| 73 | 31 | 100 | 100 | 100 | 100 | 70 | 98 | 95 | 0 | 30 | 98 | 22 |
| 74 | 31 | 100 | 98 | 80 | 100 | 70 | 100 | 95 | 20 | 40 | 98 | 21 |
| 75 | 31 | 98 | 100 | 100 | 100 | 100 | 100 | 98 | 0 | 40 | 98 | 21 |
| 76 | 31 | 98 | 98 | 80 | 90 | 65 | 75 | 60 | 0 | 30 | 95 | 21 |
| 77 | 31 | 98 | 98 | 98 | 95 | 70 | 80 | 70 | 0 | 10 | 95 | 21 |
| 78 | 31 | 60 | 70 | 60 | 60 | 60 | 65 | 10 | 0 | 0 | 70 | 21 |
| 79 | 31 | 100 | 100 | 98 | 100 | 75 | 98 | 60 | 0 | 50 | 100 | 21 |
| 82 | 31 | 70 | 40 | 60 | 60 | 50 | 70 | 40 | 0 | 0 | 70 | 22 |
| 81 | 31 | 30 | 0 | 0 | 10 | 0 | 0 | 10 | 0 | 10 | 50 | 20 |
| 83 | 31 | 100 | 100 | 100 | 80 | 70 | 95 | 80 | 0 | 0 | 95 | 22 |
| 84 | 31 | 98 | 98 | 100 | 100 | 100 | 95 | 95 | 50 | 10 | 95 | 21 |
| 85 | 31 | 98 | 98 | 100 | 95 | 98 | 98 | 95 | 60 | 10 | 98 | 21 |
| 86 | 31 | 95 | 90 | 95 | 95 | 80 | 95 | 95 | 20 | 30 | 85 | 20 |
| 87 | 31 | 95 | 100 | 100 | 100 | 75 | 95 | 90 | 10 | 10 | 95 | 20 |
| 88 | 31 | 98 | 95 | 100 | 95 | 90 | 95 | 95 | 10 | 20 | 95 | 21 |
| 89 | 31 | 100 | 100 | 100 | 90 | 60 | 100 | 100 | 20 | 20 | 95 | 20 |
| 90 | 31 | 80 | 60 | 95 | 80 | 75 | 95 | 40 | 0 | 0 | 80 | 21 |
| 91 | 31 | 95 | 98 | 98 | 98 | 75 | 95 | 90 | 0 | 20 | 98 | 21 |
| 92 | 31 | 0 | 0 | 60 | 10 | 10 | 70 | 0 | 0 | 0 | 10 | 22 |
| 93 | 31 | 95 | 80 | 95 | 98 | 70 | 80 | 70 | 0 | 30 | 80 | 22 |
| 95 | 31 | 100 | 90 | 100 | 100 | 80 | 90 | 90 | 20 | 10 | 95 | 22 |
| 97 | 31 | 100 | 70 | 100 | 100 | 50 | 80 | 60 | 10 | 0 | 80 | 22 |
| 99 | 31 | 98 | 100 | 100 | 98 | 100 | 98 | 95 | 60 | 50 | 98 | 21 |
| 101 | 31 | 100 | 100 | 100 | 100 | 70 | 98 | 98 | 10 | 30 | 90 | 22 |
| 189 | 31 | 95 | 95 | 98 | — | 70 | 100 | 90 | — | 0 | 98 | 21 |
| 207 | 31 | 95 | 95 | 100 | 100 | 60 | 100 | 70 | 0 | 0 | 100 | 21 |
| 208 | 31 | 95 | 100 | 100 | 100 | 40 | 95 | 80 | 0 | 0 | 100 | 21 |
| 209 | 31 | 100 | 95 | 98 | 98 | 90 | 100 | 95 | 0 | 0 | 100 | 17 |
| 210 | 31 | 80 | 30 | 50 | 10 | 70 | 60 | 50 | 0 | 0 | 50 | 22 |
| 211 | 31 | 70 | 70 | 70 | 90 | 20 | 90 | 50 | 0 | 20 | 98 | 20 |
| 212 | 63 | 100 | 50 | 60 | 100 | 40 | 60 | 30 | 0 | 0 | 90 | 20 |

TABLE 5-continued

Growth inhibition rate (%)

| No. | Amount of active ingredient (g/ha) | Barnyardgrass | Crabgrass | Greenfoxtail | redroot pigweed | Prickly sida | Velvetleaf | Rice | Wheat | Corn | Soybean | Date of observation |
|---|---|---|---|---|---|---|---|---|---|---|---|---|
| 213 | 125 | 98 | 70 | 50 | 80 | 60 | 70 | 60 | 30 | 0 | 95 | 20 |
| 214 | 63 | 98 | 95 | 90 | 100 | 70 | 80 | 90 | 0 | 0 | 100 | 20 |
| 215 | 31 | 100 | 60 | 70 | 95 | 50 | 50 | 70 | 0 | 30 | 95 | 20 |
| 216 | 31 | 100 | 100 | 98 | 100 | 50 | 98 | 70 | 0 | 10 | 95 | 20 |
| 217 | 31 | 100 | 100 | 98 | 100 | 70 | 80 | 90 | 40 | 0 | 98 | 21 |
| 218 | 31 | 100 | 100 | 95 | 100 | 70 | 90 | 98 | 10 | 0 | 95 | 21 |
| 219 | 31 | 100 | 100 | 100 | 100 | 70 | 100 | 80 | 0 | 0 | 100 | 21 |
| 220 | 63 | 100 | 60 | 70 | 100 | 90 | 90 | 80 | 0 | 0 | 100 | 21 |
| 221 | 63 | 100 | 50 | 50 | 80 | 40 | 60 | 20 | 0 | 0 | 100 | 21 |
| 222 | 31 | 90 | 70 | 80 | 100 | 30 | 60 | 70 | 0 | 0 | 100 | 21 |
| 223 | 31 | 100 | 100 | 90 | 90 | 70 | 95 | 70 | 0 | 0 | 100 | 21 |
| 224 | 63 | 95 | 60 | 70 | 95 | 70 | 60 | 20 | 0 | 0 | 100 | 21 |
| 225 | 31 | 30 | 0 | 20 | 0 | 0 | 0 | 0 | 0 | 0 | 50 | 21 |
| 226 | 31 | 100 | 95 | 95 | 95 | 70 | 80 | 100 | 0 | 0 | 100 | 21 |
| 227 | 63 | 100 | 100 | 100 | 100 | 60 | 100 | 30 | 0 | 0 | 95 | 21 |
| 228 | 63 | 98 | 60 | 40 | 40 | 40 | 70 | 0 | 0 | 0 | 80 | 21 |
| 229 | 63 | 100 | 100 | 100 | 100 | 98 | 100 | 95 | 50 | 60 | 98 | 21 |
| 230 | 63 | 100 | 100 | 100 | 100 | 80 | 95 | 95 | 40 | 0 | 100 | 22 |
| 231 | 63 | 100 | 70 | 40 | 80 | 40 | 80 | 50 | 0 | 0 | 100 | 22 |
| 232 | 63 | 90 | 95 | 95 | — | 70 | 90 | 95 | 0 | 0 | 90 | 21 |
| 233 | 31 | 100 | 100 | 100 | — | 60 | 100 | 80 | 0 | 0 | 100 | 21 |
| 234 | 31 | 100 | 100 | 100 | 100 | 50 | 100 | 90 | 0 | 0 | 100 | 21 |
| 235 | 31 | 100 | 100 | 100 | 100 | 50 | 100 | 90 | 40 | 30 | 100 | 21 |
| 236 | 31 | 60 | 50 | 40 | 90 | 40 | 70 | 80 | 0 | 0 | 95 | 21 |
| 238 | 63 | 100 | 98 | 98 | 100 | 98 | 100 | 90 | 10 | 0 | 98 | 17 |
| 239 | 31 | 98 | 100 | 100 | — | 80 | 100 | 85 | — | 0 | 100 | 21 |
| 241 | 31 | 100 | 98 | 100 | 100 | 90 | 100 | 90 | — | 0 | 100 | 21 |

Test Example 2

Upland field soil was put into a 1/170,000 hectare pot, and seeds of various plants (barnyardgrass, crabgrass, greenfoxtail, redroot pigweed, prickly sida, velvetleaf, rice, wheat, corn and soybean) were sown. On the day after sowing, wettable powders or emulsifiable concentrates of the compounds of the present invention prepared in accordance with a conventional preparation method, were weighed so that the active ingredients became the prescribed amounts, and diluted with water in an amount corresponding to 500 liter per 1 hectare, followed by soil application with a small sprayer.

On the 19th to 24th day after the application, the state of growth of the respective plants was visually observed, and the herbicidal effect was evaluated in accordance with a growth inhibition rate (%) of from 0 (equivalent to the non-treated area) to 100% (complete kill). The results are shown in Table 6.

TABLE 6

Growth inhibition rate (%)

| No. | Amount of active ingredient (g/ha) | Barnyardgrass | Crabgrass | Greenfoxtail | redroot pigweed | Prickly sida | Velvetleaf | Rice | Wheat | Corn | Soybean | Date of observation |
|---|---|---|---|---|---|---|---|---|---|---|---|---|
| 1 | 250 | 100 | 100 | 100 | 100 | 60 | 60 | 95 | 10 | 0 | 75 | 21 |
| 2 | 250 | 100 | 100 | 98 | 100 | 95 | 60 | 100 | 40 | 0 | — | 21 |
| 3 | 250 | 60 | 100 | 60 | 100 | 95 | 70 | 95 | 0 | 0 | 40 | 21 |
| 4 | 250 | 80 | 100 | 70 | 100 | 70 | 60 | 70 | 0 | 0 | 50 | 24 |
| 16 | 250 | 100 | 100 | 98 | 100 | 10 | 0 | 98 | 0 | 0 | — | 20 |
| 27 | 250 | 100 | 95 | 98 | 100 | 100 | 95 | 90 | 10 | 0 | 0 | 20 |
| 29 | 250 | 50 | 10 | 40 | — | 60 | 50 | 10 | 0 | 0 | 40 | 21 |
| 31 | 250 | 60 | 65 | 70 | 60 | 70 | 60 | 60 | 0 | 0 | — | 20 |
| 35 | 250 | 90 | 100 | 70 | 95 | 90 | 20 | 90 | 0 | 0 | 0 | 22 |
| 36 | 250 | 100 | 100 | 100 | 100 | 60 | 50 | 80 | 0 | 0 | 30 | 20 |
| 37 | 250 | 60 | 80 | 60 | 50 | 10 | 30 | 10 | 0 | 0 | 0 | 21 |
| 38 | 250 | 90 | 95 | 70 | 90 | 70 | 20 | 60 | 0 | 0 | 0 | 22 |
| 39 | 250 | 70 | 100 | 80 | 100 | 70 | 60 | 80 | 0 | 10 | 0 | 21 |
| 40 | 250 | 100 | 100 | 100 | 100 | 85 | 90 | 90 | 10 | 0 | 60 | 24 |
| 42 | 250 | — | 100 | — | 100 | — | 70 | — | — | 0 | — | 21 |
| 55 | 250 | 100 | 100 | 100 | 100 | 70 | 95 | 70 | 0 | 0 | 0 | 19 |
| 58 | 250 | 60 | 100 | 70 | 90 | 70 | 10 | 70 | 0 | 0 | 0 | 21 |
| 59 | 250 | 100 | 100 | 100 | 100 | 98 | 100 | 80 | 10 | 0 | 10 | 19 |
| 60 | 250 | 100 | 100 | 60 | 95 | 70 | 60 | 40 | 0 | 0 | 20 | 19 |
| 61 | 250 | 100 | 100 | 100 | 100 | 80 | 90 | 85 | 30 | 0 | 20 | 19 |
| 62 | 250 | 80 | 95 | 95 | 100 | 90 | 90 | 70 | 30 | 0 | 0 | 19 |
| 63 | 250 | 95 | 95 | 90 | 90 | 80 | 70 | 80 | 0 | 0 | 0 | 19 |

TABLE 6-continued

| | | Growth inhibition rate (%) | | | | | | | | | |
|---|---|---|---|---|---|---|---|---|---|---|---|
| No. | Amount of active ingredient (g/ha) | Barnyardgrass | Crabgrass | Greenfoxtail | redroot pigweed | Prickly sida | Velvetleaf | Rice | Wheat | Corn | Soybean | Date of observation |
| 64 | 250 | 90 | 95 | 50 | 80 | 60 | 30 | 70 | 0 | 0 | 0 | 19 |
| 65 | 250 | 0 | 10 | 10 | 20 | 0 | 0 | 0 | 0 | 0 | 0 | 21 |
| 66 | 250 | 80 | 90 | 40 | 95 | 90 | 40 | 90 | 0 | 0 | 0 | 21 |
| 67 | 250 | 60 | 70 | 40 | 50 | 70 | 60 | 60 | 0 | 0 | 20 | 20 |
| 68 | 250 | 100 | 60 | 30 | 98 | 95 | 100 | 100 | 0 | 0 | 40 | 21 |
| 69 | 250 | 70 | 95 | 50 | 100 | 70 | 70 | 70 | 0 | 0 | — | 20 |
| 70 | 250 | 70 | 80 | 50 | 100 | 65 | 70 | 40 | 0 | 0 | 0 | 20 |
| 72 | 250 | — | 0 | — | 50 | — | 30 | — | — | 0 | — | 21 |
| 73 | 250 | — | 100 | — | 100 | — | 100 | — | — | 0 | — | 21 |
| 74 | 250 | — | 90 | — | 95 | — | 70 | — | — | 0 | — | 21 |
| 75 | 250 | — | 100 | — | 100 | — | 80 | — | — | 10 | — | 21 |
| 76 | 250 | — | 100 | — | 90 | — | 30 | — | — | 0 | — | 21 |
| 77 | 250 | — | 95 | — | 90 | — | 40 | — | — | 0 | — | 21 |
| 78 | 250 | — | 95 | — | 80 | — | 50 | — | — | 0 | — | 21 |
| 79 | 250 | — | 90 | — | 90 | — | 50 | — | — | 0 | — | 21 |
| 81 | 250 | 0 | 0 | 10 | 0 | 0 | 0 | 0 | 0 | 0 | 0 | 20 |
| 82 | 250 | 30 | 70 | 20 | 50 | 80 | 20 | 10 | 0 | 0 | 0 | 21 |
| 83 | 250 | 80 | 95 | 40 | 90 | 70 | 40 | 50 | 0 | 0 | 0 | 21 |
| 84 | 250 | 98 | 100 | 100 | 100 | 98 | 98 | 98 | 0 | 30 | 50 | 21 |
| 85 | 250 | 100 | 100 | 100 | 98 | 100 | 100 | 100 | 0 | 10 | 50 | 21 |
| 86 | 250 | 95 | 100 | 95 | 100 | 90 | 95 | 90 | 0 | 0 | 0 | 19 |
| 87 | 250 | 80 | 90 | 70 | 95 | 70 | 50 | 80 | 0 | 0 | 0 | 19 |
| 88 | 250 | 100 | 100 | 98 | 100 | 95 | 100 | 95 | 0 | 0 | 0 | 20 |
| 89 | 250 | 70 | 95 | 80 | 90 | 50 | 70 | 80 | 0 | 0 | 0 | 19 |
| 90 | 250 | 100 | 100 | 100 | 100 | 98 | 100 | 100 | 0 | 10 | 30 | 21 |
| 91 | 250 | 90 | 95 | 60 | 100 | 95 | 70 | 80 | 0 | 0 | 30 | 20 |
| 92 | 250 | 80 | 95 | 70 | 70 | 60 | 50 | 80 | 0 | 0 | 0 | 20 |
| 93 | 250 | 95 | 90 | 100 | 100 | 75 | 65 | 90 | 0 | 0 | 0 | 20 |
| 95 | 250 | 100 | 95 | 100 | 100 | 95 | 80 | 98 | 0 | 0 | 0 | 20 |
| 97 | 250 | 100 | 100 | 100 | 100 | 100 | 100 | 70 | 0 | 0 | 10 | 20 |
| 99 | 250 | 100 | 100 | 100 | 95 | 100 | 100 | 100 | 0 | 0 | 40 | 20 |
| 189 | 250 | 100 | 100 | 100 | 100 | 100 | 100 | 100 | — | 0 | 10 | 20 |
| 207 | 250 | 100 | 100 | 100 | 100 | 60 | 100 | 98 | 0 | 0 | 20 | 20 |
| 208 | 250 | 100 | 100 | 100 | 100 | 30 | 50 | 98 | 0 | 0 | 0 | 20 |
| 209 | 250 | 95 | 95 | 100 | 95 | 30 | 50 | 90 | 20 | 0 | — | 20 |
| 210 | 250 | 0 | 10 | 0 | 20 | 40 | 0 | 0 | 0 | 0 | 0 | 20 |
| 211 | 250 | 60 | 98 | 60 | 100 | 70 | 40 | 50 | 0 | 0 | 0 | 20 |
| 212 | 250 | 50 | 40 | 0 | 80 | 50 | 0 | 0 | 0 | 0 | 0 | 21 |
| 213 | 250 | 50 | 40 | 20 | 30 | 0 | 0 | 0 | 0 | 0 | 0 | 21 |
| 214 | 250 | 100 | 100 | 100 | 90 | 90 | 90 | 100 | 0 | 0 | 20 | 21 |
| 215 | 250 | 90 | 95 | 70 | 60 | 40 | 0 | 90 | 0 | 0 | — | 21 |
| 216 | 250 | 95 | 100 | 100 | 100 | 80 | 90 | 80 | 0 | 0 | 0 | 21 |
| 217 | 250 | 80 | 95 | 60 | 95 | 60 | 20 | 80 | 0 | 0 | 0 | 19 |
| 218 | 250 | 90 | 80 | 90 | 100 | 50 | 30 | 80 | 0 | 0 | 0 | 19 |
| 219 | 250 | 100 | 100 | 100 | 100 | 80 | 100 | 95 | 0 | 0 | 0 | 19 |
| 220 | 250 | 95 | 95 | 100 | 100 | 95 | 95 | 100 | 0 | 0 | 0 | 19 |
| 221 | 250 | 80 | 100 | 70 | 100 | 60 | 60 | 80 | 0 | 0 | 0 | 19 |
| 222 | 250 | 95 | 100 | 80 | 100 | 50 | 80 | 90 | 0 | 0 | 0 | 19 |
| 223 | 250 | 70 | 100 | 70 | 90 | 60 | 80 | 40 | 0 | 0 | 0 | 19 |
| 224 | 250 | 100 | 100 | 98 | 100 | 75 | 70 | 98 | — | 10 | 50 | 20 |
| 225 | 250 | 0 | 0 | 0 | 30 | 0 | 0 | 0 | 0 | 0 | 0 | 19 |
| 231 | 250 | 70 | 60 | 0 | 50 | 0 | 0 | 0 | — | 0 | 0 | 20 |
| 233 | 250 | 100 | 100 | 100 | 100 | 40 | 100 | 100 | — | 0 | 50 | 20 |
| 234 | 250 | 100 | 100 | 100 | 100 | 20 | 70 | 100 | — | 0 | 0 | 20 |
| 235 | 250 | 100 | 100 | 100 | 100 | 98 | 20 | 100 | — | 0 | 0 | 20 |
| 236 | 250 | 98 | 95 | 10 | 100 | 30 | 0 | 70 | — | 0 | 0 | 20 |

Now, Formulation Examples of the present invention will be described.

Formulation Example 1

| | |
|---|---|
| (1) The compound of the present invention | 75 parts by weight |
| (2) Geropon T-77 (tradename, manufactured by Rhone-Poulenc) | 14.5 parts by weight |
| 3) NaCl | 10 parts by weight |
| 4) Dextrin | 0.5 part by weight |

The above components are placed in a high-speed mixing granulator, admixed with 20 wt % of water, granulated, and dried to obtain water-dispersible granules.

Formulation Example 2

| | |
|---|---|
| (1) Kaolin | 78 parts by weight |
| (2) Laveline FAN (tradename, manufactured by DAI-ICHI KOGYO SEIYAKU CO., LTD.) | 2 parts by weight |
| (3) Sorpol 5039 (tradename, manufactured by TOHO Chemical Industry Co., Ltd.) | 5 parts by weight |
| (4) Carplex (tradename, manufactured by DSL. Japan Co., Ltd.) | 15 parts by weight |

The mixture of the above components (1) to (4) and the compound of the present invention are mixed in a weight ratio of 9:1 to obtain a wettable powder.

Formulation Example 3

| | |
|---|---|
| (1) Hi-Filler No. 10 (tradename, manufactured by Matsumura Sangyo Co., Ltd.) | 33 parts by weight |
| (2) Sorpol 5050 (tradename, manufactured by TOHO Chemical Industry Co., Ltd.) | 3 parts by weight |
| (3) Sorpol 5073 (tradename, manufactured by TOHO Chemical Industry Co., Ltd.) | 4 parts by weight |
| (4) The compound of the present invention | 60 parts by weight |

The above compounds (1) to (4) are mixed to obtain a wettable powder.

Formulation Example 4

| | |
|---|---|
| (1) The compound of the present invention | 4 parts by weight |
| (2) Bentonite | 30 parts by weight |
| (3) Calcium carbonate | 61.5 parts by weight |
| (4) Toxanon GR-31A (tradename, manufactured by Sanyo Chemical Industries Co., Ltd.) | 3 parts by weight |
| (5) Calcium lignin sulfonate | 1.5 parts by weight |

Pulverized component (1) and components (2) and (3) are preliminarily mixed, and then components (4) and (5) and water are mixed thereto. The mixture is extruded and granulated, followed by drying and sieving to obtain granules.

Formulation Example 5

| | |
|---|---|
| (1) The compound of the present invention | 30 parts by weight |
| (2) Zieclite (tradename, manufactured by Zieclite Co., Ltd.) | 60 parts by weight |
| (3) New Kalgen WG-1 (tradename, manufactured by TAKEMOTO OIL & FAT CO., LTD.) | 5 parts by weight |
| (4) New Kalgen FS-7 (tradename, manufactured by TAKEMOTO OIL & FAT CO., LTD.) | 5 parts by weight |

Components (1), (2) and (3) are mixed and passed through a pulverizer, and then component (4) is added thereto. The mixture is kneaded and then extruded and granulated, followed by drying and sieving to obtain water dispersible granules.

Formulation Example 6

| | |
|---|---|
| (1) The compound of the present invention | 28 parts by weight |
| (2) Soprophor FL (tradename, manufactured by Rhone-Poulenc) | 2 parts by weight |
| (3) Sorpol 335 (tradename, manufactured by TOHO Chemical Industry Co., Ltd.) | 1 part by weight |
| (4) IP solvent 1620 (tradename, manufactured by Idemitsu Petrochemical Co., Ltd.) | 32 parts by weight |
| (5) Ethylene glycol | 6 parts by weight |
| (6) Water | 31 parts by weight |

The above components (1) to (6) are mixed and pulverized by a wet-grinding machine (Dyno-mill) to obtain a water-based suspension concentrate.

The invention claimed is:

1. A benzoylpyrazole compound represented by the formula (I) or its salt:

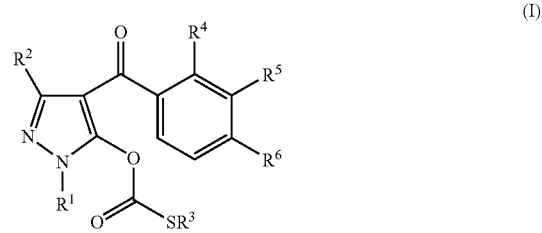

wherein $R^1$ is alkyl or cycloalkyl; $R^2$ is a hydrogen atom or alkyl; $R^3$ is alkyl, cycloalkyl, haloalkyl, alkoxyalkyl, alkoxycarbonylalkyl, alkenyl, or arylalkyl which may be substituted by $R^8$; $R^4$ is alkyl, haloalkyl, alkoxy, halogen, nitro, cyano, alkylthio, alkylsulfinyl, or alkylsulfonyl; $R^5$ is a hydrogen atom, alkyl, alkenyl, alkynyl, halogen, cyano, cyanoalkyl, cyanoalkenyl, haloalkyl, alkoxyalkyl, haloalkoxyalkyl, amino(thiocarbonyl)alkyl which may be substituted by at least one substituent selected from alkyl, cyano, cyanoalkyl, (alkylthio)carbonylalkyl, alkyl(thiocarbonyl)alkyl, —C(O)OR$^7$ and —C(O)SR$^7$, thiocyanatoalkyl, alkoxy, alkenyloxy, alkynyloxy, haloalkoxy, alkoxyalkoxy, haloalkoxyalkoxy, alkoxyhaloalkoxy, haloalkoxyhaloalkoxy, alkoxyalkoxyalkyl, alkylthio, alkoxyalkylthio, haloalkoxyalkylthio, alkoxyhaloalkylthio, haloalkoxyhaloalkylthio, alkylthioalkylthio, haloalkylthioalkylthio, alkylthiohaloalkylthio, haloalkylthiohaloalkylthio, alkylthioalkoxy, alkylsulfonyl, alkylsulfonylalkyl, alkoxycarbonylalkyl alkoxycarbonylalkoxy, heterocyclylalkyl, heterocyclyloxy, heterocyclylalkoxy, heterocyclylalkoxyalkyl, heterocyclyloxyalkyl, cycloalkyloxy, —OC(O)SR$^7$, —OC(O)OR$^7$, —C(O)OR$^7$, —C(O)SR$^7$, —C(S)OR$^7$, —C(S)SR$^7$, or aminoalkyl which may be substituted by at least one substituent selected from alkyl, cyano, cyanoalkyl, (alkylthio)carbonylalkyl, alkyl(thiocarbonyl)alkyl, —C(O)OR$^7$ and —C(O)SR$^7$; R$^6$ is haloalkyl, nitro, cyano, alkylthio, alkylsulfinyl, or alkylsulfonyl; R$^7$ is alkyl, haloalkyl, alkoxyalkyl, alkenyl, haloalkenyl, alkynyl, or arylalkyl which may be substituted by R$^{10}$; and each of R$^8$, R$^9$ and R$^{10}$ which are independent of one another, is halogen, alkyl, or alkoxy.

2. The benzoylpyrazole compound or its salt according to claim 1, wherein R$^1$ is alkyl or cycloalkyl; R$^2$ is a hydrogen atom or alkyl; R$^3$ is alkyl, cycloalkyl, haloalkyl, alkoxyalkyl, alkenyl, or arylalkyl which may be substituted by R$^8$; R$^4$ is alkyl, haloalkyl, alkoxy, halogen, nitro, cyano, alkylthio, alkylsulfinyl, or alkylsulfonyl; R$^5$ is a hydrogen atom, alkyl, halogen, cyano, cyanoalkyl, haloalkyl, alkoxyalkyl, haloalkoxyalkyl, alkoxy, haloalkoxy, alkoxyalkoxy, haloalkoxyalkoxy, alkoxyhaloalkoxy, alkoxyalkoxyalkyl, alkylthio, alkoxyalkylthio, haloalkoxyalkylthio, alkylthioalkylthio, haloalkylthioalkylthio, alkylthioalkoxy, alkylsulfonyl, alkylsulfonylalkyl, alkoxycarbonylalkyl, alkoxycarbonylalkoxy, heterocyclyloxy, heterocyclylalkoxy, heterocyclylalkoxyalkyl, —OC(O)SR$^7$, —OC(O)OR$^7$, —C(O)OR$^7$, or —C(O)SR$^7$; R$^6$ is haloalkyl, nitro, cyano, alkylthio, alkylsulfinyl, or alkylsulfonyl; R$^7$ is alkyl, haloalkyl, alkoxyalkyl, alkenyl, haloalkenyl, alkynyl, or arylalkyl which may be substituted by R$^{10}$; and each of R$^8$, R$^9$ and R$^{10}$ which are independent of one another, is halogen; alkyl; or alkoxy.

3. The benzoylpyrazole compound or its salt according to claim 2, wherein R$^1$ is alkyl or cycloalkyl; R$^2$ is a hydrogen atom or alkyl; R$^3$ is alkyl, cycloalkyl, haloalkyl, alkoxyalkyl, or arylalkyl which may be substituted by R$^8$; R$^4$ is alkyl, haloalkyl, alkoxy, halogen, nitro, cyano, alkylthio alkylsulfinyl, or alkylsulfonyl; R$^5$ is alkyl, haloalkyl, alkoxyalkyl, haloalkoxyalkyl, alkoxy, haloalkoxy, alkoxyalkoxy, haloalkoxyalkoxy, heterocyclyloxy, heterocyclylalkoxy, heterocyclylalkoxyalkyl, —OC(O)SR$^7$, —OC(O)OR$^7$, —C(O)OR$^7$, or —C(O)SR$^7$; R$^6$ is haloalkyl, nitro, cyano, alkylthio, alkylsulfinyl, or alkylsulfonyl; R$^7$ is alkyl, haloalkyl, alkoxyalkyl, alkenyl, haloalkenyl, alkynyl, or arylalkyl which may be substituted by R$^{10}$; and each of R$^8$, R$^9$ and R$^{10}$ which are independent of one another, is halogen; alkyl; or alkoxy.

4. The benzoylpyrazole compound or its salt according to claim 3, wherein R$^1$ is alkyl; R$^2$ is a hydrogen atom; R$^3$ is alkyl; R$^4$ is alkyl; R$^5$ is alkoxy, haloalkoxy, or —C(O)OR$^7$; and R$^6$ is alkylsulfonyl.

5. A process for producing a benzoylpyrazole compound represented by the formula (I) or its salt:

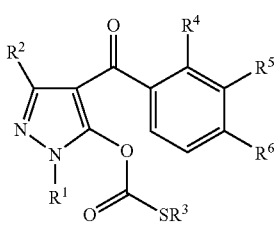

(I)

wherein R$^1$ is alkyl or cycloalkyl; R$^2$ is a hydrogen atom or alkyl; R$^3$ is alkyl, cycloalkyl, haloalkyl, alkoxyalkyl, alkoxycarbonylalkyl, alkenyl, or arylalkyl which may be substituted by R$^8$; R$^4$ is alkyl, haloalkyl, alkoxy, halogen, nitro, cyano, alkylthio, alkylsulfinyl, or alkylsulfonyl; R$^5$ is a hydrogen atom, alkyl, alkenyl, alkynyl, halogen, cyano, cyanoalkyl, cyanoalkenyl, haloalkyl, alkoxyalkyl, haloalkoxyalkyl, amino(thiocarbonyl)alkyl which may be substituted by at least one substituent selected from alkyl, cyano, cyanoalkyl, (alkylthio)carbonylalkyl, alkyl(thiocarbonyl)alkyl, —C(O)OR$^7$ and —C(O)SR$^7$, thiocyanatoalkyl, alkoxy, alkenyloxy, alkynyloxy, haloalkoxy, alkoxyalkoxy, haloalkoxyalkoxy, alkoxyhaloalkoxy, haloalkoxyhaloalkoxy, alkoxyalkoxyalkyl, alkylthio, alkoxyalkylthio, haloalkoxyalkylthio, alkoxyhaloalkylthio, haloalkoxyhaloalkylthio, alkylthioalkylthio, haloalkylthioalkylthio, alkylthiohaloalkylthio, haloalkylthiohaloalkylthio, alkylthioalkoxy, alkylsulfonyl, alkylsulfonylalkyl, alkoxycarbonylalkyl, alkoxycarbonylalkoxy, heterocyclylalkyl, heterocyclyloxy, heterocyclylalkoxy, heterocyclylalkoxyalkyl, heterocyclyloxyalkyl, cycloalkyloxy, OC(O)SR$^7$, —OC(O)OR$^7$, —C(O)OR$^7$, —C(O)SR$^7$, —C(S)OR$^7$, —C(S)SR$^7$, or aminoalkyl which may be substituted by at least one substituent selected from alkyl, cyano, cyanoalkyl, (alkylthio)carbonylalkyl, alkyl(thiocarbonyl)alkyl, —C(O)OR$^7$ and —C(O)SR$^7$; R$^6$ is haloalkyl, nitro, cyano, alkylthio, alkylsulfinyl, or alkylsulfonyl; R$^7$ is alkyl, haloalkyl, alkoxyalkyl, alkenyl, haloalkenyl, alkynyl, or arylalkyl which may be substituted by R$^{10}$; and each of R$^8$, R$^9$ and R$^{10}$ which are independent of one another, is halogen, alkyl, or alkoxy, which comprises (1) reacting a compound represented by the formula (II):

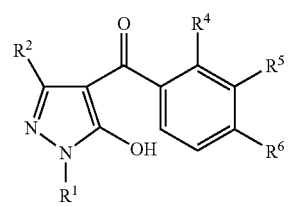

(II)

wherein R$^1$, R$^2$, R$^4$, R$^5$ and R$^6$ are as defined above, with a compound represented by the formula (III):

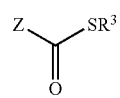

(III)

wherein R$^3$ s as defined above, and Z is a leaving group, (2) reacting a compound represented by the formula (IV-a) and/or the formula (V-a):

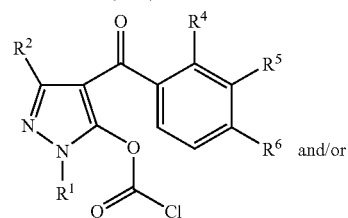

(IV-a)

and/or

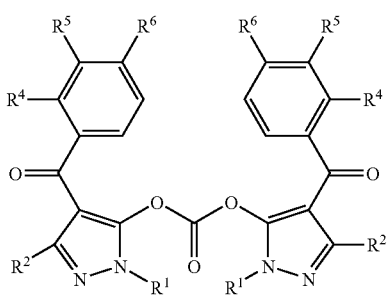

(V-a)

wherein $R^1$, $R^2$, $R^4$, $R^5$ and $R^6$ are as defined above, with a compound represented by the formula (VI-a):

$$HS-R^{3-a} \qquad (VI\text{-}a)$$

wherein $R^{3-a}$ is alkyl, cycloalkyl, haloalkyl, alkoxyalkyl, alkoxycarbonylalkyl, alkenyl, or arylalkyl which may be substituted by $R^8$, or (3) reacting a compound represented by the formula (IV-b) and/or the formula (V-b):

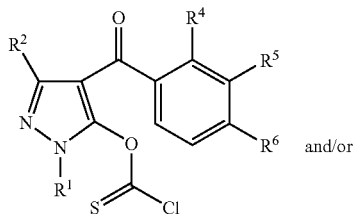

(IV-b) and/or

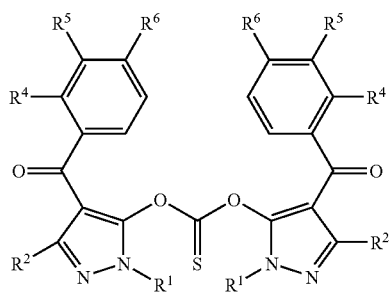

(V-b)

wherein $R^1$, $R^2$, $R^4$, $R^5$ and $R^6$ are as defined above, with a compound represented by the formula (VI-b):

$$HO-R^{3-b} \qquad (VI\text{-}b)$$

wherein $R^{3-b}$ is alkenyl.

6. A herbicide comprising the benzoylpyrazole compound or its salt as defined in claim 1 as an active ingredient.

7. A method for controlling undesired plants or inhibiting their growth, which comprises applying a herbicidally effective amount of the benzoylpyrazole compound or its salt as defined in claim 1 to the undesired plants or to a place where they grow.

* * * * *

UNITED STATES PATENT AND TRADEMARK OFFICE
CERTIFICATE OF CORRECTION

PATENT NO. : 8,030,498 B2
APPLICATION NO. : 12/094734
DATED : October 4, 2011
INVENTOR(S) : Hiroshi Shimoharada et al.

It is certified that error appears in the above-identified patent and that said Letters Patent is hereby corrected as shown below:

Col. 129, Claim 1, Line 4, replace "alkylsulfonylalkyl, alkoxycarbonylalkyl alkoxycarbonyla-"

with: --alkylsulfonylalkyl, alkoxycarbonylalkyl, alkoxycarbonyla- --

Col. 129, Claim 3, Line 39, replace "haloalkyl, alkoxy, halogen, nitro, cyano, alkylthio alkylsulfi-"

with: --haloalkyl, alkoxy, halogen, nitro, cyano, alkylthio, alkylsulfi- --

Signed and Sealed this
Thirty-first Day of January, 2012

David J. Kappos
*Director of the United States Patent and Trademark Office*